US012065486B2

(12) United States Patent
Shoemaker

(10) Patent No.: US 12,065,486 B2
(45) Date of Patent: Aug. 20, 2024

(54) VHH BASED BINDING ANTIBODIES FOR ANTHRAX AND BOTULINUM TOXINS AND METHODS OF MAKING AND USING THEREFOR

(71) Applicant: TRUSTEES OF TUFTS COLLEGE, Medford, MA (US)

(72) Inventor: Charles B. Shoemaker, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 301 days.

(21) Appl. No.: 17/221,177

(22) Filed: Apr. 2, 2021

(65) Prior Publication Data

US 2021/0221874 A1    Jul. 22, 2021

Related U.S. Application Data

(62) Division of application No. 15/534,776, filed as application No. PCT/US2015/064872 on Dec. 10, 2015, now Pat. No. 11,001,625.

(60) Provisional application No. 62/089,949, filed on Dec. 10, 2014.

(51) Int. Cl.
*A61K 39/00* (2006.01)
*C07K 16/12* (2006.01)

(52) U.S. Cl.
CPC ...... *C07K 16/1282* (2013.01); *C07K 16/1278* (2013.01); *C12Y 304/24069* (2013.01); *C12Y 304/24083* (2013.01); *A61K 2039/505* (2013.01); *C07K 2317/31* (2013.01); *C07K 2317/569* (2013.01); *C07K 2317/76* (2013.01); *G01N 2333/952* (2013.01); *G01N 2333/954* (2013.01)

(58) Field of Classification Search
None
See application file for complete search history.

(56) References Cited

U.S. PATENT DOCUMENTS

| | | |
|---|---|---|
| 5,194,596 A | 3/1993 | Tischer et al. |
| 5,196,193 A | 3/1993 | Carroll |
| 5,225,539 A | 7/1993 | Winter |
| 5,455,030 A | 10/1995 | Ladner et al. |
| 5,530,101 A | 6/1996 | Queen et al. |
| 5,585,089 A | 12/1996 | Queen et al. |
| 5,624,659 A | 4/1997 | Bigner et al. |
| 5,693,761 A | 12/1997 | Queen et al. |
| 5,693,762 A | 12/1997 | Queen et al. |
| 5,731,168 A | 3/1998 | Carter et al. |
| 5,840,526 A | 11/1998 | Casterman et al. |
| 6,015,695 A | 1/2000 | Casterman et al. |
| 6,180,370 B1 | 1/2001 | Queen et al. |
| 6,187,287 B1 | 2/2001 | Leung et al. |
| 7,345,161 B2 | 3/2008 | Masuda et al. |
| 7,745,587 B2 | 6/2010 | Devy et al. |
| 7,763,445 B2 | 7/2010 | Moore et al. |
| 7,807,184 B2 | 10/2010 | Vermeij |
| 7,867,724 B2 | 1/2011 | Alexandru et al. |
| 7,879,333 B2 | 2/2011 | Gerber |
| 7,943,345 B2 | 5/2011 | Park et al. |
| 8,114,634 B2 | 2/2012 | Park et al. |
| 8,349,326 B2 | 1/2013 | Shoemaker et al. |
| 8,865,169 B2 | 10/2014 | Shoemaker et al. |
| 8,865,871 B2 | 10/2014 | Park et al. |
| 8,975,382 B2 | 3/2015 | Revets et al. |
| 9,023,352 B2 | 5/2015 | Shoemaker et al. |
| 9,834,616 B2 | 12/2017 | Shoemaker et al. |
| 10,131,870 B2 | 11/2018 | Takeuchi et al. |
| 10,202,441 B2 | 2/2019 | Shoemaker |
| 10,550,174 B2 | 2/2020 | Stortelers et al. |
| 10,766,950 B2 | 9/2020 | Shoemaker |
| 11,001,625 B2 | 5/2021 | Shoemaker |
| 11,091,563 B2 | 8/2021 | Shoemaker et al. |
| 2004/0053340 A1 | 3/2004 | De Haard et al. |
| 2005/0287129 A1 | 12/2005 | Cicciarelli et al. |
| 2006/0018911 A1 | 1/2006 | Ault-Riche et al. |
| 2006/0149041 A1 | 7/2006 | Silence |
| 2009/0098608 A1 | 4/2009 | Park et al. |
| 2010/0092511 A1 | 4/2010 | Waldor et al. |
| 2010/0136018 A1 | 6/2010 | Dolk et al. |
| 2010/0278830 A1 | 11/2010 | Shoemaker et al. |
| 2011/0010782 A1 | 1/2011 | Horvitz et al. |

(Continued)

FOREIGN PATENT DOCUMENTS

| | | |
|---|---|---|
| CN | 103866401 A | 6/2014 |
| EP | 0239400 B1 | 8/1994 |

(Continued)

OTHER PUBLICATIONS

Buck et al. Plant Biotechnol. J. 11: 1006-1016, Epub Aug. 6, 2013.*
Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry, 1992, vol. 11, No. 5, pp. 433-444 (12 pages).
Chen et al., "Novel Chimpanzee/Human Monoclonal Antibodies That Neutralize Anthrax Lethal Factor, and Evidence for Possible Synergy with Anti-Protective Antigen Antibody," Infection and Immunity, Sep. 2009, vol. 77, No. 9, pp. 3902-3908 (7 pages).

(Continued)

*Primary Examiner* — S. Devi
(74) *Attorney, Agent, or Firm* — Melissa Hunter-Ensor; Leslie Serunian; Greenberg Traurig, LLP

(57) ABSTRACT

Methods, compositions and kits are provided for treating a subject exposed to or at risk for exposure to a disease agent, methods, compositions and kits having a pharmaceutical composition including at least one recombinant binding protein or a source of expression of the binding protein, wherein the binding protein neutralizes at least one or a plurality of disease agents that are toxins, for example at least one of a Botulinum toxin or an Anthrax toxin.

11 Claims, 10 Drawing Sheets

Specification includes a Sequence Listing.

(56) References Cited

U.S. PATENT DOCUMENTS

| | | | |
|---|---|---|---|
| 2011/0129474 A1 | 6/2011 | Shoemaker et al. | |
| 2013/0058962 A1 | 3/2013 | Shoemaker et al. | |
| 2014/0072581 A1* | 3/2014 | Dixit | C07K 16/2809 |
| | | | 435/69.6 |
| 2014/0294826 A1 | 10/2014 | Shoemaker | |
| 2015/0093384 A1 | 4/2015 | Shoemaker et al. | |
| 2016/0031971 A9 | 2/2016 | Shoemaker | |
| 2016/0159866 A1* | 6/2016 | Ichtchenko | C07K 14/33 |
| | | | 435/328 |
| 2016/0362501 A1 | 12/2016 | Shoemaker et al. | |
| 2016/0368972 A1 | 12/2016 | Shoemaker | |
| 2017/0204169 A1 | 7/2017 | Shoemaker et al. | |
| 2017/0362310 A1 | 12/2017 | Shoemaker | |
| 2019/0225675 A1 | 7/2019 | Shoemaker | |
| 2020/0129444 A1 | 4/2020 | Whitehead et al. | |
| 2021/0188953 A1 | 6/2021 | Shoemaker | |
| 2021/0363275 A1 | 11/2021 | Shoemaker et al. | |
| 2023/0192825 A1 | 6/2023 | Shoemaker | |

FOREIGN PATENT DOCUMENTS

| | | |
|---|---|---|
| EP | 0592106 B1 | 11/2004 |
| EP | 0519596 B1 | 2/2005 |
| WO | 1991009967 A1 | 7/1991 |
| WO | 2009139919 A2 | 11/2009 |
| WO | 2011068953 A2 | 6/2011 |
| WO | 2015100409 A2 | 7/2015 |
| WO | 2016040499 A1 | 3/2016 |
| WO | 2019094095 A1 | 5/2019 |
| WO | 2022006219 A2 | 1/2022 |

OTHER PUBLICATIONS

Colman, P.M., "Effects of amino acid sequence changes on antibody-antigen interactions," Research in Immunology, 1994, vol. 145, No. 1, pp. 33-36 (4 pages).

Daeron, Marc, "Fc Receptor Biology," Annual Review of Immunology, Apr. 1997, vol. 15, pp. 203-234 (32 pages).

Davies et al., "Defective Fc-Dependent Processing of Immune Complexes in Patients With Systemic Lupus Erythematosus," Arthritis & Rheumatism, Apr. 2002, vol. 46, No. 4, pp. 1028-1038 (11 pages).

Johansson et al., "Liver Cell Uptake and Degradation of Soluble Immunoglobulin G Immune Complexes In Vivo and In Vitro in Rats," Hepatology, Jul. 1996, vol. 24, pp. 169-175 (7 pages).

Lederman et al., "A Single Amino Acid Substitution in a Common African Allele of the CD4 Molecule Ablates Binding of the Monoclonal Antibody, OKT4," Molecular Immunology, 1991, vol. 28, No. 11, pp. 1171-1181 (11 pages).

Li et al., "β-Endorphin omission analogs: Dissociation of immunoreactivity from other biological activities," Proceedings of the National Academy of Sciences of the United States of America, PNAS, Jun. 1980, vol. 77, No. 6, pp. 3211-3214 (4 pages).

Little et al., "Production and Characterization of Monoclonal Antibodies to the Protective Antigen Component of Bacillus anthracis Toxin," Infection and Immunity, Jul. 1988, vol. 56, No. 7, pp. 1807-1813 (7 pages).

Lovdal et al., "Fc receptor mediated endocytosis of small soluble immunoglobulin G immune complexes in Kupffer and endothelial cells from rat liver," Journal of Cell Science, 2000, vol. 113, pp. 3255-3266 (12 pages).

Maass et al., "Three surface antigens dominate the mucosal antibody response to gastrointestinal L3-stage strongylid nematodes in field immune sheep," International Journal for Parasitology, Jul. 2007, vol. 37, Iss. 8-9, pp. 953-962 (10 pages).

Moayeri et al., "A Heterodimer of a VHH (Variable Domains of Camelid Heavy Chain-only) Antibody That Inhibits Anthrax Toxin Cell Binding Linked to a VHH Antibody That Blocks Oligomer Formation Is Highly Protective in an Anthrax Spore Challenge Model," The Journal of Biological Chemistry, Mar. 6, 2015, vol. 290, No. 10, pp. 6584-6595 (12 pages).

Moayeri et al., "Anthrax Protective Antigen Cleavage and Clearance from the Blood of Mice and Rats," Infection and Immunity, Nov. 2007, vol. 75, No. 11, pp. 5175-5184 (10 pages).

Moayeri et al., "Inflammasome Sensor Nlrp1b-Dependent Resistance to Anthrax Is Mediated by Caspase-1, IL-1 Signaling and Neutrophil Recruitment," PLoS Pathogens, Dec. 2010, vol. 6, Iss. 12, e1001222, pp. 1-9 (9 pages).

Mohamed et al., "A High-Affinity Monoclonal Antibody to Anthrax Protective Antigen Passively Protects Rabbits before and after Aerosolized Bacillus anthracis Spore Challenge," Infection and Immunity, Feb. 2005, vol. 73, No. 2, pp. 795-802 (8 pages).

Mukherjee et al., "A Novel Strategy for Development of Recombinant Antitoxin Therapeutics Tested in a Mouse Botulism Model," PLoS One, Jan. 2012, vol. 7, Iss. 1, e29941, pp. 1-12 (12 pages).

Mukherjee et al., "Human Stx2-Specific Monoclonal Antibodies Prevent Systemic Complications of Escherichia coli O157:H7 Infection," Infection and Immunity, Feb. 2002, vol. 70, No. 2, pp. 612-619 (8 pages).

Mukherjee et al., "Prolonged Prophylactic Protection from Botulism with a Single Adenovirus Treatment Promoting Serum Expression of a VHH-Based Antitoxin Protein," PLoS One, Aug. 2014, vol. 9, Iss. 8, e106422, pp. 1-13 (13 pages).

Nguyen et al., "The pharmacokinetics of an albumin-binding Fab (AB.Fab) can be modulated as a function of affinity for albumin," Protein Engineering, Design & Selection : PEDS, 2006, vol. 19, No. 7, pp. 291-297 (7 pages).

Nowakowski et al., "Potent neutralization of botulinum neurotoxin by recombinant oligoclonal antibody," Proceedings of the National Academy of Sciences of the United States of America, PNAS, Aug. 20, 2002, vol. 99, No. 17, pp. 11346-11350 (5 pages).

Park et al., "Optimized Production and Purification of Bacillus anthracis Lethal Factor," Protein Expression and Purification, Apr. 2000, vol. 18, No. 3, pp. 293-302 (10 pages).

Pomerantsev et al., "Genome Engineering in Bacillus anthracis Using Cre Recombinase," Infection and Immunity, Jan. 2006, vol. 74, No. 1, pp. 682-693 (12 pages).

Rosovitz et al., "Alanine-scanning Mutations in Domain 4 of Anthrax Toxin Protective Antigen Reveal Residues Important for Binding to the Cellular Receptor and to a Neutralizing Monoclonal Antibody," The Journal of Biological Chemistry, Aug. 15, 2003, vol. 278, No. 33, pp. 30936-30944 (9 pages).

Sepulveda et al., "Efficient Serum Clearance of Botulinum Neurotoxin Achieved Using a Pool of Small Antitoxin Binding Agents," Infection and Immunity, Feb. 2010, vol. 78, No. 2, pp. 756-763 (8 pages).

Sheoran et al., "Adenovirus Vector Expressing Stx1/Stx2-Neutralizing Agent Protects Piglets Infected with Escherichia coli O157:H7 against Fatal Systemic Intoxication," Infection and Immunity, Jan. 2015, vol. 83, No. 1, pp. 286-291 (6 pages).

Singh et al., "The Chymotrypsin-sensitive Site, FFD315, in Anthrax Toxin Protective Antigen Is Required for Translocation of Lethal Factor," The Journal of Biological Chemistry, Nov. 18, 1994, vol. 269, No. 46, pp. 29039-29046 (8 pages).

Skolnick et al., "From genes to protein structure and function: novel applications of computational approaches in the genomic era," Trends in Biotechnology, Jan. 2000, vol. 18, No. 1, pp. 34-39 (6 pages).

Tremblay et al., "A Single VHH-Based Toxin-Neutralizing Agent and an Effector Antibody Protect Mice against Challenge with Shiga Toxins 1 and 2," Infection and Immunity, Dec. 2013, vol. 81, No. 12, pp. 4592-4603 (12 pages).

Tremblay et al., "Camelid single domain antibodies (VHHs) as neuronal cell intrabody binding agents and inhibitors of Clostridium botulinum neurotoxin (BoNT) proteases," Toxicon, Nov. 2010, vol. 56, No. 6, pp. 990-998 (16 pages).

Vance et al., "Stepwise Engineering of Heterodimeric Single Domain Camelid VHH Antibodies That Passively Protect Mice from Ricin Toxin," The Journal of Biological Chemistry, Dec. 20, 2013, vol. 288, No. 51, pp. 36538-36547 (10 pages).

Yang et al., "A Novel Multivalent, Single-Domain Antibody Targeting TcdA and TcdB Prevents Fulminant Clostridium difficile Infection in Mice," The Journal of Infectious Diseases, Sep. 15, 2014, vol. 210, pp. 964-972 (9 pages).

(56) References Cited

OTHER PUBLICATIONS

English Machine Translation (Google Patents) of CN 103866401 (13 pages).
International Search Report and Written Opinion for corresponding International Patent Application No. PCT/US2015/064872, dated Apr. 15, 2016 (10 pages).
Rossolini et al., "Use of deoxyinosine-containing primers vs degenerate primers for polymerase chain reaction based on ambiguous sequence information," Molecular and Cellular Probes, 1994, vol. 8, pp. 91-98.
Sandvig et al., "Entry of ricin and Shiga toxin into cells: molecular mechanisms and medical perspectives," The EMBO Journal, 2000, vol. 19, No. 22, pp. 5943-5950.
Sehr et al., "Glucosylation and ADP Ribosylation of Rho Proteins: Effects on Nucleotide Binding, GTPase Activity, and Effector Coupling," Biochemistry, 1998, vol. 37, pp. 5296-5304.
Sikorra et al., "Identification of the Amino Acid Residues Rendering TI-VAMP Insensitive toward Botulinum Neurotoxin B," Journal of Molecular Biology, 2006, vol. 357, pp. 574-582.
Sikorra et al., "Substrate Recognition Mechanism of VAMP/Synaptobrevin-cleaving Clostridial Neurotoxins," The Journal of Biological Chemistry, Jul. 25, 2008, vol. 283, No. 30, pp. 21145-21152.
Silvaggi et al., "Structures of Clostridium botulinum Neurotoxin Serotype A Light Chain Complexed with Small-Molecule Inhibitors Highlight Active-Site Flexibility," Chemistry & Biology, May 2007, vol. 14, pp. 533-542.
Simpson, "Identification of the Major Steps in Botulinum Toxin Action," Annual Review of Pharmacology and Toxicology, 2004, vol. 44, pp. 167-193.
Snow et al., "Safety and Pharmacokinetics of a Four Monoclonal Antibody Combination against Botulinum C and D Neurotoxins," Antimicrobial Agents and Chemotherapy, Dec. 2019, vol. 63, No. 12, e01270-19, pp. 1-11.
Spears et al., "A comparison of enteropathogenic and enterohaemorrhagic *Escherichia coli* pathogenesis," FEMS Microbiology Letters, Feb. 2006, vol. 255, pp. 187-202.
Thess et al., "Sequence-engineered mRNA Without Chemical Nucleoside Modifications Enables an Effective Protein Therapy in Large Animals," Molecular Therapy, Sep. 2015, vol. 23, No. 9, pp. 1456-1464.
Thran et al., "mRNA mediates passive vaccination against infectious agents, toxins, and tumors," EMBO Molecular Medicine, 2017, vol. 9, No. 10, pp. 1434-1447.
Tomic et al., "Monoclonal Antibody Combinations Prevent Serotype A and Serotype B Inhalational Botulism in a Guinea Pig Model," Toxins, 2019, vol. 11, Article No. 208, pp. 1-15.
Tonegawa, "The genetic principle for generation of antibody diversity," The Nobel Assembly at the Karolinska Institute, 1987, retrieved from the Internet on Feb. 12, 2024, URL: <nobelprize.org/nobel_prizes/medicine/laureates/1987/press.html>.
Tremblay et al., "Camelid single domain antibodies (VHHs) as neuronal cell intrabody binding agents and inhibitors of Clostridium botulinum neurotoxin (BoNT) proteases," Toxicon, 2010, vol. 56, pp. 990-998.
Tremblay et al., "Camelid VHH Antibodies that Neutralize Botulinum Neurotoxin Serotype E Intoxication or Protease Function," Toxins, 2020, vol. 12, Article No. 611, pp. 1-18.
Tzipori et al., "The Role of the eaeA Gene in Diarrhea and Neurological Complications in a Gnotobiotic Piglet Model of Enterohemorrhagic *Escherichia coli* Infection," Infection and Immunity, Sep. 1995, vol. 63, No. 9, pp. 3621-3627.
Ulmer et al., "Heterologous Protection Against Influenza by Injection of DNA Encoding a Viral Protein," Science, Mar. 19, 1993, vol. 259, pp. 1745-1749.
Vagin et al., "Recruitment of septin cytoskeletal proteins by botulinum toxin A protease determines its remarkable stability," Journal of Cell Science, 2014, vol. 127, pp. 3294-3308.
Vattekatte et al., "Discrete analysis of camelid variable domains: sequences, structures, and in-silico structure prediction," PeerJ, 2020, vol. 8, e8408, pp. 1-28.
Von Eichel-Streiber et al., "Large clostridial cytotoxins—a family of glycosyltransferases modifying small GTP-binding proteins," Trends in Microbiology, Oct. 1996, vol. 4, No. 10, pp. 375-382.
Wahl et al., "Molecular Hybridization of Immobilized Nucleic Acids: Theoretical Concepts and Practical Considerations," Methods in Enzymology, 1987, vol. 152, pp. 399-407.
Wang et al., "A Dileucine in the Protease of Botulinum Toxin A Underlies Its Long-lived Neuroparalysis," The Journal of Biological Chemistry, Feb. 25, 2011, vol. 286, No. 8, pp. 6375-6385.
Walker, K., "Interscience Conference on Antimicrobial Agents and Chemotherapy—50th Annual Meeting—Research on Promising New Agents: Part 1," Idrugs: The Investigational Drugs Journal, Nov. 2010, vol. 13, No. 11, pp. 743-745. [Abstract].
Winn et al., "Overview of the CCP4 suite and current developments," Acta Crystallographica Section D: Biological Crystallography, 2011, vol. 67, pp. 235-242.
Wolff et al., "Direct Gene Transfer into Mouse Muscle in Vivo," Science, Mar. 23, 1990, vol. 247, pp. 1465-1468.
Yao et al., "A camelid single-domain antibody neutralizes botulinum neurotoxin A by blocking host receptor binding," Scientific Reports, 2017, vol. 7, Article No. 7438, pp. 1-12.
Zuniga et al., "A Potent Peptidomimetic Inhibitor of Botulinum Neurotoxin Serotype A Has a Very Different Conformation than SNAP-25 Substrate," Structure, Oct. 8, 2008, vol. 16, pp. 1588-1597.
Zuniga et al., "Iterative Structure-Based Peptide-Like Inhibitor Design against the Botulinum Neurotoxin Serotype A," PLoS ONE, Jun. 2010, vol. 5, No. 6, e11378, pp. 1-15.
Altschul et al., "Basic Local Alignment Search Tool," Journal of Molecular Biology, 1990, vol. 215, pp. 403-410.
Altschul et al., "Gapped BLAST and PSI-BLAST: a new generation of protein database search programs," Nucleic Acids Research, 1997, vol. 25, No. 17, pp. 3389-3402.
Bartlett, "Antibiotic-Associated Diarrhea," The New England Journal of Medicine, Jan. 2002, vol. 346, No. 5, pp. 334-339.
Benton et al., "Screening λgt Recombinant Clones by Hybridization to Single Plaques in situ," Science, Apr. 8, 1977, vol. 196, pp. 180-182.
Bilge et al., "Translocation of Ricin A-chain into Proteoliposomes Reconstituted from Golgi and Endoplasmic Reticulum," The Journal of Biological Chemistry, Oct. 1995, vol. 270, No. 40, pp. 23720-23725.
Boerlin et al., "Associations between Virulence Factors of Shiga Toxin-Producing *Escherichia coli* and Disease in Humans" Journal of Clinical Microbiology, Mar. 1999, vol. 37, No. 3, pp. 497-503.
Brown et al., "Cloning and characterization of an extracellular Ca2+-sensing receptor from bovine parathyroid," Nature, Dec. 1993, vol. 366, pp. 575-580.
Brown et al., "Identification and Characterization of a Neutralizing Monoclonal Antibody Against Botulinum Neurotoxin, Serotype F, Following Vaccination With Active Toxin," Hybridoma, 1997, vol. 16, No. 5, pp. 447-456.
Buchholz et al., "German Outbreak of *Escherichia coli* O104:H4 Associated with Sprouts," The New England Journal of Medicine, Nov. 2011, vol. 365, No. 19, pp. 1763-1770.
Butterworth et al., "Ricin and Ricinus communis agglutinin subunits are all derived from a single-size polypeptide precursor," European Journal of Biochemistry, 1983, vol. 137, pp. 57-65.
Cherla et al., "Shiga toxins and apoptosis," FEMS Microbiology Letters, 2003, vol. 228, pp. 159-166.
Cogburn et al., "Growth, Metabolic and Endocrine Responses of Broiler Cockerels Given a Daily Subcutaneous Injection of Natural or Biosynthetic Chicken Growth Hormone," The Journal of Nutrition, 1989, vol. 119, pp. 1213-1222.
Cohen, Jon, "Naked DNA Points Way to Vaccines," Science, Mar. 19, 1993, vol. 259, pp. 1691-1692.
Cohen et al., "Roles of Globotriosyl- and Galabiosylceramide in Verotoxin Binding and High Affinity Interferon Receptor," The Journal of Biological Chemistry, Dec. 1987, vol. 262, No. 35, pp. 17088-17091.

(56) References Cited

OTHER PUBLICATIONS

Cohn et al., "The Immune System: A Look from a Distance," Frontiers in Bioscience, Oct. 1996, vol. 1, pp. d318-d323.

Donohue-Rolfe et al., "Purification of Shiga Toxin and Shiga-Like Toxins I and II by Receptor Analog Affinity Chromatography with Immobilized P1 Glycoprotein and Production of Cross-Reactive Monoclonal Antibodies," Infection and Immunity, 1989, vol. 57, No. 12, pp. 3888-3893.

Dowling et al., "Phase 1 Safety and Pharmacokinetic Study of Chimeric Murine-Human Monoclonal Antibody cαStx2 Administered Intravenously to Healthy Adult Volunteers," Antimicrobial Agents and Chemotherapy, May 2005, vol. 49, No. 5, pp. 1808-1812.

Dupuy et al., "Regulation of toxin and bacteriocin synthesis in *Clostridium* species by a new subgroup of RNA polymerase σ-factors," Research in Microbiology, 2006, vol. 157, pp. 201-205.

Eubanks et al., "An in vitro and in vivo disconnect uncovered through high-throughput identification of botulinum neurotoxin A antagonists," Proceedings of the National Academy of Sciences of the United States of America, Feb. 2007, vol. 104, No. 8, pp. 2602-2607.

Eubanks et al., "Identification of a Natural Product Antagonist against the Botulinum Neurotoxin Light Chain Protease," ACS Medicinal Chemistry Letters, 2010, vol. 1, pp. 268-272.

Fernie et al., "Active and passive immunization to protect against antibiotic associated caecitis in hamsters," Developments in Biological Standardization, 1983, vol. 53, pp. 325-332.

Florin et al., "Lysosomal involvement in cellular intoxication with Clostridium difficile toxin B," Microbial Pathogenesis, Aug. 1986, vol. 1, No. 4, pp. 373-385.

Frank et al., "Epidemic Profile of Shiga-Toxin-Producing *Escherichia coli* O104:H4 Outbreak in Germany," The New England Journal of Medicine, Nov. 2011, vol. 365, No. 19, pp. 1771-1780.

Friedman et al., "Bacteriophage lambda: alive and well and still doing its thing," Current Opinion in Microbiology, 2001, vol. 4, pp. 201-207.

Friedrich et al., "*Escherichia coli* Harboring Shiga Toxin 2 Gene Variants: Frequency and Association with Clinical Symptoms," The Journal of Infectious Diseases, Jan. 2002, vol. 185, pp. 74-84.

Gibbs, "Nanobodies," Scientific American, Aug. 2005, vol. 293, No. 2, pp. 79-83.

Giesemann et al., "Cholesterol-dependent Pore Formation of Clostridium difficile Toxin A," The Journal of Biological Chemistry, Apr. 2006, vol. 281, No. 16, pp. 10808-10815.

Gronbach et al., "Safety of Probiotic *Escherichia coli* Strain Nissle 1917 Depends on Intestinal Microbiota and Adaptive Immunity of the Host," Infection and Immunity, Jul. 2010, vol. 78, No. 7, pp. 3036-3046.

Grunstein et al., "Colony hybridization: a method for the isolation of cloned DNAs that contain a specific gene," Proceedings of the National Academy of Sciences of the United States of America, Oct. 1975, vol. 72, No. 10, pp. 3961-3965.

Hedican et al., "Characteristics of O157 versus Non-O157 Shiga Toxin-Producing *Escherichia coli* Infections in Minnesota, 2000-2006," Clinical Infectious Diseases, Aug. 2009, vol. 49, pp. 358-364.

Henriques et al., "Cellular internalisation of Clostridium difficile toxin A," Microbial Pathogenesis, 1987, vol. 2, pp. 455-463.

Higgins et al., "CLUSTAL: a package for performing multiple sequence alignment on a microcomputer," Gene, 1988, vol. 73, pp. 237-244.

Hoerr et al., "In vivo application of RNA leads to induction of specific cytotoxic T lymphocytes and antibodies," European Journal of Immunology, 2000, vol. 30, pp. 1-7.

Hunt, "Shiga Toxin-Producing *Escherichia coli* (STEC)," Clinics in Laboratory Medicine, 2010, vol. 30, pp. 21-45.

Hussack et al., "Toxin-Specific Antibodies for the Treatment of Clostridium difficile: Current Status and Future Perspectives," Toxins, 2010, vol. 2, pp. 998-1018.

Janeway et al., "The interaction of the antibody molecule with specification antigen," Immunobiology: The Immune System in Health and Disease, 2001, 5th edition, 5 pages.

Adams et al., "PHENIX: a comprehensive Python-based system for macromolecular structure solution," Acta Crystallographica Section D: Biological Crystallography, 2010, vol. 66, pp. 213-221.

Adelman et al., "In Vitro Deletional Mutagenesis for Bacterial Production of the 20,000-Dalton Form of Human Pituitary Growth Hormone," DNA, 1983, vol. 2, No. 3, pp. 183-193.

Agarwal et al., "Mode of VAMP substrate recognition and inhibition of Clostridium botulinum neurotoxin F," Nature Structural & Molecular Biology, Jul. 2009, vol. 16, No. 7, pp. 789-794.

Ahmed et al., "Identification of Residues Surrounding the Active Site of Type A Botulinum Neurotoxin Important for Substrate Recognition and Catalytic Activity," The Protein Journal, 2008, vol. 27, pp. 151-162.

Baldwin et al., "The C-terminus of botulinum neurotoxin type A light chain contributes to solubility, catalysis, and stability," Protein Expression and Purification, 2004, vol. 37, pp. 187-195.

Battye et al., "iMOSFLM: a new graphical interface for diffraction-image processing with MOSFLM," Acta Crystallographica Section D: Biological Crystallography, 2011, vol. 67, pp. 271-281.

Batzer et al., "Enhanced evolutionary PCR using oligonucleotides with inosine at the 3'-terminus," Nucleic Acids Research, 1991, vol. 19, No. 18, p. 5081.

Breidenbach et al., "Substrate recognition strategy for botulinum neurotoxin serotype A," Nature, Dec. 16, 2004, vol. 432, pp. 925-929.

Brizzard et al., "Epitope Tagging of Recombinant Proteins," Current Protocols in Neuroscience, 1997, Unit 5.8, pp. 5.8.1-5.8.10.

Brunger et al., "Botulinum Neurotoxin Heavy Chain Belt as an Intramolecular Chaperone for the Light Chain," PLoS Pathogens, Sep. 2007, vol. 3, No. 9, e113, pp. 1191-1194.

Brünger, Axel T., "Free R value: a novel statistical quantity for assessing the accuracy of crystal structures," Nature, Jan. 30, 1992, vol. 355, pp. 472-475.

Chen et al., "Insights into the Different Catalytic Activities of Clostridium Neurotoxins," Biochemistry, 2012, vol. 51, pp. 3941-3947.

Chen et al., "Mechanism of Substrate Recognition by Botulinum Neurotoxin Serotype A," The Journal of Biological Chemistry, Mar. 30, 2007, vol. 282, No. 13, pp. 9621-9627.

Chen et al., "MolProbity: all-atom structure validation for macromolecular crystallography," Acta Crystallographica Section D: Biological Crystallography, 2010, vol. 66, pp. 12-21.

Chen et al., "Substrate Recognition of VAMP-2 by Botulinum Neurotoxin B and Tetanus Neurotoxin," The Journal of Biological Chemistry, Jul. 25, 2008, vol. 283, No. 30, pp. 21153-21159.

Desmyter et al., "Camelid nanobodies: killing two birds with one stone," Current Opinion in Structural Biology, 2015, vol. 32, pp. 1-8.

Dong et al., "A Single-Domain Llama Antibody Potently Inhibits the Enzymatic Activity of Botulinum Neurotoxin by Binding to the Non-Catalytic α-Exosite Binding Region," Journal of Molecular Biology, 2010, vol. 397, pp. 1106-1118.

Einhauer et al., "The FLAG™ peptide, a versatile fusion tag for the purification of recombinant proteins," Journal of Biochemical and Biophysical Methods, 2001, vol. 49, pp. 455-465.

Emsley et al., "Features and development of Coot," Acta Crystallographica Section D: Biological Crystallography, 2010, vol. 66, pp. 486-501.

Fan et al., "A three monoclonal antibody combination potently neutralizes multiple botulinum neurotoxin serotype F subtypes," PLoS ONE, 2017, vol. 12, No. 3, e0174187, pp. 1-16.

Fan et al., "Monoclonal Antibodies Targeting the Alpha-Exosite of Botulinum Neurotoxin Serotype/A Inhibit Catalytic Activity," PLoS ONE, 2015, vol. 10, No. 8, e0135306, pp. 1-23.

Fernández-Salas et al., "Plasma membrane localization signals in the light chain of botulinum neurotoxin," Proceedings of the National Academy of Sciences of the United States of America, Mar. 2, 2004, vol. 101, No. 9, pp. 3208-3213.

(56) References Cited

OTHER PUBLICATIONS

Fritze et al., "Epitope Tagging: General Method for Tracking Recombinant Proteins," Methods in Enzymology, 2000, vol. 327, pp. 3-16.
Gu et al., "Botulinum Neurotoxin Is Shielded by NTNHA in an Interlocked Complex," Science, Feb. 24, 2012, vol. 335, pp. 977-981.
Hernan et al., "Multiple Epitope Tagging of Expressed Proteins for Enhanced Detection," BioTechniques, Apr. 2000, vol. 28, No. 4, pp. 789-793.
Kabsch, Wolfgang, "XDS," Acta Crystallographica Section D: Biological Crystallography, 2010, vol. 66, pp. 125-132.
Kashmiri et al., "SDR grafting—a new approach to antibody humanization," Methods, 2005, vol. 36, pp. 25-34.
Kimmel, Alan R., "Identification and Characterization of Specific Clones: Strategy for Confirming the Validity of Presumptive Clones," Methods in Enzymology, 1987, vol. 152, pp. 507-511.
Kumaran et al., "Interactions of a potent cyclic peptide inhibitor with the light chain of botulinum neurotoxin A: Insights from X-ray crystallography," Bioorganic & Medicinal Chemistry, 2015, vol. 23, pp. 7264-7273.
Kumaran et al., "Substrate Binding Mode and Its Implication on Drug Design for Botulinum Neurotoxin A," PLoS Pathogens, Sep. 2008, vol. 4, No. 9, e1000165, pp. 1-9.
Kuroda et al., "Shape complementarity and hydrogen bond preferences in protein-protein interfaces: implications for antibody modeling and protein-protein docking," Bioinformatics, 2016, vol. 32, No. 16, pp. 2451-2456.
Lacy et al., "Crystal structure of botulinum neurotoxin type A and implications for toxicity," Nature Structural Biology, Oct. 1998, vol. 5, No. 10, pp. 898-902.
Lam et al., "Two VHH Antibodies Neutralize Botulinum Neurotoxin E1 by Blocking Its Membrane Translocation in Host Cells," Toxins, 2020, vol. 12, Article No. 616, pp. 1-14.
Lauwereys et al., "Potent enzyme inhibitors derived from dromedary heavy-chain antibodies," The EMBO Journal, 1998, vol. 17, No. 13, pp. 3512-3520.
Lawrence et al., "Shape Complementarity at Protein/Protein Interfaces," Journal of Molecular Biology, 1993, vol. 234, pp. 946-950.
Maass et al., "Alpaca (*Lama pacos*) as a convenient source of recombinant camelid heavy chain antibodies (VHHs)," Journal of Immunological Methods, 2007, vol. 324, pp. 13-25.
McCoy et al., "Phaser crystallographic software," Journal of Applied Crystallography, 2007, vol. 40, pp. 658-674.
Mizanur et al., "The C Terminus of the Catalytic Domain of Type A Botulinum Neurotoxin May Facilitate Product Release from the Active Site," The Journal of Biological Chemistry, Aug. 16, 2013, vol. 288, No. 33, pp. 24223-24233.
Nayak et al., "Safety and Pharmacokinetics of XOMA 3AB, a Novel Mixture of Three Monoclonal Antibodies against Botulinum Toxin A," Antimicrobial Agents and Chemotherapy, Sep. 2014, vol. 58, No. 9, pp. 5047-5053.
Ohtsuka et al., "An Alternative Approach to Deoxyoligonucleotides as Hybridization Probes by Insertion of Deoxyinosine at Ambiguous Codon Positions," The Journal of Biological Chemistry, Mar. 10, 1985, vol. 260, No. 5, pp. 2605-2608.
Pardon et al., "A general protocol for the generation of Nanobodies for structural biology," Nature Protocols, 2014, vol. 9, No. 3, pp. 674-693.
Riechmann et al., "Reshaping human antibodies for therapy," Nature, Mar. 24, 1988, vol. 332, pp. 323-327.
Jank et al., "Structure and mode of action of clostridial glucosylating toxins: the ABCD model," Trends in Microbiology, 2008, vol. 16, No. 5, pp. 222-229.
Jirikowski et al., "Reversal of Diabetes Insipidus in Brattleboro Rats: Intrahypothalamic Injection of Vasopressin mRNA," Science, Feb. 21, 1992, vol. 255, pp. 996-998.
Johnson et al., "Fatal Pseudomembranous Colitis Associated with a Variant Clostridium difficile Strain Not Detected by Toxin A Immunoassay," Annals of Internal Medicine, Sep. 2001, vol. 135, No. 6, pp. 434-438.
Just et al., "Glucosylation of Rho proteins by Clostridium difficile toxin B," Nature, Jun. 1995, vol. 375, pp. 500-503.
Karikó et al., "Increased Erythropoiesis in Mice Injected With Submicrogram Quantities of Pseudouridine-containing mRNA Encoding Erythropoietin," Molecular Therapy, May 2012, vol. 20, No. 5, pp. 948-953.
Karlsson et al., "Microbial recognition of target-cell glycoconjugates," Current Opinion in Structural Biology, 1995, vol. 5, pp. 622-635.
Karmali et al., "The Association Between Idiopathic Hemolytic Uremic Syndrome and Infection by Verotoxin-Producing *Escherichia coli*" The Journal of Infectious Diseases, May 1985, vol. 151, No. 5, pp. 775-782.
Kawano et al., "Relationship between pathogenicity for humans and stx genotype in Shiga toxin-producing *Escherichia coli* serotype O157," European Journal of Clinical Microbiology & Infectious Diseases, 2008, vol. 27, pp. 227-232.
Mitchell et al., "Comparative analysis of nanobody sequence and structure data," Proteins: Structure, Function, and Bioinformatics, 2018, vol. 86, pp. 697-706.
Moayeri et al., "Adenoviral Expression of a Bispecific VHH-Based Neutralizing Agent That Targets Protective Antigen Provides Prophylactic Protection from Anthrax in Mice," Clinical and Vaccine Immunology, Mar. 2016, vol. 23, No. 3, pp. 213-218.
Park et al., "Generation and Application of New Rat Monoclonal Antibodies Against Synthetic FLAG and OLLAS Tags for Improved Immunodetection," Journal of Immunological Methods, Feb. 2008, vol. 331, Nos. 1-2, pp. 27-38.
Patra et al., "Nano based drug delivery systems: recent developments and future prospects," Journal of Nanobiotechnology, 2018, vol. 16, Article No. 71, pp. 1-33.
Petsch et al., "Protective efficacy of in vitro synthesized, specific mRNA vaccines against influenza A virus infection," Nature Biotechnology, Dec. 2012, vol. 30, No. 12, pp. 1210-1216.
Pothoulakis et al., "Microbes and Microbial Toxins: Paradigms for Microbial-Mucosal Interactions II. The integrated response of the intestine to Clostridium difficile toxins," American Journal of Physiology-Gastrointestinal and Liver Physiology, 2001, vol. 280, pp. G178-G183.

* cited by examiner

Figure 4A

MSDKIIHLTDDSEDTDVLKADGAILVDFWAEWCGPCKMIAPILDEIADEYQGKLTVAKLNIDQNPGTAPKYGIRGIPTLLLFKNGEVAATKVGALSKGQLKEFLDA
NLAGSGSGGHMHHHHHHSSGLVPRGSGMKETAAAKFERQHMDSPDLGTDDDKAMAISDPNS///GAPVPYDPLEPR///AAAQVQLAESGGGLVQPGGSIGLSCV
VASERSINNYGMGWYRQAPGKQRELVAQISSGGTTNYADSVEGRFTISRDNVKRMVHLQVNSLKPEDTAVYYCNSLLRTFSWGGTQVTVSSEPKTPKPQAIA///
GGGSGGGGSGGGGSGGGGS///LQGQVQLVESGGGLVQPGGSLSVSCAASGSTARPGAMAWYRQAPGKEREIVASITPGGLTNYADSVTGRFTISRDNAKRTVYLQMNSL
QPEDTAVYYCHARIIPLGLGSEYRDHWGQGTQVTVSSAHHSEDPSARQ///GAPVPYDPLEPR///GGGS///DICLPRWGCLWED*

Figure 4B

MSDKIIHLTDDSEDTDVLKADGAILVDFWAEWCGPCKMIAPILDEIADEYQGKLTVAKLNIDQNPGTAPKYGIRGIPTLLLFKNGEVAATKVGALSKGQLKEFLDA
NLAGSGSGGHMHHHHHHSSGLVPRGSGMKETAAAKFERQHMDSPDLGTDDDKAMAISDPNS///GAPVPYDPLEPR///AAAQVQLAESGGGLVQPGGSIGLSCV
VASERSINNYGMGWYRQAPGKQRELVAQISSGGTTNYADSVEGRFTISRDNVKRMVHLQVNSLKPEDTAVYYCNSLLRTFSNGGTQVTVSSEPKTPKPQAIA///
GGGSGGGGSGGGGS///LQGQVQLAESGGGLVQPGGSLRLSCAASGRTFSGYAMGWFRQAPGKEREFVADISWSGENTYYCDSVKGRFTISRDTAKNTVYLQMN
SIKPEDTAVYYCAAEGARTHLSDSYYFPGIWAEPPVGWGQGTQVTVSSEPKTPKPQARQ///GAPVPYDPLEPR///GGGS///DICLPRWGCLWED*

| Protein | Clone | K_D (nM) | EC₅₀ (nM) | IC₅₀ (nM) | C-group | Comments |
|---|---|---|---|---|---|---|
| JHD-B6 | JHP-18 | 66 +/- 2 | 0.5 | 10 | 1 | |
| JHE-D9 | JHP-25 | 13 +/- 1 | 5 | N/A | 1 | Non-neutralizing |
| JIJ-A12 | JIX-2 | 45 +/- 8 | 2 | N/A | 1 | Non-neutralizing |
| JIJ-B8 | JJS-2 | 8 +/- 8 | 0.4 | N/A | 2 | Non-neutralizing |
| JIJ-D3 | JIX-7 | 18 +/- 0.7 | 0.3 | 9 | 1 | |
| JIJ-E9 | JIX-10 | 12 +/- 1 | 0.4 | 30 | 1 | |
| JIJ-F11 | JIX-15 | 200 +/- 20 | 20 | N/A | 1 | Non-neutralizing |
| JIK-B8 | JIX-20 | 0.13 +/- 0.06 | 0.2 | 1 | 1 | |
| JIK-B10 | JIX-26 | 9 +/- 1 | 0.2 | 8 | 1 | |
| JIK-B12 | JIX-31 | 12 +/- 3 | 0.3 | 6 | 1 | |
| JIK-F4 | JIX-37 | 7 +/- 1 | 0.2 | 3 | 1 | |
| JKH-A4 | JKT-1 | 9 ± 0.5 | 0.5 | N/A | 2 | Non-neutralizing |
| JKH-C7 | JKT-3 | 7 ± 2 | 2 | 5 | 3 | |
| JKH-D12 | JKT-5 | 1 ± 0.4 | 0.3 | N/A | 2 | Non-neutralizing |
| JKM-A6 | JKT-8 | 20 ± 5 | 0.3 | N/A | 2 | Non-neutralizing |
| JKO-A4 | JKT-10 | 10 ± 2.2 | 0.3 | N/A | 2 | Non-neutralizing |
| JKO-B8 | JKT-11 | 200 ± 70 | >100 | N/A | 1 | Non-neutralizing |
| JKO-E12 | JKT-13 | 0.2 ± 0.07 | 0.1 | 0.2 | 1 | |
| JKO-H2 | JKT-15 | 4 ± 1 | 0.6 | N/A | 4 | Poor binding to PA63 |
| VNA1-PA | JKD-11 | ND | ND | 0.5 | | JIK-B8+ JIJ-B8 |
| VNA2-PA | JKU-1 | 0.07 | 1.0 | 0.5 | | JIK-B8+ JKH-C7 |

Figure 6

VHH BASED BINDING ANTIBODIES FOR ANTHRAX AND BOTULINUM TOXINS AND METHODS OF MAKING AND USING THEREFOR

CROSS REFERENCE TO RELATED APPLICATIONS

This AIA application, filed on Apr. 2, 2021, is a divisional of application U.S. Ser. No. 15/534,776, filed on Jun. 9, 2017, now U.S. Pat. No. 11,001,625, which is the U.S. national stage application pursuant to 35 U.S.C. § 371 of International PCT Application No. PCT/US2015/064872, filed on Dec. 10, 2015, designating the United States and published in English, which claims priority to and benefit of U.S. provisional application No. 62/089,949, filed on Dec. 10, 2014, the contents of all of which are incorporated by reference herein in their entireties.

GOVERNMENT SUPPORT

This invention was made with government support under grant numbers AI057159 and AI093467 awarded by the National Institutes of Health. The government has certain rights in the invention.

SEQUENCE LISTING

The application contains a Sequence Listing which has been submitted electronically in ASCII format and is hereby incorporated by reference in its entirety. The ASCII copy, created on Dec. 23, 2020, is named 167774_011402_US_SL.txt and is 216,354 bytes in size.

TECHNICAL FIELD

The present invention generally relates to compositions and methods to prevent or treat exposure to Anthrax toxin or to Botulinum toxins by VHH based neutralizing antibodies.

BACKGROUND

The disease, Anthrax is caused by the gram-positive bacterium *Bacillus anthracis* and is a major bioterror concern. Following introduction into a host in spore form and germination of the spore, the bacterium divides and manifests disease and lethality primarily through the action of two toxins, anthrax lethal toxin (LT) and edema toxin (ET). Anthrax toxins have a common receptor-binding component, protective antigen (PA), which is responsible for transport of the lethal factor metalloprotease (LF) or edema factor adenylate cyclase (EF) or both into the host cell cytosol. Injection of the toxins into animals replicates symptoms of anthrax disease.

PA acts as a 'gateway' that allows translocation and action of both LT and ET toxins and hence PA has been the primary target of therapeutics including antibodies developed for treatment of anthrax. PA binds to two cellular receptors as an 83 kDa polypeptide (PA83) and is rapidly cleaved by cell surface proteases such as furin to a 63 kDa (PA63) form which associates as heptamers or octamers that provide the binding sites for LF or EF. The oligomer bound to one or more molecules of LF/EF is then rapidly translocated. PA63 form of the Anthrax toxin is competent for endocytosis. When PA is cleaved prior to exposure to cells, or produced as PA63, it rapidly oligomerizes and the pre-formed oligomer binds and transports LF/EF into cells. The PA63 oligomer undergoes a conformational change in acidic endosomes to a heat and SDS-stable form, which allows the translocation of LF and EF through a central pore into the cytosol. LF and EF then act on their substrates and manifest toxic effects.

During anthrax infection, the accumulation of anthrax toxins in the blood leads to lethality. Antibodies against PA are considered a primary therapeutic for treatment of the disease. The majority of neutralizing antibodies developed against PA act on the receptor-binding domain to inhibit interaction of the toxin with cells. A few antibodies have been identified which neutralize PA by other mechanisms.

Botulinum toxin is a neurotoxin produced by the bacterium *Clostridium botulinum*. Botulinum toxin is released by *C. botulinum* spores, which are commonly found in soil and water. The *C. botulinum* spores produce botulinum toxin on exposure to low oxygen levels and certain temperatures. Botulinum toxin can cause Botulism, which is a serious and life-threatening paralytic illness in humans and animals. The early symptoms of Botulism are weakness, trouble seeing, feeling tired, and trouble speaking followed by weakness of the arms, chest muscles and legs. Botulinum toxin is an acute lethal toxin with an estimated human median lethal dose (LD-50) of 1.3-2.1 ng/kg intravenously or intramuscularly and 10-13 ng/kg when inhaled. Antibodies against Botulinum toxins are considered a primary therapeutic for treatment of the disease.

A need exists for generating high affinity binding agents that treat both routine incidents of disease and toxicity. The production of antibodies and their storage is a costly and lengthy process. In fact, development of a single antibody therapeutic agent often requires years of clinical study. Yet multiple, different therapeutic antibodies are necessary for the effective treatment of patients exposed to a bio-terrorist assault with a potential weapon such as Anthrax or Botulism. Developing and producing multiple antibodies each of which can bind to a different target (e.g. microbial pathogens, viral pathogens, and toxins) is often a difficult task because it involves separately producing, storing and transporting each of the multiplicity of antibodies of which each is specific for one pathogen or toxin. Production and stockpiling a sufficient amount of antibodies to protect large populations is a challenge and has not currently been achieved. The shelf life of antibodies is often relatively short (e.g., weeks or months), and accordingly freshly prepared batches of present therapeutic antibodies have to be produced to replace expiring antibodies.

Accordingly, there is a need for a cost effective and efficient way to provide alternatives to current therapeutic agents. Further a need exists for alternative therapeutics that are easier to develop and produce, have a longer shelf life, and bind as a single agent to multiple targets on the same disease agent, as well as to different disease agents.

SUMMARY

An aspect of invention provides a pharmaceutical composition for treating a subject at risk for exposure to or exposed to at least one disease agent, the pharmaceutical composition including: at least one recombinant binding protein that neutralizes the disease agent and treats the subject for exposure to the disease agent, the binding protein including at least one amino acid sequence selected from the group of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17. SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, and SEQ ID NO: 143.

In some embodiments, the composition comprises at least one nucleotide sequence that encodes a recombinant binding protein having an amino acid sequence selected from the group consisting of: SEQ ID NO: 2, SEQ ID NO: 4 SEQ ID NO: 6, SEQ ID NO: 8, SEQ ID NO: 10, SEQ ID NO: 12, SEQ ID NO: 14 SEQ ID NO: 16, SEQ ID NO: 18, SEQ ID NO: 20, SEQ ID NO: 22, SEQ ID NO: 24 SEQ ID NO: 26, SEQ ID NO: 28, SEQ ID NO: 30, SEQ ID NO: 32, SEQ ID NO: 34 SEQ ID NO: 36, SEQ ID NO: 38, SEQ ID NO: 40, SEQ ID NO: 42, SEQ ID NO: 44 SEQ ID NO: 46, SEQ ID NO: 48, SEQ ID NO: 50, SEQ ID NO: 52, SEQ ID NO: 54 SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, and SEQ ID NO: 144. In an embodiment of the composition, the binding protein is heteromultimeric and has a plurality of binding regions. In another embodiment of the composition, the binding regions are not identical, and each binding region has affinity to specifically bind and neutralize a non-overlapping portion of the disease agent.

In an embodiment of the composition, the binding protein further includes at least one of: a tag epitope that has affinity to bind an antibody; and a linker that separates the binding regions, and the linker including at least one selected from the group of: a peptide, a protein, a sugar, and a nucleic acid. In an embodiment of the composition, the disease agent is a toxin selected from a plant lectin and a bacterial toxin. In some embodiments, the bacterial toxin is at least one selected from a *B. anthracis* toxin, a *C. botulinum* B toxin, and a *C. botulinum* E toxin. In an embodiment of the composition, the bacterial toxin is a *B. anthracis* toxin and the binding protein binds to and neutralizes at least one selected from: an Anthrax protective antigen, an Anthrax lethal toxin, and an Anthrax edema toxin. In some embodiments, the binding protein inhibits or prevents endocytosis of the toxin. In some embodiments, the Anthrax protective antigen is a cell surface generated antigen.

In various embodiments of the composition, the binding protein comprises an amino acid sequence that is substantially identical to a binding protein having an amino acid sequence as set forth in a SEQ ID NO: listed above, and has at least 50% identity, at least 60% identity, at least 65% identity, at least 70% identity, at least 75% identity, at least 80% identity, at least 85% identity, at least 90% identity, or and at least 95% identity to the amino acid sequence as set forth in a SEQ ID NO: listed above. In some embodiments, the nucleotide sequence encodes a binding protein comprising an amino acid sequence that is substantially identical to a binding protein having an amino acid sequence as set forth in a SEQ ID NO: listed above, and has at least 50% identity, at least 60% identity, at least 65% identity, at least 70% identity, at least 75% identity, at least 80% identity, at least 85% identity, at least 90% identity, or and at least 95% identity to a nucleotide sequence encoding a binding protein having an amino acid sequence as set forth in a SEQ ID NO: as listed above.

An aspect of the invention provides a method for treating a subject at risk for exposure to or exposed to at least one disease agent, the method including: administering to the subject at least one binding protein having at least one binding region including an amino acid sequence selected from: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, and SEQ ID NO: 143, and measuring a decrease in at least one symptom associated with exposure to disease agent.

In an embodiment of the method, measuring the symptom further comprises analyzing an amount of remediation of at least one symptom selected from fever, chills, swelling of neck, soreness of neck glands, sore throat, painful swallowing, hoarseness, nausea, vomiting, bloody vomiting, diarrhea, bloody diarrhea, constipation, headache, flushing, red eyes, stomach pain, fainting, swelling of abdomen, double vision, blurred vision, drooping eyelids, slurred speech, dry mouth, and muscle weakness.

An aspect of the invention provides a method of identifying a therapeutic binding protein for treating a subject at risk for exposure to or exposed to at least one disease agent, the method including: contacting a first sample of a disease agent with a test protein and measuring an amount of binding of the disease agent to the test protein under conditions for the disease agent to interact with the test protein; and comparing the amount of binding to that of a second sample of the disease agent not contacted by the test protein and otherwise identical, such that presence of the therapeutic binding protein is identified by an increase of binding of the disease agent in the first sample compared to the second sample.

In an embodiment of the method, the test protein is a plurality of proteins. In some embodiments, the disease agent is in vitro. In other embodiments, the disease agent is in a cell.

An embodiment of the method further includes contacting the disease agent to a mammalian subject and measuring a decrease in at least one symptom of the disease agent. In some embodiments, the disease agent is a toxin selected from a plant lectin and a bacterial toxin. In some embodiments, the bacterial toxin is at least one selected from a *B. anthracis* toxin, a *C. botulinum* B toxin, and a *C. botulinum* E toxin. In some embodiments, the bacterial toxin is a *B. anthracis* toxin and the binding protein binds to and neutralizes Anthrax protective antigen. In an embodiment, the binding protein inhibits or prevents endocytosis of the toxin. In an embodiment of the method, the Anthrax protective antigen is a cell surface generated antigen.

An aspect of the invention provides a method for treating a subject at risk for exposure to or exposed to at least one disease agent, the method including: administering to the subject a source of expression of a binding protein having a nucleotide sequence encoding the binding protein, such that the nucleotide sequence comprises at least one selected from the group consisting of: a naked nucleic acid vector, bacterial vector, and a viral vector, such that the nucleotide sequence encodes a binding protein having an amino acid sequence selected from the group consisting of: SEQ ID NO: 2. SEQ ID NO: 4 SEQ ID NO: 6. SEQ ID NO: 8. SEQ ID NO: 10. SEQ ID NO: 12. SEQ ID NO: 14 SEQ ID NO: 16. SEQ ID NO: 18. SEQ ID NO: 20. SEQ ID NO: 22. SEQ ID NO: 24 SEQ ID NO: 26. SEQ ID NO: 28. SEQ ID NO: 30. SEQ ID NO: 32. SEQ ID NO: 34 SEQ ID NO: 36. SEQ ID NO: 38. SEQ ID NO: 40. SEQ ID NO: 42. SEQ ID NO: 44 SEQ ID NO: 46. SEQ ID NO: 48. SEQ ID NO: 50. SEQ ID NO: 52. SEQ ID NO: 54 SEQ ID NO: 56. SEQ ID NO: 58. SEQ ID NO: 60. SEQ ID NO: 62. SEQ ID NO: 64 SEQ ID NO: 66. SEQ ID NO: 68. SEQ ID NO: 70. SEQ ID NO: 72. SEQ ID NO: 74. SEQ ID NO: 76. SEQ ID NO: 78. SEQ ID NO: 80. SEQ ID NO: 82. SEQ ID NO: 84. SEQ ID NO: 86. SEQ ID NO: 88. SEQ ID NO: 90. SEQ ID NO: 92. SEQ ID NO: 94. SEQ ID NO: 96. SEQ ID NO: 98, SEQ ID NO: 100. SEQ ID NO: 102. SEQ ID NO: 104. SEQ ID NO: 106. SEQ ID NO: 108. SEQ ID NO: 110. SEQ ID NO: 112. SEQ ID NO: 114. SEQ ID NO: 116. SEQ ID NO: 118. SEQ ID NO: 120. SEQ ID NO: 122. SEQ ID NO: 124. SEQ ID NO: 126. SEQ ID NO: 128. SEQ ID NO: 130. SEQ ID NO: 132. SEQ ID NO: 134. SEQ ID NO: 136. SEQ ID NO: 138. SEQ ID NO: 140. SEQ ID NO: 142, and SEQ ID NO: 144.

An aspect of the invention provides a kit for treating a subject exposed to or at risk for exposure to a disease agent including: a unit dosage of a pharmaceutical composition for treating a subject at risk for exposure to or exposed to at least one disease agent, the pharmaceutical composition including: at least one recombinant binding protein that neutralizes the disease agent thereby treating the subject for exposure to the disease agent, such that the binding protein includes at least one amino acid sequence selected from the group of: SEQ ID NO: 1. SEQ ID NO: 3. SEQ ID NO: 5. SEQ ID NO: 7. SEQ ID NO: 9. SEQ ID NO: 11. SEQ ID NO: 13. SEQ ID NO: 15. SEQ ID NO: 17. SEQ ID NO: 19. SEQ 25 ID NO: 21. SEQ ID NO: 23. SEQ ID NO: 25. SEQ ID NO: 27. SEQ ID NO: 29. SEQ ID NO: 31. SEQ ID NO: 33. SEQ ID NO: 35. SEQ ID NO: 37. SEQ ID NO: 39. SEQ ID NO: 41. SEQ ID NO: 43. SEQ ID NO: 45. SEQ ID NO: 47. SEQ ID NO: 49. SEQ ID NO: 51. SEQ ID NO: 53. SEQ ID NO: 55. SEQ ID NO: 57. SEQ ID NO: 59. SEQ ID NO: 61. SEQ ID NO: 63. SEQ ID NO: 65. SEQ ID NO: 67. SEQ ID NO: 69. SEQ ID NO: 71. SEQ ID NO: 73. SEQ ID NO: 75. SEQ ID NO: 77. SEQ ID NO: 79. SEQ ID NO: 81. SEQ ID NO: 83. SEQ ID NO: 85. SEQ ID NO: 87. SEQ ID NO: 89. SEQ ID NO: 91. SEQ ID NO: 93. SEQ ID NO: 95. SEQ ID NO: 97. SEQ ID NO: 99. SEQ ID NO: 101. SEQ ID NO: 103. SEQ ID NO: 105. SEQ ID NO: 107. SEQ ID NO: 109. SEQ ID NO: 111. SEQ ID NO: 113. SEQ ID NO: 115. SEQ ID NO: 117. SEQ ID NO: 119. SEQ ID NO: 121. SEQ ID NO: 123. SEQ ID NO: 125, SEQ ID NO: 127. SEQ ID NO: 129. SEQ ID NO: 131. SEQ ID NO: 133. SEQ ID NO: 135. SEQ ID NO: 137. SEQ ID NO: 139. SEQ ID NO: 141, and SEQ ID NO: 143. In an embodiment of the kit, the recombinant binding protein is encoded by at least one nucleotide sequence selected from the group consisting of: SEQ ID NO: 2. SEQ ID NO: 4 SEQ ID NO: 6. SEQ ID NO: 8. SEQ ID NO: 10. SEQ ID NO: 12. SEQ ID NO: 14 SEQ ID NO: 16. SEQ ID NO: 18. SEQ ID NO: 20. SEQ ID NO: 22. SEQ ID NO: 24 SEQ ID NO: 26. SEQ ID NO: 28. SEQ ID NO: 30. SEQ ID NO: 32. SEQ ID NO: 34 SEQ ID NO: 36. SEQ ID NO: 38. SEQ ID NO: 40, SEQ ID NO: 42. SEQ ID NO: 44 SEQ ID NO: 46. SEQ ID NO: 48. SEQ ID NO: 50. SEQ ID NO: 52. SEQ ID NO: 54 SEQ ID NO: 56. SEQ ID NO: 58. SEQ ID NO: 60. SEQ ID NO: 62. SEQ ID NO: 64. SEQ ID NO: 66, SEQ ID NO: 68. SEQ ID NO: 70. SEQ ID NO: 72. SEQ ID NO: 74. SEQ ID NO: 76. SEQ ID NO: 78. SEQ ID NO: 80. SEQ ID NO: 82. SEQ ID NO: 84. SEQ ID NO: 86. SEQ ID NO: 88. SEQ ID NO: 90. SEQ ID NO: 92. SEQ ID NO: 94. SEQ ID NO: 96. SEQ ID NO: 98. SEQ ID NO: 100. SEQ ID NO: 102. SEQ ID NO: 104. SEQ ID NO: 106. SEQ ID NO: 108. SEQ ID NO: 110. SEQ ID NO: 112. SEQ ID NO: 114. SEQ ID NO: 116. SEQ ID NO: 118. SEQ ID NO: 120. SEQ ID NO: 122. SEQ ID NO: 124. SEQ ID NO: 126. SEQ ID NO: 128. SEQ ID NO: 130. SEQ ID NO: 132. SEQ ID NO: 134. SEQ ID NO: 136, SEQ ID NO: 138. SEQ ID NO: 140. SEQ ID NO: 142, and SEQ ID NO: 144.

An aspect of the invention provides a method for detecting a presence of a toxin in a sample, the method including: contacting and incubating an aliquot of the sample to an amount of at least one binding protein that specifically binds the toxin, such that the binding protein includes a binding region having an amino acid sequence selected from: SEQ ID NO: 1. SEQ ID NO: 3. SEQ ID NO: 5. SEQ ID NO: 7. SEQ ID NO: 9. SEQ ID NO: 11. SEQ ID NO: 13. SEQ ID NO: 15. SEQ ID NO: 17. SEQ ID NO: 19. SEQ ID NO: 21. SEQ ID NO: 23. SEQ ID NO: 25. SEQ ID NO: 27. SEQ ID NO: 29. SEQ ID NO: 31. SEQ ID NO: 33. SEQ ID NO: 35. SEQ ID NO: 37. SEQ ID NO: 39. SEQ ID NO: 41. SEQ ID NO: 43. SEQ ID NO: 45. SEQ ID NO: 47. SEQ ID NO: 49. SEQ ID NO: 51. SEQ ID NO: 53. SEQ ID NO: 55. SEQ ID NO: 57. SEQ ID NO: 59. SEQ ID NO: 61. SEQ ID NO: 63. SEQ ID NO: 65. SEQ ID NO: 67. SEQ ID NO: 69. SEQ ID NO: 71. SEQ ID NO: 73. SEQ ID NO: 75. SEQ ID NO: 77. SEQ ID NO: 79. SEQ ID NO: 81. SEQ ID NO: 83. SEQ ID NO: 85. SEQ ID NO: 87. SEQ ID NO: 89. SEQ ID NO: 91. SEQ ID NO: 93. SEQ ID NO: 95. SEQ ID NO: 97. SEQ ID NO: 99. SEQ ID NO: 101. SEQ ID NO: 103. SEQ ID NO: 105. SEQ ID NO: 107. SEQ ID NO: 109. SEQ ID NO: 111. SEQ ID NO: 113. SEQ ID NO: 115. SEQ ID NO: 117. SEQ ID NO: 119. SEQ ID NO: 121. SEQ ID NO: 123. SEQ ID NO: 125. SEQ ID NO: 127. SEQ ID NO: 129. SEQ ID NO: 131. SEQ ID NO: 133. SEQ ID NO: 135. SEQ ID NO: 137. SEQ ID NO: 139. SEQ ID NO: 141, and SEQ ID NO: 143, such that the toxin is selected from the group of: a *B. anthracis* toxin, a *C. botulinum* B toxin and a (botulinum E toxin, and SEQ ID NO: 1. SEQ ID NO: 3 SEQ ID NO: 5. SEQ ID NO: 7. SEQ ID NO: 9. SEQ ID NO: 11. SEQ ID NO: 13. SEQ ID NO: 15. SEQ ID NO: 73. SEQ ID NO: 75.

SEQ ID NO: 77. SEQ ID NO: 79. SEQ ID NO: 81. SEQ ID NO: 83. SEQ ID NO: 85. SEQ ID NO: 87. SEQ ID NO: 89. SEQ ID NO: 91. SEQ ID NO: 93. SEQ ID NO: 95. SEQ ID NO: 97. SEQ ID NO: 99. SEQ ID NO: 101. SEQ ID NO: 103, and SEQ ID NO: 105 are amino acid sequences of binding proteins that specifically bind a B. anthracis toxin, and SEQ ID NO: 17. SEQ ID NO: 19. SEQ ID NO: 21. SEQ ID NO: 23. SEQ ID NO: 25. SEQ ID NO: 27. SEQ ID NO: 29. SEQ ID NO: 31. SEQ ID NO: 33. SEQ ID NO: 35. SEQ ID NO: 37. SEQ ID NO: 39. SEQ ID NO: 41. SEQ ID NO: 43. SEQ ID NO: 45. SEQ ID NO: 47. SEQ ID NO: 107. SEQ ID NO: 109. SEQ ID NO: 111. SEQ ID NO: 113. SEQ ID NO: 115. SEQ ID NO: 117. SEQ ID NO: 119. SEQ ID NO: 121. SEQ ID NO: 123. SEQ ID NO: 125. SEQ ID NO: 131. SEQ ID NO: 133. SEQ ID NO: 135, and SEQ ID NO: 137 are amino acid sequences of binding proteins that specifically bind a B. botulinum B toxin, and SEQ ID NO: 49. SEQ ID NO: 51. SEQ ID NO: 53. SEQ ID NO: 55. SEQ ID NO: 57. SEQ ID NO: 59. SEQ ID NO: 61. SEQ ID NO: 63. SEQ ID NO: 65. SEQ ID NO: 67. SEQ ID NO: 69. SEQ ID NO: 71. SEQ ID NO: 127. SEQ ID NO: 129. SEQ ID NO: 139. SEQ ID NO: 141, and SEQ ID NO: 143 are amino acid sequences of binding proteins that specifically bind a B. botulinum E toxin under conditions to form a complex; separating the complex from unbound binding protein; and measuring amount of complex formed.

In an embodiment of the method, the sample is at least one selected from: a medical sample, a food sample, a beverage sample, a water sample, and an environmental sample. In another embodiment of the invention, the medical sample is at least one selected from: blood, plasma, tissue, stool, urine, perspiration, serum, semen, breast milk, cerebrospinal fluid, skin and hair. An embodiment of the method further includes, analyzing the extent of complex formation, such that the extent of complex formation is a function of extent of toxin present in the sample.

BRIEF DESCRIPTION OF THE DRAWINGS

FIG. 1C shows a single group (POST) received antibody 2 hours after toxin was administered. Control groups were injected with PBS instead of antibody. Heterodimers JKC-5 and VNA1 (JKD-11) contain the VHHs JIK-B8 and JIJ-B8, both with high affinity for PA but only JIK-B8 having anthrax neutralizing properties. VNA2 contains JIK-B8 and JKH-C7, both potent anthrax neutralizing VHHs. Heterodimers VNA1 and VNA2 also contain a carboxyl albumin-binding-peptide (ABP) which prolongs in vivo serum persistence of similar VNAs in mice. Antibody 14B7 is a previously described neutralizing monoclonal antibody, which binds to the same receptor-interacting domain as JIK-B8. Animals were monitored for 10 days post for signs of malaise and survival.

FIG. 2A shows data obtained using C57BL/6J mice treated with VNA2 heterodimeric VNA or 14B7 mAb control (15 µg/injection/IV) at indicated times before or after spore infection. FIG. 2D shows data from C57BL/6J mice (n=5/group, except PBS controls, n=15), treated with heterodimeric VNA2-PA subcutaneously (SC) at indicated times and doses before or after spore infection ($2 \times 10^7$ spores, also SC at a distal site). Control mice were treated with PBS at 15 min, one hour and four hours post infection (n=5) or at five minutes (n=5) and eight hours (n=5) post infection. Neutralizing mAb 14B7 was used as a positive control in these studies. Mice were monitored for survival and signs of malaise for 10 days.

FIG. 3 includes the following VHHs containing complementarity determining regions (CDRs), CDR1, CDR2 and CDR3: JIJ B8 (SEQ ID NO: 151) comprises CDR 1: SGSIARPGA (SEQ ID NO: 170); CDR2: SITPGGLTN (SEQ ID NO: 171); and CDR3: HARIIPLGLGSEYRDH (SEQ ID NO: 172); JIK-B8 (SEQ ID NO: 155) comprises CDR 1: ASERSINNYG (SEQ ID NO: 173); CDR2: QIS-SGGTTN (SEQ ID NO: 174); and CDR3: NSLLRTFS (SEQ ID NO: 175); JKH-A4 (SEQ ID NO: 159) comprises CDR 1: SGLTFGNYA (SEQ ID NO: 176); CDR2: SISRSG-SNTW (SEQ ID NO: 177); and CDR3: AGGSYN-SDWWNYMY (SEQ ID NO: 178); JHK-C7 (SEQ ID NO: 160) comprises CDR 1: SGRTFSGYA (SEQ ID NO: 179); CDR2: DISWSGHNTY (SEQ ID NO: 180); and CDR3: AEGARTHLSDSYYFPGLWAEPPVGY (SEQ ID NO: 181); JKH-D12 (SEQ ID NO: 161) comprises CDR 1: SGRTFTSYY (SEQ ID NO: 182); CDR2: SIGWTDDNTY (SEQ ID NO: 183); and CDR3: AADYGSGIRAWYNWIY (SEQ ID NO: 184); JKM-A6 (SEQ ID NO: 162) comprises CDR 1: SGATLDTYI (SEQ ID NO: 185); CDR2: CINRSGTT (SEQ ID NO: 186); and CDR3: AADASYRT-CGGSWWNWAY (SEQ ID NO: 187); JKO-A4 (SEQ ID NO: 163) comprises CDR 1: SGFTFSSYT (SEQ ID NO: 188); CDR2: DINGGGDRTD (SEQ ID NO: 189); and CDR3: AKDLSYVSGTYFAND (SEQ ID NO: 190); JKO-B8 (SEQ ID NO: 164) comprises CDR 1: SGIIFDYYSV (SEQ ID NO: 191); CDR2: TITGDGSPN (SEQ ID NO: 192); and CDR3: HAKRTIGTKSEY (SEQ ID NO: 193);

Figure 1A:
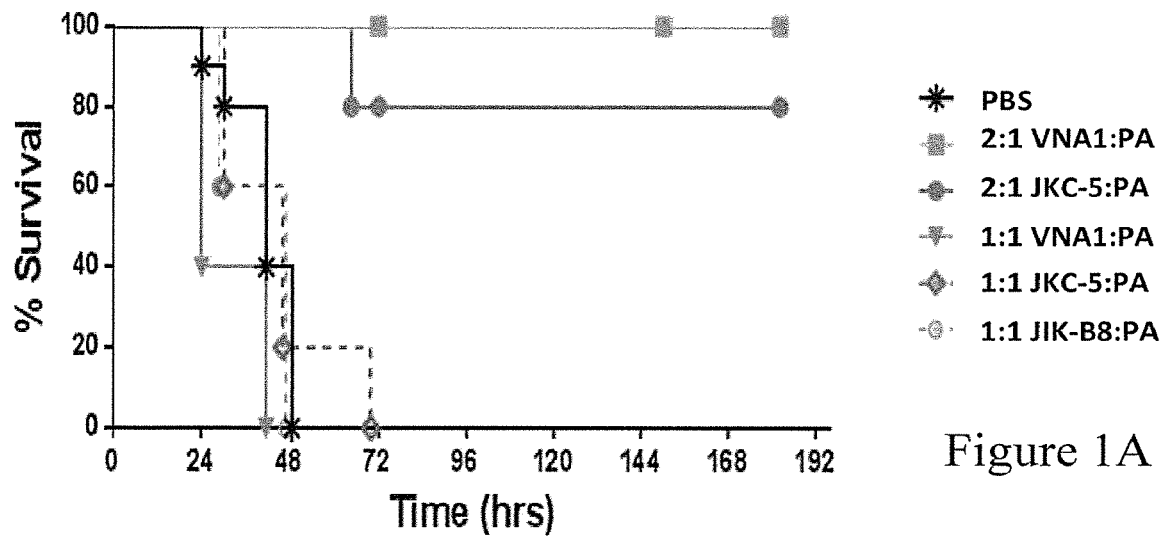
FIG. 1A-FIG. 1C are Meyer-Kaplan survival plots showing percent survival (% survival, ordinate) of subjects as a function of time in days (abscissa) following contact with LT and VHH binding/neutralizing agents as indicated. Balb/cJ mice were injected intravenously with antibody (Ab) at indicated molar ratios (Ab:toxin) 10 min prior to injection with LT (45 µg for each toxin component, IV).
Figure 1B:
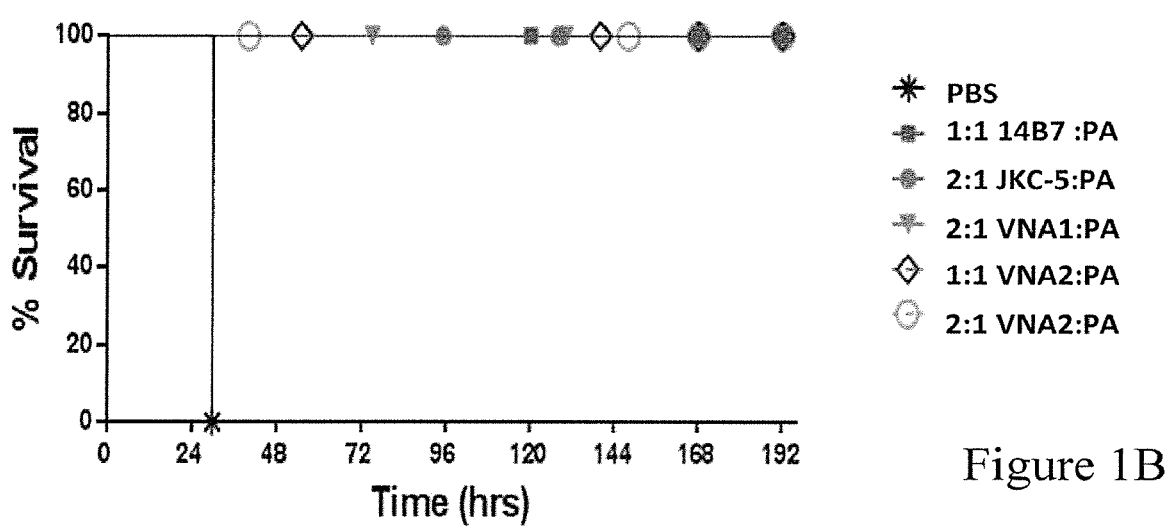

JKO-E12 (SEQ ID NO: 165) comprises CDR 1: SRMSFSRRP (SEQ ID NO: 194); CDR2: TISSFGDTTN (SEQ ID NO: 195); and CDR3: NTLLATYA (SEQ ID NO: 196); and JKO-H2 (SEQ ID NO: 166) comprises CDR 1: SGRTFSSYV (SEQ ID NO: 197); CDR2: AISRNGGKTY (SEQ ID NO: 198); and CDR3: AAAVAASAEFVTARSNFYEY (SEQ ID NO: 199).

FIG. 4A and FIG. 4B are amino acid sequences of fusion proteins that contain partial translation products of the two VNAs SEQ ID NOs: 103 and 105. FIG. 4A (SEQ ID NO: 167) shows a fusion protein containing VNA1-PA (SEQ ID NO: 103), and FIG. 4B (SEQ ID NO: 168) shows a fusion protein containing VNA2-PA (SEQ ID NO: 105). The proteins are expressed in E. coli and tested as anthrax antitoxins. Proteins VNA1-PA (SEQ ID NO: 103) and VNA2-PA (SEQ ID NO: 105), respectively, are the same as previously named JKD-11 and JKU-1, respectively, in U.S. provisional application Ser. No. 62/089,949 filed Dec. 10, 2014. Both VNA fusion proteins shown in FIGS. 4A and 4B contain an amino terminal thioredoxin fusion partner and hexahistidine (SEQ ID NO: 169) encoded by the pET32b expression vector. In FIGS. 4A and 4B, the VHH sequences are flanked by E-tag peptides (underlined) and separated by the unstructured spacer ((GGGGS)$_3$) (SEQ ID NO: 145). The 14 amino acid albumin-binding-peptide (ABP), DICLPRWGCLEWED (SEQ ID NO: 146) described in Nguyen A, et al. (2006) Protein engineering, design & selection: PEDS 19: 291-297 is located at the carboxyl end of the fusion protein, separated from the second E-tag by a GGGGS (SEQ ID NO: 147) spacer.

FIG. 5A-FIG. 5D, respectively, are Meyer-Kaplan survival plots showing percent survival (% survival, ordinate) after BoNT/B toxin exposure of each of four amounts, respectively, subjects as a function of time in days (abscissa) following treatment with a preparation of BoNT/B neutralizing VHH heterodimers as indicated. In FIG. 5A-FIG. 5D, an amount of BoNT/B, toxin of 10, 40, 100 and 500 LD50, respectively, was administered by intraperitoneal injection to groups of five C57BL/6J mice. The mice receiving the toxin were treated with 2 μg of one of BoNT/B neutralizing VHH heterodimers (SEQ ID NO: 131, SEQ ID NO: 133, SEQ ID NO: 135, or SEQ ID NO: 137). Mice were monitored at least five times per day for survival and symptoms of botulism for seven days.

FIG. 6 is a table of the VHH names and binding properties. The first eleven VHHs were obtained by panning using PA83 bound to plastic, after which the $K_D$ values for these VHHs were assessed by SPR PROTEON™. The second group of nine VHHs were obtained by panning using 14B7-bound PA83, and the $K_D$ values were assessed by SPR BIACORE™. The $K_D$ for JIK-B8, obtained as an internal reference for SPR BIACORE™ group, was observed to be 1±0.7. $EC_{50}$ values were assessed by dilution ELISAs, and $IC_{50S}$ were assessed by toxin neutralization assays on macrophages and competition groups (C-groups) by competition ELISA. N/A refers to antibodies that were observed to not neutralize toxin and thus have no measurable $IC_{50}$.

Figure 7A:
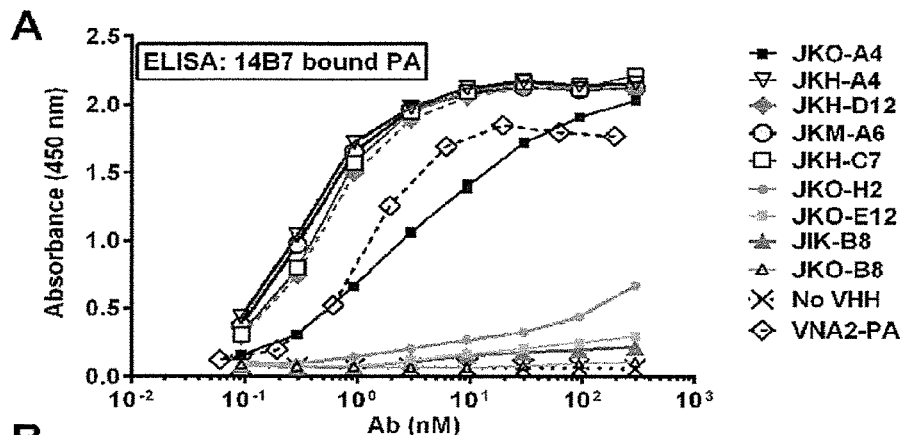
Figure 7B:
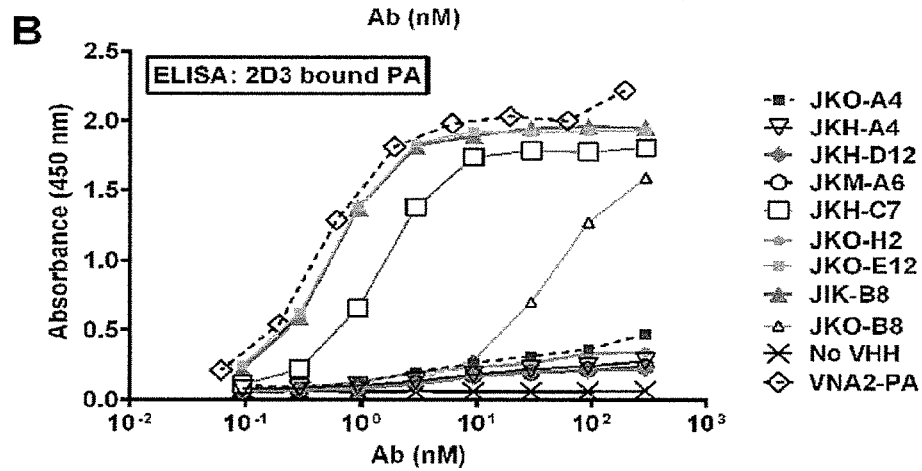
Figure 7C:
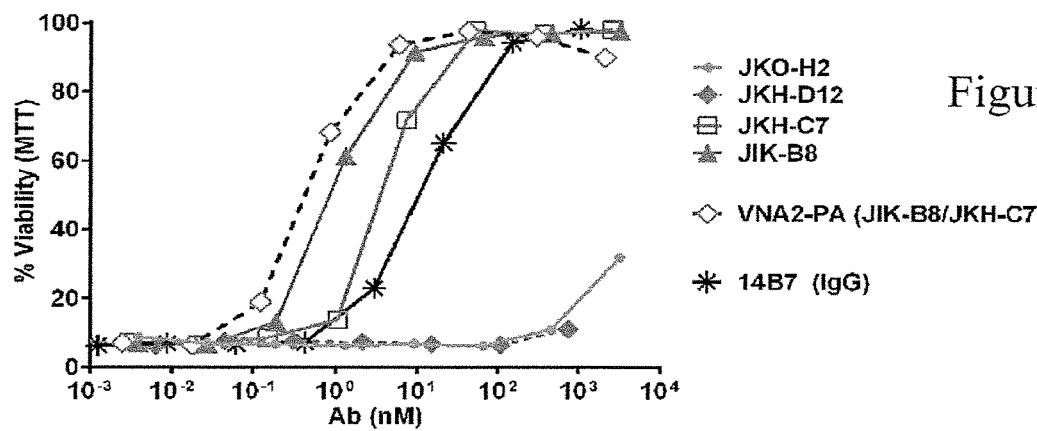

FIG. 7A-FIG. 7C are graphs showing the results of competition ELISAs and neutralization assays. Data in FIG. 7A and FIG. 7B were obtained using 14B7- or 2D3-captured PA which was bound to plates and an increasing concentration per plate of each VHH was then added and binding was assessed with an HRP-conjugated anti-Hisx6 or E-tag antibody using standard ELISA protocols. FIG. 7C shows representative neutralization assays for each of the four VHHs representing the four competition groups, a heteromultimer of two neutralizing VHHs, and mAb 14B7, with viability of the ordinate as a function of antibody concentration. All data were obtained from assays are representative of at least two separate repetitions.

DETAILED DESCRIPTION

Anthrax is a toxigenic disease, which rapidly progresses to lethality for the host if left untreated. The bioterrorist attacks utilizing Bacillus anthracis spores highlighted the need for cost-effective treatments that could be produced on a large scale if necessary. Almost all the therapeutics developed against the disease focus on the anthrax toxins, which have been demonstrated to be the primary virulence determinants. Examples herein describe a novel recombinant anti-toxin consisting of a heterodimer of two camelid anti-anthrax PA heavy chain VHH binding domains as an efficient therapeutic agent. A number of antibodies have been produced against the PA receptor-binding component of the tripartite toxin, and protection in animal models is demonstrated by data herein. Most antibodies target the same epitope of the toxin, which is the dominant neutralizing antigenic region, and only differ in varying affinities and clearance rates.

Anthrax disease is caused by a complex toxin that contains a protective antigen (PA), a lethal factor (LF) and an edema factor (EF). Recombinant engineered proteins as antibodies against PA are described herein which are protective against the disease. Heavy-chain-only Ab $V_H$ (VHH) domains with affinity for PA were obtained from immunized alpacas and were screened for anthrax neutralizing activity in macrophage toxicity assays.

Two classes of neutralizing VHHs were identified that recognized distinct and non-overlapping epitopes. One class of VHHs recognized were observed that domain 4 of PA at a neutralizing site that blocks PA binding to cells. Another class of VHHs recognized a novel, conformational epitope. A VHH antibody described herein was observed to inhibit conversion of the PA63 oligomer from "pre-pore" conformation to a SDS and heat-resistant "pore" conformation. The antibody described herein was observed to prevent endocytosis of cell surface generated PA63 subunit. The monomer neutralizing VHHs administered at 2:1 molar ratio to PA were observed to be effective in protecting mice from a lethal anthrax toxin challenge. The highest affinity members of different anti-PA VHH classes were expressed as two heterodimeric VHH-based neutralizing agents (VNAs). VNAs were observed to have improved neutralizing potency in cell assays and to have protected mice from anthrax toxin challenge with better efficacy than their corresponding monomer VHHs. The VNA2-PA (JKU-1) which was observed to be most efficient consists of a heterodimer of the novel oligomer-inhibiting VHH (JKH-C7) and a receptor blocking VHH (JIK-B8). This VNA2-PA was observed to protect mice against toxin challenge at 1:1 molar ratio to toxin and increased survival times were observed at submolar ratios. Furthermore, the antibody also provided protection against A35 spore challenge. VNA2-PA (JKU-1) has potential as an anthrax therapeutic, and its simple and stable nature is amenable to administration by genetic delivery or by respiratory routes.

The novel VHH-based VNA described herein consists of two anti-toxin VHHs targeting independent epitopes of PA and inhibiting the action of the toxin at two different functional steps. The VHH based VNA agent described herein is more effective in vivo by a factor of at least about 20-50 fold compared to the well-characterized neutralizing antibody 14B7 which acts on the same epitope as the approved human anti-PA antibody, RAXIBACUMAB (Abthrax) in protecting against anthrax toxin challenge and spore infection. The affinity is 0.07 nM in contrast to the 2.78 nM affinity of Abthrax, a commercially available monoclonal antibody, RAXIBACUMAB, that neutralizes toxins produced by *B. anthracis* (Human Genome Sciences, Rockville, MD).

An antitoxin strategy herein uses VNAs consisting of two or more, linked, toxin neutralizing, VHHs recognizing non-overlapping epitopes on PA. An advantage of covalently linking VHHs together is a resulting increased toxin binding affinity and increase in potency of neutralization through targeting of two different steps in the interaction of the toxin with cells. A benefit of the conformational epitope of the VNA, JKH-C7 arm is the extremely low likelihood of easily circumventing the PA-antibody interaction through a small number of mutations in genes encoding PA. The bulk of previously available anti-PA neutralizing antibodies target the same receptor-binding epitope that the JIK-B8 arm of the VNA targets, and the receptor-binding epitope can be destroyed by genetic manipulation of the PA antigen to eliminate reactivity with these neutralizing antibodies. The complex conformational epitope for the JKH-C7 VHH arm of the antibody described herein is unlikely to be easily disrupted without impact on PA function.

The presence of toxins in the circulation causes a wide variety of human and animal illnesses. Antitoxins are therapeutic agents that prevent toxin infection or reduce further development of negative symptoms in patients that have been exposed to a toxin (a process referred to as "intoxication"). Typically, antitoxins are antisera obtained from large animals (e.g., sheep, horse, and pig) that were immunized with inactivated or non-functional toxin.

More recently, antitoxin therapies have been developed using combinations of antitoxin monoclonal antibodies including yeast-displayed single-chain variable fragment antibodies generated from vaccinated humans or mice. See Nowakowski et al. 2002. Proc Natl Acad Sci USA 99: 11346-11350; Mukherjee et al. 2002. Infect Immun 70: 612-619; Mohamed et al. 2005 Infect Immun 73: 795-802; Walker, K. 2010 Interscience Conference on Antimicrobial Agents and Chemotherapy—50th Annual Meeting—Research on Promising New Agents: Part 1. IDrugs 13: 743-745. Antisera and monoclonal antibodies are difficult to produce economically at scale, usually requiring long development times and resulting in problematic quality control, shelf-life and safety issues. New therapeutic strategies to develop and prepare antitoxins are needed.

Antitoxins function through two key mechanisms, neutralization of toxin function and clearance of the toxin from the body. Toxin neutralization occurs through biochemical processes including inhibition of enzymatic activity and prevention of binding to cellular receptors. Antibody mediated serum clearance occurs subsequent to the binding of multiple antibodies to the target antigen (Daeron M. 1997 Annu Rev Immunol 15: 203-234; Davies et al. 2002 Arthritis Rheum 46: 1028-1038; Johansson et al. 1996 Hepatology 24: 169-175; and Lovdal et al. 2000 J Cell Sci 113 (Pt 18): 3255-3266). Multimeric antibody decoration of the target is necessary to permit binding to the Fc receptors which have only low affinity (Davies et al. 2002 Arthritis Rheum 46: 1028-1038 and Lovdal et al. 2000 J Cell Sci 113 (Pt 18): 3255-3266). Without being limited by any particular theory or mechanism of action, it is here envisioned that an ideal antitoxin therapeutic would both promote toxin neutralization to immediately block further toxin activity and would also accelerate toxin clearance to eliminate future pathology if neutralization becomes reversed.

Effective clearance of botulinum neurotoxin (BoNT), a National Institute of Allergy and Infectious Diseases (NIAID) Category A priority pathogen, is believed by some researchers to require three or more antibodies bound to the toxin. Nowakowski et al. 2002. Proc Natl Acad Sci USA 99: 11346-11350 determined that effective protection of mice against high dose challenge of BoNT serotype A (BoNT/A) requires co-administration of three antitoxin monoclonal antibodies, and that all three antibodies presumably promote clearance. Administration of a pool of three or more small binding agents, each produced with a common epitopic tag, reduced serum levels of a toxin when co-administered with an anti-tag monoclonal antibody (Shoemaker et al. U.S. published application 2010/0278830 A1 published Nov. 4, 2010 and Sepulveda et al. 2009 Infect Immun 78: 756-763, each of which is incorporated herein in its entirety). The tagged binding agents directed the binding of anti-tag monoclonal antibody to multiple sites on the toxin, thus indirectly decorating the toxin with antibody Fc domains and leading to clearance of the toxin through the liver.

Pools of scFv domain binding agents with specificity for BoNT/A and each containing a common epitopic tag (E-tag), had been shown to be effective for decorating the botulinum toxin with multiple anti-tag antibodies (Shoemaker et al. U.S. utility patent publication number 2010/0278830 published Nov. 4, 2010 and U.S. continuation-in-part patent publication number 2011/0129474 published Jun. 2, 2011, each of which is incorporated herein by reference in its entirety). Administration of binding agents and clearance antibodies to subjects resulted in clearance via the liver with an efficacy in mouse assays equivalent to conventional polyclonal antitoxin sera. Ibid. and Sepulveda et al. 2009 Infect Immun 78: 756-763. The tagged scFvs toxin targeting agents and the anti-tag monoclonal antibodies were effective to treat subjects at risk for or having been contacted with a disease agent.

The use of small binding agents to direct the decoration of toxin with antibody permits new strategies for the development of agents with improved therapeutic and commercial properties. Examples herein show that a single recombinant heterodimeric binding protein/agent which contains two or more high-affinity BoNT binding agents (camelid heavy-chain-only Ab VH (VHH) domains) and two epitopic tags, co-administered with an anti-tag mAb, protected subjects from negative symptoms and lethality caused by botulism. Further, the binding protein was observed to have antitoxin efficacy equivalent to and greater than conventional BoNT antitoxin serum in two different in vivo assays. Examples herein compare neutralizing or non-neutralizing binding agents administered with or without clearing antibody, and show the relative contributions of toxin neutralization and toxin clearance to antitoxin efficacy. Examples herein show that both toxin neutralization and toxin clearance contribute significantly to antitoxin efficacy in subjects. Toxin neutralization or toxin clearance using heterodimer binding protein antitoxins was observed herein to sufficiently protect subjects from BoNT lethality in a therapeutically relevant, post-intoxication assay. Methods in further Examples herein include an optional clearing antibody for example a monoclonal anti-E-tag antibody.

It was observed in Examples herein that VHH binding agents that neutralized toxin function significantly improved the antitoxin efficacy and even obviated the need for clearing antibody in a clinically relevant post-intoxication BoNT/A assay.

Pharmaceutical Compositions

An aspect of the present invention provides pharmaceutical compositions, wherein these compositions comprise an antigen from a toxin of *B. anthracis* or *C. botulinum* peptide or protein, and optionally further include an adjuvant, and optionally further include a pharmaceutically acceptable carrier. In various embodiments, the compositions include at least one atoxic protein or a source of expression of the protein, such that the protein elicits an immune response specific for a *B. anthracis* or *C. botulinum* toxin.

In certain embodiments, these compositions optionally further comprise one or more additional therapeutic agents. In certain embodiments, the additional therapeutic agent or agents are selected from the group consisting of antibiotics particularly antibacterial compounds, anti-viral compounds, anti-fungals, and include one or more of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's The Science and Practice of Pharmacy Ed.* by LWW $21^{st}$ EQ. PA, 2005 discloses various carriers used in formulating pharmaceutical compositions and known techniques for the preparation thereof. Carriers are selected to prolong dwell time for example following any route of administration, including IP, IV, subcutaneous, mucosal, sublingual, inhalation or other form of intranasal administration, or other route of administration.

Some examples of materials that can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, according to the methods of treatment of the present invention, the immunization is promoted by contacting the subject with a pharmaceutical composition, as described herein. Thus, the invention provides methods for immunization comprising administering a therapeutically effective amount of a pharmaceutical composition comprising active agents that include an immunogenic toxin protein of *B. anthracis* or *C. botulinum* to a subject in need thereof, in such amounts and for such time as is necessary to achieve the desired result. It will be appreciated that this encompasses administering an inventive vaccine as described herein, as a preventive or therapeutic measure to promote immunity to infection by *B. anthracis* or *C. botulinum*, to minimize complications associated with the slow development of immunity (especially in compromised patients such as those who are nutritionally challenged, or at risk patients such as the elderly or infants).

In certain embodiments of the present invention a "therapeutically effective amount" of the pharmaceutical composition is that amount effective for promoting production of antibodies and activity in serum specific for the toxins of *B. anthracis* or *C. botulinum*, or disappearance of disease symptoms, such as amount of antigen or toxin or bacterial cells in feces or in bodily fluids or in other secreted products. The compositions, according to the method of the present invention, may be administered using any amount and any route of administration effective for generating an antibody response. Thus, the expression "amount effective for promoting immunity", as used herein, refers to a sufficient amount of composition to result in antibody production or remediation of a disease symptom characteristic of infection by *B. anthracis* or *C. botulinum*.

The exact dosage is chosen by the individual physician in view of the patient to be treated. Dosage and administration are adjusted to provide sufficient levels of the active agent(s) or to maintain the desired effect. Additional factors which may be taken into account include the severity of the disease state; contact to infectious agent in the past or potential future contact; age, weight and gender of the patient; diet, time and frequency of administration; drug combinations; reaction sensitivities; and tolerance/response to therapy. Long acting pharmaceutical compositions might be administered every three to four days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for one dose to be administered to the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs or piglets or other suitable animals. The animal models described herein including that of chronic or recurring infection by *B. anthracis* or *C. botulinum* is also used to achieve a desirable concentration range and route of administration. Such information can then be used to determine useful doses and routes for administration in humans.

A therapeutically effective dose refers to that amount of active agent which ameliorates at least one symptom or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and from animal studies are used in formulating a range of dosage for human use.

The therapeutic dose shown in examples herein is at least about 1 µg per kg, at least about 5, 10, 50, 100, 500 µg per kg, at least about 1 mg/kg, 5, 10, 50 or 100 mg/kg body weight of the purified toxin vaccine per body weight of the subject, although the doses may be more or less depending on age, health status, history of prior infection, and immune status of the subject as would be known by one of skill in the art of immunization. Doses may be divided or unitary per day and may be administered once or repeated at appropriate intervals.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, rectally, mucosally, sublingually, parenterally, intracisternally, intravaginally, intraperitoneally, bucally, sublingually, ocularly, or intranasally, depending on preventive or therapeutic objectives and the severity and nature of a pre-existing infection.

In various embodiments of the invention herein, it was observed that high titers of antibodies, sufficient for protection against a lethal dose of *B. anthracis* or *C. botulinum* toxin, were produced after administration of the engineered atoxic toxin proteins provided herein. Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. Administration may be therapeutic, or it may be prophylactic.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized prior to addition of spores, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral, mucosal or sublingual administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Substantially Identical Amino Acid and Nucleotide Sequences for VHHs

There is a large body of information in the literature supporting the fact that closely related antibody (Ab) sequences are capable of performing the same binding and therapeutic functions such that this is now generally accepted by those with ordinary skill in immunological sciences and is even a dogma. The creation of Abs with small numbers of amino acid sequence variations occurs naturally within mammals and other some other animal species during the process of 'affinity maturation' in which cells producing Abs that bind a newly encountered antigen (Ag) are expanded such that progeny cells contain random mutations within portions of the Ab coding DNA that results in new, related Ab sequences. The cells expressing Abs that have gained improved binding properties for the new Ag are then selected and expanded, increasing the amount of the improved antibody in the animal. This process continues through multiple generations of mutation and selection until Abs with greatly improved binding properties result, thus providing, for example, better immunity against pathogens possessing the new Ag. This process of Ab affinity maturation is widely accepted in the literature and clearly demonstrates that related Ab amino acid sequences can possess similar target binding properties and perform similar therapeutic functions in vivo.

In examples herein, there are numerous examples of related Ab sequences performing similar functions and providing similar therapeutic benefits. The Abs described herein are mostly heavy-chain only Abs (HcAbs) from Camelids. The $V_H$ region from the DNA is isolated encoding these Abs and expressed as single-domain Abs called VHHs. Alpacas are immunized with a selected Ag multiple times to permit the animal to undergo affinity maturation of the HcAbs they produce recognizing this Ag. The HcAbs are then isolated and the DNA encoding the VHH regions are closed for expression of soluble VHHs that bind the Ag and have potential therapeutic or diagnostic properties. During this process, many examples of closely related VHHs are isolated presumably different which are intermediates resulting from the alpacas' affinity maturation process. These related VHHs are screened and most promising members of each homology group is identified, and becomes a lead candidate for further development.

VHHs, like all mammalian antibodies, consist of four well-conserved 'framework' regions (FRs) which are important to form the antibody structure. Between the FRs (FR1, FR2, FR3 and FR4) are three much less well-conserved 'complementarity determining regions' or CDRs which form the interactions with the Ags. These binding regions must bind to widely varying structures (epitopes) on different Ags, therefore, the CDRs must also vary widely so as to interact and bind to these Ags. The third CDR, CDR3, is generally the longest and most diverse of the CDRs within VHHs, both in size and sequence. CDR3 in VHHs can range in size from about 7 to about 28 amino acid residues [1]. The CDR3 regions of VHHs from the same alpacas selected for their binding to a common target Ag, prove to be very similar in their size and have many amino acid identities; the chance that this occurred by random chance are astronomical. Therefore, these VHHs resulted from affinity maturation of a common precursor VHH within the animal and are classified as being a 'homology group'. The individual VHHs within a homology group are classified for binding to a target the members of the VHH homology group 'compete' with each other for binding, thus demonstrating that they bind to the same region on the target.

Since the FRs are critical for sustaining the structure of the VHH and the positioning of the CDRs for binding to their target Ag, the FRs must not vary too much in sequence. Some variation, particular when replacement amino acids are related in properties, is permissible and these changes can often be found naturally within VHHs that have undergone affinity maturation in an animal. In addition to the FRs, the CDRs also must not vary too much in sequence or their Ag binding affinity will be compromised. An excellent way to estimate how much amino acid sequence variation is tolerated within VHHs without compromising their Ag binding character is to observe the variation that occurs naturally within affinity matured homology groups of VHHs isolated from the same animals and shown to bind to the same Ag.

An example of VHH sequence relatedness necessary to retain common Ag binding properties is described in U.S. Pat. No. 8,349,326, issued Jan. 8, 2014 and represented in FIG. 5. In this example, the substantial identity of five different VHH sequences shown in the patent, JDO-E9, JDQ-B2, JDQ-B5, JDQ-C5, and JDQ-F9 is represented as a phylogenic tree. These sequences are substantially different from each other and form a clear homology group when their sequences are compared to the sequences of seven random VHHs. All five members of this homology group had been selected for their binding to Botulinum neurotoxin serotype A (BoNT/A), all had clearly related CDR3 regions, and all were found to compete with each other for binding to BoNT/A. Therefore, these sequences had a common binding site. Despite their common clonal origin and common Ag binding sites, these VHHs of 108 amino acid length contained as many as 26 amino acid differences. This implied that VHHs containing up to 24% amino acid sequence variation had retained their ability to bind to the same region of BoNT/A.

Another example that describes acceptable amount of VHH sequence variation within related VHHs having the same Ag binding character is described in Tremblay et al., 2013 Infect Immun 81: 4592-4603. Proteins in large homology group are described containing 11 VHH sequences, Stx-A3, A4, A5, D4, F1, G6, H3, H5, H9, H10, and H12 with closely related CDR3 sequences of identical size, and the unusual property of cross-specific binding to two different Shiga toxins, Stx1 and Stx2. Two of the more distantly related members of this homology group, VHHs Stx-A4, Stx-A5 are characterized as having common Ag binding character. These two related VHHs have 32 amino acid changes in their full 120 or 121 residue VHH sequence. Therefore, 26% amino acid variation in sequence does not result in the loss of their common Ag binding property.

A portion of the data herein was published as follows, "Prolonged prophylactic protection from botulism with a single adenovirus treatment promoting serum expression of a VHH-based antitoxin protein" by co-authors Mukherjee J, Dmitriev I, Debatis M, Tremblay J M, Beamer G, Kashentseva E A, Curiel D T, Shoemaker C B, in the journal PLoS ONE 9(8): e106422 2014 Aug. doi:10.1371/journal. pone.0106422; "Adenovirus vector expressing Stx1/2-neutralizing agent protects piglets infected with *E. coli* O157: H7 against fatal systemic intoxication" by co-authors Sheoran A S, Dmitriev I P, Kashentseva E A, Cohen O, Mukherjee J, Debatis M, Shearer J, Tremblay J M, Beamer G, Curiel D T, Shoemaker C B, Tzipori S, in the journal Infect Immun. 2014 Nov. 3. pii: IAI.02360-14; and "A heterodimer of a VHH (variable domains of camelid heavy chain-only) antibody that inhibits anthrax toxin cell binding linked to a VHH antibody that blocks oligomer formation is highly protective in an anthrax spore challenge model" by co-authors Moayeri M, Leysath C E, Tremblay J M, Vrentas C, Crown D, Leppla S H, Shoemaker C B, in the journal J Biol Chem. 2015 Mar. 6; 290(10):6584-95 which appeared online Jan. 6, 2015. These papers are hereby incorporated in their entireties herein.

The invention now having been fully described, it is further exemplified by the following claims.

EXAMPLES

Example 1: Toxins and Spores

Endotoxin-free mutant PA proteins, including wild type PA83, PA63, and LF were purified from *B. anthracis* as described in Park, S., et al., 2000 Protein expression and purification 18, 293-302. The PAΔΔ is a mutant from which amino acid residues at positions 162-167 and 304-317 of the amino acid sequences have been genetically deleted, such that the protein cannot be cleaved by furin and accumulates on the cell surface. PAdFF is a mutant in which phenylalanine residues at positions 313 and 314 have been deleted thereby making the protein unable to translocate LF and EF (Singh, Y., et al., 1994 The Journal of biological chemistry 269, 29039-29046). Concentrations of LT correspond to the concentration of each toxin component (i.e. 1 μg/mL LT is 1 μg/mL PA+1 μg/mL LF). Spores of the non-encapsulated, toxigenic Sterne-like strain A35 (Pomerantsev, A. P., et al., 2006 Infection and immunity 74, 682-693) used to infect mice were prepared as described in Moayeri, M., et al., 2010 PLoS pathogens 6, e1001222.

Example 2: Reagents

Rabbit anti-PA83 polyclonal serum #5308 and neutralizing anti-PA mouse monoclonal antibody (mAb) 14B7, which blocks binding of PA (both PA83 and PA63) to its cellular receptors was manufactured as described in Rosovitz, M. J., et al., 2003 The Journal of biological chemistry 278, 30936-30944. Antibodies against the N-terminus of MEK1 (Calbiochem-EMD Biosciences, San Diego, CA), horse radish peroxidase (HRP)-conjugated and non-conjugated anti-E-tag polyclonal antibodies (Bethyl Labs, Montgomery, TX) and various IR-dye tagged secondary antibodies (Rockland Labs, Boyertown, PA) were purchased. The dye 3-(4,5-dimethyl-2-thiazolyl)-2,5-diphenyl tetrazolium bromide (MTT) was purchased from Sigma (St. Louis, MO).

Example 3: VHH-Display Library Preparation from Genes Expressed in Immunized Alpacas Three alpacas were immunized with PA83 (100 μg) by five successive multi-site subcutaneous (SC) injections at three week intervals. For the first immunization, the adjuvant was alum/CpG and subsequent immunizations used alum. All alpacas achieved ELISA anti-PA titers of 1:1,000,000. Blood was obtained from the alpacas for lymphocyte preparation seven days after the fifth immunization, and RNA was extracted using the RNEASY kit (Qiagen, Valencia, CA). Two VHH-display phage libraries were prepared as described in Maass, D. R., et al., 2007 International journal for parasitology 37, 953-962 and Tremblay, J. M., et al., 2010 Toxicon 56, 990-998. The forward and reverse primers used to amplify the VHH coding region repertoire contained Not1 and Asc1 sites, which were used to ligate the JSC vector for gene III phage display. The first library (JIG-2) was constructed using RNA obtained from peripheral blood lymphocytes (PBLs) of one immunized alpaca and contained about $1\times10^7$ independent clones, and the second library (JKF-1) was generated from RNA obtained from a pool of PBLs of the other two alpacas, and contained about $3\times10^7$ independent clones.

Example 4: ELISAs

Purified VHH preparations were serially diluted onto ELISA plates coated with 1 μg/ml of each of the different PA proteins, incubated for one hour at room temperature, washed and then incubated for one hour with HRP-anti-E-tag. Bound HRP was detected using 3,3',5,5'-tetramethylbenzidine (Sigma) and values were plotted as a function of the input VHH concentration. $EC_{50}$ values were calculated for the VHH concentration that secreted in a signal equal to 50% of the maximum signal.

Example 5: Anti-PA VHH Identification and Preparation

Phage library panning, phage recovery and clone fingerprinting were performed as described in Mukherjee, J., et al., 2012 PLoS ONE 7, e29941, Maass, D. R., et al., 2007 International journal for parasitology 37, 953-962 and Tremblay, J. M., et al., 2010 Toxicon 56, 990-998, as follows. The first panning process utilized the JIG-2 VHH-display library and employed purified PA83 or PA63 coated onto Nunc Immunotubes at 10 μg/ml for the first low stringency pan and 1 μg/ml for the second high stringency pan. After two panning cycles, 70% of random clones selected on each target produced a signal two-fold greater than background. The clones that produced strongest 'bug supernatant' ELISA (Tremblay, J. M., et al., 2013 Infection and immunity 81, 4592-4603) signals on plates coated with 0.5 μg/ml PA83 were fingerprinted. The VHHs that had been panned on PA83 or PA63 were observed to recognize both PA83 and PA63. VHH coding sequences were determined for 24 clones displaying clear unique fingerprints (Tremblay, J. M., et al., 2013 Infection and immunity 81, 4592-4603). Sequence alignments showed 11 distinct homology groups. Amino acid sequences of clones representing each group are shown in FIG. 3. A second panning process using the JKF-1 library was performed similar to the first panning process and PA83 was used as the target. About 300 colonies were picked randomly and screened by bug supernatant ELISA on replica plates coated with either 0.5 μg/ml PA, or 3 μg/ml 14B7 mAb (Little, S. F., et al., 1988 Infection and immunity 56, 1807-1813) followed by 1 μg/ml PA83. Screening on 14B7-captured PA83 was performed to block binding of VHHs recognizing the dominant epitope (C-group 1, FIG. 6) that was identified following the screening of the first library. About 70% of clones recognized PA83 and about 20% recognized 14B7-captured PA83. From data obtained by ELISA and DNA fingerprinting, about 70 different VHH coding sequences were obtained. The alignment of these 70 different VHH coding sequences led to the identification of eight new homology groups not previously identified in the first screen (VHHs: JKH-A4, JKH-C7, JKH-D12, JKM-A6, JKO-A4, JKO-B8, JKO-E12, AND JKO-H12 in FIGS. 3 and 6). At least one VHH from each homology group was selected for protein expression. Expression and purification of VHHs in *E. coli* as recombinant thioredoxin (Trx) fusion proteins containing hexahistidine (SEQ ID NO: 169) was performed as previously described in Tremblay, J. M., et al., 2010 Toxicon 56, 990-998. VHH heterodimers were genetically engineered to be linked by a 15-amino acid flexible spacer ((GGGGS)$_3$) (SEQ ID NO: 145). All VHHs were expressed with a carboxyl-terminal E-tag epitope. Competition ELISA analysis was performed as previously described, with minor modifications (Mukherjee, J., et al., 2012 PLoS ONE 7, e29941).

Example 6: Affinity Analyses

The kinetic parameters of the VHHs were assessed by performing surface plasmon resonance, using either a PROTEON™ XPR36 Protein Interaction Array System (Bio-Rad, Hercules, CA; VHHs: JHD-B6, JHE-D9, JIJ-A12, JIJ-B8, JIJ-D3, JIJ-E9, JIJ-F11, JIK-B8, JIK-B10, JIK-B12, and JIK-F4 in FIG. 6) or a BIACORE™ 3000 (GE Healthcare; VHHs: JKH-A4, JKH-C7, JKH-D12, JKM-A6, JKO-A4, JKO-B8, JKO-E12, and JKO-H12 in FIG. 6). In each assay, the VHH was immobilized to the chip (GLH for PROTEON™, CM5 for BIACORE™) by amine coupling chemistry, involving sequential activation of the chip surface with a mixture of 1-ethyl-3-(3-dimethylaminopropyl) carbodiimide (EDC) and sulfo-N-hydoxysuccinimide (sulfo-NHS), injection of PA83 at pH 5 (sodium acetate buffer), and deactivation with an ethanolamine injection.

For the PROTEON™ data set, a range of PA concentrations was passed over the chip surface at 100 µL/min for 60 s, and dissociation was recorded for 600 s or 1200 s. Running buffer for these assays was 10 mM Hepes, pH 7.4, 150 mM NaCl, 0.005% TWEEN® 20. The surface was regenerated between runs with a 30 s injection of 50 mM HCl at 50 µL/min. Data were evaluated with PROTEON™ Manager software (version 3.1.0.6) using the Langmuir interaction model to obtain $K_D$ values. Reported values are the mean of at least four replicates.

For the BIACORE™ data set, VHHs were passed over the PA immobilized on the chip surface at 100 nM and 100 l/min for 60 s, and dissociation was recorded for 600 s or 1200 s. Running buffer for these assays was 10 mM Hepes, pH 7.4, 150 mM NaCl, 0.005% TWEEN® 20. The surface was regenerated between runs with a 30 s injection of 10 mM glycine (pH 3) at 50 µl/min. Dissociation and association phases of each curve were fit separately using BIAevaluation software (GE) using the 1:1 Langmuir model to obtain $K_D$ values. Reported values are the mean of three replicates. A series of four replicates at 100 nM through 2 µM JKO-B8 resulted in comparable $K_D$ values at each concentration. A negative control VHH (anti-EF) did not exhibit any binding to the PA-coated chip. JIK-B8 was run at the beginning and end of the series to provide a point of comparison to the PROTEON™ data set.

Example 7: Toxicity and Neutralization Assays

RAW264.7 mouse macrophages were grown in Dulbecco's modified Eagle medium (DMEM) supplemented with 10% fetal bovine serum, 10 mM HEPES, and 50 µg/mL gentamicin (all purchased from Life Technologies, Grand Island, NY). For neutralization assays PA83 and LF (250 ng/ml) in serum-free Dulbecco's Modified Eagle Medium were incubated with each of various dilutions of antibody in 96-well plates for one hour prior to addition to RAW264.7 macrophages. Viability was assessed by MTT staining as described in Chen, Z., et al., 2009 Infection and immunity 77, 3902-3908, at a time point when greater than 90% of toxin-treated controls were observed to be lysed by assessment by light microscopy. In certain experiments PA83 or PA63 (1 µg/ml) were pre-bound to antibodies or were added to cells at 37° C. or 4° C. followed after one hour by washing with serum-free DMEM at the same temperature and addition of medium containing LF or antibodies prepared in LF (1 µg/ml). Cells were then incubated at 37° C. for 12-16 hours. Viability was then assessed by MTT staining relative to untreated cell controls.

Example 8: Mouse Studies

For toxin challenge, Balb/cJ mice (female, 8 weeks old, Jackson Laboratories, Bar Harbor, ME) were treated with antibody agents by the IV route at the doses (molar ratios relative to PA) and times described in brief description of the figures. Mice were challenged with LT (45 µg, IV) and monitored for 10 days for survival. For spore challenges, C57BL/6J mice (8 weeks old, female, Jackson Laboratories) were challenged with the lethal dose of $2 \times 10^7$ spores (SC, 200 µl) before or after antibody administration (SC) at various doses and times as noted in brief description of the figures.

Example 9: Ethics Statement

All examples were performed under protocols approved by Tufts University and National Institute of Allergy and Infectious Diseases (NIAID) Animal Care and Use Committees. Work with alpacas was performed at Tufts under approved protocol Tuskegee University School of Veterinary Medicine (TUSVM) and Institutional Animal Care and Use Committee (IACUC) Protocol #G2011-08. Mouse studies were performed at NIAID under approved protocols LPD8E and LPD9E.

Example 10: Anthrax PA-Binding VHHs

VHH-display phage libraries were prepared from genetic material obtained from three alpacas, which had been immunized with purified anthrax PA83. Two separate libraries were selected for clones binding to PA83 or, to PA83 immobilized on mAb 14B7. The mAb 14B7 is a well-characterized neutralizing mAb that binds to an immunodominant epitope through which PA binds to its receptor.

Figure 3:
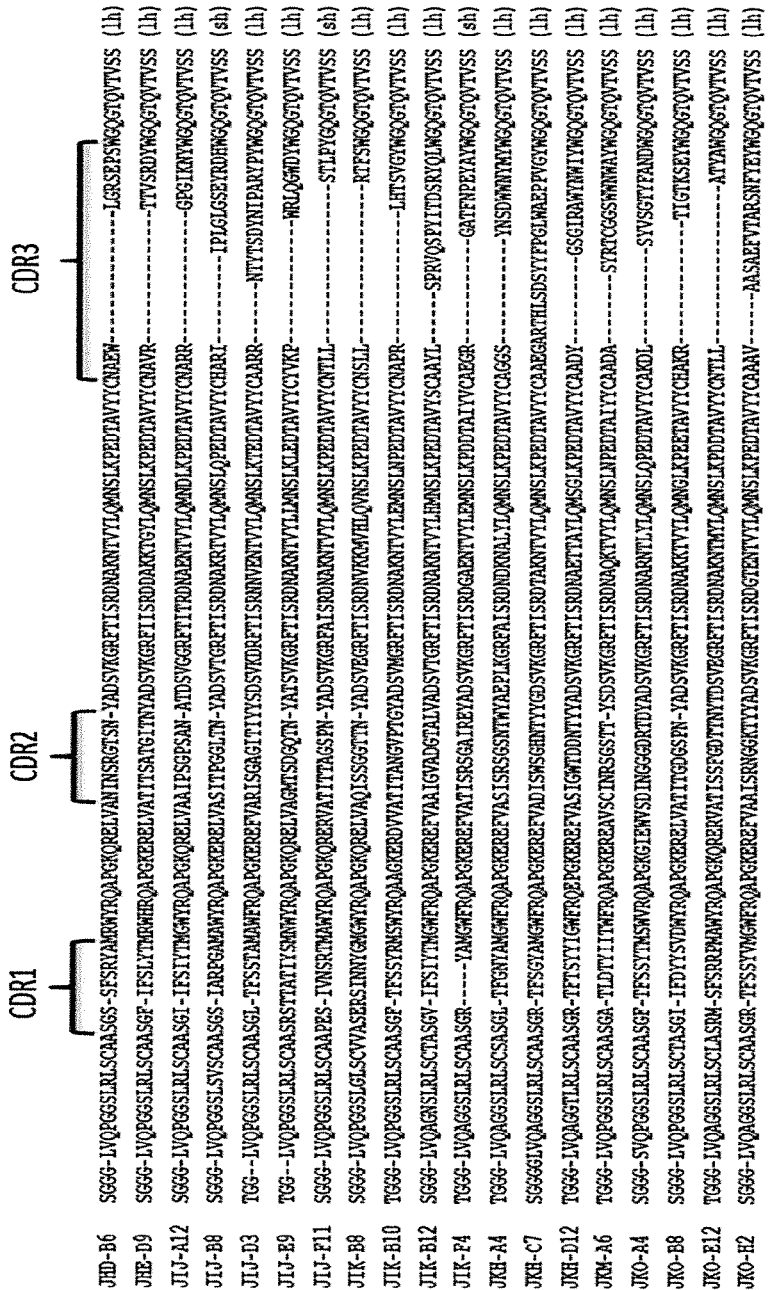
FIG. 3 shows amino acid sequences SEQ ID NOS 148-166 of VHHs selected for binding to anthrax PA. Sequences shown begin within framework 1 at the site of the primer binding employed in coding sequence DNA amplification from the immune alpaca cDNA and continue through the end of framework 4. The expression in parentheses at the right end indicates that the VHH contains a long hinge (lh) or a short hinge (sh). The locations of each of the three complementarity determining regions (CDRs) are indicated at the top end.

Of total clones obtained and sequenced, 19 VHHs with apparently unrelated sequences were identified (FIG. 3). Competition assays between the various VHHs, and with 14B7 and 2D3 mAbs, which bind distinct immunodominant regions of PA83 (Little, S. F., et al., 1988 Infection and immunity 56, 1807-1813) showed that the identified VHHs fall into four distinct competition groups (identified as 1, 2, 3, and 4 in FIG. 6) and thus likely each protein in a group binds to one of four non-overlapping epitopes on PA. Ten of the 11 VHHs selected by binding to PA83-coated tubes (VHHs: JHD-B6, JHE-D9, JIJ-A12, JIJ-B8, JIJ-D3, JIJ-E9, JIJ-F11, JIK-B8, JIK-B10, JIK-B12, and JIK-F4 in FIG. 6) competed with 14B7. Eight unique PA-binding VHHs, including six that bind PA83 at sites different than 14B7 (FIG. 7A and FIG. 7B) were subsequently selected by binding to 14B7-immobilized (and thereby blocked) PA (VHHs: JKH-A4, JKH-C7, JKH-D12, JKM-A6, JKO-A4, JKO-B8, JKO-E12, and JKO-H12 in FIG. 6). Binding of one of the VHH, clone JIJ-B8 was not blocked by either mAb, and binding of another clone JKO-H2 was inhibited by both mAbs (FIG. 7A and FIG. 7B). The VHHs were characterized for PA affinity by dilution ELISA (for $EC_{50}$) and by surface plasmon resonance (for $K_D$) (FIG. 6). A selected VHH representative of each of the four epitope competition groups is illustrated by a shaded portion in FIG. 6. These are JIK-B8 (C-group 1), JKH-C7 (C-group 3), JKH-D12 (C-group 2), and JKO-H2 (C-group 4).

Example 11: Anthrax Toxin Neutralization

Cell-based anthrax toxin neutralization assays were performed on each of the 19 unique VHHs, and the data showed potencies ranging from $IC_{50}$ of about 200 pM to no activity in an assay using PA at 1.25 nM (FIG. 6; representative assay with antibodies from each competition group shown in FIG. 7C). VHHs recognizing the immunodominant PA domain (group 1) differed widely in their ability to neutralize the toxin, with four of 12 showing no neutralizing ability. VHHs JIK-B8 and JKO-E12 of the C-group 1 class displayed the highest affinity and lowest $IC_{50}$ values. One VHH recognized a second epitope (JKH-C7, group 3, FIG. 6) showed potent anthrax neutralizing activity (FIG. 7C). VHHs that had been characterized as recognizing C-group 2 and C-group 4 showed weak or undetectable toxin neutralizing activity (FIG. 7C). VHH JKO-H2 (group 4) displayed no recognition of PA63, suggesting that furin cleavage either removes the epitope or alters it in a manner that it cannot be recognized.

Example 12: Heterodimeric VHH-Based Neutralizing Agents (VNAs) Protect Against Anthrax Toxin and Spore Infection in Mice Linking toxin-neutralizing VHHs into heteromultimeric VNAs has been found to improve toxin affinity and, more importantly, to substantially improve in vivo antitoxin efficacy (Mukherjee, J., et al., 2012 PLoS ONE 7, e29941; Tremblay, J. M., et al., 2013 Infection and immunity 81, 4592-460; Vance, D. J., et al., 2013 The Journal of biological chemistry 288, 36538-36547; Yang, Z., et al., 2014 The Journal of infectious diseases 2014 Sep. 15; 210(6):964-72).

Figure 1C:
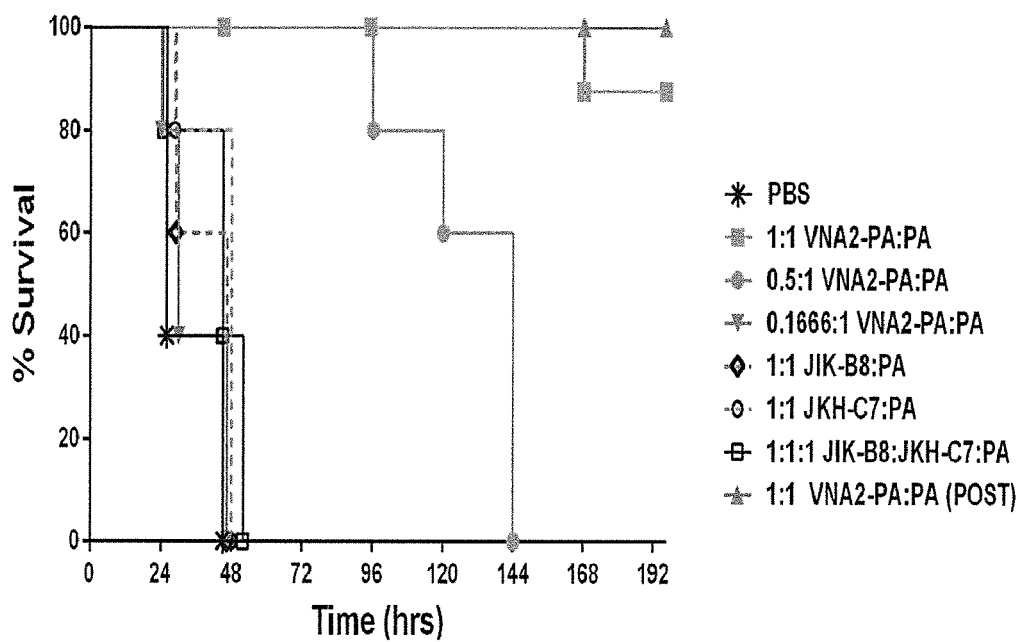
Figure 2A:
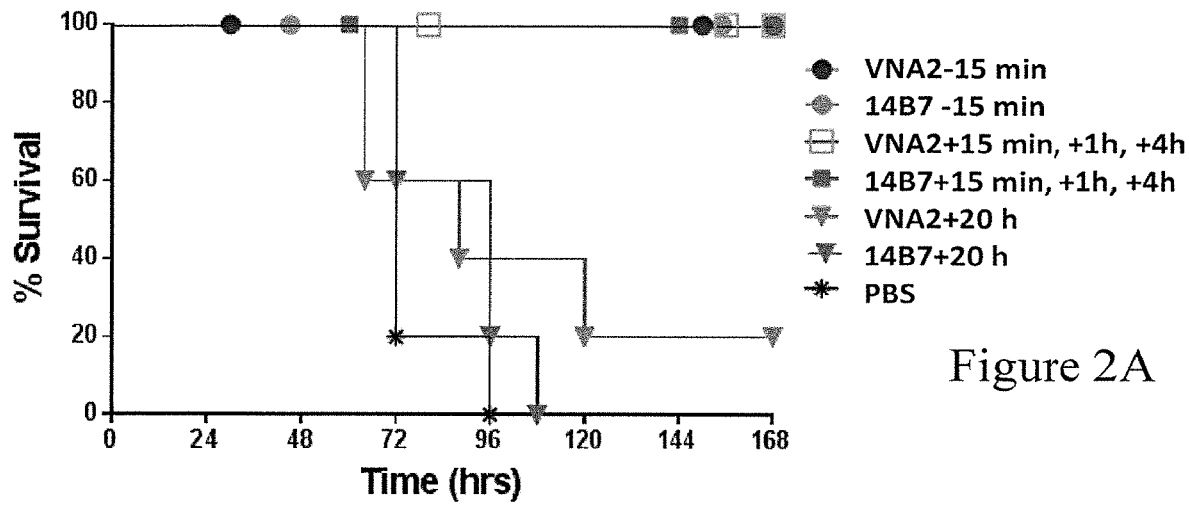
FIG. 2A and FIG. 2D are Meyer-Kaplan survival plots showing percent survival (% survival, ordinate) of subjects as a function of time in days (abscissa) following contact with A35 Sterne-like toxigenic B. anthracis strain spores ($2 \times 10^7$ spores, SC) and VHH binding/neutralizing agents.
Figure 2B:
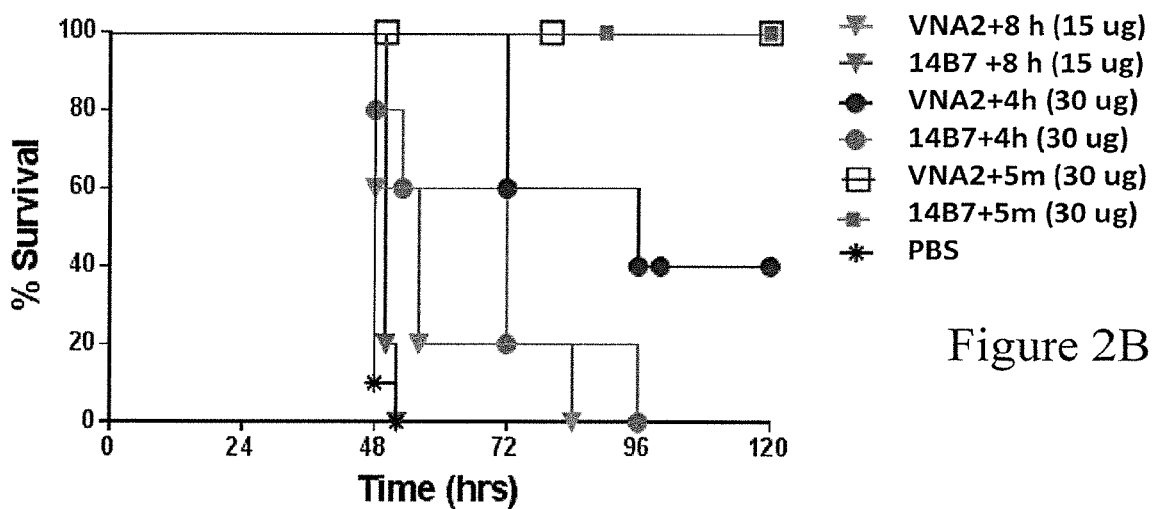
FIG. 2B shows data obtained after antibody was administered post-infection at indicated times and doses. Control mice were treated with PBS at 15 min, 1 hour and 4 hours post infection.
Figure 2C:
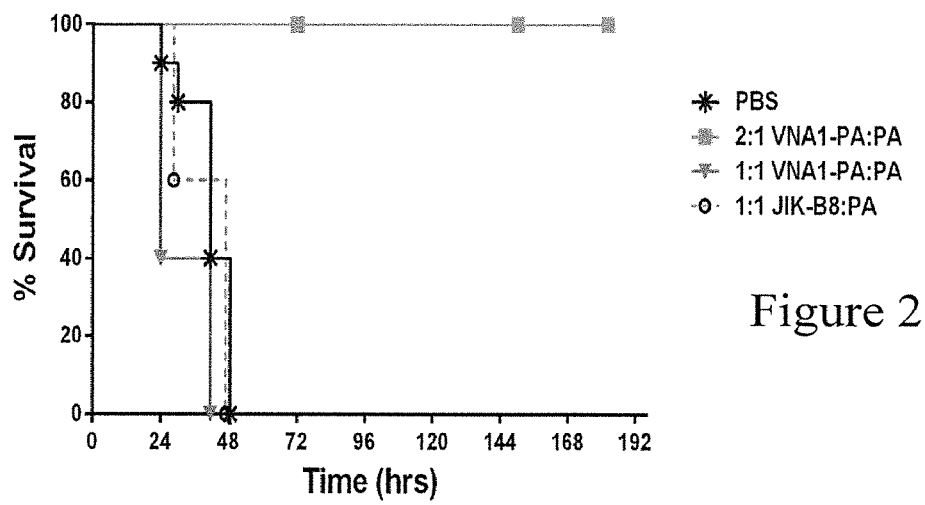
FIG. 2C contains data from Balb/cJ mice injected intravenously (IV) with antibody at indicated molar ratios (Ab:toxin) 10 minutes prior to injection with LT (45 µg for each toxin component). Control groups received PBS instead of antibody. Animals were monitored for 10 days post treatment for signs of malaise and survival.
Figure 2D:
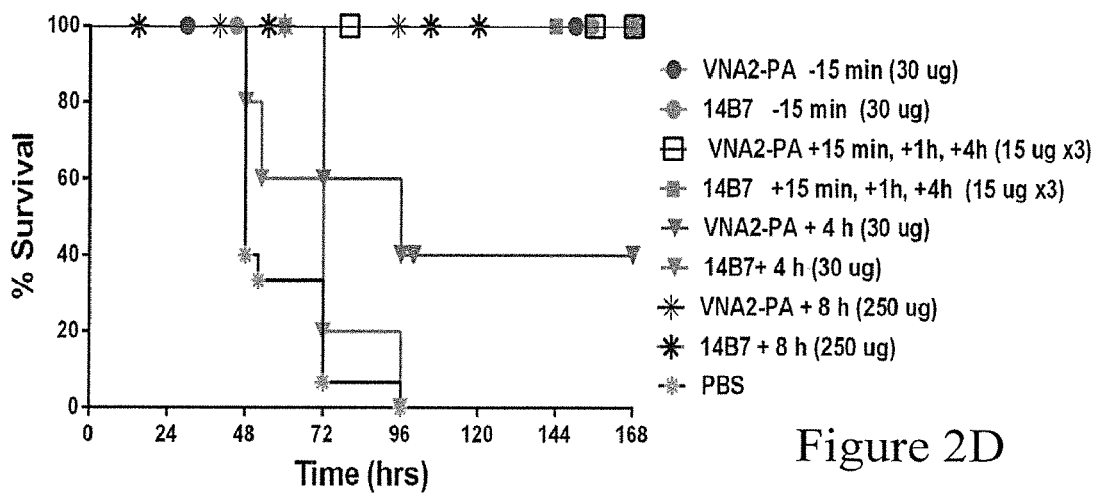

A heterodimeric VNA (VNA2-PA) was prepared to contain the two, potent neutralizing VHHs, JIK-B8 and JKH-C7, separated by a short unstructured peptide, was expressed and purified (amino acid sequence shown in FIG. 4A). This construct, VNA2-PA, was observed to have potent neutralizing toxin activity (FIG. 7C). VNA2-PA was compared to monomeric VHHs for the ability to protect mice from anthrax toxin. The toxin dose between 1-2 LD100 (45 µg LT) was administered by IV route for the Balb/cJ strain. Treatment doses were selected to test efficacy at various molar ratios of agent to toxin. Heterodimeric VNAs each bind at two separate sites on each toxin, so a dose that can fully occupy both binding sites must be present at a 2:1 molar ratio agent:toxin. Each single monomer VHH was observed as not able to protect mice or provide any beneficial effect at a 1:1 molar ratio, with percent survivals as low as that for mice administered control PBS. The heterodimeric VNA2-PA in contrast was highly protective at 1:1 (FIG. 1C) yielding 100% protection for the entire time course. Thus, VNA2-PA was able to shift the time to death significantly even at submolar ratios to toxin. Importantly, the heterodimer offered greater protection against toxin than a pool of the two VHHs used in a 1:1:1 ratio with toxin, providing evidence of the improved in vivo efficacy of the heterodimer form (FIG. 1C). VNA2-PA treatment two hour post-toxin administration was also highly protective (FIG. 1C). This finding was surprising in light of the fact that the bulk of PA has been shown to be cleaved to PA63 and removed from circulation by two hours after a bolus administration (Moayeri, M., et al., 2007 Infection and immunity 75, 5175-5184). Thus, it is here envisioned that a significant amount of active PA not measurable in circulation (plasma) may remain accessible to antibody at crucial tissue sites. A second VHH heterodimer engineered by the methods herein, VNA1-PA, incorporating as component monomers the neutralizing JIK-B8 VHH with a non-neutralizing VHH (JIJ-B8) was observed to fail to provide any protection if administered 1:1, but was fully protective in this assay if administered at a two-fold molar excess (FIG. 4B and FIG. 2C).

VNA2-PA was tested with 14B7 mAb control for protection of C57BL/6J mice against infection with a single LD100 dose of the A35 Sterne-like toxigenic B. anthracis strain. Antibody provided 15 min prior to subcutaneous spore infection or at three sequential times of dosing, at 15, 60 and 240 min post-infection, was also fully protective (FIG. 2A-FIG. 2D).

A single administration of the VNA2-PA antibody at the lower dose of 30 µg at four hours post infection resulted in survival of 2/5 mice. Mice treated with this dose of 14B7 died during the time course, likely because only one third the number of antibody molecules were present compared to VNA2-PA. Increasing the time gap between spore infection and antibody administration to eight hours resulted in a complete loss of protection unless antibody was increased to a much higher dose of 250 µg, at which dose a surprising full protection of the entire mouse group was observed (FIG. 2A-FIG. 2D).

Example 13: Heterodimeric VHH-Based Neutralizing Agents (VNAs) Protect Against BoNT/B Toxin in Mice BoNT/B neutralizing heterodimer VHHs were tested for the ability to protect mice from BoNT/B lethality. An amount of BoNT/B toxin of 10, 40, 100 and 500 LD50 respectively was administered by intraperitoneal injection to groups of five C57BL/6J mice. The mice receiving the toxin were treated with 2 µg of one of BoNT/B neutralizing VHH heterodimers (SEQ ID NO: 131, SEQ ID NO: 133, SEQ ID NO: 135, or SEQ ID NO: 137). Mice were monitored at least five times per day for survival and symptoms of botulism for seven days.

Figure 5A:
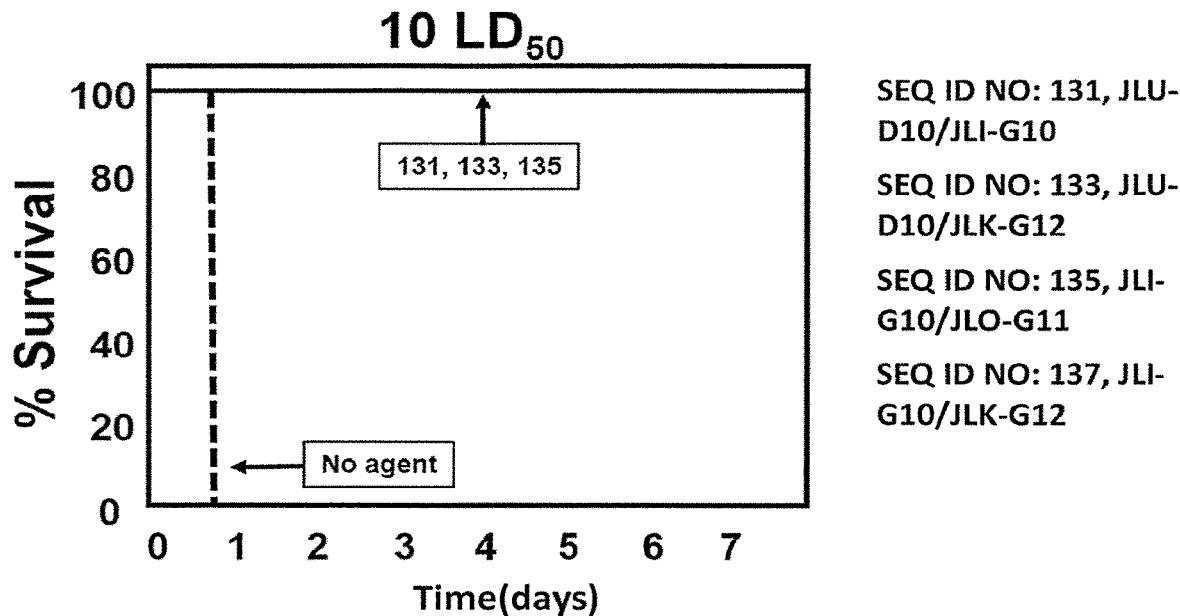
Figure 5B:
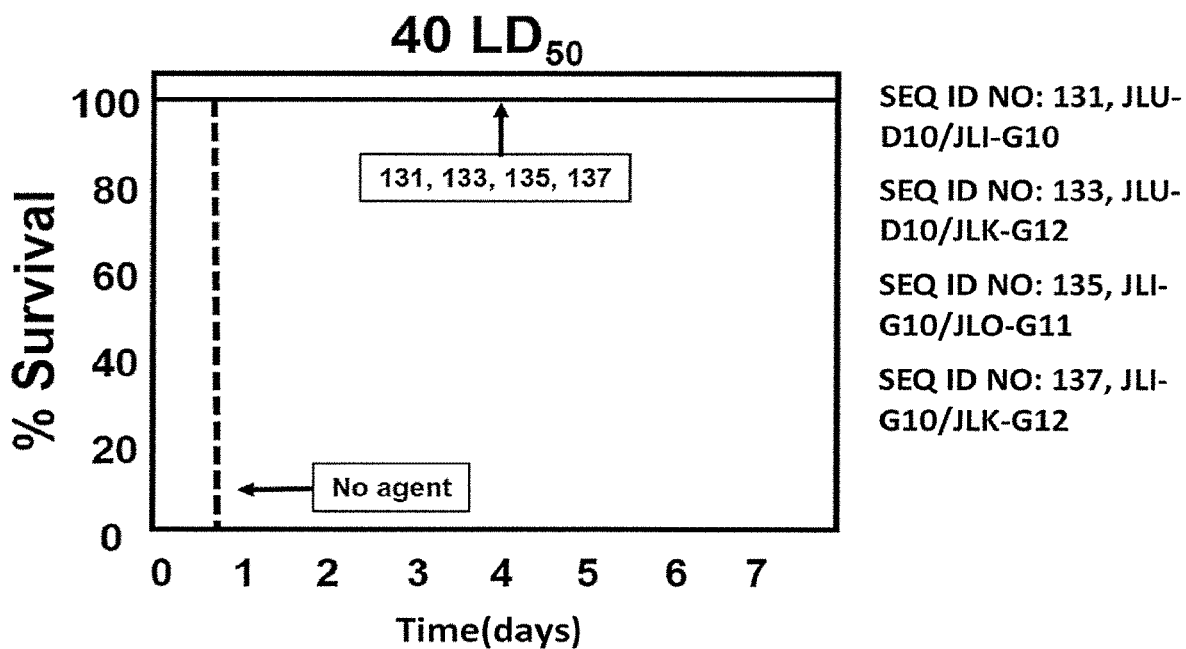
Figure 5C:
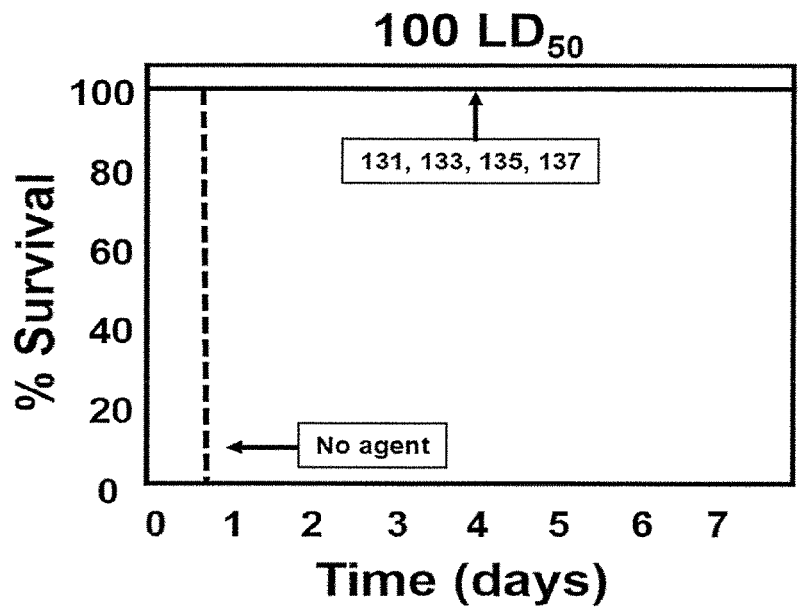

Mice contacted with BoNT/B toxin of 10, 40 and 100 LD50 respectively by intraperitoneal injection were treated with 2 µg of one of BoNT/B neutralizing VHH heterodimers SEQ ID NO: 131, SEQ ID NO: 133, SEQ ID NO: 135, or SEQ ID NO: 137. It was observed that the treated mice were fully protected, having a survival rate of 100%. In contrast, control mice untreated with VHH heterodimers died within 24 hours as shown in FIG. 5A-FIG. 5C.

Figure 5D:
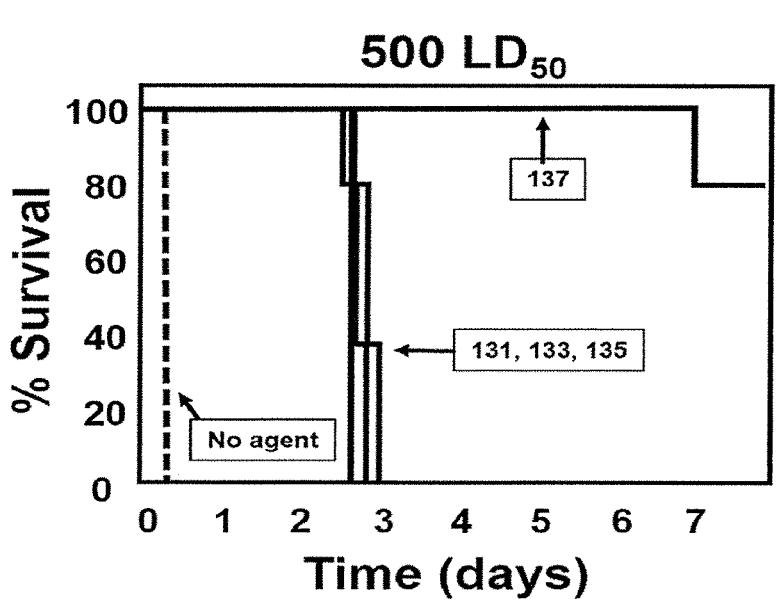

At the even greater BoNT/B toxin concentration of 500 LD50, VHH heterodimers SEQ ID NO: 131, SEQ ID NO: 133 and SEQ ID NO: 135 provided protection for two days and VHH heterodimer SEQ ID NO: 137 showed 100% survival rate till day 7 and 80% survival rate thereafter (FIG. 5D).

Appendices of Toxin-Binding VHH Proteins and Encoding Nucleic Acids

Appendix B

Anthrax Protective Antigen (PA) Positive VHHs

Included in Appendix B are the following: 8 anthrax protective antigen (PA)-binding VHHs; 16 BoNT/B-binding VHHs; and 12 BoNT/E-binding VHHs:

JKH-A4,
SEQ ID NO: 1
QVQLAETGGGLVQAGGSLRLSCSASGLTFGNYAMGWFRQAPGKEREFVASISRSGSN
TWYAEPLKGRFAISRDNDKNALYLQMNSLKPEDTAVYYCAGGSYNSDWWNYMYWGQG
TQVTVSSEPKTPKPQ

SEQ ID NO: 2
CAGGTGCAGCTGGCGGAGACGGGGGGAGGATTGGTGCAGGCTGGGGGCTCGCTGAGA
CTCTCCTGTTCAGCCTCTGGGCTCACCTTCGGGAACTATGCCATGGCTGGTTCCGC
CAGGCTCCAGGGAAGGAGCGTGAGTTTGTAGCATCTATTTCTCGGAGTGGTAGTAAC
ACATGGTATGCAGAACCCCTGAAGGGCCGATTCGCCATCTCCAGAGACAACGACAAG
AACGCGCTCTATCTGCAAATGAACAGCCTGAAACCTGAGGACACGGCCGTTTATTAC
TGTGCTGGAGGATCTTATAATAGTGACTGGTGGAACTATATGTACTGGGGCCAGGGG
ACCCAGGTCACTGTCTCCTCAGAACCCAAGACACCAAAACCACAA

JKH-C7,
SEQ ID NO: 3
QVQLVESGGGLVQAGGSLRLSCAASGRTFSGYAMGWFRQAPGKEREFVADISWSGH
NTYYGDSVKGRFTISRDTAKNTVYLQMNSLKPEDTAVYYCAAEGARTHLSDSYYFPG
LWAEPPVGYWGQGTQVTVSSEPKTPKPQ

SEQ ID NO: 4
CAGGTGCAGCTGGTGGAGTCGGGTGGGGGAGGACTGGTGCAGGCTGGGGGCTCTCTG
AGACTCTCCTGTGCAGCCTCTGGACGCACCTTCAGTGGCTATGCCATGGGCTGGTTC
CGCCAGGCTCCGGGGAAGGAGCGTGAGTTTGTAGCCGATATTAGCTGGAGTGGTCAT
AACACGTACTATGGAGACTCCGTGAAGGGCCGATTCACCATCTCCAGAGACACCGCC
AAGAACACGGTGTATCTGCAAATGAACAGCCTGAAACCTGAGGACACGGCCGTTTAT
TACTGTGCAGCGGAGGGGCCCGTACACACCTTAGTGATAGTTACTACTTCCCGGGC
CTCTGGGCCGAACCCCCCGTGGGCTACTGGGGCCAGGGGACCCAGGTCACTGTCTCC
TCAGAACCCAAGACACCAAAACCACAA

JKH-D12,
SEQ ID NO: 5
QVQLVETGGGLVQAGGTLRLSCAASGRTFTSYYIGWFRQEPGKEREFVASIGWTDDN
TYYADSVKGRFTISRDNAETTAYLQMSGLKPEDTAVYYCAADYGSGIRAWYNWIYWG
QGTQVTVSSEPKTPKPQ

SEQ ID NO: 6
CAGGTGCAGCTGGTGGAGACCGGGGGAGGATTGGTGCAGGCTGGGGGCACTCTGAGA
CTCTCCTGTGCAGCCTCTGGACGTACCTTCACGAGCTATTACATTGGCTGGTTCCGC
CAGGAACCAGGGAAGGAGCGTGAGTTTGTAGCAAGTATCGGCTGGACCGATGATAAC
ACATACTATGCAGACTCCGTGAAGGGCCGATTCACCATCTCCAGAGACAACGCCGAG
ACCACGGCCATATCTGCAAATGTCGGGCCTGAAACCTGAGGACACGGCCGTTTATTAC
TGTGCAGCCGACTACGGGTCAGGGATACGGGCCTGGTATAATTGGATTTACTGGGGC
CAGGGGACCCAGGTCACCGTCTCCTCAGAACCCAAGACACCAAAACCACAA

JKM-A6,
SEQ ID NO: 7
QLQLAETGGGLVQPGGSLRLSCAASGATLDTYIITWFRQAPGKEREAVSCINRSGST
TYSDSVKGRFTISRDNAQKTVYLQMNSLNPEDTAIYYCAADSYRTCGGSWWNWAYW
GQGTQVTVSSEPKTPKPQ

SEQ ID NO: 8
CAGTTGCAGCTCGCGGAGACGGGAGGAGGCTTGGTGCAGCCTGGGGGGTCTCTGAGA
CTCTCCTGTGCAGCCTCTGGCGCCACTTTGGATACTTATATCATAACCTGGTTCCGC
CAGGCCCCAGGGAAGGAGCGTGAGGCCGTCTCATGTATTAATCGTAGTGGTAGCACG
ACCTATTCAGACTCCGTGAAGGGCCGATTCACCATCTCCAGAGACAACGCCCAGAAA
ACGGTGTATCTGCAGATGAACAGCCTGAACCCTGAGGACACAGCCATTTATTACTGC
GCAGCGGATGCTTCGTACCGTACTTGCGGCGGGAGTTGGTGGAATTGGGCGTACTGG
GGCCAGGGGACCCAGGTCACCGTCTCCTCAGAACCCAAGACACCAAAACCACAA

JKO-A4,
SEQ ID NO: 9
QVQLAESGGGSVQPGGSLRLSCAASGFTFSSYTMSWVRQAPGKGIEWVSDINGGGDR
TDYADSVKGRFTISRDNARNTLYLQMNSLQPEDTAVYYCAKDLSYVSGTYFANDWGQ
GTQVTVSSEPKTPKPQ

SEQ ID NO: 10
CAGGTGCAGCTCGCGGAGTCTGGAGGAGGCTCGGTGCAACCTGGGGGGTCTCTGAGA
CTCTCCTGTGCAGCCTCTGGATTCACCTTCAGTAGTTATACTATGAGCTGGGTCCGC
CAGGCTCCAGGAAAGGGGATCGAGTGGGTCTCAGATATTAATGGGGGTGGTGATAGA
ACAGACTATGCAGACTCCGTGAAGGGCCGATTCACCATCTCCAGAGACAACGCCAGG
AACACGCTGTATCTGCAAATGAACAGCCTGCAACCTGAGGACACGGCCGTGTATTAC
TGTGCAAAAGATCTGAGCTACGTTAGTGGTACTTATTTCGCAACGACTGGGGCCAG
GGGACCCAGGTCACCGTCTCCTCCGAACCCAAGACACCAAAACCACAA

JKO-B8,
SEQ ID NO: 11
QLQLAESGGGLVQPGGSLRLSCTASGIIFDYYSVDWYRQAPGKERELVATITGDGSP
NYADSVKGRFTISRDNAKKTVYLQMNGLKPEETAVYYCHAKRTIGTKSEYWGQTQV
TVSSEPKTPKPQ

-continued

```
                                                   SEQ ID NO: 12
CAGTTGCAGCTGGCGGAGTCGGGGGGAGGCTTGGTGCAGCCTGGGGGGTCTCTGAGA
CTCTCCTGTACAGCCTCTGGAATCATCTTCGATTACTATTCCGTGGACTGGTACCGC
CAGGCTCCAGGGAAGGAGCGCGAATTGGTCGCAACTATTACGGGTGATGGTAGCCCG
AACTATGCGGACTCTGTCAAGGGCCGATTCACCATCTCCAGAGACAACGCCAAGAAG
ACGGTGTATCTGCAAATGAACGGCCTGAAACCTGAGGAAACGGCCGTCTATTACTGT
CATGCCAAAGGACTATAGGGACCAAATCTGAGTACTGGGGCCAGGGGACCCAGGTC
ACTGTCTCCTCAGAACCCAAGACACCAAAACCACAA

JKO-E12,
                                                   SEQ ID NO: 13
QVQLAETGGGLVQAGGSLRLSCLASRMSFSRRPMAWYRQAPGKQRERVATISSFGDT
TNYTDSVEGRETISRDNAKNTMYLQMNSLKPDDTAVYYCNTLLATYAWGQGTQVTVS
SEPKTPKPQ

SEQ ID NO: 14
CAGGTGCAGCTCGCGGAGACCGGGGGAGGCTTGGTGCAGGCTGGGGGGTTCTCTGAGA
CTCTCCTGTTTAGCCTCTAGAATGAGCTTTAGTAGGCGCCCCATGGCCTGGTACCGC
CAGGCTCCAGGCAAGCAGCGCGAAAGGGTCGCAACTATTAGTAGTTTCGGTGATACC
ACAAACTATACAGACTCCGTGGAGGGCCGATTCACCATCTCCAGGGACAATGCCAAG
AACACGATGTATCTGCAAATGAACAGCCTGAAACCTGACGACACGGCCGTGTATTAC
TGTAACACATTACTCGCTACGTACGCCTGGGGCCAGGGGACCCAGGTCACCGTCTCC
TCAGAACCCAAGACACCAAAACCACAA

JKO-H2,
                                                   SEQ ID NO: 15
QVQLAESGGGLVQAGGSLRLSCAASGRTFSSYVMGWFRQAPGKEREFVAAISRNGGK
TYYADSVKGRFTISRDGTENTVYLQMNSLKPEDTAVYYCAAAVAASAEFVTARSNFY
EYWGQGTQVTVSSEPKTPKPQ

SEQ ID NO: 16
CAGGTGCAGCTGGCGGAGTCGGGGGGAGGATTGGTGCAGGCTGGGGGCTCTCTGAGA
CTCTCCTGTGCAGCCTCTGGACGCACCTTCAGTAGCTATGTCATGGGCTGGTTCCGC
CAGGCTCCAGGGAAGGAGCGTGAGTTTGTGGCCGCTATTAGCGAAATGGTGGTAAG
ACCTACTATGCAGACTCCGTGAAGGGCCGATTCACCATCTCAAGAGACGGCACCGAG
AACACGGTGTATCTGCAAATGAACAGCCTGAAACCTGAGGACACGGCCGTTTATTAC
TGCGCAGCAGCCGTAGCCGCTTCTGCCGAGTTTGTTACGGCTCGCTCGAATTTTTAT
GAATATTGGGGTCAGGGGACCCAGGTCACTGTCTCCTCAGAACCCAAGACACCAAAA
CCACAA
```

New BoNT/B-Binding VHHs

```
JLB-B7,
                                                   SEQ ID NO: 17
QVQLVETGGGLVQAGGSLRLSCEASGSVVTIKEMGWYRQAPGKEREQERDLVAAIGIGGV
TYYATSVKGRFTISRDSAKTTLRLQMSSLRPEDTAMYYCAVITDRNTGGYPDYWGQGTQV
TVTAEPKTPKPQ

SEQ ID NO: 18
CAGGTGCAGCTGGTGGAGACGGGTGGAGGCTTGGTGCAGGCTGGGGGGTCTCTGAGACTC
TCCTGTGAAGCCTCTGGAAGCGTCGTCACCATCAAAGAGATGGGCTGGTACCGACAGGCT
CCAGGAAAGGAGCGCGAACAGGAGCGCGACTTGGTCGCAGCAATTGGCATTGGTGGTGTC
ACATACTACGCAACCTCTGTGAAGGGCCGATTCACCATCTCCAGACAGTGCCAAGACT
ACGCTGCGTCTGCAAATGAGCAGCCTGAGACCTGAGGACACGGCCATGTATTATTGTGCG
GTCATAACTGACAGGAACACCGGTGGTTACCCGGACTACTGGGGCCAGGGGACCCAGGTC
ACTGTTACCGCAGAACCCAAGACACCAAAACCACAA

JLI-G10,
                                                   SEQ ID NO: 19
QVQLVESGGGLVQAGGSLRLSCAASILTYDLDYYYIGWVRQAPGKEREGVSCISSTDGAT
YYADSVKGRFTISRNNAKNTVYLQMNNLKPEDTAIYYCAAAPLAGRYCPASHEYGYWGQG
TQVTVSSEPKTPKPQ

SEQ ID NO: 20
CAGGTGCAGCTGGTGGAGTCCGGTGGAGGCTTGGTGCAGGCTGGGGGGTCTCTGAGACTC
TCCTGTGCAGCCTCTATACTCACTTATGATTTGGATTATTATTACATAGGCTGGGTCCGC
CAGGCCCCAGGGAAGGAGCGTGAGGGGTCTCATGATTATTAGTAGTACTGATGGTGCCACA
TACTATGCAGACTCCGTGAAGGGCCGATTCACCATCTCCAGAAACAACGCCAAGAACACG
GTGTATCTGCAAATGAACAACCTAAAACCTGAGGACACAGCCATTTATTATTGTGCAGCA
GCCCCCCTGGCTGGGCGCTACTGTCCCGCCTCGCATGAGTATGGCTACTGGGGTCAGGGG
ACCCAGGTCACCGTCTCGTCAGAACCCAAGACACCAAAACCACAA

JLI-H11,
                                                   SEQ ID NO: 21
QVQLVESGGGLVQPGESLRLSCGASGMSLDYYAIAWYRQAPGKEREGVSCISVSGSSAQY
LDSVRGRFIISKDNTKSTAYLQMNSLKPEDTAVYYCAALADCAGYASLTFDFDSWGQGTQ
VAVSSAHHSEDPS
```

-continued

SEQ ID NO: 22
CAGGTGCAGCTCGTGGAGTCGGGTGGAGGCTTGGTGCAGCCTGGGGAGTCTCTGAGACTC
TCCTGTGGAGCCTCTGGAATGAGTTTGGATTACTATGCCATAGCCTGGTACCGCCAGGCC
CCAGGGAAGGAGCGTGAGGGGGTCTCATGTATTAGTGTTAGTGGCAGTAGCGCACAATAT
TTAGACTCCGTGAGGGGTCGCTTCATCATCTCCAAAGACAACACCAAGACGGGCTAT
CTGCAAATGAACAGCCTGAAGCCTGAAGACACAGCCGTTTATTACTGCGCAGCCCTGGCC
GACTGTGCAGGCTATGCCAGTCTTACCTTTGACTTTGATTCTTGGGGCCAGGGGACCCAG
GTCGCCGTCTCCTCGGCGCACCACAGCGAAGACCCCTCG

JLJ-F9,
SEQ ID NO: 23
QVQLVESGGGLVQAGGSLRLSCAPSRLTLDFFAIAWFRQAPGKEREGVSCISSHDGSTYY
TDSVKGRFTISKDNAKNTVYLQMNSLKPEDTAVYYCALDHNVGTCQLTQAEYDYWGQGTQ
VTVSSAHHSEDPS

SEQ ID NO: 24
CAGGTGCAGCTGGTGGAGTCCGGTGGAGGCTTGGTGCAGGCTGGGGGGTCTCTGAGACTC
TCCTGTGCACCCTCGCGATTAACTTTGGATTTCTTTGCCATAGCCTGGTTCCGCCAGGCC
CCAGGGAAGGAGCGTGAGGGGGTCTCATGTATTAGTAGTCATGATGGTAGCACATACTAC
ACAGACTCCGTGAAGGGCCGATTCACCATCTCCAAAGACAACGCCAAGAACACGGTGTAT
CTGCAAATGAACAGCCTGAAGCCTGAGGACACAGCCGTTTATTACTGTGCCCTAGACCAT
AACGTGGGTACCTGCCAACTCACCCAAGCTGAGTATGACTACTGGGGCCAGGGGACCCAG
GTCACCGTCTCCTCGGCGCACCACAGCGAAGACCCCTCG

JLJ-G3,
SEQ ID NO: 25
QVQLVESGGGLVQSGGSLRLSCAASGSIDSLYHMGWYRQAPGKERELVARVQDGGSTAYK
DSVKGRFTISRDFSRSTMYLQMNSLKPEDTAIYYCAAKSTISTPLSWGQGTQVTVSSEPK
TPKPQ

SEQ ID NO: 26
CAGGTGCAGCTGGTGGAGTCCGGGGGAGGCTTGGTGCAGTCTGGGGGGTCTCTGAGACTC
TCCTGTGCAGCCTCTGGAAGTATCGATAGTCTCTATCATATGGGCTGGTACCGCCAGGCT
CCAGGGAAGGAGCGCGAGTTGGTCGCACGAGTTCAAGATGGGGGTAGCACAGCGTACAAA
GACTCTGTGAAGGGGCGATTCACCATCTCCAGAGACTTTTCCAGGAGCACGATGTATCTG
CAAATGAACAGCCTGAAACCTGAGGACACGGCCATCTATTACTGTGCGGCGAAGAGTACA
ATTAGCACCCCCTTGTCCTGGGGCCAGGGGACCCAGGTCACCGTCTCCTCGGAACCCAAG
ACACCAAAACCACAA

JLK-D7,
SEQ ID NO: 27
QVQLVESGGGLVQAGGSLRLSCAASGFTLGHNQVAWFRQAPGKEREGVACISATGASTHY
ADPVKGRFTVSRDNTKNVVYLQVNSLKPEDTANYCASRFSLMSIDASMCLSAPQYDRWG
QGTQVRISSEPKTPKPQ

SEQ ID NO: 28
CAGGTGCAGCTGGTGGAGTCCGGTGGAGGCTTGGTGCAGGCTGGGGGGTCTCTGAGACTC
TCCTGTGCAGCCTCTGGATTCACTTTGGGACATAATCAAGTAGCCTGGTTCCGCCAGGCC
CCAGGCAAGGAGCGTGAGGGGGTCGCGTGTATTAGCGCCACCGGTGCTAGCACACACTAT
GCAGACCCCGTGAAGGGCCGATTTACCGTCTCCAGAGACAACACCAAGAACGTGGTGTAT
CTGCAAGTGAACAGCCTGAAACCTGAGGACACGGCCAATTATGTCTGTGCAAGCAGATTC
TCCCTTATGTCGATCGATGCGAGCATGTGCCTTTCGGCGCCTCAGTATGACCGCTGGGGC
CAGGGGACCCAGGTCAGAATCTCCTCAGAACCCAAGACACCAAAACCACAA

JLK-F7,
SEQ ID NO: 29
QVQLVETGGLVQPGGSLRLSCTASGFTLGHHRVGWFRQAPGKEREGVACISATGLSSHYS
DEVIGRFTVSRDNDNNVVYLQVNGLKPEDTAVYYCASRFSLNSVDANMCLSEPQYDNWGQ
GTPVRISSEPKTPKPQ

SEQ ID NO: 30
CAGGTGCAGCTGGTGGAGACGGGTGGCTTGGTGCAGCCTGGGGGGTCTCTGAGACTCTCC
TGTACAGCCTCTGGATTCACTTTGGGACACCATCGCGTTGGCTGGTTCCGCCAGGCCCCA
GGAAAGGAGCGTGAGGGGGTCGCGTGTATTAGCGCCACTGGTCTTAGTTCACACTATTCA
GACTTCGTGATCGGCCGATTTACCGTCTCCAGAGACAACGACAACAACGTGGTGTATCTA
CAAGTGAACGGCCTGAAACCTGAGGACACAGCCGTTTATTACTGTGCAAGCAGATTCTCC
CTTAATTCGGTCGATGCGAATATGTGCCTTTCGGAGCCTCAGTATGACAACTGGGGCCAG
GGGACCCCGGTCAGAATCTCCTCAGAACCCAAGACACCAAAACCACAA

JLK-G12,
SEQ ID NO: 31
QVQLVESGGGLVQAGGSLRLSCAASEFRAEHFAVGWFRQAPGKEREGVSCVDASGDSTAY
ADSVKGRFTISRDNNKNVVYLQMDSLEPEDTGDYYCGASYFTVCAKSMRKIEYRYWGQGT
QVTVSSEPKTPKPQ

SEQ ID NO: 32
CAGGTGCAGCTGGTGGAGTCCGGTGGAGGCTTGGTGCAGGCTGGGGGGTCTCTGAGACTC
TCCTGTGCAGCCTCTGAATTCCGTGCGGAGCATTTTGCCGTGGGCTGGTTCCGCCAGGCC
CCAGGGAAGGAGCGTGAGGGGGTCTCATGTGTAGACGCGAGTGGTGATAGTACAGCATAT
GCGGACTCTGTGAAGGGCCGATTCACCATCTCCAGAGACAACAACAAGAACGTAGTGTAT
CTGCAAATGGACAGCCTGGAACCTGAAGACACAGGAGATTATTATTGTGGAGCCTCGTAC

-continued
TTTACTGTCTGCGCCAAGAGCATGCGGAAAATTGAATATAGGTACTGGGGCCAGGGGACC
CAGGTCACCGTCTCCTCAGAACCCAAGACACCAAAACCACAA JLO-C8,
SEQ ID NO: 33
QVQLAESGGGLVQPGGSLRLSCAASGRALNYYVIGWFRQAPGKEREGVSCIASSEAYTDY
ADSVQGRFTISRDKALNTVYLDMKRLKPDDTAVYYCAARLRDPNWCGRNADEYDSWGQGT
QVTVSSEPKTPKPQ SEQ ID NO: 34
CAGGTGCAGCTCGCGGAGTCAGGCGGAGGCTTGGTGCAGCCTGGGGGGTCTCTGAGACTC
TCCTGTGCAGCCTCTGGACGCGCTTTGAATTATTATGTCATAGGCTGGTTCCGCCAGGCC
CCAGGGAAGGAGCGTGAGGGGGTCTCATGTATTGCGAGTAGCGAAGCCTACACAGACTAT
GCAGACTCCGTGCAAGGCCGATTCACCATCTCGAGAGACAAGGCTCTGAATACGGTGTAT
TTGGATATGAAGCGCCTGAAACCTGACGACACAGCCGTTTATTATTGTGCAGCCCGGTTG
CGTGATCCTAATTGGTGCGGGCGGAATGCGGATGAGTATGACTCCTGGGGCCAGGGGACC
CAGGTCACCGTCTCCTCAGAACCCAAGACACCAAAACCACAA JLO-G7,
SEQ ID NO: 35
QVQLVESGGGLVQAGGSLRLSCAASGFPFGSYYMSWVRQAPGKGPEWVSDISNGGIITRY
SDSVKGRFTISRDNAKNILYLQMNSLKPEDTALYFCATGTGRDWSREYRGQGTQVTVSSE
PKTPKPQ SEQ ID NO: 36
CAGGTGCAGCTGGTGGAGTCCGGTGGAGGCTTGGTGCAGGCTGGGGGGTCTCTGAGACTC
TCCTGTGCAGCCTCTGGATTCCCCTTCGGTAGTTACTACATGAGCTGGGTCCGCCAGGCT
CCAGGAAAGGGGCCCGAGTGGGTCTCAGATATTAGCAATGGTGGTATTATTACAAGGTAT
TCAGACTCCGTGAAGGGCCGATTCACCATCTCCCGAGACAACGCCAAGAACATATTGTAT
CTGCAAATGAACAGCCTGAAACCTGAAGACACGGCCCTGTATTTCTGTGCGACAGGGACC
GGTAGAGACTGGAGCAGGGAGTACCGGGGCCAGGGGACCCAGGTCACCGTCTCCTCAGAA
CCCAAGACACCAAAACCACAA JLO-G11,
SEQ ID NO: 37
QVQLAESGGGLVQPGGSLRLSCEASGFHLEHFAVGWFRQAPGKEREGVSCISASGDSTTY
ADSVKGRSTISKDNAKNAVYLQMDSLRPEDTGDYYCAASHFSVCGKNIRKIEYRYWGQGT
PVTVSSEPKTPKPQ SEQ ID NO: 38
CAGGTGCAGCTCGCGGAGTCTGGTGGAGGCTTGGTGCAGCCTGGGGGGTCTCTGAGACTC
TCCTGTGAAGCCTCAGGATTCCATTTGGAGCATTTTGCCGTAGGCTGGTTCCGCCAGGCC
CCAGGGAAGGAGCGTGAGGGGGTCTCATGTATAAGCGCGAGTGGTGATAGTACAACGTAT
GCAGACTCCGTGAAGGGCCGATCCACCATCTCCAAAGACAACGCCAAGAACGCGGTGTAT
CTGCAAATGGACAGCCTGAGACCCGAGGACACAGGCGATTATTACTGTGCAGCCTCGCAC
TTCAGTGTCTGCGGCAAGAACATTCGGAAAATTGAGTATAGGTACTGGGGCCAGGGGACC
CCGGTCACCGTCTCCTCAGAACCCAAGACACCAAAACCACAA JLU-A4,
SEQ ID NO: 39
QVQLVETGGGLVQPGGSLRLSCVVSGLTENSNYMSWVRQAPGKGPELVSYINSEDGSTFY
ADSVKGRFTISRDNNENTLYLQMSSLKPEDTARYYCALGIAGATRGQGTQVTVSSEPKTP
KPQ SEQ ID NO: 40
CAGGTGCAGCTCGTGGAGACCGGGGGAGGCTTGGTGCAGCCGGGGGGGTCTCTGAGACTC
TCCTGTGTAGTGTCTGGATTAACCTTCAATAGCAACTACATGAGTTGGGTCCGCCAGGCT
CCAGGGAAGGGGCCCGAGTTGGTCTCATATATTAATTCTGAAGATGGTAGTACCTTTTAT
GCAGACTCCGTGAAGGGCCGATTCACCATCTCGCGAGACAACAACGAGAATACACTGTAT
CTGCAAATGAGCAGCCTGAAGCCTGAGGACACGGCCCGCTATTACTGTGCACTGGGGATC
GCTGGTGCAACTCGGGGCCAGGGGACCCAGGTCACCGTCTCCTCAGAACCCAAGACACCA
AAACCACAA JLU-D10,
SEQ ID NO: 41
QVQLVESGGGLVQPGGSLRLSCAASGFTLDSYAIGWFRQAPGKEREGVACISASGSGTDY
VDSVKGRFTVSRDQAKSMVFLQMNNMKPEDAAVYYCAADYRPRPLPIQAPCTMTGGNYWG
QGTQVTVSSEPKTPKPQ SEQ ID NO: 42
CAGGTGCAGCTCGTGGAGTCAGGGGGAGGCTTGGTGCAGCCTGGGGGGTCTCTGAGACTC
TCCTGTGCAGCCTCTGGATTCACTTTAGATAGTTATGCAATAGGCTGGTTCCGCCAGGCC
CCAGGGAAGGAGCGTGAGGGGGTCGCATGTATTAGTGCTAGTGGTAGTGGCACGGACTAT
GTAGACTCCGTGAAGGGCCGATTCACCGTCTCCAGAGACCAGGCCAAGAGCATGGTGTTT
CTGCAAATGAACAACATGAAACCTGAGGACGCAGCCGTTTATTACTGTGCAGCAGATTAT
CGGCCGAGGCCCCTGCCGATTCAGGCGCCGTGTACAATGACAGGTGGCAACTACTGGGGC
CAGGGGACCCAGGTCACCGTCTCCTCAGAACCCAAGACACCAAAACCACAA JLU-H6,
SEQ ID NO: 43
QVQLVESGGGLVQPGGSLTLSCVASGSNLDYFAIGWFRQAPGKEREGVSCISTSSDMSKY -continued
```
ADSVKGRFTISRDNTRNTVYLQMNSLEPEDTAVYYCAAKRRRYGLDRDMCLMDSVGMDVW
GKGTLVTVSSAHHSEDPS
```

SEQ ID NO: 44
```
CAGGTGCAGCTGGTGGAGTCGGGGGGAGGCTTGGTGCAGCCTGGGGGGTCTCTGACACTC
TCCTGTGTAGCCTCTGGATCCAATTTGGATTATTTTGCGATAGGCTGGTTCCGCCAGGCC
CCAGGGAAGGAGCGTGAGGGGGTCTCATGTATTAGTACGAGTAGTGACATGTCAAAGTAT
GCAGACTCCGTGAAGGGCCGCTTCACCATCTCCAGAGACAACACCAGGAACACGGTGTAT
CTGCAAATGAACAGCCTGGAACCCGAAGATACGGCCGTTTATTATTGTGCAGCAAAGCGC
CGCCGATATGGTCTCGATCGTGATATGTGTCTTATGGATTCGGTCGGCATGGACGTGTGG
GGCAAAGGGACCCTGGTCACCGTCTCCTCGGCGCACCACAGCGAAGACCCCTCG
```

JLU-H9,
SEQ ID NO: 45
```
QVQLVESGGGLVQPGGSLRLSCAAPGFTLDYYAIGWFRQAPGKEREGVSCIRSRGDRTNY
ADSVKGRFTVSRDNAKNTAYLQMNNLKPEDTGVYFCAAAPRTTVQDLCVTPLLGGADWVS
WGQGTQVTVSSEPKTPKPQ
```

SEQ ID NO: 46
```
CAGGTGCAGCTCGTGGAGTCAGGAGGAGGCTTGGTGCAGCCTGGGGGTCTCTGAGACTC
TCCTGTGCAGCTCCTGGATTCACTTTGGATTATTATGCCATAGGCTGGTTCCGCCAGGCC
CCAGGGAAGGAGCGTGAGGGGGTCTCATGTATTCGTAGTCGGTGATCGGACAAATTAT
GCAGACTCCGTGAAGGGCCGATTCACCGTCTCCAGAGACAACGCCAAGAACACGGCGTAT
CTGCAAATGAACAACCTGAAACCTGAGGACACAGGCGTTTATTTCTGTGCAGCTGCTCCG
AGGACTACTGTTCAGGATTTGTGTGTAACCCCTCTTTTGGGGGTGCTGACTGGGTTTCC
TGGGGCCAGGGGACCCAGGTCACCGTCTCCTCGGAACCCAAGACACCAAAACCACAA
```

JLU-H10,
SEQ ID NO: 47
```
QLQLVESGGGLVQPGGSLRLSCAASGFPLGDYTVGWFRQAPGKEREGVSCISKGSRGLRY
GDSVKGRFTVARDNAKSTVTLQMDSLKPEDTAVYSCAAGPAMENQCHMVDNYFTYWGQGT
QVTVSSAHHSEDPS
```

SEQ ID NO: 48
```
CAGTTGCAGCTGGTGGAGTCTGGCGGAGGCTTGGTGCAGCCTGGGGGGTCTCTGAGACTC
TCCTGTGCAGCCTCTGGATTCCCTTTGGGTGATTATACCGTGGGCTGGTTCCGCCAGGCC
CCAGGGAAGGAGCGTGAGGGGGTCTCATGTATTAGTAAAGGTAGTAGAGGCTTAAGATAC
GGAGACTCCGTGAAGGCCGATTCACCGTTGCCAGAGACAACGCCAAGAGCACGGTAACT
CTGCAAATGGACAGCCTGAAACCGGAGGACACAGCCGTTTATTCTTGTGCTGCAGGGCCG
GCCATGTTCAATCAATGTCATATGGTCGACAATTACTTTACATACTGGGGTCAGGGGACC
CAGGTCACCGTCTCCTCGGCGCACCACAGCGAAGACCCCTCG
```

New BoNT/E-binding VHHs

JLD-B12,
SEQ ID NO: 49
```
QVQLVETGGGLVQAGGSLRLSCAASGRTFSNYAMGWFRQAPGKEREFVAAISWSGAHTYY
ADSVKGRFTISRDNAKSTMYLQMNSLKPEDTAVYYCNADLERYSDFGREVDDYWGQGTQV
TVSSEPKTPKPQ
```

SEQ ID NO: 50
```
CAGGTGCAGCTCGTGGAGACAGGTGGAGGATTGGTGCAGGCTGGGGGGGTCTCTGAGACTC
TCCTGTGCAGCCTCTGGACGCACCTTCAGTAACTATGCCATGGGCTGGTTCCGCCAGGCT
CCAGGGAAGGAGCGTGAGTTTGTCGCAGCTATTAGCTGGAGTGGTGCTCACACATACTAT
GCAGACTCCGTGAAGGGCCGATTCACCATCTCCAGAGACAACGCCAAGAGCACGATGTAT
CTGCAAATGAACAGCCTGAAACCTGAGGACACGGCCGTCTATTACTGTAATGCAGATCTC
GAGCGGTATAGTGACTTCGGTAGGAGGTGGATGACTACTGGGGCCAGGGGACCCAGGTC
ACCGTCTCCTCAGAACCCAAGACACCAAAACCACAA
```

JLE-A12,
SEQ ID NO: 51
```
QVQLVESGGGLVQPGGSLRLSCTASGLTLAKWTINWFRQAPGKEREGISCISSSSGSTYY
ADSVKGRFTISRDNAENTVYLQMS SLKPEDTAVYYCAADS FKGCTFLSSTTHYNNMDYWG
KGTLVTVSSAHHSEDPS
```

SEQ ID NO: 52
```
CAGGTGCAGCTCGTGGAGTCGGGTGGAGGCTTGGTGCAGCCTGGGGGGTCTCTGAGACTC
TCGTGTACAGCCTCTGGATTAACTTTGGCTAAGTGGACCATCAACTGGTTCCGCCAGGCC
CCAGGGAAGGAGCGCGAGGGGATCTCATGTATTAGTAGCAGTAGTGGTAGCACATACTAT
GCAGACTCCGTGAAGGGCCGATTCACCATCTCCAGAGACAACGCCGAAAACACGGTATAT
CTGCAAATGAGCAGCCTGAAACCTGAGGACACGGCCGTTTATTACTGTGCAGCGGATTCT
TTTAAGGGCTGTACGTTCCTCAGTAGTACTACCCATTACAACAACATGGACTACTGGGGC
AAAGGGACCCTGGTCACCGTCTCCTCAGCGCACCACAGCGAAGACCCCTCG
```

JLE-B10,
SEQ ID NO: 53
```
QVQLVESGGGLVQSGGSLRLSCAASRRTASNYAVAWFRQAPGKEREFVAAIGWSDDVTYY
ADSVKGRFTVSRDNAKNTVYLQMNGLEPEDTAVYYCTTNGDRYSRTASSYHYWGQGTQV
TVSSAHHSEDPS
```

-continued

SEQ ID NO: 54
CAGGTGCAGCTCGTGGAGTCGGGTGGGGGATTGGTGCAGTCTGGGGGCTCTCTGAGACTC
TCCTGTGCAGCCTCTAGACGCACCGCCAGTAACTATGCCGTGGCCTGGTTCCGCCAGGCT
CCAGGAAAGGAGCGTGAGTTTGTAGCAGCGATTGGCTGGAGTGATGATGTCACGTATTAC
GCAGACTCCGTGAAGGGCCGATTCACCGTCTCCAGAGACAACGCCAAGAACACGGTGTAT
CTGCAAATGAACGGCCTGGAACCTGAGGACACGGCCGTTTATTACTGTACAACAAATGGT
GATAGATACAGTTACAGGACGGCATCCAGCTATCACTACTGGGGCCAGGGGACCCAGGTC
ACCGTCTCCTCAGCGCACCACAGCGAAGACCCCTCG

JLE-C7,
                                                     SEQ ID NO: 55
QVQLAETGGGSVQTGGSLRLSCAASGLPFRNYAMAWERQAPGKEREFVAAISREGGRTYY
ADFVKGRFTISRDNGRNTIYLEMNSLASEDTAIYYCAGVEGAYTYRTGASYTYWGQGTQV
TVSSEPKTPKPQ

SEQ ID NO: 56
CAGGTGCAGCTCGCGGAGACTGGGGGAGGATCGGTGCAGACTGGGGGCTCTCTGAGGCTC
TCCTGTGCAGCCTCTGGACTGCCCTTCAGAAACTATGCCATGGCCTGGTTCCGCCAGGCT
CCAGGGAAGGAGCGTGAGTTTGTAGCAGCTATTAGTCGGGAAGGCGGGAGGACATACTAT
GCAGACTTCGTGAAGGGCCGATTCACCATCTCCAGAGACAACGGCAGGAACACGATATAT
CTGGAGATGAACAGCCTGGCATCGGAGGATACGGCCATTTATTACTGTGCCGGTGTCGAG
GGTGCTTATACTTATCGTACCGGGGCCTCGTATACTTACTGGGGCCAGGGGACCCAGGTC
ACCGTCTCCTCAGAACCCAAGACACCAAAACCACAA

JLE-E5,
                                                     SEQ ID NO: 57
QVQLVETGGGLVQAGGSLRLSCAASGRSYAMGWFRQGPGKEREFVATISWSSTNTWYADS
VKGRFTISRDNAKNTVYLQMNSLKPEDTAVYYCAASHRESDYPMRSEDGMDYWGKGTLVT
VSSEPKTPKPQ

SEQ ID NO: 58
CAGGTGCAGCTGGTGGAGACGGGGGGAGGATTGGTGCAGGCTGGGGGCTCTCTGAGACTC
TCCTGTGCAGCCTCTGGACGCAGTTATGCCATGGGCTGGTTCCGCCAGGGTCCAGGGAAG
GAGCGTGAGTTTGTAGCCACTATCAGTTGGAGTAGTACTAACACATGGTATGCAGATTCC
GTGAAGGGCCGATTCACCATCTCTAGAGACAACGCCAAGAACACGGTGTATCTGCAAATG
AACAGCCTGAAACCTGAGGACACGGCTGTTTATTACTGTGCAGCGAGCCATCGTTTTAGC
GACTATCCCATGAGGTCAGAGGACGGCATGGACTACTGGGGCAAAGGGACCCTGGTCACC
GTCTCCTCAGAACCCAAGACACCAAAACCACAA

JLE-E9,
                                                     SEQ ID NO: 59
QVQLVETGGGLVQAGGSLRLSCAASGRTFSSYSMGWFRQAPGKEREYVAAVNSNGDSTFY
ADSIKGRFTVSRDAAKNTVYLQMNSLKPEDTALYYCAAVYGRYTYQSPKSYEYWGQGTQV
TVSSEPKTPKPQ

SEQ ID NO: 60
CAGGTGCAGCTGGTGGAGACGGGAGGAGGATTGGTGCAGGCTGGGGGCTCTCTGAGACTC
TCGTGTGCAGCCTCTGGACGCACCTTCAGTAGCTATTCCATGGGCTGGTTCCGCCAGGCT
CCAGGGAAGGAGCGTGAGTATGTAGCAGCAGTTAACTCCAATGGCGACAGTACATTCTAT
GCCGACTCCATTAAGGGCCGATTCACCGTCTCCAGAGACAACGCCAAGAACACAGTCTAT
CTGCAAATGAACAGCCTGAAACCTGAGGACACGGCCCTTTATTACTGTGCAGCTGTCTAC
GGTAGATACACTTACCAGTCCCCAAAATCGTATGAGTACTGGGGCCAGGGGACCCAGGTC
ACCGTCTCCTCAGAACCCAAGACACCAAAACCACAA

JLE-G6,
                                                     SEQ ID NO: 61
QLQLVETGGGLVKPGGSLRLSCVVSGFTEDDYRMAWVRQAPGKELEWVSSIDSWSINTYY
EDSVKGRFTISTDNAKNTLYLQMSSLKPEDTAVYYCAAEDRLGVPTINAHPSKYDYNYWG
QGTQVTVSSEPKTPKPQ

SEQ ID NO: 62
CAGTTGCAGCTCGTGGAGACTGGTGGAGGCTTGGTGAAGCCTGGGGGTTCTCTGAGACTC
TCCTGTGTAGTCTCCGGATTCACTTTTGATGATTATCGCATGGCTTGGGTCCGCCAGGCT
CCAGGGAAGGAGCTGGAGTGGGTGTCCAGTATAGATAGTTGGAGTATCAACACATACTAT
GAAGACTCCGTGAAGGGCCGGTTCACCATCTCCACAGACAACGCCAAGAATACACTGTAT
CTGCAAATGAGCAGCCTGAAACCTGAGGACACGGCCGTGTATTACTGTGCAGCAGAGGAC
CGCTTAGGTGTACCGACTATTAACGCCCACCCTTCAAAATATGATTATAACTACTGGGGG
CAGGGGACCCAGGTCACCGTCTCCTCAGAACCCAAGACACCAAAACCACAA

JLE-H5,
                                                     SEQ ID NO: 63
QVQLVESGGGLVQAGGSLRLSCAASGRTFTSYAMGWFRQAPGKEREFVASISWRGSYTYY
SDSVKGRFTISRDYAENTMYLQMNSLKPEXTGRYYCATLTGDVSVGEYDNRGQGTQVTVS
SAHHSEDPS

SEQ ID NO: 64
CAGGTGCAGCTGGTGGAGTCCGGTGGAGGCTTGGTGCAGGCTGGGGGTCTCTGAGACTC
TCCTGTGCAGCCTCTGGACGCACCTTCACTAGTTATGCCATGGGCTGGTTCCGCCAGGCT
CCAGGGAAGGAGCGTGAGTTTGTAGCGTCTATTAGCTGGCGCGGTAGTTACACATACTAT
TCAGACTCCGTGAAGGGCCGATTCACCATCTCCAGAGATTACGCCGAGAACACGATGTAT

-continued
```
CTGCAAATGAACAGCCTGAAACCTGAGGNNACGGGCAGATATTACTGTGCAACCTTAACC
GGCGACGTGAGTGTCGGCGAGTATGACAACCGGGGCCAGGGGACCCAGGTCACTGTCTCC
TCAGCGCACCACAGCGAAGACCCCTCG
```

JLF-H5,

SEQ ID NO: 65
```
QVQLVESGGGSVQPGGSLRLSCVASGFTFTNYAMAWVRQVSGKGLEGVAAISSEGFIYIP
DSVKGRFTISRDNAKNTVYLQMDNLQSEDTAIYHCAAVDWKRVAAMNSYNMDYWGKGTPV
TVSAEPKTPKPQ
```

SEQ ID NO: 66
```
CAGGTGCAGCTGGTGGAGTCGGGGGGAGGCTCGGTGCAGCCTGGGGGTCTCTGAGACTC
TCCTGTGTAGCCTCTGGATTCACCTTCACTAATTACGCGATGGCCTGGGTCCGCCAGGTA
TCAGGGAAGGGGCTCGAGGGTGTGGCCGCTATTAGTAGTGAGGGTTTCATATATATCCCA
GACTCAGTGAAGGGCCGATTCACCATCTCCAGAGACAACGCCAAGAACACGGTGTATCTA
CAAATGGACAACCTCCAGTCTGAGGATACGGCCATATATCACTGTGCGGCAGTTGATTGG
AAACGGGTCGCCGCGATGAACAGCTACAACATGGACTACTGGGGAAAAGGGACCCCGGTC
ACCGTCTCCGCAGAACCCAAGACACCAAAACCACAA
```

JLG-G8,

SEQ ID NO: 67
```
QLQLVESGGGLVQAGGSLRLSCAASGRTESSYAMGWFRQAPGKEREHVAAISWSGGYTYY
ANSVKGRFTISRDNAKNTVYLQMNSLKPEDTAVYYCNGVQDHSDSLQNWGQGTQVTVSSE
PKTPKPQ
```

SEQ ID NO: 68
```
CAGTTGCAGCTGGTGGAGTCGGGCGGAGGATTGGTGCAGGCTGGGGGGTCTCTGAGACTC
TCCTGTGCAGCCTCTGGACGCACCTTCAGTAGCTATGCCATGGGCTGGTTCCGCCAGGCT
CCAGGGAAGGAACGTGAGCATGTCGCAGCTATTAGCTGGAGTGGTGGTTACACATACTAT
GCAAACTCCGTGAAGGGCCGATTCACCATCTCCAGAGACAACGCCAAGAACACGGTGTAT
CTGCAAATGAACAGCCTGAAACCTGAGGACACGGCCGTCTATTACTGTAATGGAGTTCAG
GACCATAGCGACTCCCTTCAGAACTGGGGCCAGGGGACCCAGGTCACCGTCTCCTCAGAA
CCCAAGACACCAAAACCACAA
```

JLG-G12,

SEQ ID NO: 69
```
QLQLVETGGGLVQAGGSLRLSCAASGRTESSYAVGWFRQAPGKEREFVAAISWSGSYAYY
ADSVKGRFTISRDNAKNTVYLQMNSLKPEDTAVYYCNGDLEGYSNHETGDYWGQGTQVTV
SSEPKTPKPQ
```

SEQ ID NO: 70
```
CAGTTGCAGCTGGTGGAGACGGGAGGAGGATTGGTGCAGGCTGGGGGGTCTCTGAGACTC
TCCTGTGCAGCCTCTGGACGCACCTTCAGTAGTTATGCCGTGGGCTGGTTCCGCCAGGCT
CCAGGGAAGGAGCGTGAGTTTGTCGCAGCTATTAGCTGGAGTGGTAGTTACGCATACTAT
GCAGACTCCGTGAAGGGCCGATTCACCATCTCCAGAGACAACGCCAAGAACACGGTGTAT
CTGCAAATGAACAGCCTGAAACCTGAGGACACGGCCGTCTATTACTGTAATGGAGATCTT
GAGGGTTATAGCAACCATGAAACCGGGACTACTGGGGCCAGGGGACCCAGGTCACCGTC
TCCTCAGAACCCAAGACACCAAAACCACAA
```

JLH-H4,

SEQ ID NO: 71
```
QLQLAESGGGLVQAGGSLRLSCAASGRTFSSYAMGWFRQAPGKEREFVAAISWIGGYTYY
ASSVKGRFTISRDNAKNTMYLQMNSLKPEDTAVYYCNADLESYSEYPESYYWGQGTQVTV
SSEPKTPKPQ
```

SEQ ID NO: 72
```
CAGTTGCAGCTGGCGGAGTCGGGAGGAGGATTGGTGCAGGCTGGGGGGTCTCTGAGACTC
TCCTGTGCAGCCTCTGGACGCACCTTCAGTAGCTATGCCATGGGCTGGTTCCGCCAGGCT
CCAGGGAAGGAGCGTGAGTTTGTCGCAGCTATTAGCTGGAGTGGTGGTTACACATACTAT
GCAAGCTCCGTGAAGGGCCGATTCACCATCTCCAGAGACAATGCCAAAAACACGATGTAT
CTGCAAATGAACAGCCTGAAACCGGAGGACACGGCCGTCTATTACTGTAATGCAGATTTA
GAATCCTATAGCGAGTATCCCGAGAGCTACTACTGGGGCCAGGGGACCCAGGTCACCGTC
TCCTCAGAACCCAAGACACCAAAACCACAA
```

Appendix C

Included in Appendix C are the following: Amino acid and nucleic acid sequences of 2 anthrax edema factor (EF)-binding VHHs; 7 anthrax lethal factor (LF)-binding VHHs; and 6 VHHs binding both anthrax EF and LF (EF/LF cross-specific)

New Anthrax EF-Binding VHHs

JMN-E2,

SEQ ID NO: 73
```
QVQLAESGGGLVQAGGSLTLSCAASGLNFDKYAIGWYRQAPGKEREGVSCISKYYNH
RMYSDSVKGRFTVSSNYAKNTVYLQMTNLKPEDTAVYYCAAGCIDPEDWGQGTQVTV
SSEPKTPKPQ
```

-continued

```
                                               SEQ ID NO: 74
CAGGTGCAGCTGGCGGAGTCGGGGGGAGGCTTGGTGCAGGCTGGGGGGTCTCTGACA
CTCTCCTGTGCAGCCTCTGGCCTCAATTTCGATAAATATGCCATAGGCTGGTACCGC
CAGGCCCCAGGGAAGAGCGTGAGGGGGTTTCATGTATTAGTAAGTATTACAATCAT
CGGATGTATAGTGACTCCGTGAAGGGCCGATTCACCGTCTCCAGTAACTATGCCAAG
AACACGGTGTACCTGCAAATGACCAATCTGAAACCGGAGGATACGGCCGTTTATTAC
TGTGCGGCAGGGTGTATTGACCCGGAAGATTGGGGCCAGGGGACCCAGGTCACCGTC
TCCTCAGAACCCAAGACACCAAAACCACAA

JMN-F3,
                                               SEQ ID NO: 75
QVQLVETGGGQVQTGGSLRLSCAASEPTFTPKVVGWFRQAPVKERDEVATITIRTGR
TLYADSVKGRFTISGDGANNTVYLQMNGLKPEDTAVYYCAASLPLAIPPTQASAYEY
WGLGTQVTVSSEPKTPKPQ

SEQ ID NO: 76
CAGGTGCAGCTGGTGGAGACCGGGGGAGGCCAGGTGCAGACTGGGGGATCTCTGAGA
CTCTCTTGCGCAGCCTCTGAACCCACCTTCACTCCGAAAGTTGTGGGCTGGTTCCGC
CAGGCTCCAGTGAAGGAGCGTGACTTTGTAGCAACTATAACAATCCGTACCGGTCGC
ACACTCTATGCAGATTCCGTGAAGGGCCGATTCACCATCTCCGGAGACGGCGCCAAC
AATACGGTGTATCTACAAATGAACGGCCTGAAACCTGAGGACACGGCCGTTTATTAC
TGCGCCGCATCTCTTCCGCTAGCAATACCACCGACGCAGGCTTCGGCATATGAATAC
TGGGGCCTGGGGACCCAGGTCACCGTCTCCTCAGAACCCAAGACACCAAAACCACAA
```

New Anthrax LF-Binding VHHs

JMO-A2,
                                               SEQ ID NO: 77
QVQLVETGGGLVQPGGSLRLSCSVSGLHERFANMGWFRQAPGKQRELVAYITTGDNT
NYVDHVKGRFTISRDNAKNTVYLQMNSLKPEDTAVYYCNIVNALGEENPRNDWGQGT
QVTVSSEPKTPKPQ

```
                                               SEQ ID NO: 78
CAGGTGCAGCTGGTGGAGACGGGGGGAGGCTTGGTGCAGCCTGGGGGGTCTCTGAGA
CTCTCCTGTTCAGTCTCTGGCCTCCACTTCAGGTTCGCGAACATGGGATGGTTTCGC
CAGGCTCCAGGGAAGCAGCGCGAGTTGGTCGCATATATTACTACTGGTGATAACACT
AACTATGTAGACCACGTGAAGGGCCGATTCACCATCTCCAGAGACAACGCCAAGAAC
ACGGTGTATCTGCAAATGAACAGCCTGAAACCTGAAGACACGGCCGTCTACTACTGT
AATATAGTCAATGCGCTGGGGGAGTTCAATCCCCGAAACGACTGGGGCCAGGGGACC
CAGGTCACCGTCTCCTCAGAACCCAAGACACCAAAACCACAA
```

JMO-B3,
                                               SEQ ID NO: 79
QVQLVETGGGWVQAGGSLRLSCAASGRAASGNAMAWFRQAPGKEREFVALISWSGGR
PYYANSVKGRFAISRDNATNTVYLQMNRLKPEDTAVYYCAASPTIAILPTPYDYWGQ
GTQVTVSSEPKTPKPQ

```
                                               SEQ ID NO: 80
CAGGTGCAGCTGGTGGAGACGGGTGGGGGTGGGTACAGGCTGGGGGCTCTCTGAGA
CTCTCCTGTGCAGCCTCTGGACGCGCCGCCAGTGGAAATGCCATGGCCTGGTTCCGC
CAGGCTCCAGGAAAGGAGCGTGAGTTTGTAGCATTGATTAGTTGGAGTGGTGGTCGC
CCATACTATGCAAACTCCGTGAAGGGCCGATTCGCCATCTCCAGAGACAACGCCACG
AATACGGTGTATCTGCAAATGAACAGACTGAAACCTGAGGACACGGCCGTTTATTAC
TGTGCAGCGTCGCCTACCATAGCGATACTACCTACTCCGTATGACTACTGGGGCCAG
GGGACCCAGGTCACCGTCTCCTCAGAACCCAAGACACCAAAACCACAA
```

JMO-B9,
                                               SEQ ID NO: 81
QVQLVETGGGLVQAGASLRLSCAASGRTFSTDHMGWFRQAPQKEREFVAAINAWSGL
SIYYADSVKGRFTISRDNDKKTAYLQMNSLKPEDTAVYYCAAKEMGRGWVPQSSDDY
DAWGQGTQVTVSSEPKTPKPQ

```
                                               SEQ ID NO: 82
CAGGTGCAGCTGGTGGAGACGGGGGGAGGATTGGTGCAGGCTGGGGCCTCTCTGAGA
CTCTCCTGTGCAGCCTCTGGACGCACCTTCAGTACCGATCACATGGGCTGGTTCCGC
CAGGCTCCACAGAAGGAGCGTGAGTTTGTGGCAGCAATAAATGCATGGAGTGGACTC
AGCATTTACTATGCAGACTCCGTGAAGGGCCGATTCACCATCTCCAGAGACAACGAC
AAGAAAACGGCATATCTACAAATGAACAGCCTGAAACCTGAGGACACGGCCGTTTAT
TACTGTGCAGCCAAGGAGATGGGTAGGGGTTGGGTGCCACAGAGCTCAGACGACTAT
GACGCCTGGGGCCAGGGGACCCAGGTCACCGTCTCCTCAGAACCCAAGACACCAAAA
CCACAA
```

JMO-C1,
                                               SEQ ID NO: 83
QVQLVETGGGLVQAGGSLRLSCAVSGRTESSYAMAWFRQAPGKERDFVAAISWSGGA
PHYEDSVKGRFTISRDNAKNMVYLQMNSLKPDDTAVYYCAAAKAGYYSGSYYVGGGM
YDYWGQGTQVTVSSEPKTPKPQ

```
                                                SEQ ID NO: 84
CAGGTGCAGCTGGTGGAGACTGGAGGAGGATTGGTGCAGGCTGGGGGCTCTCTGAGA
CTCTCCTGTGCAGTCTCTGGACGCACCTTCAGTAGCTATGCCATGGCCTGGTTCCGC
CAGGCTCCAGGGAAGGAGCGTGATTTTGTAGCAGCTATTAGCTGGAGTGGTGGTGCC
CCACACTATGAAGACTCCGTGAAGGGCCGATTCACCATCTCCAGAGACAACGCCAAG
AACATGGTATATCTCCAAATGAACAGCCTGAAACCTGACGACACGGCCGTTTACTAC
TGTGCAGCAGCGAAAGCAGGATACTATAGTGGTAGTTACTACGTGGGGGGGGTATG
TATGACTACTGGGGCCAGGGGACCCAGGTCACCGTCTCCTCAGAACCCAAGACACCA
AAACCACAA
```

JMO-C10,
```
                                                SEQ ID NO: 85
QVQLVETGGLVQAGGSLRLSCAASGSIGRVDNMGWYRQTPGKERERVAIITGGGTAI
YADTVKGRFTVSRDNAKNTIYLQMNSVKPEDTAVYFCNADISRSIESIVYRSYWGQG
TQVTVSSEPKTPKPQ
```
```
                                                SEQ ID NO: 86
CAGGTGCAGCTGGTGGAGACAGGAGGCTTGGTGCAGGCTGGGGGGTCTCTGAGACTC
TCCTGTGCAGCCTCCGGAAGCATCGGCAGGGTCGATAACATGGGCTGGTACCGCCAA
ACTCCAGGGAAGAGCGCGAGCGGGTCGCAATCATTACTGGAGGCGGTACCGCGATC
TATGCAGACACCGTGAAGGGCCGATTCACCGTCTCCAGAGACAACGCCAAGAACACA
ATATATCTACAAATGAACAGCGTGAAACCTGAGGACACAGCCGTCTATTTCTGTAAT
GCCGACATCAGTCGTAGTATTGAGTCCATCGTCTATCGTTCCTACTGGGGCCAGGGG
ACCCAGGTCACCGTCTCCTCAGAACCCAAGACACCAAAACCACAA
```

JMO-F4,
```
                                                SEQ ID NO: 87
QVQLVETGGGLVQPGGSLRLSCAASGNIFSINAMGWYRQAPGKQRELVAAISNSGST
NYEDSVKGRFTVSRDNAKNTVYLQMNSLKPEDTAVYYCNAFDLVAGTRLGSWGQGTQ
VTVSSEPKTPKPQ
```
```
                                                SEQ ID NO: 88
CAGGTGCAGCTGGTGGAGACGGGGGGAGGCTTGGTGCAGCCTGGGGGGTCTCTGAGA
CTCTCCTGTGCAGCCTCTGGAAACATCTTCAGTATCAATGCCATGGGCTGGTACCGC
CAGGCTCCAGGGAAGCAGCGCGAGTTGGTCGCAGCTATTAGTAATAGTGGTAGCACA
AACTATGAAGACTCCGTGAAGGGCCGATTCACCGTCTCCAGAGACAACGCCAAGAAC
ACGGTGTATCTGCAAATGAACAGCCTGAAACCTGAGGACACGGCCGTCTATTACTGT
AATGCCTTCGATTTAGTAGCTGGTACTAGGCTGGGGTCCTGGGGCCAGGGGACCCAG
GTCACCGTCTCCTCGGAACCCAAGACACCAAAACCACAA
```

JMO-F12,
```
                                                SEQ ID NO: 89
QVQLVESGGGLVQPGGSLRLSCAASEFTLEHAAVGWFRQAPGKEREGVSCISSRDSN
TYYADSVKGRFTISRDNAENTVYLQMNSLKPEDTAVYYCATDVPCWDGSNWSLGHEY
DYWGQGTQVTVSSEPKTPKPQ
```
```
                                                SEQ ID NO: 90
CAGGTGCAGCTGGTGGAGTCGGGGGGAGGCTTGGTGCAGCCTGGGGGGTCTCTGAGA
CTCTCCTGTGCAGCCTCTGAATTCACTTTGGAACATGCCGCCGTAGGCTGGTTCCGC
CAGGCCCCAGGGAAGGAGCGCGAGGGGGTCTCTTGTATTAGTAGTCGTGATAGTAAC
ACATACTATGCAGACTCCGTGAAGGGCCGATTCACCATCTCCAGAGACAATGCCGAA
AACACGGTATATCTGCAAATGAACAGCCTGAAACCTGAGGACACGGCCGTTTATTAC
TGTGCGACAGATGTCCCCTGCTGGGACGGTAGTAACTGGTCCCTCGGTCATGAGTAT
GACTACTGGGGCCAGGGGACCCAGGTCACCGTCTCCTCAGAACCCAAGACACCAAAA
CCACAA
```

New Anthrax EF/LF-Binding (Cross-Specific) VHHs

JMO-G1,
```
                                                SEQ ID NO: 91
QVQLVETGGGLVQPGGSLRLSCAASGSISSINAMGWYRQAPGKQRELVAAITIRGNT
VYGDSVKGRFTVSRDNAKNTVYLQMNSLKPEDTAVYYCNAKSTPSLYAAGYGVDYWG
EGTLVTVSSEPKTPKPQ
```
```
                                                SEQ ID NO: 92
CAGGTGCAGCTGGTGGAGACGGGGGGAGGCTTGGTGCAGCCTGGGGGGTCTCTGAGA
CTCTCCTGTGCAGCCTCTGGAAGCATCTCCAGTATCAATGCCATGGGCTGGTACCGC
CAGGCTCCAGGGAAGCAGCGCGAGTTGGTCGCGGCTATTACTATTCGTGGTAACACA
GTCTATGGAGACTCCGTGAAGGGCCGATTCACCGTCTCCAGAGACAACGCCAAGAAC
ACGGTGTATCTGCAAATGAACAGCCTGAAACCTGAGGACACGGCCGTCTATTACTGT
AATGCCAAGTCGACCCCGAGCTTGTACGCCGCCGGCTACGGCGTGGACTACTGGGGC
GAAGGGACCCTAGTCACCGTCTCCTCAGAACCCAAGACACCAAAACCACAA
```

JMO-C9,
```
                                                SEQ ID NO: 93
QVQLVETGGGLVQAGGSLRLSCAASGNISSINAMAWYRQAPGQQRELVAGITSGGRT
QYTDSVKGRFTISRDNAKNTVYLQMESLKPEDTAVYYCNAKSPPSTWATGGGMNYWG
KGTLVTVSSEPKTPKPQ
```

-continued

```
                                           SEQ ID NO: 94
CAGGTGCAGCTGGTGGAGACGGGGGGAGGCTTGGTGCAGGCTGGGGGTCTCTGAGA
CTCTCCTGTGCAGCCTCTGGGAACATCTCCAGTATCAATGCCATGGCCTGGTACCGC
CAGGCTCCAGGGCAGCAGCGCGAGCTGGTCGCAGGGATTACTAGTGGTGGCAGGACA
CAATATACAGACTCCGTGAAGGGCCGATTCACCATCTCCAGAGACAACGCCAAGAAC
ACGGTGTATCTGCAAATGGAGAGTCTGAAACCTGAGGACACAGCCGTCTATTACTGT
AATGCAAAAGCCCTCCCAGTACCTGGGCCACGGGGGGGGCATGAACTACTGGGGC
AAAGGGACCCTGGTCACCGTCTCCTCAGAACCCAAGACACCAAAACCACAA

JMN-D10,
                                           SEQ ID NO: 95
QVQLVETGGALVQAGGSLRLSCAASETSSVSLSWMGWYRQAPGKERELVAGINRDRP
KYKESVKGRFTISRDNAQNTVYLQMNSLKPEDTAVYYCNTVPPRGDYWGQGTQVTVS
SEPKTPKPQ

SEQ ID NO: 96
CAGGTGCAGCTGGTGGAGACAGGAGGAGCCTTGGTGCAGGCGGGGGGTCTCTGAGA
CTCTCCTGTGCAGCCTCTGAGACATCTTCAGTATCGCTATCATGGATGGGCTGGTAC
CGCCAGGCTCCTGGGAAGGAGCGCGAGTTGGTCGCAGGCATTAATCGTGATAGGCCA
AAGTATAAAGAGTCCGTGAAGGGCCGATTCACCATCTCCAGAGACAACGCCCAGAAT
ACGGTGTATCTGCAAATGAACAGCCTGAAACCTGAGGACACAGCCGTCTATTACTGT
AATACGGTTCCACCACGCGGCGACTACTGGGGCCAGGGGACCCAGGTCACCGTCTCC
TCAGAACCCAAGACACCAAAACCACAA

JMN-E12,
                                           SEQ ID NO: 97
QVQLVESGGGLVQPGGSLRVSCVASGNISSVAAMAWYRQRPEKRRELVAVITNSGGT
AYTDSVRGRFTISRDNVKSTVYLQMNNLKPEDTAVYYCNARGLDAGSGRIDYWGQGT
QVTVSSEPKTPKPQ

SEQ ID NO: 98
CAGGTGCAGCTGGTGGAGTCCGGTGGAGGCTTGGTGCAGCCTGGGGGTCTCTGAGA
GTCTCCTGTGTAGCCTCTGGAAACATCTCCAGTGTCGCTGCCATGGCCTGGTACCGC
CAGAGACCAGAGAAGCGCCGCGAATTGGTCGCAGTCATTACTAACAGCGGTGGCACA
GCCTATACAGACTCCGTGAGGGGCCGATTCACCATCTCCAGAGACAATGTCAAGTCA
ACGGTGTATCTACAAATGAATAACCTGAAACCTGAGGACACAGCCGTGTATTACTGT
AATGCGAGGGGGTTAGACGCCGGGTCAGGGCGCATTGACTACTGGGGCCAGGGAACC
CAGGTCACCGTCTCCTCAGAACCCAAGACACCAAAACCACAA

JMN-F1,
                                           SEQ ID NO: 99
QVQLVESGGGLAQTGGSLNLSCAASGPTFSGYGMGWFRQAPGKEREFLAVIRWSVGN
TLYAESVKGRFTISRDKVKNTGYLQIDNLKPEDTAVYYCAAGAYVTTRSRDYAYWGQ
GTQVTVSSEPKTPKPQ

SEQ ID NO: 100
CAGGTGCAGCTGGTGGAGTCGGGGGGAGGATTGGCGCAGACTGGGGGCTCTCTGAAC
CTCTCCTGTGCAGCCTCTGGACCGACTTTCAGCGGCTATGGTATGGGCTGGTTCCGC
CAGGCTCCAGGGAAGGAGCGTGAATTTCTAGCGGTAATTCGCTGGAGTGTAGGTAAT
ACATTGTATGCAGAGTCCGTCAAGGGCCGATTCACCATCTCCAGAGACAAGGTCAAG
AACACGGGGTATCTGCAAATAGACAACCTGAAACCCGAGGACACGGCCGTTTATTAC
TGTGCAGCGGGGCGTACGTAACTACGAGGTCCCGCGACTATGCCTACTGGGGCCAG
GGGACCCAGGTCACCGTCTCCTCAGAACCCAAGACACCAAAACCACAA

JLO-A4,
                                           SEQ ID NO: 101
QVQLVETGGRQVQTGDSLNLSCAASEHTFSPKVMGWERQAPGKGREFVATITIRGGR
TLYADSVKGRFAISKDGAKNTVYLQMNSLKPEDTAVYYCAASRELAIPPTQPSAYDH
WGQGTQVTVSSAHHSEDPS

SEQ ID NO: 102
CAGGTGCAGCTCGTGGAGACCGGCGGACGTCAGGTGCAGACTGGGGACTCTCTGAAC
CTCTCTTGCGCAGCTTCTGAACACACCTTCAGTCCTAAAGTTATGGGGTGGTTCCGC
CAGGCTCCAGGCAAGGGGCGTGAGTTTGTAGCAACTATCACAATCCGTGGCGGTCGC
ACACTCTATGCAGATTCCGTGAAGGGCCGATTTGCCATCTCCAAAGACGGCGCCAAG
AATACGGTGTATCTGCAAATGAACAGTCTGAAACCTGAGGACACGGCCGTTTATTAC
TGTGCAGCAAGTCGTGAGCTAGCGATACCACCGACGCAGCCTTCGGCATACGACCAC
TGGGGCCAGGGGACCCAGGTCACCGTCTCCTCAGCGCACCACAGCGAAGACCCCTCG
```

Appendix D
Included in Appendix D are 2 anthrax PA-binding VNAs
New Anthrax PA-Binding VNAs

```
VNA1-PA (JKD-11)
                                           SEQ ID NO: 103
QVQLAESGGGLVQPGGSLGLSCVVASERSINNYGMGWYRQAPGKQRELVAQISSGGT
TNYADSVEGRFTISRDNVKKMVHLQVNSLKPEDTAVYYCNSLLRTFSWGQGTQVTVS
SEPKTPKPQAIAGGGGSGGGGSGGGGSLQGQVQLVESGGGLVQPGGSLSVSCAASGS
```

-continued
IARPGAMAWYRQAPGKERELVASITPGGLTNYADSVTGRFTISRDNAKRTVYLQMNS
LQPEDTAVYYCHARIIPLGLGSEYRDHWGQGTQVTVSSAHHSEDPS SEQ ID NO: 104
CAGGTGCAGCTGGCGGAGTCGGGCGGAGGCTTGGTGCAGCCTGGGGGGTCTCTGGGA
CTCTCCTGTGTAGTCGCCTCTGAAAGAAGCATCAATAATTATGGCATGGGCTGGTAC
CGCCAGGCTCCAGGGAAGCAGCGCGAGTTGGTCGCGCAAATTAGTAGTGGTGGTACC
ACAAATTATGCAGACTCCGTAGAGGGCCGATTCACCATCTCCAGAGACAACGTCAAG
AAAATGGTGCATCTTCAAGTGAACAGCCTGAAACCTGAGGACACGGCCGTCTATTAC
TGTAATTCGCTACTCCGAACTTTTTCCTGGGGCCAGGGGACCCAGGTCACCGTCTCC
TCGGAACCCAAGACACCAAAACCACAAGCGATCGCTGGTGGAGGCGGTTCAGGCGGA
GGTGGCTCTGGCGGTGGCGGTTCCCTGCAGGGTCAGTGCAGCTSGYGGAGTCCGGG
GGCGGCTTGGTGCAGCCCGGGGGGTCTCTGAGTGTCTCCTGTGCAGCCTCTGGAAGC
ATCGCAAGACCAGGTGCCATGGCCTGGTACCGCCAGGCTCCAGGGAAGGAGCGCGAG
TTGGTCGCGTCTATTACGCCTGGTGGTCTTACAAACTATGCGGACTCCGTGACGGGC
CGATTCACCATTTCCAGAGACAACGCCAAGAGGACGGTGTATCTGCAGATGAACAGC
CTCCAACCCGAGGACACGGCCGTCTATTACTGTCATGCACGAATAATTCCCCTAGGA
CTTGGGTCCGAATACAGGGACCACTGGGGCCAGGGGACTCAGGTCACCGTCTCCTCA
GCGCACCACAGCGAAGACCCCTCG VNA2-PA (JKU-1)
SEQ ID NO: 105
QVQLAESGGGLVQPGGSLGLSCVVASERSINNYGMGWYRQAPGKQRELVAQISSGGT
TNYADSVEGRETISRDNVKKMVHLQVNSLKPEDTAVYYCNSLLRTFSWGQGTQVTVS
SEPKTPKPQAIAGGGGGGGSGGGGSLQGQVQLAESGGGGLVQAGGSLRLSCAASG
RTFSGYAMGWFRQAPGKEREFVADISWSGHNTYYGDSVKGRFTISRDTAKNTVYLQM
NSLKPEDTAVYYCAAEGARTHLSDSYYFPGLWAEPPVGYWGQGTQVTVSSEPKTPKP SEQ ID NO: 106
CAGGTGCAGCTGGCGGAGTCGGGCGGAGGCTTGGTGCAGCCTGGGGGGTCTCTGGGA
CTCTCCTGTGTAGTCGCCTCTGAAAGAAGCATCAATAATTATGGCATGGGCTGGTAC
CGCCAGGCTCCAGGGAAGCAGCGCGAGTTGGTCGCGCAAATTAGTAGTGGTGGTACC
ACAAATTATGCAGACTCCGTAGAGGGCCGATTCACCATCTCCAGAGACAACGTCAAG
AAAATGGTGCATCTTCAAGTGAACAGCCTGAAACCTGAGGACACGGCCGTCTATTAC
TGTAATTCGCTACTCCGAACTTTTTCCTGGGGCCAGGGGACCCAGGTCACCGTCTCC
TCGGAACCCAAGACACCAAAACCACAAGCGATCGCTGGTGGAGGCGGTTCAGGCGGA
GGTGGCTCTGGCGGTGGCGGTTCCCTGCAGGGTCAGTGCAGCTCGGGAGTCGGGT
GGGGGAGGACTGGTGCAGGCTGGGGGCTCTCTGAGACTCTCCTGTGCAGCCTCTGGA
CGCACCTTCAGTGGCTATGCCATGGGCTGGTTCCGCCAGGCTCCGGGGAAGGAGCGT
GAGTTTGTAGCCGATATTAGCTGGAGTGGTCATAACACGTACTATGGAGACTCCGTG
AAGGGCCGATTCACCATCTCCAGAGACACCGCCAAGAACACGGTGTATCTGCAAATG
AACAGCCTGAAACCTGAGGACACGGCCGTTTATTACTGTGCAGCGGAGGGGCCCGT
ACACACCTTAGTGATAGTTACTACTTCCCGGGCCTCTGGGCCGAACCCCCCGTGGGC
TACTGGGGCCAGGGGACCCAGGTCACTGTCTCCTCAGAACCCAAGACACCAAAACCA
CAA

Appendix E

Included in Appendix E are 10 BoNT/B-protease light chain (BLc) binding VHHs; 2 BoNT/E-protease light chain (ELc) binding VHHs; 4 BoNT/B-binding VHH heterodimers; and 3 BoNT/E-binding VHH heterodimers.

New BoNT/B-Protease Light Chain (BLc) Binding VHHs

JLS-G8,
SEQ ID NO: 107
QVQLVESGGGSVQAGGSLRLTCTGSGRSFALYYMAWFRQAPGKEREFVAAISHNSLSAIV
ADSLKGRFTISRDNARNQVVLQMNSLKPEDTAVYYCAADFSPSTYNTNYYRTGSYQYWGQ
GTQVTVSSEPKTPKPQ

SEQ ID NO: 108
CAGGTGCAGCTGGTGGAGTCGGGGGGAGGATCGGTGCAGGCTGGGGGCTCTCTGAGACTC
ACCTGTACAGGCTCTGGACGCAGTTTCGCGCTCTATTACATGGCCTGGTTCCGCCAGGCT
CCAGGGAAGGAGCGTGAGTTTGTAGCAGCTATCAGCCACAATTCGTTAAGCGCAATCGTT
GCAGACTCCCTAAAGGGCCGATTCACCATCTCCAGAGACAACGCCAGAAACCAGGTGGTT
CTACAAATGAACAGCCTGAAACCTGAGGACACGGCCGTTTATTACTGTGCAGCAGACTTT
TCGCCCTCGACCTATAATACAAATTACTACCGCACCGGTTCGTATCAGTATTGGGGCCAG
GGGACCCAGGTCACCGTCTCCTCAGAACCCAAGACACCAAAACCACAA

JND-A12,
SEQ ID NO: 109
QVQLVETGGGLVQAGGSLGLSCAASGLSFNWYDVGWFRQAPGKEREFVASRSSGGGSTYY
GDSVKGRESISTDNAKNTAYLQMNSLKPEDTAVYYCAADWTGRAGESVGYYRPDEYDYWG
QGTQVTVSEEPKTPKPQ

SEQ ID NO: 110
CAGGTGCAGCTGGTGGAGACGGGAGGAGGATTGGTGCAGGCTGGGGGCTCTCTGGGACTC
TCCTGTGCAGCCTCTGGACTGTCCTTTAATTGGTATGACGTGGGCTGGTTCCGCCAGGCT
CCAGGGAAGGAGCGTGAGTTTGTAGCGTCTCGTAGCTCGGGTGGTGGTAGTACATATTAT
GGAGACTCCGTGAAGGGCCGATTCAGCATCTCCACAGACAATGCCAAGAACACGGCGTAT
CTGCAAATGAACAGCCTAAAACCTGAGGACACGGCCGTTTACTACTGTGCAGCAGATTGG
ACAGGCCGCGCAGGCTTCAGTGTTGGTTACTACCGGCCCGATGAGTATGACTACTGGGGC

-continued
CAGGGGACCCAGGTCACCGTCTCCGAAGAACCCAAGACACCAAAACCACAA

JND-B4,
SEQ ID NO: 111
QVQLVETGGGLVQPGGSLRLSCVASGFTLDSYAIGWFRQAPGKEREGVSCMSSGDGSTYY
TNSVKGRFTISRDNAQNTVYLQMNSLKPEDTAVYYCAADGFDYCSAYVPGRGMNYSGKGT
LVTVSSEPKTPKPQ

SEQ ID NO: 112
CAGGTGCAGCTGGTGGAGACGGGGGGAGGCTTGGTGCAGCCTGGGGGGTCTCTGAGACTC
TCCTGTGTAGCCTCTGGATTCACTTTGGATTCATATGCCATAGGCTGGTTCCGCCAGGCC
CCAGGGAAGGAGCGTGAGGGGGTCTCATGTATGAGTAGTGGTGATGGTAGCACATACTAT
ACAAACTCCGTGAAGGGCCGATTCACCATCTCCAGAGACAACGCCCAGAACACGGTGTAT
CTGCAAATGAACAGCCTGAAACCTGAGGACACAGCCGTTTATTACTGTGCAGCAGATGGG
TTTGACTATTGTTCAGCTTATGTGCCCGGGAGAGGCATGAACTACTCGGGCAAAGGGACC
CTGGTCACCGTCTCCTCAGAACCCAAGACACCAAAACCACAA

JND-C7,
SEQ ID NO: 113
QVQLVETGGGLVQPGGSLRLSCAGSGFTLDNYAVGWFRQAPGKEREGVSCISSSDDNTDY
SDSVKGRFTISRDNAKDTVYLQMNSLKPEDTAIYYCAAESPTFGFSCTVATDPYDYWGQG
TQVTVSSEPKTPKPQ

SEQ ID NO: 114
CAGGTGCAGCTGGTGGAGACGGGTGGAGGCTTGGTGCAGCCTGGGGGGTCTCTGAGACTC
TCCTGTGCAGGCTCTGGATTCACTTTGGATAATTATGCCGTCGGCTGGTTCCGCCAGGCC
CCAGGGAAGGAGCGTGAGGGGGTCTCATGTATTAGTAGTAGTGATGATAACACTGACTAT
TCAGACTCCGTGAAGGGCCGATTCACCATCTCCAGAGACAACGCCAAGGACACGGTCTAT
CTGCAAATGAACAGCCTGAAACCTGAGGACACAGCGATTTATTACTGTGCAGCAGAAAGC
CCGACGTTCGGGTTCAGCTGTACGGTAGCCACTGATCCATATGACTACTGGGGCCAGGGG
ACCCAGGTCACCGTCTCCTCAGAACCCAAGACACCAAAACCACAA

JND-E4,
SEQ ID NO: 115
QVQLVETGGGLVQPGGSLRLSCAASGFTLDGYAAGWFRQAPGKERELVSWISSTDGSTYY
AASVKGRFTVSRDNAKNTVYLQMNSLKPEDTAVYYCTAGLGLDVSDYVYDYWGQGTQVTV
SSEPKTPKPQ

SEQ ID NO: 116
CAGGTGCAGCTGGTGGAGACGGGGGGAGGCTTGGTGCAGCCTGGGGGGTCTCTGAGGCTC
TCCTGTGCAGCCTCTGGATTCACTTTGGATGGCTATGCCGCAGGCTGGTTCCGCCAGGCC
CCAGGGAAGGAGCGTGAGTTGGTCTCATGGATTAGTAGCACTGATGGTAGCACATACTAT
GCAGCCTCCGTGAAGGGCCGATTCACCGTCTCCAGAGACAACGCCAAGAACACGGTGTAT
CTACAAATGAACAGCCTGAAACCTGAGGACACAGCCGTTTATTACTGTACAGCAGGTCTA
GGGCTTGACGTTAGCGACTATGTATATGACTACTGGGGCCAGGGGACCCAGGTCACCGTC
TCCTCAGAACCCAAGACACCAAAACCACAA

JND-E5,
SEQ ID NO: 117
QVQLVESGGGLVQPGGSLRLSCAASGFTLDYYGIGWVRQAPGKEREEVSCITSGGLTNYPD
SVKGRFTISRDNAKNTVYLQMNSLKPEDTAVYYCAIDRVGVCAMEDFGSWGQGTQVTVSS
EPKTPKPQ

SEQ ID NO: 118
CAGGTGCAGCTGGTGGAGTCGGGCGGCTTGGTGCAGCCTGGGGGGTCTCTGAGACTCTCC
TGTGCAGCCTCTGGATTCACTTTGGATTATTATGGCATAGGCTGGGTCCGCCAGGCCCCA
GGGAAGGAGCGTGAGGAGGTCTCATGTATTACTAGTGGTGGTCTCACAAACTATCCAGAC
TCCGTGAAGGGCCGATTCACCATCTCCAGAGACAACGCCAAGAACACAGTGTATCTGCAA
ATGAACAGCCTGAAACCTGAGGACACGGCCGTTTATTACTGTGCAATCGACCGTGTGGGA
GTATGCGCGATGGAGGACTTTGGTTCCTGGGGCCAGGGGACCCAGGTCACCGTCTCCTCG
GAACCCAAGACACCAAAACCACAA

JND-E9,
SEQ ID NO: 119
QVQLVETGGGLVQAGDSLRLSCAASGRTENYYAMAWFRQAPGKEREFVAFINWSGDSTYY
AGSVKGRFTISRDNAKNTVYLQMNNLKPEDTAVYSCAAEFGTFSYLQGDDYSYWGQGTQV
TVSSEPKTPKPQ

SEQ ID NO: 120
CAGGTGCAGCTGGTGGAGACAGGTGGAGGATTGGTGCAGGCTGGGGACTCTCTGAGACTC
TCCTGTGCAGCCTCTGGACGCACCTTCAATTACTATGCCATGGCCTGGTTCCGCCAGGCC
CCAGGAAAGGAGCGTGAATTTGTAGCATTTATTAACTGGAGCGGCGATAGTACATACTAT
GCAGGCTCCGTGAAGGGCCGATTCACCATCTCCAGAGACAACGCCAAGAACACGGTGTAT
CTGCAAATGAACAACCTGAAACCTGAGGACACGGCCGTTTATTCCTGTGCAGCAGAATTC
GGTACATTTTCCTACTTGCAAGGCGATGACTATAGCTACTGGGGCCAGGGGACCCAGGTC
ACCGTCTCCTCAGAACCCAAGACACCAAAACCACAA

JND-F3,
SEQ ID NO: 121
QVQLVESGGGLVQAGGSLRLSCAASGRSFSSYRMGWFRQAPGKERELVAGISWSGSSTWY

-continued
ADSVKGRFTISRDNAKNTVYLQMNSLKPEDTAVYYCAADGLGTDWSDAIWDYWGQTQVT
VSSEPKTPKPQ SEQ ID NO: 122
CAGGTGCAGCTGGTGGAGTCTGGAGGAGGATTGGTGCAGGCTGGGGGCTCTCTGAGACTC
TCCTGTGCAGCCTCTGGACGCAGCTTCAGTAGCTATCGCATGGGCTGGTTCCGCCAGGCT
CCAGGGAAGGAGCGTGAGCTTGTAGCAGGTATTAGCTGGAGTGGAAGTAGTACATGGTAT
GCAGACTCCGTGAAGGGCCGATTCACCATCTCCAGAGACAACGCCAAGAACACGGTGTAT
CTGCAAATGAACAGCCTGAAACCCGAGGACACGGCCGTTTATTACTGTGCAGCAGATGGG
CTAGGGACGGATTGGAGCGATGCCATATGGGACTACTGGGGCCAGGGGACCCAGGTCACC
GTCTCCTCAGAACCCAAGACACCAAAACCACAA JND-F7,
SEQ ID NO: 123
QVQLVESGGGLVQAGGSLRLSCAASGRNFSHYAMGWFRQAPGKAREFVATINRDGDSTYY
TNSVKGRFTISRENAKNTYLQMNSLKPEDTAVYYCGVQYSWSGTSIYWREYEYAYWGQG
AQVTVSSEPKTPKPQ SEQ ID NO: 124
CAGGTGCAGCTGGTGGAGTCGGGGGGAGGATTGGTGCAGGCTGGGGGCTCTCTGAGACTC
TCCTGTGCAGCCTCTGGACGCAATTTCAGTCACTATGCCATGGGCTGGTTCCGCCAGGCT
CCAGGGAAGGCGCGTGAGTTTGTAGCAACTATTAACCGGGATGGTGATAGCACATACTAT
ACGAACTCCGTGAAGGGCCGATTCACCATCTCCAGAGAGAACGCCAAGAACACGGGATAT
CTGCAAATGAACAGCCTGAAACCTGAGGACACGGCCGTTTATTACTGTGGAGTACAATAC
TCGTGGTCGGGTACAAGTATTTACTGGAGGGAGTATGAGTATGCCTACTGGGGCCAGGGG
GCCCAGGTCACCGTCTCCTCAGAACCCAAGACACCAAAACCACAA JNE-B10,
SEQ ID NO: 125
QVQLVESGGGLVQPGGSLRLSCAASGFPFHAYYMSWVRQAPGKGLEWVSHIGNGGIITRY
ADSVKGRFTISRDNAKNTLYLQMTNLKPEDTALYYCTLGTRDDLGPERGQGTQVTVSSEP
KTPKPQ SEQ ID NO: 126
CAGGTGCAGCTGGTGGAGTCGGGTGGAGGCTTGGTGCAGCCTGGGGGGTCTCTGAGACTC
TCCTGTGCAGCCTCTGGATTCCCCTTCCATGCCTACTACATGAGCTGGGTCCGCCAGGCT
CCAGGAAAGGGGCTCGAGTGGGTCTCCCATATTGGCAATGGTGGTATTATTACACGCTAT
GCAGACTCCGTGAAGGGCCGGTTCACCATCTCCAGAGACAACGCCAAGAACACGCTGTAT
CTGCAAATGACCAACCTGAAACCTGAGGACACGGCCCTGTATTATTGTACCCTGGGGACC
CGCGACGACCTGGGGCCTGAGAGGGGCCAGGGGACCCAGGTCACCGTCTCCTCAGAACCC
AAGACACCAAAACCACAA New BoNT/E-Protease Light Chain (ELc) Binding VHHs JNB-B12,
SEQ ID NO: 127
QVQLVESGGGLVQPGGSLRLSCAASEGIFSVDAMGWYRQVPGKQRELVARITRGGSIIYA
DSVKGRFTISRDSAKNTVYLQMNSLKPEDTAVYYCNRLYRGTLTFGQGTQVTVSSAHHSE
DPS SEQ ID NO: 128
CAGGTGCAGCTCGTGGAGTCGGGTGGAGGCTTGGTGCAGCCTGGGGGGTCTCTGAGACTC
TCCTGTGCAGCCTCTGAGGGAATCTTCAGTGTTGATGCCATGGGCTGGTACCGCCAGGTT
CCAGGGAAGCAGCGCGAGTTGGTCGCACGAATTACCCGTGGTGGTAGCATAATTTATGCA
GACTCCGTGAAGGGCCGATTCACCATCTCCAGAGACAGCGCCAAGAACACGGTGTATCTG
CAAATGAACAGCCTGAAACCTGAGGACACGGCCGTCTATTACTGTAATCGCCTTTATAGG
GGTACCCTAACGTTCGGCCAGGGGACCCAGGTCACCGTCTCCTCAGCGCACCACAGCGAA
GACCCCTCG JNC-D5,
SEQ ID NO: 129
QVQLVETGGGLVQAGGSLRLSCAASGRTESIYAMGWFRQAPGREREFVASISRMGWSTYY
GDSVKGRFTASRDNAKNTLYLQMNSLELEDTAVYFCAASASALRVNQWDYWGQGTQVTVS
SEPKTPKPQ SEQ ID NO: 130
CAGGTGCAGCTGGTGGAGACCGGCGGAGGATTGGTGCAGGCTGGGGGCTCTCTGAGACTC
TCCTGTGCAGCCTCTGGACGCACCTTCAGTATCTATGCCATGGGCTGGTTCCGCCAGGCT
CCAGGGAGGGAGCGTGAGTTTGTAGCGTCTATTAGTCGGATGGGTTGGAGCACATATTAT
GGGGACTCCGTGAAGGGCCGATTCACCGCCTCCAGAGACAACGCCAAGAACACGCTGTAT
CTACAAATGAACAGCCTCGAACTTGAGGACACGGCCGTATATTTTTGTGCGGCATCTGCG
AGTGCGTTACGAGTTAATCAGTGGGACTACTGGGGCCAGGGGACCCAGGTCACCGTCTCC
TCAGAACCCAAGACACCAAAACCACAA New BoNT/B-Binding VHH Heterodimers JLU-D10/JLI-G10,
SEQ ID NO: 131
QVQLVESGGGLVQPGGSLRLSCAASGFTLDSYAIGWFRQAPGKEREGVACISASGSGTDY
VDSVKGRFTVSRDQAKSMVFLQMNNMKPEDAAVYYCAADYRPRPLPIQAPCTMTGGNYWG
QGTQVTVSSEPKTPKPQAIAGGGGSGGGGSGGGGSLQGQVQLVESGGGLVQAGGSLRLSC
AASILTYDLDYYYIGWVRQAPGKEREGVSCISSTDGATYYADSVKGRFTISRNNAKNTVY
LQMNNLKPEDTAIYYCAAAPLAGRYCPASHEYGYWGQGTQVTVSSAHHSEDPS SEQ ID NO: 132
CAGGTGCAGCTCGTGGAGTCAGGGGGAGGCTTGGTGCAGCCTGGGGGTCTCTGAGACTC
TCCTGTGCAGCCTCTGGATTCACTTTAGATAGTTATGCAATAGGCTGGTTCCGCCAGGCC
CCAGGGAAGGAGCGTGAGGGGGTCGCATGTATTAGTGCTAGTGGTAGTGGCACGGACTAT
GTAGACTCCGTGAAGGGCCGATTCACCGTCTCCAGAGACCAGGCCAAGAGCATGGTGTTT
CTGCAAATGAACAACATGAAACCTGAGGACGCAGCCGTTTATTACTGTGCAGCAGATTAT
CGGCCGAGGCCCCTGCCGATTCAGGCGCCGTGTACAATGACAGGTGGCAACTACTGGGGC
CAGGGGACCCAGGTCACCGTCTCCTCAGAACCCAAGACACCAAAACCACAAGCGATCGCT
GGTGGAGGCGGTTCAGGCGGAGGTGGCTCTGGCGGTGGCGGTTCCCTGCAGGGTCAGGTG
CAGCTCGTGGAGTCCGGTGGAGGCTTGGTGCAGGCTGGGGGGTCTCTGAGACTCTCCTGT
GCAGCCTCTATACTCACTTATGATTTGGATTATTATTACATAGGCTGGGTCCGCCAGGCC
CCAGGGAAGGAGCGTGAGGGGGTCTCATGTATTAGTAGTACTGATGGTGCCACATACTAT
GCAGACTCCGTGAAGGGCCGATTCACCATCTCCAGAAACAACGCCAAGAACACGGTGTAT
CTGCAAATGAACAACCTAAAACCTGAGGACACAGCCATTTATTATTGTGCAGCAGCCCCC
CTGGCTGGGCGCTACTGTCCCGCCTCGCATGAGTATGGCTACTGGGGTCAGGGGACCCAG
GTCACCGTCTCGTCAGCGCACCACAGCGAAGACCCCTCG JLU-D10/JLK-G12,
SEQ ID NO: 133
QVQLVESGGGLVQPGGSLRLSCAASGFTLDSYAIGWFRQAPGKEREGVACISASGSGTDY
VDSVKGRFTVSRDQAKSMVFLQMNNMKPEDAAVYYCAADYRPRPLPIQAPCTMTGGNYWG
QGTQVTVSSEPKTPKPQAIAGGGGSGGGGSGGGGSLQGQVQLXESGGGLVQAGGSLRLSC
AASEFRAEHFAVGWFRQAPGKEREGVSCVDASGDSTAYADSVKGRFTISRDNNKNVVYLQ
MDSLEPEDTGDYYCGASYFTVCAKSMRKIEYRYWGQGTQVTVSSEPKTPKPQ SEQ ID NO: 134
CAGGTGCAGCTCGTGGAGTCAGGGGGAGGCTTGGTGCAGCCTGGGGGTCTCTGAGACTC
TCCTGTGCAGCCTCTGGATTCACTTTAGATAGTTATGCAATAGGCTGGTTCCGCCAGGCC
CCAGGGAAGGAGCGTGAGGGGGTCGCATGTATTAGTGCTAGTGGTAGTGGCACGGACTAT
GTAGACTCCGTGAAGGGCCGATTCACCGTCTCCAGAGACCAGGCCAAGAGCATGGTGTTT
CTGCAAATGAACAACATGAAACCTGAGGACGCAGCCGTTTATTACTGTGCAGCAGATTAT
CGGCCGAGGCCCCTGCCGATTCAGGCGCCGTGTACAATGACAGGTGGCAACTACTGGGGC
CAGGGGACCCAGGTCACCGTCTCCTCAGAACCCAAGACACCAAAACCACAAGCGATCGCT
GGTGGAGGCGGTTCAGGCGGAGGTGGCTCTGGCGGTGGCGGTTCCCTGCAGGGTCAGKTG
CAGCTSGYGGAGTCCGGTGGAGGCTTGGTGCAGGCTGGGGGGTCTCTGAGACTCTCCTGT
GCAGCCTCTGAATTCCGTGCGGAGCATTTTGCCGTGGGCTGGTTCCGCCAGGCCCCAGGG
AAGGAGCGTGAGGGGGTCTCATGTGTAGACGCGAGTGGTGATAGTACAGCATATGCGGAC
TCTGTGAAGGGCCGATTCACCATCTCCAGAGACAACAACAAGAACGTAGTGTATCTGCAA
ATGGACAGCCTGGAACCTGAAGACACAGGAGATTATTATTGTGGAGCCTCGTACTTTACT
GTCTGCGCCAAGAGCATGCGGAAAATTGAATATAGGTACTGGGGCCAGGGGACCCAGGTC
ACCGTCTCCTCAGAACCCAAGACACCAAAACCACAA JLI-G10/JLO-G11,
SEQ ID NO: 135
QVQLVESGGGLVQAGGSLRLSCAASILTYDLDYYYIGWVRQAPGKEREGVSCISSTDGAT
YYADSVKGRFTISRNNAKNTVYLQMNNLKPEDTAIYYCAAAPLAGRYCPASHEYGYWGQG
TQVTVSSAHHSEDPSAIAGGGGSGGGGSGGGGSLQGQVQLVESGGGLVQPGGSLRLSCEA
SGFHLEHFAVGWFRQAPGKEREGVSCISASGDSTTYADSVKGRSTISKDNAKNAVYLQMD
SLRPEDTGDYYCAASHFSVCGKNIRKIEYRYWGQGTPVTVSSEPKTPKPQ SEQ ID NO: 136
CAGGTGCAGCTGGTGGAGTCCGGTGGAGGCTTGGTGCAGGCTGGGGGTCTCTGAGACTC
TCCTGTGCAGCCTCTATACTCACTTATGATTTGGATTATTATTACATAGGCTGGTCCGC
CAGGCCCCAGGGAAGGAGCGTGAGGGGGTCTCATGTATTAGTAGTACTGATGGTGCCACA
TACTATGCAGACTCCGTGAAGGGCCGATTCACCATCTCCAGAAACAACGCCAAGAACACG
GTGTATCTGCAAATGAACAACCTAAAACCTGAGGACACAGCCATTTATTATTGTGCAGCA
GCCCCCCTGGCTGGGCGCTACTGTCCCGCCTCGCATGAGTATGGCTACTGGGGTCAGGGG
ACCCAGGTCACCGTCTCGTCAGCGCACCACAGCGAAGACCCCTCGGCGATCGCTGGTGGA
GGCGGTTCAGGCGGAGGTGGCTCTGGCGGTGGCGGTTCCCTGCAGGGTCAGGTGCAGCTG
GTGGAGTCTGGTGGAGGCTTGGTGCAGCCTGGGGGTCTCTGAGACTCTCCTGTGAAGCC
TCAGGATTCCATTTGGAGCATTTTGCCGTGGGCTGGTTCCGCCAGGCCCCAGGGAAGGAG
CGTGAGGGGGTCTCATGTATAAGCGCGAGTGGTGATAGTACAACGTATGCAGACTCCGTG
AAGGGCCGATCACCATCTCCAAAGACAACGCCAAGAACGCGGTGTATCTGCAAATGGAC
AGCCTGAGACCCGAGGACACAGCCGATTATTACTGTGCAGCCTCGCACTTCAGTGTCTGC
GGCAAGAACATTCGGAAAATTGAATATAGGTACTGGGGCCAGGGGACCCCGGTCACCGTC
TCCTCAGAACCCAAGACACCAAAACCACAA JLI-G10/JLK-G12,
SEQ ID NO: 137
QVQLVESGGGLVQAGGSLRLSCAASILTYDLDYYYIGWVRQAPGKEREGVSCISSTDGAT
YYADSVKGRFTISRNNAKNTVYLQMNNLKPEDTAIYYCAAAPLAGRYCPASHEYGYWGQG -continued
TQVTVSSAHHSEDPSAIAGGGGSGGGGSGGGGSLQGQVQLAESGGGLVQAGGSLRLSCAA
SEFRAEHFAVGWERQAPGKEREGVSCVDASGDSTAYADSVKGRFTISRDNNKNVVYLQMD
SLEPEDTGDYYCGASYFTVCAKSMRKIEYRYWGQGTQVTVSSEPKTPKPQ SEQ ID NO: 138
CAGGTGCAGCTGGTGGAGTCCGGTGGAGGCTTGGTGCAGGCTGGGGGGTCTCTGAGACTC
TCCTGTGCAGCCTCTATACTCACTTATGATTTGGATTATTATTACATAGGCTGGGTCCGC
CAGGCCCCAGGGAAGGAGCGTGAGGGGGTCTCATGTATTAGTAGTACTGATGGTGCCACA
TACTATGCAGACTCCGTGAAGGGCCGATTCACCATCTCCAGAAACAACGCCAAGAACACG
GTGTATCTGCAAATGAACAACCTAAAACCTGAGGACACAGCCATTTATTATTGTGCAGCA
GCCCCCCTGGCTGGGCGCTACTGTCCCGCCTCGCATGAGTATGGCTACTGGGGTCAGGGG
ACCCAGGTCACCGTCTCGTCAGCGCACCACAGCGAAGACCCCTCGGCGATCGCTGGTGGA
GGCGGTTCAGGCGGAGGTGGCTCTGGCGGTGGCGGTTCCCTGCAGGGTCAGGTGCAGCTG
GCGGAGTCCGGTGGAGGCTTGGTGCAGGCTGGGGGGTCTCTGAGACTCTCCTGTGCAGCC
TCTGAATTCCGTGCGGAGCATTTTGCCGTGGGCTGGTTCCGCCAGGCCCCAGGGAAGGAG
CGTGAGGGGGTCTCATGTGTAGACGCGAGTGGTGATAGTACAGCATATGCGGACTCTGTG
AAGGGCCGATTCACCATCTCCAGAGACAACAACAAGAACGTAGTGTATCTGCAAATGGAC
AGCCTGGAACCTGAAGACACAGGAGATTATTATTGTGGAGCCTCGTACTTTACTGTCTGC
GCCAAGAGCATGCGGAAAATTGAATATAGGTACTGGGGCCAGGGGACCCAGGTCACCGTC
TCCTCAGAACCCAAGACACCAAAACCACAA New BoNT/E-Binding VHH Heterodimers JLE-E5/JLE-E9,
SEQ ID NO: 139
QVQLVETGGGLVQAGGSLRLSCAASGRSYAMGWFRQGPGKEREFVATISWSSTNTWYADS
VKGRFTISRDNAKNTVYLQMNSLKPEDTAVYYCAASHRFSDYPMRSEDGMDYWGKGTLVT
VSSEPKTPKPQAIAGGGGSGGGGSGGGGSLQGQVQLVETGGGLVQAGGSLRLSCAASGRT
FSSYSMGWFRQAPGKEREYVAAVNSNGDSTFYADSIKGRFTVSRDAAKNTVYLQMNSLKP
EDTALYYCAAVYGRYTYQSPKSYEYWGQGTQVTVSSEPKTPKPQ SEQ ID NO: 140
CAGGTGCAGCTGGTGGAGACGGGGGGAGGATTGGTGCAGGCTGGGGGGCTCTCTGAGACTC
TCCTGTGCAGCCTCTGGACGCAGTTATGCCATGGGCTGGTTCCGCCAGGGTCCAGGGAAG
GAGCGTGAGTTTGTAGCCACTATCAGTTGGAGTAGTACTAACACATGGTATGCAGATTCC
GTGAAGGGCCGATTCACCATCTCTAGAGACAACGCCAAGAACACGGTGTATCTGCAAATG
AACAGCCTGAAACCTGAGGACACGGCTGTTTATTACTGTGCAGCGAGCCATCGTTTTAGC
GACTATCCCATGAGGTCAGAGGACGGCATGGACTACTGGGGCAAAGGGACCCTGGTCACC
GTCTCCTCAGAACCCAAGACACCAAAACCACAAGCGATCGCTGGTGGAGGCGGTTCAGGC
GGAGGTGGCTCTGGCGGTGGCGGTTCCCTGCAGGGTCAGGTGCAGCTGGTGGAGACGGGA
GGAGGATTGGTGCAGGCTGGGGGCTCTCTGAGACTCTCGTGTGCAGCCTCTGGACGCACC
TTCAGTAGCTATTCCATGGGCTGGTTCCGCCAGGCTCCAGGGAAGGAGCGTGAGTATGTA
GCAGCAGTTAACTCCAATGGCGACAGTACATTCTATGCCGACTCCATTAAGGGCCGATTC
ACCGTCTCCAGAGACGCCGCCAAGAACACAGTCTATCTGCAAATGAACAGCCTGAAACCT
GAGGACACGGCCCTTTATTACTGTGCAGCTGTCTACGGTAGATACACTTACCAGTCCCCA
AAATCGTATGAGTACTGGGGCCAGGGGACCCAGGTCACCGTCTCCTCAGAACCCAAGACA
CCAAAACCACAA JLE-E5/JLE-G6,
SEQ ID NO: 141
QVQLVETGGGLVQAGGSLRLSCAASGRSYAMGWFRQGPGKEREFVATISWSSTNTWYADS
VKGRFTISRDNAKNTVYLQMNSLKPEDTAVYYCAASHRESDYPMRSEDGMDYWGKGTLVT
VSSEPKTPKPQAIAGGGGSGGGGSGGGGSLQGQVQLVETGGGLVKPGGSLRLSCVVSGFT
FDDYRMAWVRQAPGKELEWVSSIDSWSINTYYEDSVKGRFTISTDNAKNTLYLQMSSLKP
EDTAVYYCAAEDRLGVPTINAHPSKYDYNYWGQGTQVTVSSEPKTPKPQ SEQ ID NO: 142
CAGGTGCAGCTGGTGGAGACGGGGGGAGGATTGGTGCAGGCTGGGGGGCTCTCTGAGACTC
TCCTGTGCAGCCTCTGGACGCAGTTATGCCATGGGCTGGTTCCGCCAGGGTCCAGGGAAG
GAGCGTGAGTTTGTAGCCACTATCAGTTGGAGTAGTACTAACACATGGTATGCAGATTCC
GTGAAGGGCCGATTCACCATCTCTAGAGACAACGCCAAGAACACGGTGTATCTGCAAATG
AACAGCCTGAAACCTGAGGACACGGCTGTTTATTACTGTGCAGCGAGCCATCGTTTTAGC
GACTATCCCATGAGGTCAGAGGACGGCATGGACTACTGGGGCAAAGGGACCCTGGTCACC
GTCTCCTCAGAACCCAAGACACCAAAACCACAAGCGATCGCTGGTGGAGGCGGTTCAGGC
GGAGGTGGCTCTGGCGGTGGCGGTTCCCTGCAGGGTCAGGTGCAGCTGGTGGAGACTGGT
GGAGGCTTGGTGAAGCCTGGGGGTTCTCTGAGACTCTCCTGTGTAGTCTCCGGATTCACT
TTTGATGATTATCGCATGGCTTGGGTCCGCCAGGCTCCAGGGAAGGAGCTGGAGTGGGTG
TCCAGTATAGATAGTTGGAGTATCAACACATACTATGAAGACTCCGTGAAGGGCCGGTTC
ACCATCTCCACAGACAACGCCAAGAATACACTGTATCTGCAAATGAGCAGCCTGAAACCT
GAGGACACGGCCGTGTATTACTGTGCAGCAGAGGACCGCTTAGGTGTACCGACTATTAAC
GCCCACCCTTCAAAATATGATTATAACTACTGGGGGCAGGGGACCCAGGTCACCGTCTCC
TCAGAACCCAAGACACCAAAACCACAA JLE-G6/JLE-E9,
SEQ ID NO: 143
QLQLVETGGGLVKPGGSLRLSCVVSGFTEDDYRMAWVRQAPGKELEWVSSIDSWSINTYY
EDSVKGRFTISTDNAKNTLYLQMSSLKPEDTAVYYCAAEDRLGVPTINAHPSKYDYNYWG
QGTQVTVSSEPKTPKPQAIAGGGGSGGGGSGGGGSLQGQVQLVETGGGLVQAGGSLRLSC -continued AASGRTESSYSMGWFRQAPGKEREYVAAVNSNGDSTFYADSIKGRFTVSRDAAKNTVYLQ
MNSLKPEDTALYYCAAVYGRYTYQSPKSYEYWGQGTQVTVSSEPKTPKPQ

SEQ ID NO: 144

CAGTTGCAGCTCGTGGAGACTGGTGGAGGCTTGGTGAAGCCTGGGGGTTCTCTGAGACTC
TCCTGTGTAGTCTCCGGATTCACTTTTGATGATTATCGCATGGCTTGGGTCCGCCAGGCT
CCAGGGAAGGAGCTGGAGTGGGTGTCCAGTATAGATAGTTGGAGTATCAACACATACTAT
GAAGACTCCGTGAAGGGCCGGTTCACCATCTCCACAGACAACGCCAAGAATACACTGTAT
CTGCAAATGAGCAGCCTGAAACCTGAGGACACGGCCGTGTATTACTGTGCAGCAGAGGAC
CGCTTAGGTGTACCGACTATTAACGCCCACCCTTCAAAATATGATTATAACTACTGGGGG
CAGGGGACCCAGGTCACCGTCTCCTCAGAACCCAAGACACCAAAACCACAAGCGATCGCT
GGTGGAGGCGGTTCAGGCGGAGGTGGCTCTGGCGGTGGCGGTTCCCTGCAGGGTCAGGTG
CAGCTGGTGGAGACGGGAGGAGGATTGGTGCAGGCTGGGGGCTCTCTGAGACTCTCGTGT
GCAGCCTCTGGACGCACCTTCAGTAGCTATTCCATGGGCTGGTTCCGCCAGGCTCCAGGG
AAGGAGCGTGAGTATGTAGCAGCAGTTAACTCCAATGGCGACAGTACATTCTATGCCGAC
TCCATTAAGGGCCGATTCACCGTCTCCAGAGACGCCGCCAAGAACACAGTCTATCTGCAA
ATGAACAGCCTGAAACCTGAGGACACGGCCCTTTATTACTGTGCAGCTGTCTACGGTAGA
TACACTTACCAGTCCCCAAAATCGTATGAGTACTGGGGCCAGGGGACCCAGGTCACCGTC
TCCTCAGAACCCAAGACACCAAAACCACAA

---

What is claimed is:

1. A recombinant binding protein that specifically binds to a botulinum toxin B, wherein the binding protein comprises the amino acid sequence selected from the group consisting of SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, and a combination thereof.

2. A binding protein dimer or multimer comprising two or more of the binding proteins of claim 1, or a binding region thereof, wherein each of the binding proteins, or the binding region thereof, in the dimer or the multimer specifically binds to a non-overlapping portion of the botulinum toxin B.

3. The binding protein dimer or multimer of claim 2, which further comprises at least one of a tag epitope that is specifically bound by an anti-tag antibody and a linker that separates the binding proteins, or the binding region thereof, wherein the linker comprises a peptide or a protein.

4. The binding protein dimer or multimer of claim 3, wherein the linker is a peptide comprising GGGGS as set forth in SEQ ID NO: 147 or (GGGGS)$_3$ as set forth in SEQ ID NO: 145.

5. A pharmaceutical composition comprising the binding protein of claim 1, and a pharmaceutically acceptable carrier or diluent.

6. A pharmaceutical composition comprising the binding protein dimer or the multimer of claim 2, and a pharmaceutically acceptable carrier or diluent.

7. A method of detecting the presence of botulinum toxin B in a test sample, the method comprising:

incubating the test sample with an amount of the binding protein of claim 1 that specifically binds to the botulinum toxin B under conditions to form a complex of the binding protein and the botulinum toxin B in the test sample, separating the complex from the unbound binding protein, and analyzing the extent of the complex formation, and/or measuring the amount of the complex formed.

8. The method of claim 7, wherein the test sample is a food sample, a beverage sample, a water sample, or an environmental sample.

9. The method of claim 7, wherein the test sample is selected from blood, plasma, tissue, stool, saliva, or serum.

10. A pharmaceutical composition for treating botulinum toxin B infection or for ameliorating a symptom of botulism due to botulinum toxin B in a mammalian subject in need thereof, the composition comprising a botulinum toxin B-neutralizing recombinant heterodimeric VHH comprising the amino acid sequence selected from the group consisting of SEQ ID NO: 131, SEQ ID NO: 133, SEQ ID NO: 135 and SEQ ID NO: 137 and a pharmaceutically acceptable carrier or diluent.

11. A method of treating botulinum toxin B infection or ameliorating a symptom of botulism due to botulinum toxin B in a mammalian subject in need thereof, the method comprising administering to the subject an effective amount of a pharmaceutical composition comprising a botulinum toxin B-neutralizing recombinant heterodimeric VHH comprising the amino acid sequence selected from the group consisting of SEQ ID NO: 131, SEQ ID NO: 133, SEQ ID NO: 135 and SEQ ID NO: 137 and a pharmaceutically acceptable carrier or diluent.

* * * * *

SEQUENCE LISTING

<160> NUMBER OF SEQ ID NOS: 259

<210> SEQ ID NO 1
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Ala Glu Thr Gly Gly Gly Leu Val Gln Ala Gly Gly
1               5                   10                  15

Ser Leu Arg Leu Ser Cys Ser Ala Ser Gly Leu Thr Phe Gly Asn Tyr
            20                  25                  30

Ala Met Gly Trp Phe Arg Gln Ala Pro Gly Lys Glu Arg Glu Phe Val
        35                  40                  45

Ala Ser Ile Ser Arg Ser Gly Ser Asn Thr Trp Tyr Ala Glu Pro Leu
    50                  55                  60

Lys Gly Arg Phe Ala Ile Ser Arg Asp Asn Asp Lys Asn Ala Leu Tyr
65                  70                  75                  80

Leu Gln Met Asn Ser Leu Lys Pro Glu Asp Thr Ala Val Tyr Tyr Cys
                85                  90                  95

Ala Gly Gly Ser Tyr Asn Ser Asp Trp Trp Asn Tyr Met Tyr Trp Gly
            100                 105                 110

Gln Gly Thr Gln Val Thr Val Ser Ser Glu Pro Lys Thr Pro Lys Pro
        115                 120                 125

Gln

<210> SEQ ID NO 2
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
caggtgcagc tggcggagac ggggggagga ttggtgcagg ctgggggctc gctgagactc        60
tcctgttcag cctctgggct caccttcggg aactatgcca tgggctggtt ccgccaggct       120
ccagggaagg agcgtgagtt tgtagcatct atttctcgga gtggtagtaa cacatggtat       180
gcagaacccc tgaagggccg attcgccatc tccagagaca acgacaagaa cgcgctctat    240
ctgcaaatga acagcctgaa acctgaggac acggccgttt attactgtgc tggaggatct    300
tataatagtg actggtggaa ctatatgtac tggggccagg ggacccaggt cactgtctcc    360
tcagaaccca agacaccaaa accacaa                                        387

<210> SEQ ID NO 3
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Gln Ala Gly
1               5                   10                  15

Gly Ser Leu Arg Leu Ser Cys Ala Ala Ser Gly Arg Thr Phe Ser Gly
            20                  25                  30

Tyr Ala Met Gly Trp Phe Arg Gln Ala Pro Gly Lys Glu Arg Glu Phe
        35                  40                  45

Val Ala Asp Ile Ser Trp Ser Gly His Asn Thr Tyr Tyr Gly Asp Ser
    50                  55                  60

Val Lys Gly Arg Phe Thr Ile Ser Arg Asp Thr Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Glu Gly Ala Arg Thr His Leu Ser Asp Ser Tyr Tyr Phe
            100                 105                 110

Pro Gly Leu Trp Ala Glu Pro Pro Val Gly Tyr Trp Gly Gln Gly Thr
        115                 120                 125

Gln Val Thr Val Ser Ser Glu Pro Lys Thr Pro Lys Pro Gln
    130                 135                 140

<210> SEQ ID NO 4
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caggtgcagc tggtggagtc gggtggggga ggactggtgc aggctggggg ctctctgaga     60
ctctcctgtg cagcctctgg acgcaccttc agtggctatg ccatgggctg gttccgccag    120
gctccgggga aggagcgtga gtttgtagcc gatattagct ggagtggtca taacacgtac    180
tatggagact ccgtgaaggg ccgattcacc atctccagag acaccgccaa gaacacggtg    240
tatctgcaaa tgaacagcct gaaacctgag gacacggccg tttattactg tgcagcggag    300
ggggcccgta cacaccttag tgatagttac tacttcccgg gcctctgggc cgaacccccc    360
gtgggctact ggggccaggg gacccaggtc actgtctcct cagaacccaa gacaccaaaa    420
ccacaa                                                                426

<210> SEQ ID NO 5
<211> LENGTH: 131
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 5

Gln Val Gln Leu Val Glu Thr Gly Gly Gly Leu Val Gln Ala Gly Gly
1               5                   10                  15

Thr Leu Arg Leu Ser Cys Ala Ala Ser Gly Arg Thr Phe Thr Ser Tyr
            20                  25                  30

Tyr Ile Gly Trp Phe Arg Gln Glu Pro Gly Lys Glu Arg Glu Phe Val
        35                  40                  45

Ala Ser Ile Gly Trp Thr Asp Asp Asn Thr Tyr Tyr Ala Asp Ser Val
    50                  55                  60

Lys Gly Arg Phe Thr Ile Ser Arg Asp Asn Ala Glu Thr Thr Ala Tyr
65                  70                  75                  80

Leu Gln Met Ser Gly Leu Lys Pro Glu Asp Thr Ala Val Tyr Tyr Cys
                85                  90                  95

Ala Ala Asp Tyr Gly Ser Gly Ile Arg Ala Trp Tyr Asn Trp Ile Tyr
            100                 105                 110

Trp Gly Gln Gly Thr Gln Val Thr Val Ser Ser Glu Pro Lys Thr Pro
        115                 120                 125

Lys Pro Gln
    130

<210> SEQ ID NO 6
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caggtgcagc tggtggagac cggggggagga ttggtgcagg ctggggggcac tctgagactc      60 tcctgtgcag cctctggacg taccttcacg agctattaca ttggctggtt ccgccaggaa     120
ccagggaagg agcgtgagtt tgtagcaagt atcggctgga ccgatgataa cacatactat     180
gcagactccg tgaagggccg attcaccatc tccagagaca cgccgagac cacggcatat      240 ctgcaaatgt cgggcctgaa acctgaggac acggccgttt attactgtgc agccgactac     300
gggtcaggga tacgggcctg gtataattgg atttactggg gccaggggac ccaggtcacc     360
gtctcctcag aacccaagac accaaaacca caa                                   393

<210> SEQ ID NO 7
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Leu Gln Leu Ala Glu Thr Gly Gly Gly Leu Val Gln Pro Gly Gly
1               5                   10                  15

Ser Leu Arg Leu Ser Cys Ala Ala Ser Gly Ala Thr Leu Asp Thr Tyr
            20                  25                  30

Ile Ile Thr Trp Phe Arg Gln Ala Pro Gly Lys Glu Arg Glu Ala Val
        35                  40                  45

Ser Cys Ile Asn Arg Ser Gly Ser Thr Thr Tyr Ser Asp Ser Val Lys
    50                  55                  60

Gly Arg Phe Thr Ile Ser Arg Asp Asn Ala Gln Lys Thr Val Tyr Leu
65                  70                  75                  80

Gln Met Asn Ser Leu Asn Pro Glu Asp Thr Ala Ile Tyr Tyr Cys Ala
                85                  90                  95

Ala Asp Ala Ser Tyr Arg Thr Cys Gly Gly Ser Trp Trp Asn Trp Ala
            100                 105                 110

Tyr Trp Gly Gln Gly Thr Gln Val Thr Val Ser Ser Glu Pro Lys Thr
        115                 120                 125

Pro Lys Pro Gln
    130

<210> SEQ ID NO 8
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cagttgcagc tcgcggagac gggaggaggc ttggtgcagc ctgggggttc tctgagactc      60
tcctgtgcag cctctggcgc cactttggat acttatatca taacctggtt ccgccaggcc    120
ccagggaagg agcgtgaggc cgtctcatgt attaatcgta gtggtagcac gacctattca    180
gactccgtga agggccgatt caccatctcc agagacaacg cccagaaaac ggtgtatctg    240
cagatgaaca gcctgaaccc tgaggacaca gccatttatt actgcgcagc ggatgcttcg    300
taccgtactt gcggcgggag ttggtggaat tgggcgtact ggggccaggg gacccaggtc    360
accgtctcct cagaacccaa gacaccaaaa ccacaa                               396

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Ala Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Ile Glu Trp Val
        35                  40                  45

Ser Asp Ile Asn Gly Gly Gly Asp Arg Thr Asp Tyr Ala Asp Ser Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Gln Pro Glu Asp Thr Ala Val Tyr Tyr Cys
                85                  90                  95

Ala Lys Asp Leu Ser Tyr Val Ser Gly Thr Tyr Phe Ala Asn Asp Trp
            100                 105                 110

Gly Gln Gly Thr Gln Val Thr Val Ser Ser Glu Pro Lys Thr Pro Lys
        115                 120                 125

Pro Gln
    130

<210> SEQ ID NO 10
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcagc tcgcggagtc tggaggaggc tcggtgcaac ctggggggtc tctgagactc     60
tcctgtgcag cctctggatt caccttcagt agttatacta tgagctgggt ccgccaggct    120
ccaggaaagg ggatcgagtg gtctcagat attaatgggg gtggtgatag aacagactat    180
gcagactccg tgaagggccg attcaccatc tccagagaca cgccaggaa cacgctgtat    240 ctgcaaatga acagcctgca acctgaggac acggccgtgt attactgtgc aaaagatctg    300
agctacgtta gtggtactta tttcgcgaac gactggggcc aggggaccca ggtcaccgtc    360
tcctccgaac caagacacc aaaaccacaa                                      390

<210> SEQ ID NO 11
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Leu Gln Leu Ala Glu Ser Gly Gly Gly Leu Val Gln Pro Gly Gly
1               5                   10                  15

Ser Leu Arg Leu Ser Cys Thr Ala Ser Gly Ile Ile Phe Asp Tyr Tyr
            20                  25                  30

Ser Val Asp Trp Tyr Arg Gln Ala Pro Gly Lys Glu Arg Glu Leu Val
        35                  40                  45

Ala Thr Ile Thr Gly Asp Gly Ser Pro Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Gly Leu Lys Pro Glu Glu Thr Ala Val Tyr Tyr Cys His
                85                  90                  95

Ala Lys Arg Thr Ile Gly Thr Lys Ser Glu Tyr Trp Gly Gln Gly Thr
            100                 105                 110

Gln Val Thr Val Ser Ser Glu Pro Lys Thr Pro Lys Pro Gln
        115                 120                 125

<210> SEQ ID NO 12
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cagttgcagc tggcggagtc gggggggaggc ttggtgcagc ctggggggtc tctgagactc     60
tcctgtacag cctctggaat catcttcgat tactattccg tggactggta ccgccaggct    120
ccagggaagg agcgcgaatt ggtcgcaact attcgggtg atggtagccc gaactatgcg    180
gactctgtca agggccgatt caccatctcc agagacaacg ccaagaagac ggtgtatctg    240

```
caaatgaacg gcctgaaacc tgaggaaacg ccgtctatt actgtcatgc caaaaggact    300 ataggggacca aatctgagta ctggggccag gggacccagg tcactgtctc ctcagaaccc    360
aagacaccaa aaccacaa                                                   378
```

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Ala Glu Thr Gly Gly Gly Leu Val Gln Ala Gly Gly
1               5                   10                  15

Ser Leu Arg Leu Ser Cys Leu Ala Ser Arg Met Ser Phe Ser Arg Arg
            20                  25                  30

Pro Met Ala Trp Tyr Arg Gln Ala Pro Gly Lys Gln Arg Glu Arg Val
        35                  40                  45

Ala Thr Ile Ser Ser Phe Gly Asp Thr Thr Asn Tyr Thr Asp Ser Val
    50                  55                  60

Glu Gly Arg Phe Thr Ile Ser Arg Asp Asn Ala Lys Asn Thr Met Tyr
65                  70                  75                  80

Leu Gln Met Asn Ser Leu Lys Pro Asp Asp Thr Ala Val Tyr Tyr Cys
                85                  90                  95

Asn Thr Leu Leu Ala Thr Tyr Ala Trp Gly Gln Gly Thr Gln Val Thr
            100                 105                 110

Val Ser Ser Glu Pro Lys Thr Pro Lys Pro Gln
        115                 120
```

<210> SEQ ID NO 14
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
caggtgcagc tcgcggagac cggggggaggc ttggtgcagg ctggggggttc tctgagactc    60 tcctgtttag cctctagaat gagctttagt aggcgcccca tggcctggta ccgccaggct   120
ccaggcaagc agcgcgaaag ggtcgcaact attagtagtt tcggtgatac acaaaactat   180
acagactccg tggagggccg attcaccatc tccagggaca atgccaagaa cacgatgtat   240
ctgcaaatga acagcctgaa acctgacgac acggccgtgt attactgtaa cacattactc   300
gctacgtacg cctggggcca ggggacccag gtcaccgtct cctcagaacc caagacacca   360
aaaccacaa                                                            369
```

<210> SEQ ID NO 15
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Ala Glu Ser Gly Gly Gly Leu Val Gln Ala Gly Gly
1               5                   10                  15
```

-continued

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Ala Ala Ile Ser Arg Asn Gly Gly Lys Thr Tyr Tyr Ala Asp Ser Val
    50                  55                  60

Lys Gly Arg Phe Thr Ile Ser Arg Asp Gly Thr Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Val Ala Ala Ser Ala Glu Phe Val Thr Ala Arg Ser Asn
            100                 105                 110

Phe Tyr Glu Tyr Trp Gly Gln Gly Thr Gln Val Thr Val Ser Ser Glu
        115                 120                 125

Pro Lys Thr Pro Lys Pro Gln
    130                 135

<210> SEQ ID NO 16
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
caggtgcagc tggcggagtc ggggggagga ttggtgcagg ctgggggctc tctgagactc      60
tcctgtgcag cctctggacg caccttcagt agctatgtca tgggctggtt ccgccaggct    120
ccagggaagg agcgtgagtt tgtggccgct attagccgaa atggtggtaa gacctactat    180
gcagactccg tgaagggccg attcaccatc tcaagagacg gcaccgagaa cacggtgtat    240
ctgcaaatga acagcctgaa acctgaggac acggccgttt attactgcgc agcagccgta    300
gccgcttctg ccgagtttgt tacggctcgc tcgaattttt atgaatattg gggtcagggg    360
acccaggtca ctgtctcctc agaacccaag acaccaaaac cacaa                    405

<210> SEQ ID NO 17
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Thr Gly Gly Gly Leu Val Gln Ala Gly Gly
1               5                   10                  15

Ser Leu Arg Leu Ser Cys Glu Ala Ser Gly Ser Val Val Thr Ile Lys
            20                  25                  30

Glu Met Gly Trp Tyr Arg Gln Ala Pro Gly Lys Glu Arg Glu Gln Glu
        35                  40                  45

Arg Asp Leu Val Ala Ala Ile Gly Ile Gly Val Thr Tyr Tyr Ala
    50                  55                  60

Thr Ser Val Lys Gly Arg Phe Thr Ile Ser Arg Asp Ser Ala Lys Thr
65                  70                  75                  80

Thr Leu Arg Leu Gln Met Ser Ser Leu Arg Pro Glu Asp Thr Ala Met
                85                  90                  95

Tyr Tyr Cys Ala Val Ile Thr Asp Arg Asn Thr Gly Gly Tyr Pro Asp
            100                 105                 110

Tyr Trp Gly Gln Gly Thr Gln Val Thr Val Thr Ala Glu Pro Lys Thr
        115                 120                 125

Pro Lys Pro Gln
    130

<210> SEQ ID NO 18
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
caggtgcagc tggtggagac gggtggaggc ttggtgcagg ctggggggtc tctgagactc     60
tcctgtgaag cctctggaag cgtcgtcacc atcaaagaga tgggctggta ccgacaggct    120
ccaggaaagg agcgcgaaca ggagcgcgac ttggtcgcag caattggcat tggtggtgtc    180
acatactacg caacctctgt gaagggccga ttcaccatct ccagagacag tgccaagact    240
acgctgcgtc tgcaaatgag cagcctgaga cctgaggaca cggccatgta ttattgtgcg    300
gtcataactg acaggaacac cggtggttac ccggactact ggggccaggg gacccaggtc    360
actgttaccg cagaacccaa gacaccaaaa ccacaa                              396

<210> SEQ ID NO 19
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Leu Val Gln Ala Gly Gly
1               5                   10                  15

Ser Leu Arg Leu Ser Cys Ala Ala Ser Ile Leu Thr Tyr Asp Leu Asp
            20                  25                  30

Tyr Tyr Tyr Ile Gly Trp Val Arg Gln Ala Pro Gly Lys Glu Arg Glu
        35                  40                  45

Gly Val Ser Cys Ile Ser Ser Thr Asp Gly Ala Thr Tyr Tyr Ala Asp
    50                  55                  60

Ser Val Lys Gly Arg Phe Thr Ile Ser Arg Asn Asn Ala Lys Asn Thr
65                  70                  75                  80

Val Tyr Leu Gln Met Asn Asn Leu Lys Pro Glu Asp Thr Ala Ile Tyr
                85                  90                  95

Tyr Cys Ala Ala Ala Pro Leu Ala Gly Arg Tyr Cys Pro Ala Ser His
            100                 105                 110

Glu Tyr Gly Tyr Trp Gly Gln Gly Thr Gln Val Thr Val Ser Ser Glu
        115                 120                 125

Pro Lys Thr Pro Lys Pro Gln
    130                 135

<210> SEQ ID NO 20
<211> LENGTH: 405
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 20

```
caggtgcagc tggtggagtc cggtggaggc ttggtgcagg ctggggggtc tctgagactc      60
tcctgtgcag cctctatact cacttatgat ttggattatt attacatagg ctgggtccgc     120
caggccccag ggaaggagcg tgaggggtc tcatgtatta gtagtactga tggtgccaca      180
tactatgcag actccgtgaa gggccgattc accatctcca gaaacaacgc caagaacacg     240
gtgtatctgc aaatgaacaa cctaaaacct gaggacacag ccatttatta ttgtgcagca     300
gcccccctgg ctgggcgcta ctgtcccgcc tcgcatgagt atggctactg ggtcagggg      360
acccaggtca ccgtctcgtc agaacccaag acaccaaaac cacaa                     405
```

<210> SEQ ID NO 21
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Gln Val Gln Leu Val Glu Ser Gly Gly Gly Leu Val Gln Pro Gly Glu
1               5                   10                  15
Ser Leu Arg Leu Ser Cys Gly Ala Ser Gly Met Ser Leu Asp Tyr Tyr
            20                  25                  30
Ala Ile Ala Trp Tyr Arg Gln Ala Pro Gly Lys Glu Arg Glu Gly Val
        35                  40                  45
Ser Cys Ile Ser Val Ser Gly Ser Ala Gln Tyr Leu Asp Ser Val
    50                  55                  60
Arg Gly Arg Phe Ile Ile Ser Lys Asp Asn Thr Lys Ser Thr Ala Tyr
65                  70                  75                  80
Leu Gln Met Asn Ser Leu Lys Pro Glu Asp Thr Ala Val Tyr Tyr Cys
                85                  90                  95
Ala Ala Leu Ala Asp Cys Ala Gly Tyr Ala Ser Leu Thr Phe Asp Phe
            100                 105                 110
Asp Ser Trp Gly Gln Gly Thr Gln Val Ala Val Ser Ser Ala His His
        115                 120                 125
Ser Glu Asp Pro Ser
    130
```

<210> SEQ ID NO 22
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
caggtgcagc tcgtggagtc gggtggaggc ttggtgcagc ctggggagtc tctgagactc      60
tcctgtggag cctctggaat gagtttggat tactatgcca tagcctggta ccgccaggcc     120
ccagggaagg agcgtgaggg ggtctcatgt attagtgtta gtggcagtag cgcacaatat     180
ttagactccg tgaggggtcg cttcatcatc tccaaagaca acaccaagag cacggcgtat     240
ctgcaaatga acagcctgaa gcctgaagac acagccgttt attactgcgc agccctggcc     300
gactgtgcag gctatgccag tcttaccttt gactttgatt cttggggcca ggggacccag     360
```
gtcgccgtct cctcggcgca ccacagcgaa gacccctcg                             399

<210> SEQ ID NO 23
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Glu Ser Gly Gly Gly Leu Val Gln Ala Gly Gly
1               5                   10                  15

Ser Leu Arg Leu Ser Cys Ala Pro Ser Arg Leu Thr Leu Asp Phe Phe
            20                  25                  30

Ala Ile Ala Trp Phe Arg Gln Ala Pro Gly Lys Glu Arg Glu Gly Val
        35                  40                  45

Ser Cys Ile Ser Ser His Asp Gly Ser Thr Tyr Tyr Thr Asp Ser Val
    50                  55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Asp His Asn Val Gly Thr Cys Gln Leu Thr Gln Ala Glu Tyr
            100                 105                 110

Asp Tyr Trp Gly Gln Gly Thr Gln Val Thr Val Ser Ser Ala His His
        115                 120                 125

Ser Glu Asp Pro Ser
    130

<210> SEQ ID NO 24
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
caggtgcagc tggtggagtc cggtggaggc ttggtgcagg ctgggggggtc tctgagactc      60 tcctgtgcac cctcgcgatt aactttggat ttctttgcca tagcctggtt ccgccaggcc     120
ccagggaagg agcgtgaggg ggtctcatgt attagtagtc atgatggtag cacatactac     180
acagactccg tgaagggccg attcaccatc tccaaagaca acgccaagaa cacggtgtat     240
ctgcaaatga acagcctgaa gcctgaggac acagccgttt attactgtgc cctagaccat     300
aacgtgggta cctgccaact cacccaagct gagtatgact actggggcca ggggacccag     360
gtcaccgtct cctcggcgca ccacagcgaa gacccctcg                             399

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Leu Val Gln Ser Gly Gly
1               5                   10                  15

Ser Leu Arg Leu Ser Cys Ala Ala Ser Gly Ser Ile Asp Ser Leu Tyr
            20                  25                  30

His Met Gly Trp Tyr Arg Gln Ala Pro Gly Lys Glu Arg Glu Leu Val
            35                  40                  45

Ala Arg Val Gln Asp Gly Gly Ser Thr Ala Tyr Lys Asp Ser Val Lys
 50                  55                  60

Gly Arg Phe Thr Ile Ser Arg Asp Phe Ser Arg Ser Thr Met Tyr Leu
 65                  70                  75                  80

Gln Met Asn Ser Leu Lys Pro Glu Asp Thr Ala Ile Tyr Tyr Cys Ala
             85                  90                  95

Ala Lys Ser Thr Ile Ser Thr Pro Leu Ser Trp Gly Gln Gly Thr Gln
            100                 105                 110

Val Thr Val Ser Ser Glu Pro Lys Thr Pro Lys Pro Gln
            115                 120                 125

<210> SEQ ID NO 26
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
caggtgcagc tggtggagtc cggggggaggc ttggtgcagt ctggggggtc tctgagactc      60
tcctgtgcag cctctggaag tatcgatagt ctctatcata tgggctggta ccgccaggct     120
ccagggaagg agcgcgagtt ggtcgcacga gttcaagatg ggggtagcac agcgtacaaa     180
gactctgtga agggcgatt caccatctcc agagactttt ccaggagcac gatgtatctg     240
caaatgaaca gcctgaaacc tgaggacacg gccatctatt actgtgcggc gaagagtaca     300
attagcaccc ccttgtcctg gggccagggg acccaggtca ccgtctcctc ggaacccaag     360
acaccaaaac cacaa                                                     375

<210> SEQ ID NO 27
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Leu Val Gln Ala Gly Gly
  1               5                  10                  15

Ser Leu Arg Leu Ser Cys Ala Ala Ser Gly Phe Thr Leu Gly His Asn
            20                  25                  30

Gln Val Ala Trp Phe Arg Gln Ala Pro Gly Lys Glu Arg Glu Gly Val
            35                  40                  45

Ala Cys Ile Ser Ala Thr Gly Ala Ser Thr His Tyr Ala Asp Pro Val
 50                  55                  60

Lys Gly Arg Phe Thr Val Ser Arg Asp Asn Thr Lys Asn Val Val Tyr
 65                  70                  75                  80

Leu Gln Val Asn Ser Leu Lys Pro Glu Asp Thr Ala Asn Tyr Val Cys
             85                  90                  95

Ala Ser Arg Phe Ser Leu Met Ser Ile Asp Ala Ser Met Cys Leu Ser
            100                 105                 110

Ala Pro Gln Tyr Asp Arg Trp Gly Gln Gly Thr Gln Val Arg Ile Ser

<210> SEQ ID NO 28
<211> LENGTH: 411
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
caggtgcagc tggtggagtc cggtggaggc ttggtgcagg ctggggggtc tctgagactc      60
tcctgtgcag cctctggatt cactttggga cataatcaag tagcctggtt ccgccaggcc     120
ccaggcaagg agcgtgaggg ggtcgcgtgt attagcgcca ccgtgctag cacacactat      180
gcagaccccg tgaagggccg atttaccgtc tccagagaca acaccaagaa cgtggtgtat     240
ctgcaagtga acagcctgaa acctgaggac acggccaatt atgtctgtgc aagcagattc     300
tcccttatgt cgatcgatgc gagcatgtgc ctttcggcgc tcagtatga ccgctggggc      360
caggggaccc aggtcagaat ctcctcagaa cccaagacac caaaaccaca a              411
```

<210> SEQ ID NO 29
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Gln Val Gln Leu Val Glu Thr Gly Gly Leu Val Gln Pro Gly Gly Ser
1               5                   10                  15

Leu Arg Leu Ser Cys Thr Ala Ser Gly Phe Thr Leu Gly His His Arg
            20                  25                  30

Val Gly Trp Phe Arg Gln Ala Pro Gly Lys Glu Arg Glu Gly Val Ala
        35                  40                  45

Cys Ile Ser Ala Thr Gly Leu Ser Ser His Tyr Ser Asp Phe Val Ile
    50                  55                  60

Gly Arg Phe Thr Val Ser Arg Asp Asn Asp Asn Val Val Tyr Leu
65                  70                  75                  80

Gln Val Asn Gly Leu Lys Pro Glu Asp Thr Ala Val Tyr Tyr Cys Ala
                85                  90                  95

Ser Arg Phe Ser Leu Asn Ser Val Asp Ala Asn Met Cys Leu Ser Glu
            100                 105                 110

Pro Gln Tyr Asp Asn Trp Gly Gln Gly Thr Pro Val Arg Ile Ser Ser
        115                 120                 125

Glu Pro Lys Thr Pro Lys Pro Gln
    130                 135

<210> SEQ ID NO 30
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
caggtgcagc tggtggagac gggtggcttg gtgcagcctg gggggtctct gagactctcc    60
tgtacagcct ctggattcac tttgggacac catcgcgttg ctggttccg ccaggcccca    120 ggaaaggagc gtgaggggt cgcgtgtatt agcgccactg gtcttagttc acactattca    180
gacttcgtga tcggccgatt taccgtctcc agagacaacg acaacaacgt ggtgtatcta    240
caagtgaacg gcctgaaacc tgaggacaca gccgtttatt actgtgcaag cagattctcc    300
cttaattcgg tcgatgcgaa tatgtgcctt tcggagcctc agtatgacaa ctggggccag    360
gggaccccgg tcagaatctc ctcagaaccc aagcaccaa aaccacaa              408
```

```
<210> SEQ ID NO 31
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

Gln Val Gln Leu Val Glu Ser Gly Gly Gly Leu Val Gln Ala Gly Gly
1               5                   10                  15

Ser Leu Arg Leu Ser Cys Ala Ala Ser Glu Phe Arg Ala Glu His Phe
            20                  25                  30

Ala Val Gly Trp Phe Arg Gln Ala Pro Gly Lys Glu Arg Glu Gly Val
        35                  40                  45

Ser Cys Val Asp Ala Ser Gly Asp Ser Thr Ala Tyr Ala Asp Ser Val
    50                  55                  60

Lys Gly Arg Phe Thr Ile Ser Arg Asp Asn Lys Asn Val Val Tyr
65                  70                  75                  80

Leu Gln Met Asp Ser Leu Glu Pro Glu Asp Thr Gly Asp Tyr Tyr Cys
                85                  90                  95

Gly Ala Ser Tyr Phe Thr Val Cys Ala Lys Ser Met Arg Lys Ile Glu
            100                 105                 110

Tyr Arg Tyr Trp Gly Gln Gly Thr Gln Val Thr Val Ser Ser Glu Pro
        115                 120                 125

Lys Thr Pro Lys Pro Gln
    130

```
<210> SEQ ID NO 32
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
caggtgcagc tggtggagtc cggtggaggc ttggtgcagg ctgggggtc tctgagactc    60 tcctgtgcag cctctgaatt ccgtgcggag cattttgccg tgggctggtt ccgccaggcc    120
ccagggaagg agcgtgaggg ggtctcatgt gtagacgcga gtggtgatag tacagcatat    180
gcggactctg tgaagggccg attcaccatc tccagagaca caacaagaa cgtagtgtat    240 ctgcaaatgg acagcctgga acctgaagac acaggagatt attattgtgg agcctcgtac    300
tttactgtct gcgccaagag catgcggaaa attgaatata ggtactgggg ccaggggacc    360
caggtcaccg tctcctcaga acccaagaca ccaaaaccac aa                     402

<210> SEQ ID NO 33
```

-continued

<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Ala Glu Ser Gly Gly Gly Leu Val Gln Pro Gly Gly
1               5                   10                  15

Ser Leu Arg Leu Ser Cys Ala Ala Ser Gly Arg Ala Leu Asn Tyr Tyr
            20                  25                  30

Val Ile Gly Trp Phe Arg Gln Ala Pro Gly Lys Glu Arg Glu Gly Val
        35                  40                  45

Ser Cys Ile Ala Ser Ser Glu Ala Tyr Thr Asp Tyr Ala Asp Ser Val
    50                  55                  60

Gln Gly Arg Phe Thr Ile Ser Arg Asp Lys Ala Leu Asn Thr Val Tyr
65                  70                  75                  80

Leu Asp Met Lys Arg Leu Lys Pro Asp Asp Thr Ala Val Tyr Tyr Cys
                85                  90                  95

Ala Ala Arg Leu Arg Asp Pro Asn Trp Cys Gly Arg Asn Ala Asp Glu
            100                 105                 110

Tyr Asp Ser Trp Gly Gln Gly Thr Gln Val Thr Val Ser Ser Glu Pro
        115                 120                 125

Lys Thr Pro Lys Pro Gln
    130

<210> SEQ ID NO 34
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caggtgcagc tcgcggagtc aggcggaggc ttggtgcagc ctgggggtc tctgagactc      60
tcctgtgcag cctctggacg cgctttgaat tattatgtca taggctggtt ccgccaggcc    120
ccagggaagg agcgtgaggg ggtctcatgt attgcgagta gcgaagccta cacagactat    180
gcagactccg tgcaaggccg attcaccatc tcgagagaca ggctctgaa tacggtgtat    240
ttggatatga agcgcctgaa acctgacgac acagccgttt attattgtgc agcccggttg    300
cgtgatccta attggtgcgg gcggaatgcg gatgagtatg actcctgggg ccaggggacc    360
caggtcaccg tctcctcaga acccaagaca ccaaaaccac aa                       402

<210> SEQ ID NO 35
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Pro Phe Gly Ser Tyr
            20                  25                  30

Tyr Met Ser Trp Val Arg Gln Ala Pro Gly Lys Gly Pro Glu Trp Val

```
                    35                  40                  45
Ser Asp Ile Ser Asn Gly Gly Ile Ile Thr Arg Tyr Ser Asp Ser Val
         50                  55                  60

Lys Gly Arg Phe Thr Ile Ser Arg Asp Asn Ala Lys Asn Ile Leu Tyr
 65                  70                  75                  80

Leu Gln Met Asn Ser Leu Lys Pro Glu Asp Thr Ala Leu Tyr Phe Cys
                 85                  90                  95

Ala Thr Gly Thr Gly Arg Asp Trp Ser Arg Glu Tyr Arg Gly Gln Gly
            100                 105                 110

Thr Gln Val Thr Val Ser Ser Glu Pro Lys Thr Pro Lys Pro Gln
        115                 120                 125

<210> SEQ ID NO 36
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
caggtgcagc tggtggagtc cggtggaggc ttggtgcagg ctgggggtc tctgagactc     60 tcctgtgcag cctctggatt ccccttcggt agttactaca tgagctgggt ccgccaggct    120
ccaggaaagg ggcccgagtg ggtctcagat attagcaatg gtggtattat tacaaggtat    180
tcagactccg tgaagggccg attcaccatc tcccgagaca cgccaagaa catattgtat    240 ctgcaaatga acagcctgaa acctgaagac acggccctgt atttctgtgc gacagggacc    300
ggtagagact ggagcaggga gtaccggggc caggggaccc aggtcaccgt ctcctcagaa    360
cccaagacac aaaaccaca a                                                381

<210> SEQ ID NO 37
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Ala Glu Ser Gly Gly Gly Leu Val Gln Pro Gly Gly
  1               5                  10                  15

Ser Leu Arg Leu Ser Cys Glu Ala Ser Gly Phe His Leu Glu His Phe
             20                  25                  30

Ala Val Gly Trp Phe Arg Gln Ala Pro Gly Lys Glu Arg Glu Gly Val
         35                  40                  45

Ser Cys Ile Ser Ala Ser Gly Asp Ser Thr Thr Tyr Ala Asp Ser Val
     50                  55                  60

Lys Gly Arg Ser Thr Ile Ser Lys Asp Asn Ala Lys Asn Ala Val Tyr
 65                  70                  75                  80

Leu Gln Met Asp Ser Leu Arg Pro Glu Asp Thr Gly Asp Tyr Tyr Cys
                 85                  90                  95

Ala Ala Ser His Phe Ser Val Cys Gly Lys Asn Ile Arg Lys Ile Glu
            100                 105                 110

Tyr Arg Tyr Trp Gly Gln Gly Thr Pro Val Thr Val Ser Ser Glu Pro
        115                 120                 125

Lys Thr Pro Lys Pro Gln
        130
```

<210> SEQ ID NO 38
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
caggtgcagc tcgcggagtc tggtggaggc ttggtgcagc ctgggggtc tctgagactc      60
tcctgtgaag cctcaggatt ccatttggag cattttgccg taggctggtt ccgccaggcc   120
ccagggaagg agcgtgaggg ggtctcatgt ataagcgcga gtggtgatag tacaacgtat   180
gcagactccg tgaagggccg atccaccatc tccaaagaca cgccaagaa cgcggtgtat   240
ctgcaaatgg acagcctgag acccgaggac acaggcgatt attactgtgc agcctcgcac   300
ttcagtgtct gcggcaagaa cattcggaaa attgagtata ggtactgggg ccaggggacc   360
ccggtcaccg tctcctcaga acccaagaca ccaaaaccac aa                     402
```

<210> SEQ ID NO 39
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Thr Gly Gly Gly Leu Val Gln Pro Gly Gly
1               5                   10                  15
Ser Leu Arg Leu Ser Cys Val Val Ser Gly Leu Thr Phe Asn Ser Asn
            20                  25                  30
Tyr Met Ser Trp Val Arg Gln Ala Pro Gly Lys Gly Pro Glu Leu Val
        35                  40                  45
Ser Tyr Ile Asn Ser Glu Asp Gly Ser Thr Phe Tyr Ala Asp Ser Val
    50                  55                  60
Lys Gly Arg Phe Thr Ile Ser Arg Asp Asn Glu Asn Thr Leu Tyr
65                  70                  75                  80
Leu Gln Met Ser Ser Leu Lys Pro Glu Asp Thr Ala Arg Tyr Tyr Cys
                85                  90                  95
Ala Leu Gly Ile Ala Gly Ala Thr Arg Gly Gln Gly Thr Gln Val Thr
            100                 105                 110
Val Ser Ser Glu Pro Lys Thr Pro Lys Pro Gln
        115                 120

<210> SEQ ID NO 40
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
caggtgcagc tcgtggagac cggggggaggc ttggtgcagc cggggggggtc tctgagactc      60
tcctgtgtag tgtctggatt aaccttcaat agcaactaca tgagttgggt ccgccaggct    120
ccagggaagg ggcccgagtt ggtctcatat attaattctg aagatggtag tacctttat    180
gcagactccg tgaagggccg attcaccatc tcgcgagaca caacgagaa tacactgtat    240
```

```
ctgcaaatga gcagcctgaa gcctgaggac acggcccgct attactgtgc actggggatc    300
gctggtgcaa ctcggggcca ggggacccag gtcaccgtct cctcagaacc caagacacca    360
aaaccacaa                                                             369
```

<210> SEQ ID NO 41
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Ser Tyr
            20                  25                  30

Ala Ile Gly Trp Phe Arg Gln Ala Pro Gly Lys Glu Arg Glu Gly Val
        35                  40                  45

Ala Cys Ile Ser Ala Ser Gly Ser Gly Thr Asp Tyr Val Asp Ser Val
    50                  55                  60

Lys Gly Arg Phe Thr Val Ser Arg Asp Gln Ala Lys Ser Met Val Phe
65                  70                  75                  80

Leu Gln Met Asn Asn Met Lys Pro Glu Asp Ala Ala Val Tyr Tyr Cys
                85                  90                  95

Ala Ala Asp Tyr Arg Pro Arg Pro Leu Pro Ile Gln Ala Pro Cys Thr
            100                 105                 110

Met Thr Gly Gly Asn Tyr Trp Gly Gln Gly Thr Gln Val Thr Val Ser
        115                 120                 125

Ser Glu Pro Lys Thr Pro Lys Pro Gln
    130                 135

<210> SEQ ID NO 42
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
caggtgcagc tcgtggagtc aggggggaggc ttggtgcagc ctgggggggtc tctgagactc    60 tcctgtgcag cctctggatt cactttagat agttatgcaa taggctggtt ccgccaggcc    120
ccagggaagg agcgtgaggg ggtcgcatgt attagtgcta gtggtagtgg cacggactat    180
gtagactccg tgaagggccg attcaccgtc tccagagacc aggccaagag catggtgttt    240
ctgcaaatga acaacatgaa acctgaggac gcagccgttt attactgtgc agcagattat    300
cggccgaggc ccctgccgat tcaggcgccg tgtacaatga caggtggcaa ctactggggc    360
caggggaccc aggtcaccgt ctcctcagaa cccaagacac caaaaccaca a             411
```

<210> SEQ ID NO 43
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 43

Gln Val Gln Leu Val Glu Ser Gly Gly Gly Leu Val Gln Pro Gly Gly
 1               5                  10                  15

Ser Leu Thr Leu Ser Cys Val Ala Ser Gly Ser Asn Leu Asp Tyr Phe
             20                  25                  30

Ala Ile Gly Trp Phe Arg Gln Ala Pro Gly Lys Glu Arg Glu Gly Val
         35                  40                  45

Ser Cys Ile Ser Thr Ser Ser Asp Met Ser Lys Tyr Ala Asp Ser Val
     50                  55                  60

Lys Gly Arg Phe Thr Ile Ser Arg Asp Asn Thr Arg Asn Thr Val Tyr
 65                  70                  75                  80

Leu Gln Met Asn Ser Leu Glu Pro Glu Asp Thr Ala Val Tyr Tyr Cys
                 85                  90                  95

Ala Ala Lys Arg Arg Arg Tyr Gly Leu Asp Arg Asp Met Cys Leu Met
            100                 105                 110

Asp Ser Val Gly Met Asp Val Trp Gly Lys Gly Thr Leu Val Thr Val
                115                 120                 125

Ser Ser Ala His His Ser Glu Asp Pro Ser
            130                 135

<210> SEQ ID NO 44
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caggtgcagc tggtggagtc gggggggaggc ttggtgcagc ctgggggggtc tctgacactc      60
tcctgtgtag cctctggatc caatttggat tattttgcga taggctggtt ccgccaggcc     120
ccagggaagg agcgtgaggg ggtctcatgt attagtacga gtagtgacat gtcaaagtat     180
gcagactccg tgaagggccg cttcaccatc tccagagaca acaccaggaa cacggtgtat     240
ctgcaaatga acagcctgga acccgaagat acggccgttt attattgtgc agcaaagcgc     300
cgccgatatg gtctcgatcg tgatatgtgt cttatggatt cggtcggcat ggacgtgtgg     360
ggcaaaggga ccctggtcac cgtctcctcg gcgcaccaca gcgaagaccc ctcg           414

<210> SEQ ID NO 45
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Glu Ser Gly Gly Gly Leu Val Gln Pro Gly Gly
 1               5                  10                  15

Ser Leu Arg Leu Ser Cys Ala Ala Pro Gly Phe Thr Leu Asp Tyr Tyr
             20                  25                  30

Ala Ile Gly Trp Phe Arg Gln Ala Pro Gly Lys Glu Arg Glu Gly Val
         35                  40                  45

Ser Cys Ile Arg Ser Arg Gly Asp Arg Thr Asn Tyr Ala Asp Ser Val
     50                  55                  60

Lys Gly Arg Phe Thr Val Ser Arg Asp Asn Ala Lys Asn Thr Ala Tyr
 65                  70                  75                  80
```

Leu Gln Met Asn Asn Leu Lys Pro Glu Asp Thr Gly Val Tyr Phe Cys
                85                  90                  95

Ala Ala Ala Pro Arg Thr Thr Val Gln Asp Leu Cys Val Thr Pro Leu
            100                 105                 110

Leu Gly Gly Ala Asp Trp Val Ser Trp Gly Gln Gly Thr Gln Val Thr
        115                 120                 125

Val Ser Ser Glu Pro Lys Thr Pro Lys Pro Gln
    130                 135

<210> SEQ ID NO 46
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caggtgcagc tcgtggagtc aggaggaggc ttggtgcagc ctggggggtc tctgagactc     60
tcctgtgcag ctcctggatt cactttggat tattatgcca taggctggtt ccgccaggcc    120
ccagggaagg agcgtgaggg ggtctcatgt attcgtagtc gtggtgatcg gacaaattat    180
gcagactccg tgaagggccg attcaccgtc tccagagaca acgccaagaa cacggcgtat    240
ctgcaaatga acaacctgaa acctgaggac acaggcgttt attctgtgc agctgctccg     300 aggactactg ttcaggattt gtgtgtaacc cctctttgg ggggtgctga ctgggtttcc     360
tggggccagg ggacccaggt caccgtctcc tcggaaccca agacaccaaa accacaa       417

<210> SEQ ID NO 47
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Gly Asp Tyr
            20                  25                  30

Thr Val Gly Trp Phe Arg Gln Ala Pro Gly Lys Glu Arg Glu Gly Val
        35                  40                  45

Ser Cys Ile Ser Lys Gly Ser Arg Gly Leu Arg Tyr Gly Asp Ser Val
    50                  55                  60

Lys Gly Arg Phe Thr Val Ala Arg Asp Asn Ala Lys Ser Thr Val Thr
65                  70                  75                  80

Leu Gln Met Asp Ser Leu Lys Pro Glu Asp Thr Ala Val Tyr Ser Cys
                85                  90                  95

Ala Ala Gly Pro Ala Met Phe Asn Gln Cys His Met Val Asp Asn Tyr
            100                 105                 110

Phe Thr Tyr Trp Gly Gln Gly Thr Gln Val Thr Val Ser Ser Ala His
        115                 120                 125

His Ser Glu Asp Pro Ser
    130

<210> SEQ ID NO 48
<211> LENGTH: 402

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cagttgcagc tggtggagtc tggcggaggc ttggtgcagc ctgggggtc tctgagactc     60 tcctgtgcag cctctggatt ccctttgggt gattataccg tgggctggtt ccgccaggcc   120
ccagggaagg agcgtgaggg ggtctcatgt attagtaaag gtagtagagg cttaagatac   180
ggagactccg tgaaaggccg attcaccgtt gccagagaca acgccaagag cacggtaact   240
ctgcaaatgg acagcctgaa accggaggac acagccgttt attcttgtgc tgcagggccg   300
gccatgttca tcaatgtca tatggtcgac aattacttta catactgggg tcaggggacc   360
caggtcaccg tctcctcggc gcaccacagc gaagacccct cg                      402

<210> SEQ ID NO 49
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ala His Thr Tyr Tyr Ala Asp Ser Val
    50                  55                  60

Lys Gly Arg Phe Thr Ile Ser Arg Asp Asn Ala Lys Ser Thr Met Tyr
65                  70                  75                  80

Leu Gln Met Asn Ser Leu Lys Pro Glu Asp Thr Ala Val Tyr Tyr Cys
                85                  90                  95

Asn Ala Asp Leu Glu Arg Tyr Ser Asp Phe Gly Arg Glu Val Asp Asp
            100                 105                 110

Tyr Trp Gly Gln Gly Thr Gln Val Thr Val Ser Ser Glu Pro Lys Thr
        115                 120                 125

Pro Lys Pro Gln
    130

<210> SEQ ID NO 50
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
caggtgcagc tcgtggagac aggtggagga ttggtgcagg ctgggggtc tctgagactc     60 tcctgtgcag cctctggacg caccttcagt aactatgcca tgggctggtt ccgccaggct   120
ccagggaagg agcgtgagtt tgtcgcagct attagctgga gtggtgctca cacatactat   180
gcagactccg tgaagggccg attcaccatc tccagagaca acgccaagag cacgatgtat   240
```

```
ctgcaaatga acagcctgaa acctgaggac acggccgtct attactgtaa tgcagatctc    300
gagcggtata gtgacttcgg tagggaggtg gatgactact ggggccaggg gacccaggtc    360
accgtctcct cagaacccaa gacaccaaaa ccacaa                              396
```

<210> SEQ ID NO 51
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Val Gln Leu Val Glu Ser Gly Gly Gly Leu Val Gln Pro Gly Gly
1               5                   10                  15

Ser Leu Arg Leu Ser Cys Thr Ala Ser Gly Leu Thr Leu Ala Lys Trp
            20                  25                  30

Thr Ile Asn Trp Phe Arg Gln Ala Pro Gly Lys Glu Arg Glu Gly Ile
        35                  40                  45

Ser Cys Ile Ser Ser Ser Gly Ser Thr Tyr Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Ser Phe Lys Gly Cys Thr Phe Leu Ser Ser Thr Thr His
            100                 105                 110

Tyr Asn Asn Met Asp Tyr Trp Gly Lys Gly Thr Leu Val Thr Val Ser
        115                 120                 125

Ser Ala His His Ser Glu Asp Pro Ser
    130                 135
```

<210> SEQ ID NO 52
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
caggtgcagc tcgtggagtc gggtggaggc ttggtgcagc ctggggggtc tctgagactc     60
tcgtgtacag cctctggatt aactttggct aagtggacca tcaactggtt ccgccaggcc    120
ccagggaagg agcgcgaggg gatctcatgt attagtagca gtagtggtag cacatactat    180
gcagactccg tgaagggccg attcaccatc tccagagaca cgccgaaaa cacggtatat    240 ctgcaaatga gcagcctgaa acctgaggac acggccgttt attactgtgc agcggattct    300
tttaagggct gtacgttcct cagtagtact acccattaca caacatgga ctactggggc    360 aaagggaccc tggtcaccgt ctcctcagcg caccacagcg aagacccctc g             411
```

<210> SEQ ID NO 53
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Glu Ser Gly Gly Gly Leu Val Gln Ser Gly Gly
1               5                   10                  15

Ser Leu Arg Leu Ser Cys Ala Ala Ser Arg Arg Thr Ala Ser Asn Tyr
            20                  25                  30

Ala Val Ala Trp Phe Arg Gln Ala Pro Gly Lys Glu Arg Glu Phe Val
        35                  40                  45

Ala Ala Ile Gly Trp Ser Asp Asp Val Thr Tyr Tyr Ala Asp Ser Val
    50                  55                  60

Lys Gly Arg Phe Thr Val Ser Arg Asp Asn Ala Lys Asn Thr Val Tyr
65                  70                  75                  80

Leu Gln Met Asn Gly Leu Glu Pro Glu Asp Thr Ala Val Tyr Tyr Cys
                85                  90                  95

Thr Thr Asn Gly Asp Arg Tyr Ser Tyr Arg Thr Ala Ser Ser Tyr His
            100                 105                 110

Tyr Trp Gly Gln Gly Thr Gln Val Thr Val Ser Ser Ala His His Ser
        115                 120                 125

Glu Asp Pro Ser
    130

<210> SEQ ID NO 54
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caggtgcagc tcgtggagtc gggtggggga ttggtgcagt ctgggggctc tctgagactc      60
tcctgtgcag cctctagacg caccgccagt aactatgccg tggcctggtt ccgccaggct     120
ccaggaaagg agcgtgagtt tgtagcagcg attggctgga gtgatgatgt cacgtattac     180
gcagactccg tgaagggccg attcaccgtc tccagagaca acgccaagaa cacggtgtat     240
ctgcaaatga acggcctgga acctgaggac acggccgttt attactgtac aacaaatggt     300
gatagataca gttacaggac ggcatccagc tatcactact ggggccaggg gacccaggtc     360
accgtctcct cagcgcacca cagcgaagac ccctcg                               396

<210> SEQ ID NO 55
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Ala Glu Thr Gly Gly Gly Ser Val Gln Thr Gly Gly
1               5                   10                  15

Ser Leu Arg Leu Ser Cys Ala Ala Ser Gly Leu Pro Phe Arg Asn Tyr
            20                  25                  30

Ala Met Ala Trp Phe Arg Gln Ala Pro Gly Lys Glu Arg Glu Phe Val
        35                  40                  45

Ala Ala Ile Ser Arg Glu Gly Gly Arg Thr Tyr Tyr Ala Asp Phe Val
    50                  55                  60

Lys Gly Arg Phe Thr Ile Ser Arg Asp Asn Gly Arg Asn Thr Ile Tyr
65                  70                  75                  80

```
Leu Glu Met Asn Ser Leu Ala Ser Glu Asp Thr Ala Ile Tyr Tyr Cys
            85                  90                  95

Ala Gly Val Glu Gly Ala Tyr Thr Tyr Arg Thr Gly Ala Ser Tyr Thr
            100                 105                 110

Tyr Trp Gly Gln Gly Thr Gln Val Thr Val Ser Ser Glu Pro Lys Thr
        115                 120                 125

Pro Lys Pro Gln
    130
```

<210> SEQ ID NO 56
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
caggtgcagc tcgcggagac tgggggagga tcggtgcaga ctgggggctc tctgaggctc      60
tcctgtgcag cctctggact gcccttcaga aactatgcca tggcctggtt ccgccaggct     120
ccagggaagg agcgtgagtt tgtagcagct attagtcggg aaggcgggag gacatactat     180
gcagacttcg tgaagggccg attcaccatc tccagagaca acggcaggaa cacgatatat     240
ctggagatga acagcctggc atcggaggat acgccatttt attactgtgc cggtgtcgag     300
ggtgcttata cttatcgtac cggggcctcg tatacttact ggggccaggg gacccaggtc     360
accgtctcct cagaacccaa gacaccaaaa ccacaa                               396
```

<210> SEQ ID NO 57
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Ser Tyr Ala Met Gly
            20                  25                  30

Trp Phe Arg Gln Gly Pro Gly Lys Glu Arg Glu Phe Val Ala Thr Ile
        35                  40                  45

Ser Trp Ser Ser Thr Asn Thr Trp Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Ala Ala Ser
            85                  90                  95

His Arg Phe Ser Asp Tyr Pro Met Arg Ser Glu Asp Gly Met Asp Tyr
            100                 105                 110

Trp Gly Lys Gly Thr Leu Val Thr Val Ser Ser Glu Pro Lys Thr Pro
        115                 120                 125

Lys Pro Gln
    130
```

<210> SEQ ID NO 58
<211> LENGTH: 393
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 58

```
caggtgcagc tggtggagac ggggggagga ttggtgcagg ctgggggctc tctgagactc      60
tcctgtgcag cctctggacg cagttatgcc atgggctggt tccgccaggg tccagggaag     120
gagcgtgagt ttgtagccac tatcagttgg agtagtacta acacatggta tgcagattcc     180
gtgaagggcc gattcaccat ctctagagac aacgccaaga acacggtgta tctgcaaatg     240
aacagcctga aacctgagga cacggctgtt tattactgtg cagcgagcca tcgttttagc     300
gactatccca tgaggtcaga ggacggcatg gactactggg gcaaagggac cctggtcacc     360
gtctcctcag aacccaagac accaaaacca caa                                  393
```

<210> SEQ ID NO 59
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gln Val Gln Leu Val Glu Thr Gly Gly Gly Leu Val Gln Ala Gly Gly
 1               5                  10                  15
Ser Leu Arg Leu Ser Cys Ala Ala Ser Gly Arg Thr Phe Ser Ser Tyr
            20                  25                  30
Ser Met Gly Trp Phe Arg Gln Ala Pro Gly Lys Glu Arg Glu Tyr Val
        35                  40                  45
Ala Ala Val Asn Ser Asn Gly Asp Ser Thr Phe Tyr Ala Asp Ser Ile
    50                  55                  60
Lys Gly Arg Phe Thr Val Ser Arg Asp Ala Ala Lys Asn Thr Val Tyr
65                  70                  75                  80
Leu Gln Met Asn Ser Leu Lys Pro Glu Asp Thr Ala Leu Tyr Tyr Cys
                85                  90                  95
Ala Ala Val Tyr Gly Arg Tyr Thr Tyr Gln Ser Pro Lys Ser Tyr Glu
            100                 105                 110
Tyr Trp Gly Gln Gly Thr Gln Val Thr Val Ser Ser Glu Pro Lys Thr
        115                 120                 125
Pro Lys Pro Gln
    130
```

<210> SEQ ID NO 60
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
caggtgcagc tggtggagac gggaggagga ttggtgcagg ctgggggctc tctgagactc      60
tcgtgtgcag cctctggacg caccttcagt agctattcca tgggctggtt ccgccaggct     120
ccagggaagg agcgtgagta tgtagcagca gttaactcca atggcgacag tacattctat     180
gccgactcca ttaagggccg attcaccgtc tccagagacg ccgccaagaa cacagtctat     240
ctgcaaatga acagcctgaa acctgaggac acggcccttt attactgtgc agctgtctac     300
```

```
ggtagataca cttaccagtc cccaaaatcg tatgagtact ggggccaggg gacccaggtc    360
accgtctcct cagaacccaa gacaccaaaa ccacaa                              396
```

<210> SEQ ID NO 61
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Gln Leu Gln Leu Val Glu Thr Gly Gly Gly Leu Val Lys Pro Gly Gly
1               5                   10                  15

Ser Leu Arg Leu Ser Cys Val Val Ser Gly Phe Thr Phe Asp Asp Tyr
            20                  25                  30

Arg Met Ala Trp Val Arg Gln Ala Pro Gly Lys Glu Leu Glu Trp Val
        35                  40                  45

Ser Ser Ile Asp Ser Trp Ser Ile Asn Thr Tyr Tyr Glu Asp Ser Val
    50                  55                  60

Lys Gly Arg Phe Thr Ile Ser Thr Asp Asn Ala Lys Asn Thr Leu Tyr
65                  70                  75                  80

Leu Gln Met Ser Ser Leu Lys Pro Glu Asp Thr Ala Val Tyr Tyr Cys
                85                  90                  95

Ala Ala Glu Asp Arg Leu Gly Val Pro Thr Ile Asn Ala His Pro Ser
            100                 105                 110

Lys Tyr Asp Tyr Asn Tyr Trp Gly Gln Gly Thr Gln Val Thr Val Ser
        115                 120                 125

Ser Glu Pro Lys Thr Pro Lys Pro Gln
    130                 135
```

<210> SEQ ID NO 62
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
cagttgcagc tcgtggagac tggtggaggc ttggtgaagc ctgggggttc tctgagactc    60
tcctgtgtag tctccggatt cacttttgat gattatcgca tggcttgggt ccgccaggct    120
ccagggaagg agctggagtg ggtgtccagt atagatagtt ggagtatcaa cacatactat    180
gaagactccg tgaagggccg gttcaccatc tccacagaca acgccaagaa tacactgtat    240
ctgcaaatga gcagcctgaa acctgaggac acggccgtgt attactgtgc agcagaggac    300
cgcttaggtg taccgactat taacgcccac ccttcaaaat atgattataa ctactggggg    360
caggggaccc aggtcaccgt ctcctcagaa cccaagacac caaaaccaca a              411
```

<210> SEQ ID NO 63
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (90)..(90)

<223> OTHER INFORMATION: Any amino acid

<400> SEQUENCE: 63

Gln Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Thr Ser Tyr
            20                  25                  30
Ala Met Gly Trp Phe Arg Gln Ala Pro Gly Lys Glu Arg Glu Phe Val
        35                  40                  45
Ala Ser Ile Ser Trp Arg Gly Ser Tyr Thr Tyr Tyr Ser Asp Ser Val
    50                  55                  60
Lys Gly Arg Phe Thr Ile Ser Arg Asp Tyr Ala Glu Asn Thr Met Tyr
65                  70                  75                  80
Leu Gln Met Asn Ser Leu Lys Pro Glu Xaa Thr Gly Arg Tyr Tyr Cys
                85                  90                  95
Ala Thr Leu Thr Gly Asp Val Ser Val Gly Glu Tyr Asp Asn Arg Gly
            100                 105                 110
Gln Gly Thr Gln Val Thr Val Ser Ser Ala His His Ser Glu Asp Pro
        115                 120                 125
Ser

<210> SEQ ID NO 64
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (269)..(270)
<223> OTHER INFORMATION: a, c, t, g, unknown or other

<400> SEQUENCE: 64
caggtgcagc tggtggagtc cggtggaggc ttggtgcagg ctgggggtc tctgagactc      60
tcctgtgcag cctctggacg caccttcact agttatgcca tgggctggtt ccgccaggct    120
ccagggaagg agcgtgagtt tgtagcgtct attagctggc gcggtagtta cacatactat    180
tcagactccg tgaagggccg attcaccatc tccagagatt acgccgagaa cacgatgtat    240
ctgcaaatga acagcctgaa acctgaggnn acgggcagat attactgtgc aaccttaacc    300
ggcgacgtga gtgtcggcga gtatgacaac cggggccagg ggacccaggt cactgtctcc    360
tcagcgcacc acagcgaaga cccctcg                                        387

<210> SEQ ID NO 65
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Ser Val Gln Pro Gly Gly
1               5                   10                  15
Ser Leu Arg Leu Ser Cys Val Ala Ser Gly Phe Thr Phe Thr Asn Tyr
            20                  25                  30
Ala Met Ala Trp Val Arg Gln Val Ser Gly Lys Gly Leu Glu Gly Val
        35                  40                  45

Ala Ala Ile Ser Ser Glu Gly Phe Ile Tyr Ile Pro Asp Ser Val Lys
            50                  55                  60

Gly Arg Phe Thr Ile Ser Arg Asp Asn Ala Lys Asn Thr Val Tyr Leu
 65                  70                  75                  80

Gln Met Asp Asn Leu Gln Ser Glu Asp Thr Ala Ile Tyr His Cys Ala
                85                  90                  95

Ala Val Asp Trp Lys Arg Val Ala Ala Met Asn Ser Tyr Asn Met Asp
            100                 105                 110

Tyr Trp Gly Lys Gly Thr Pro Val Thr Val Ser Ala Glu Pro Lys Thr
                115                 120                 125

Pro Lys Pro Gln
    130

<210> SEQ ID NO 66
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
caggtgcagc tggtggagtc ggggggaggc tcggtgcagc tggggggtc tctgagactc      60 tcctgtgtag cctctggatt caccttcact aattacgcga tggcctgggt ccgccaggta    120
tcagggaagg ggctcgaggg tgtggccgct attagtagtg agggtttcat atatatccca    180
gactcagtga aggccgatt caccatctcc agagacaacg ccaagaacac ggtgtatcta    240
caaatggaca acctccagtc tgaggatacg gccatatatc actgtgcggc agttgattgg    300
aaacgggtcg ccgcgatgaa cagctacaac atggactact ggggaaaagg daccccggtc    360
accgtctccg cagaacccaa gacaccaaaa ccacaa                              396

<210> SEQ ID NO 67
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Leu Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu His Val
        35                  40                  45

Ala Ala Ile Ser Trp Ser Gly Gly Tyr Thr Tyr Tyr Ala Asn Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Asn Gly Val Gln Asp His Ser Asp Ser Leu Gln Asn Trp Gly Gln Gly
            100                 105                 110

Thr Gln Val Thr Val Ser Ser Glu Pro Lys Thr Pro Lys Pro Gln
        115                 120                 125

<210> SEQ ID NO 68
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
cagttgcagc tggtggagtc gggcggagga ttggtgcagg ctggggggtc tctgagactc      60
tcctgtgcag cctctggacg caccttcagt agctatgcca tgggctggtt ccgccaggct     120
ccagggaagg aacgtgagca tgtcgcagct attagctgga gtggtggtta cacatactat     180
gcaaactccg tgaagggccg attcaccatc tccagagaca acgccaagaa cacggtgtat     240
ctgcaaatga acagcctgaa acctgaggac acggccgtct attactgtaa tggagttcag     300
gaccatagcg actcccttca gaactggggc caggggaccc aggtcaccgt ctcctcagaa     360
cccaagacac aaaaccaca a                                                 381

<210> SEQ ID NO 69
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Leu Gln Leu Val Glu Thr Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Val Gly Trp Phe Arg Gln Ala Pro Gly Lys Glu Arg Glu Phe Val
        35                  40                  45

Ala Ala Ile Ser Trp Ser Gly Ser Tyr Ala Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Gly Asp Leu Glu Gly Tyr Ser Asn His Glu Thr Gly Asp Tyr Trp
            100                 105                 110

Gly Gln Gly Thr Gln Val Thr Val Ser Ser Glu Pro Lys Thr Pro Lys
        115                 120                 125

Pro Gln
    130

<210> SEQ ID NO 70
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
cagttgcagc tggtggagac gggaggagga ttggtgcagg ctggggggtc tctgagactc      60
tcctgtgcag cctctggacg caccttcagt agtatgccg tgggctggtt ccgccaggct     120
ccagggaagg agcgtgagtt tgtcgcagct attagctgga gtggtagtta cgcatactat     180

```
gcagactccg tgaagggccg attcaccatc tccagagaca acgccaagaa cacggtgtat    240
ctgcaaatga acagcctgaa acctgaggac acggccgtct attactgtaa tggagatctt    300
gagggttata gcaaccatga aaccggggac tactggggcc aggggaccca ggtcaccgtc    360
tcctcagaac ccaagacacc aaaaccacaa                                     390
```

```
<210> SEQ ID NO 71
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Leu Gln Leu Ala Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Thr Gly Gly Tyr Thr Tyr Ala Ser Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Asp Leu Glu Ser Tyr Ser Glu Tyr Pro Glu Ser Tyr Tyr Trp
            100                 105                 110

Gly Gln Gly Thr Gln Val Thr Val Ser Ser Glu Pro Lys Thr Pro Lys
        115                 120                 125

Pro Gln
    130
```

```
<210> SEQ ID NO 72
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cagttgcagc tggcggagtc gggaggagga ttggtgcagg ctggggggtc tctgagactc     60
tcctgtgcag cctctggacg caccttcagt agctatgcca tgggctggtt ccgccaggct    120
ccagggaagg agcgtgagtt tgtcgcagct attagctgga ctggtggtta cacatactat    180
gcaagctccg tgaagggccg attcaccatc tccagagaca atgccaaaaa cacgatgtat    240
ctgcaaatga acagcctgaa accggaggac acggccgtct attactgtaa tgcagattta    300
gaatcctata gcgagtatcc cgagagctac tactggggcc aggggaccca ggtcaccgtc    360
tcctcagaac ccaagacacc aaaaccacaa                                     390
```

```
<210> SEQ ID NO 73
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 73

Gln Val Gln Leu Ala Glu Ser Gly Gly Gly Leu Val Gln Ala Gly Gly
1               5                   10                  15

Ser Leu Thr Leu Ser Cys Ala Ala Ser Gly Leu Asn Phe Asp Lys Tyr
            20                  25                  30

Ala Ile Gly Trp Tyr Arg Gln Ala Pro Gly Lys Glu Arg Glu Gly Val
        35                  40                  45

Ser Cys Ile Ser Lys Tyr Tyr Asn His Arg Met Tyr Ser Asp Ser Val
50                  55                  60

Lys Gly Arg Phe Thr Val Ser Ser Asn Tyr Ala Lys Asn Thr Val Tyr
65                  70                  75                  80

Leu Gln Met Thr Asn Leu Lys Pro Glu Asp Thr Ala Val Tyr Tyr Cys
                85                  90                  95

Ala Ala Gly Cys Ile Asp Pro Glu Asp Trp Gly Gln Gly Thr Gln Val
            100                 105                 110

Thr Val Ser Ser Glu Pro Lys Thr Pro Lys Pro Gln
        115                 120

<210> SEQ ID NO 74
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtgcagc tggcggagtc ggggggaggc ttggtgcagg ctggggggtc tctgacactc     60
tcctgtgcag cctctggcct caatttcgat aaatatgcca taggctggta ccgccaggcc    120
ccagggaaag agcgtgaggg ggtttcatgt attagtaagt attacaatca tcggatgtat    180
agtgactccg tgaagggccg attcaccgtc tccagtaact atgccaagaa cacggtgtac    240
ctgcaaatga ccaatctgaa accggaggat acggccgttt attactgtgc ggcagggtgt    300
attgacccgg aagattgggg ccaggggacc caggtcaccg tctcctcaga acccaagaca    360
ccaaaaccac aa                                                        372

<210> SEQ ID NO 75
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Glu Thr Gly Gly Gly Gln Val Gln Thr Gly Gly
1               5                   10                  15

Ser Leu Arg Leu Ser Cys Ala Ala Ser Glu Pro Thr Phe Thr Pro Lys
            20                  25                  30

Val Val Gly Trp Phe Arg Gln Ala Pro Val Lys Glu Arg Asp Phe Val
        35                  40                  45

Ala Thr Ile Thr Ile Arg Thr Gly Arg Thr Leu Tyr Ala Asp Ser Val
50                  55                  60

Lys Gly Arg Phe Thr Ile Ser Gly Asp Gly Ala Asn Asn Thr Val Tyr
65                  70                  75                  80

Leu Gln Met Asn Gly Leu Lys Pro Glu Asp Thr Ala Val Tyr Tyr Cys

```
                85                  90                  95
Ala Ala Ser Leu Pro Leu Ala Ile Pro Pro Thr Gln Ala Ser Ala Tyr
            100                 105                 110

Glu Tyr Trp Gly Leu Gly Thr Gln Val Thr Val Ser Ser Glu Pro Lys
        115                 120                 125

Thr Pro Lys Pro Gln
        130

<210> SEQ ID NO 76
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
caggtgcagc tggtggagac cggggggaggc caggtgcaga ctgggggatc tctgagactc      60
tcttgcgcag cctctgaacc caccttcact ccgaaagttg tgggctggtt ccgccaggct     120
ccagtgaagg agcgtgactt tgtagcaact ataacaatcc gtaccggtcg cacactctat     180
gcagattccg tgaagggccg attcaccatc tccggagacg cgccaacaa tacggtgtat      240 ctacaaatga acggcctgaa acctgaggac acggccgttt attactgcgc cgcatctctt     300
ccgctagcaa taccaccgac gcaggcttcg gcatatgaat actggggcct ggggacccag     360
gtcaccgtct cctcagaacc caagacacca aaaccacaa                            399

<210> SEQ ID NO 77
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Glu Thr Gly Gly Gly Leu Val Gln Pro Gly Gly
1               5                   10                  15

Ser Leu Arg Leu Ser Cys Ser Val Ser Gly Leu His Phe Arg Phe Ala
            20                  25                  30

Asn Met Gly Trp Phe Arg Gln Ala Pro Gly Lys Gln Arg Glu Leu Val
        35                  40                  45

Ala Tyr Ile Thr Thr Gly Asp Asn Thr Asn Tyr Val Asp His Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Val Asn Ala Leu Gly Glu Phe Asn Pro Arg Asn Asp Trp Gly Gln
            100                 105                 110

Gly Thr Gln Val Thr Val Ser Ser Glu Pro Lys Thr Pro Lys Pro Gln
        115                 120                 125

<210> SEQ ID NO 78
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 78

```
caggtgcagc tggtggagac gggggaggc ttggtgcagc tggggggtc tctgagactc    60
tcctgttcag tctctggcct ccacttcagg ttcgcgaaca tgggatggtt tcgccaggct   120
ccagggaagc agcgcgagtt ggtcgcatat attactactg gtgataacac taactatgta   180
gaccacgtga agggccgatt caccatctcc agagacaacg ccaagaacac ggtgtatctg   240
caaatgaaca gcctgaaacc tgaagacacg gccgtctact actgtaatat agtcaatgcg   300
ctgggggagt tcaatccccg aaacgactgg ggccagggga cccaggtcac cgtctcctca   360
gaacccaaga caccaaaacc acaa                                         384
```

<210> SEQ ID NO 79
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Gln Val Gln Leu Val Glu Thr Gly Gly Gly Trp Val Gln Ala Gly Gly
1               5                   10                  15

Ser Leu Arg Leu Ser Cys Ala Ala Ser Gly Arg Ala Ala Ser Gly Asn
            20                  25                  30

Ala Met Ala Trp Phe Arg Gln Ala Pro Gly Lys Glu Arg Glu Phe Val
        35                  40                  45

Ala Leu Ile Ser Trp Ser Gly Gly Arg Pro Tyr Tyr Ala Asn Ser Val
    50                  55                  60

Lys Gly Arg Phe Ala Ile Ser Arg Asp Asn Ala Thr Asn Thr Val Tyr
65                  70                  75                  80

Leu Gln Met Asn Arg Leu Lys Pro Glu Asp Thr Ala Val Tyr Tyr Cys
                85                  90                  95

Ala Ala Ser Pro Thr Ile Ala Ile Leu Pro Thr Pro Tyr Asp Tyr Trp
            100                 105                 110

Gly Gln Gly Thr Gln Val Thr Val Ser Ser Glu Pro Lys Thr Pro Lys
        115                 120                 125

Pro Gln
    130
```

<210> SEQ ID NO 80
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
caggtgcagc tggtggagac gggtggggg tgggtacagg ctgggggctc tctgagactc    60
tcctgtgcag cctctggacg cgccgccagt ggaaatgcca tggcctggtt ccgccaggct   120
ccaggaaagg agcgtgagtt tgtagcattg attagttgga gtggtggtcg cccatactat   180
gcaaactccg tgaagggccg attcgccatc tccagagaca cgccacgaa tacggtgtat   240
ctgcaaatga acagactgaa acctgaggac acggccgttt attactgtgc agcgtcgcct   300
accatagcga tactacctac tccgtatgac tactgggggcc aggggaccca ggtcaccgtc   360
tcctcagaac ccaagacacc aaaaccacaa                                   390
```

<210> SEQ ID NO 81
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Glu Thr Gly Gly Gly Leu Val Gln Ala Gly Ala
1               5                   10                  15

Ser Leu Arg Leu Ser Cys Ala Ala Ser Gly Arg Thr Phe Ser Thr Asp
            20                  25                  30

His Met Gly Trp Phe Arg Gln Ala Pro Gln Lys Glu Arg Glu Phe Val
        35                  40                  45

Ala Ala Ile Asn Ala Trp Ser Gly Leu Ser Ile Tyr Tyr Ala Asp Ser
    50                  55                  60

Val Lys Gly Arg Phe Thr Ile Ser Arg Asp Asn Asp Lys Lys Thr Ala
65                  70                  75                  80

Tyr Leu Gln Met Asn Ser Leu Lys Pro Glu Asp Thr Ala Val Tyr Tyr
                85                  90                  95

Cys Ala Ala Lys Glu Met Gly Arg Gly Trp Val Pro Gln Ser Ser Asp
            100                 105                 110

Asp Tyr Asp Ala Trp Gly Gln Gly Thr Gln Val Thr Val Ser Ser Glu
        115                 120                 125

Pro Lys Thr Pro Lys Pro Gln
    130                 135

<210> SEQ ID NO 82
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caggtgcagc tggtggagac ggggggagga ttggtgcagg ctggggcctc tctgagactc      60
tcctgtgcag cctctggacg cacctttcagt accgatcaca tgggctggtt ccgccaggct    120
ccacagaagg agcgtgagtt tgtggcagca ataaatgcat ggagtggact cagcatttac    180
tatgcagact ccgtgaaggg ccgattcacc atctccagag acaacgacaa gaaaacggca    240
tatctacaaa tgaacagcct gaaacctgag gacacggccg tttattactg tgcagccaag    300
gagatgggta ggggttgggt gccacagagc tcagacgact atgacgcctg gggccagggg    360
acccaggtca ccgtctcctc agaacccaag acaccaaaac cacaa                    405

<210> SEQ ID NO 83
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Glu Thr Gly Gly Gly Leu Val Gln Ala Gly Gly
1               5                   10                  15

Ser Leu Arg Leu Ser Cys Ala Val Ser Gly Arg Thr Phe Ser Ser Tyr

```
                20                  25                  30
Ala Met Ala Trp Phe Arg Gln Ala Pro Gly Lys Glu Arg Asp Phe Val
            35                  40                  45

Ala Ala Ile Ser Trp Ser Gly Gly Ala Pro His Tyr Glu Asp Ser Val
        50                  55                  60

Lys Gly Arg Phe Thr Ile Ser Arg Asp Asn Ala Lys Asn Met Val Tyr
65                  70                  75                  80

Leu Gln Met Asn Ser Leu Lys Pro Asp Asp Thr Ala Val Tyr Tyr Cys
                85                  90                  95

Ala Ala Ala Lys Ala Gly Tyr Tyr Ser Gly Ser Tyr Tyr Val Gly Gly
            100                 105                 110

Gly Met Tyr Asp Tyr Trp Gly Gln Gly Thr Gln Val Thr Val Ser Ser
            115                 120                 125

Glu Pro Lys Thr Pro Lys Pro Gln
            130                 135

<210> SEQ ID NO 84
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caggtgcagc tggtggagac tggaggagga ttggtgcagg ctgggggctc tctgagactc      60
tcctgtgcag tctctggacg caccttcagt agctatgcca tggcctggtt ccgccaggct     120
ccagggaagg agcgtgattt tgtagcagct attagctgga gtggtggtgc cccacactat     180
gaagactccg tgaagggccg attcaccatc tccagagaca cgccaagaa catggtatat     240 ctccaaatga acagcctgaa acctgacgac acggccgttt actactgtgc agcagcgaaa     300
gcaggatact atagtggtag ttactacgtg ggggggggta tgtatgacta ctggggccag     360
gggacccagg tcaccgtctc ctcagaaccc aagacaccaa aaccacaa                  408

<210> SEQ ID NO 85
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Glu Thr Gly Gly Gly Leu Val Gln Ala Gly Gly Ser
1               5                   10                  15

Leu Arg Leu Ser Cys Ala Ala Ser Gly Ser Ile Gly Arg Val Asp Asn
            20                  25                  30

Met Gly Trp Tyr Arg Gln Thr Pro Gly Lys Glu Arg Glu Arg Val Ala
        35                  40                  45

Ile Ile Thr Gly Gly Gly Thr Ala Ile Tyr Ala Asp Thr Val Lys Gly
    50                  55                  60

Arg Phe Thr Val Ser Arg Asp Asn Ala Lys Asn Thr Ile Tyr Leu Gln
65                  70                  75                  80

Met Asn Ser Val Lys Pro Glu Asp Thr Ala Val Tyr Phe Cys Asn Ala
                85                  90                  95

Asp Ile Ser Arg Ser Ile Glu Ser Ile Val Tyr Arg Ser Tyr Trp Gly
            100                 105                 110
```

Gln Gly Thr Gln Val Thr Val Ser Ser Glu Pro Lys Thr Pro Lys Pro
            115                 120                 125

Gln

<210> SEQ ID NO 86
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caggtgcagc tggtggagac aggaggcttg gtgcaggctg gggggtctct gagactctcc      60
tgtgcagcct ccggaagcat cggcagggtc gataacatgg gctggtaccg ccaaactcca     120
gggaaagagc gcgagcgggt cgcaatcatt actggaggcg gtaccgcgat ctatgcagac     180
accgtgaagg gccgattcac cgtctccaga gacaacgcca agaacacaat atatctacaa     240
atgaacagcg tgaaacctga ggacacagcc gtctatttct gtaatgccga catcagtcgt     300
agtattgagt ccatcgtcta tcgttcctac tggggccagg ggacccaggt caccgtctcc     360
tcagaaccca agacaccaaa accacaa                                          387

<210> SEQ ID NO 87
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Glu Thr Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Asn Ser Gly Ser Thr Asn Tyr Glu Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Phe Asp Leu Val Ala Gly Thr Arg Leu Gly Ser Trp Gly Gln Gly
            100                 105                 110

Thr Gln Val Thr Val Ser Ser Glu Pro Lys Thr Pro Lys Pro Gln
        115                 120                 125

<210> SEQ ID NO 88
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
caggtgcagc tggtggagac ggggggaggc ttggtgcagc tggggggtc tctgagactc       60

```
tcctgtgcag cctctggaaa catcttcagt atcaatgcca tgggctggta ccgccaggct    120
ccagggaagc agcgcgagtt ggtcgcagct attagtaata gtggtagcac aaactatgaa    180
gactccgtga agggccgatt caccgtctcc agagacaacg ccaagaacac ggtgtatctg    240
caaatgaaca gcctgaaacc tgaggacacg gccgtctatt actgtaatgc cttcgattta    300
gtagctggta ctaggctggg gtcctggggc caggggaccc aggtcaccgt ctcctcggaa    360
cccaagacac aaaaccaca a                                               381
```

```
<210> SEQ ID NO 89
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Leu Glu His Ala
            20                  25                  30

Ala Val Gly Trp Phe Arg Gln Ala Pro Gly Lys Glu Arg Glu Gly Val
        35                  40                  45

Ser Cys Ile Ser Ser Arg Asp Ser Asn Thr Tyr Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Thr Asp Val Pro Cys Trp Asp Gly Ser Asn Trp Ser Leu Gly His
            100                 105                 110

Glu Tyr Asp Tyr Trp Gly Gln Gly Thr Gln Val Thr Val Ser Ser Glu
        115                 120                 125

Pro Lys Thr Pro Lys Pro Gln
    130                 135
```

```
<210> SEQ ID NO 90
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
caggtgcagc tggtggagtc gggggggaggc ttggtgcagc ctggggggtc tctgagactc     60
tcctgtgcag cctctgaatt cactttggaa catgccgccg taggctggtt ccgccaggcc    120
ccagggaagg agcgcgaggg ggtctcttgt attagtagtc gtgatagtaa cacatactat    180
gcagactccg tgaagggccg attcaccatc tccagagaca atgccgaaaa cacggtatat    240
ctgcaaatga acagcctgaa acctgaggac acggccgttt attactgtgc gacagatgtc    300
ccctgctggg acggtagtaa ctggtccctc ggtcatgagt atgactactg gggccagggg    360
acccaggtca ccgtctcctc agaacccaag acaccaaaac acaa                     405
```

```
<210> SEQ ID NO 91
<211> LENGTH: 131
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 91

Gln Val Gln Leu Val Glu Thr Gly Gly Gly Leu Val Gln Pro Gly Gly
1               5                   10                  15

Ser Leu Arg Leu Ser Cys Ala Ala Ser Gly Ser Ile Ser Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ile Arg Gly Asn Thr Val Tyr Gly Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Ser Thr Pro Ser Leu Tyr Ala Ala Gly Tyr Gly Val Asp Tyr
            100                 105                 110

Trp Gly Glu Gly Thr Leu Val Thr Val Ser Ser Glu Pro Lys Thr Pro
        115                 120                 125

Lys Pro Gln
    130

<210> SEQ ID NO 92
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
caggtgcagc tggtggagac ggggggaggc ttggtgcagc ctggggggtc tctgagactc      60
tcctgtgcag cctctggaag catctccagt atcaatgcca tgggctggta ccgccaggct     120
ccagggaagc agcgcgagtt ggtcgcggct attactattc gtggtaacac agtctatgga     180
gactccgtga agggccgatt caccgtctcc agagacaacg ccaagaacac ggtgtatctg     240
caaatgaaca gcctgaaacc tgaggacacg gccgtctatt actgtaatgc caagtcgacc     300
ccgagcttgt acgccgccgg ctacggcgtg gactactggg gcgaagggac cctagtcacc     360
gtctcctcag aacccaagac accaaaacca caa                                  393

<210> SEQ ID NO 93
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Gln Val Gln Leu Val Glu Thr Gly Gly Gly Leu Val Gln Ala Gly Gly
1               5                   10                  15

Ser Leu Arg Leu Ser Cys Ala Ala Ser Gly Asn Ile Ser Ser Ile Asn
            20                  25                  30

Ala Met Ala Trp Tyr Arg Gln Ala Pro Gly Gln Gln Arg Glu Leu Val
        35                  40                  45

```
Ala Gly Ile Thr Ser Gly Gly Arg Thr Gln Tyr Thr Asp Ser Val Lys
    50                  55                  60

Gly Arg Phe Thr Ile Ser Arg Asp Asn Ala Lys Asn Thr Val Tyr Leu
 65                  70                  75                  80

Gln Met Glu Ser Leu Lys Pro Glu Asp Thr Ala Val Tyr Tyr Cys Asn
                 85                  90                  95

Ala Lys Ser Pro Pro Ser Thr Trp Ala Thr Gly Gly Met Asn Tyr
            100                 105                 110

Trp Gly Lys Gly Thr Leu Val Thr Val Ser Ser Glu Pro Lys Thr Pro
        115                 120                 125

Lys Pro Gln
    130

<210> SEQ ID NO 94
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
caggtgcagc tggtggagac ggggggaggc ttggtgcagg ctggggggtc tctgagactc      60
tcctgtgcag cctctgggaa catctccagt atcaatgcca tggcctggta ccgccaggct     120
ccagggcagc agcgcgagct ggtcgcaggg attactagtg gtggcaggac acaatataca     180
gactccgtga aggccgatt caccatctcc agagacaacg ccaagaacac ggtgtatctg      240
caaatggaga gtctgaaacc tgaggacaca gccgtctatt actgtaatgc aaaaagccct     300
cccagtacct gggccacggg gggggcatg aactactggg gcaaagggac cctggtcacc      360
gtctcctcag aacccaagac accaaaacca caa                                  393

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Glu Thr Gly Gly Ala Leu Val Gln Ala Gly Gly
 1               5                  10                  15

Ser Leu Arg Leu Ser Cys Ala Ala Ser Glu Thr Ser Ser Val Ser Leu
            20                  25                  30

Ser Trp Met Gly Trp Tyr Arg Gln Ala Pro Gly Lys Glu Arg Glu Leu
        35                  40                  45

Val Ala Gly Ile Asn Arg Asp Arg Pro Lys Tyr Lys Glu Ser Val Lys
    50                  55                  60

Gly Arg Phe Thr Ile Ser Arg Asp Asn Ala Gln Asn Thr Val Tyr Leu
 65                  70                  75                  80

Gln Met Asn Ser Leu Lys Pro Glu Asp Thr Ala Val Tyr Tyr Cys Asn
                 85                  90                  95

Thr Val Pro Pro Arg Gly Asp Tyr Trp Gly Gln Gly Thr Gln Val Thr
            100                 105                 110

Val Ser Ser Glu Pro Lys Thr Pro Lys Pro Gln
        115                 120
```

<210> SEQ ID NO 96
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
caggtgcagc tggtggagac aggaggagcc ttggtgcagg cggggggtc tctgagactc      60
tcctgtgcag cctctgagac atcttcagta tcgctatcat ggatgggctg gtaccgccag    120
gctcctggga aggagcgcga gttggtcgca ggcattaatc gtgataggcc aaagtataaa    180
gagtccgtga agggccgatt caccatctcc agagacaacg cccagaatac ggtgtatctg    240
caaatgaaca gcctgaaacc tgaggacaca gccgtctatt actgtaatac ggttccacca    300
cgcggcgact actggggcca ggggacccag gtcaccgtct cctcagaacc caagacacca    360
aaaccacaa                                                             369
```

<210> SEQ ID NO 97
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Gln Val Gln Leu Val Glu Ser Gly Gly Gly Leu Val Gln Pro Gly Gly
1               5                   10                  15
Ser Leu Arg Val Ser Cys Val Ala Ser Gly Asn Ile Ser Ser Val Ala
            20                  25                  30
Ala Met Ala Trp Tyr Arg Gln Arg Pro Glu Lys Arg Arg Glu Leu Val
        35                  40                  45
Ala Val Ile Thr Asn Ser Gly Gly Thr Ala Tyr Thr Asp Ser Val Arg
    50                  55                  60
Gly Arg Phe Thr Ile Ser Arg Asp Asn Val Lys Ser Thr Val Tyr Leu
65                  70                  75                  80
Gln Met Asn Asn Leu Lys Pro Glu Asp Thr Ala Val Tyr Tyr Cys Asn
                85                  90                  95
Ala Arg Gly Leu Asp Ala Gly Ser Gly Arg Ile Asp Tyr Trp Gly Gln
            100                 105                 110
Gly Thr Gln Val Thr Val Ser Ser Glu Pro Lys Thr Pro Lys Pro Gln
        115                 120                 125
```

<210> SEQ ID NO 98
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
caggtgcagc tggtggagtc cggtggaggc ttggtgcagc tggggggtc tctgagagtc      60
tcctgtgtag cctctggaaa catctccagt gtcgctgcca tggcctggta ccgccagaga    120
ccagagaagc gccgcgaatt ggtcgcagtc attactaaca gcggtggcac agcctataca    180
gactccgtga ggggccgatt caccatctcc agagacaatg tcaagtcaac ggtgtatcta    240
caaatgaata acctgaaacc tgaggacaca gccgtgtatt actgtaatgc gaggggggtta    300
```

```
gacgccgggt cagggcgcat tgactactgg ggccagggaa cccaggtcac cgtctcctca    360
gaacccaaga caccaaaacc acaa                                            384
```

<210> SEQ ID NO 99
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Gln Val Gln Leu Val Glu Ser Gly Gly Gly Leu Ala Gln Thr Gly Gly
1               5                  10                  15

Ser Leu Asn Leu Ser Cys Ala Ala Ser Gly Pro Thr Phe Ser Gly Tyr
            20                  25                  30

Gly Met Gly Trp Phe Arg Gln Ala Pro Gly Lys Glu Arg Glu Phe Leu
        35                  40                  45

Ala Val Ile Arg Trp Ser Val Gly Asn Thr Leu Tyr Ala Glu Ser Val
    50                  55                  60

Lys Gly Arg Phe Thr Ile Ser Arg Asp Lys Val Lys Asn Thr Gly Tyr
65                  70                  75                  80

Leu Gln Ile Asp Asn Leu Lys Pro Glu Asp Thr Ala Val Tyr Tyr Cys
                85                  90                  95

Ala Ala Gly Ala Tyr Val Thr Thr Arg Ser Arg Asp Tyr Ala Tyr Trp
            100                 105                 110

Gly Gln Gly Thr Gln Val Thr Val Ser Ser Glu Pro Lys Thr Pro Lys
        115                 120                 125

Pro Gln
    130
```

<210> SEQ ID NO 100
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
caggtgcagc tggtggagtc ggggggagga ttggcgcaga ctgggggctc tctgaacctc    60
tcctgtgcag cctctggacc gactttcagc ggctatggta tgggctggtt ccgccaggct    120
ccagggaagg agcgtgaatt tctagcggta attcgctgga gtgtaggtaa tacattgtat    180
gcagagtccg tcaagggccg attcaccatc tccagagaca aggtcaagaa cacgggtat    240 ctgcaaatag acaacctgaa acccgaggac acggccgttt attactgtgc agcggggcg    300 tacgtaacta cgaggtcccg cgactatgcc tactggggcc aggggaccca ggtcaccgtc    360
tcctcagaac ccaagacacc aaaaccacaa                                     390
```

<210> SEQ ID NO 101
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Glu Thr Gly Gly Arg Gln Val Thr Gly Asp
1               5                   10                  15

Ser Leu Asn Leu Ser Cys Ala Ala Ser Glu His Thr Phe Ser Pro Lys
            20                  25                  30

Val Met Gly Trp Phe Arg Gln Ala Pro Gly Lys Gly Arg Glu Phe Val
        35                  40                  45

Ala Thr Ile Thr Ile Arg Gly Gly Arg Thr Leu Tyr Ala Asp Ser Val
    50                  55                  60

Lys Gly Arg Phe Ala Ile Ser Lys Asp Gly Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Arg Glu Leu Ala Ile Pro Pro Thr Gln Pro Ser Ala Tyr
            100                 105                 110

Asp His Trp Gly Gln Gly Thr Gln Val Thr Val Ser Ser Ala His His
        115                 120                 125

Ser Glu Asp Pro Ser
    130

<210> SEQ ID NO 102
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
caggtgcagc tcgtggagac cggcggacgt caggtgcaga ctggggactc tctgaacctc      60
tcttgcgcag cttctgaaca caccttcagt cctaaagtta tggggtggtt ccgccaggct     120
ccaggcaagg ggcgtgagtt tgtagcaact atcacaatcc gtggcggtcg cacactctat     180
gcagattccg tgaagggccg atttgccatc tccaaagacg gcgccaagaa tacggtgtat     240
ctgcaaatga acagtctgaa acctgaggac acggccgttt attactgtgc agcaagtcgt     300
gagctagcga taccaccgac gcagccttcg catacgacc actggggcca ggggacccag     360
gtcaccgtct cctcagcgca ccacagcgaa gacccctcg                            399

<210> SEQ ID NO 103
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Ala Glu Ser Gly Gly Gly Leu Val Gln Pro Gly Gly
1               5                   10                  15

Ser Leu Gly Leu Ser Cys Val Val Ala Ser Glu Arg Ser Ile Asn Asn
            20                  25                  30

Tyr Gly Met Gly Trp Tyr Arg Gln Ala Pro Gly Lys Gln Arg Glu Leu
        35                  40                  45

Val Ala Gln Ile Ser Ser Gly Gly Thr Thr Asn Tyr Ala Asp Ser Val
    50                  55                  60

Glu Gly Arg Phe Thr Ile Ser Arg Asp Asn Val Lys Lys Met Val His
65                  70                  75                  80

Leu Gln Val Asn Ser Leu Lys Pro Glu Asp Thr Ala Val Tyr Tyr Cys 85                  90                  95
Asn Ser Leu Leu Arg Thr Phe Ser Trp Gly Gln Gly Thr Gln Val Thr
                    100                 105                 110

Val Ser Ser Glu Pro Lys Thr Pro Lys Pro Gln Ala Ile Ala Gly Gly
                115                 120                 125

Gly Gly Ser Gly Gly Gly Ser Gly Gly Gly Ser Leu Gln Gly
        130                 135                 140

Gln Val Gln Leu Val Glu Ser Gly Gly Leu Val Gln Pro Gly Gly
145                 150                 155                 160

Ser Leu Ser Val Ser Cys Ala Ala Ser Gly Ser Ile Ala Arg Pro Gly
                165                 170                 175

Ala Met Ala Trp Tyr Arg Gln Ala Pro Gly Lys Glu Arg Glu Leu Val
                180                 185                 190

Ala Ser Ile Thr Pro Gly Gly Leu Thr Asn Tyr Ala Asp Ser Val Thr
                195                 200                 205

Gly Arg Phe Thr Ile Ser Arg Asp Asn Ala Lys Arg Thr Val Tyr Leu
            210                 215                 220

Gln Met Asn Ser Leu Gln Pro Glu Asp Thr Ala Val Tyr Tyr Cys His
225                 230                 235                 240

Ala Arg Ile Ile Pro Leu Gly Leu Gly Ser Glu Tyr Arg Asp His Trp
                245                 250                 255

Gly Gln Gly Thr Gln Val Thr Val Ser Ser Ala His His Ser Glu Asp
            260                 265                 270

Pro Ser

<210> SEQ ID NO 104
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
caggtgcagc tggcggagtc gggcggaggc ttggtgcagc tgggggggtc tctgggactc      60
tcctgtgtag tcgcctctga agaagcatc aataattatg catgggctg gtaccgccag     120
gctccaggga agcagcgcga gttggtcgcg caaattagta gtggtggtac acaaattat     180
gcagactccg tagagggccg attcaccatc tccagagaca cgtcaagaa aatggtgcat     240
cttcaagtga acagcctgaa acctgaggac acggccgtct attactgtaa ttcgctactc     300
cgaactttttt cctggggcca ggggacccag gtcaccgtct cctcggaacc caagacacca     360
aaaccacaag cgatcgctgg tggaggcggt tcaggcggag gtggctctgg cggtggcggt     420
tccctgcagg gtcagktgca gctsgyggag tccgggggcg gcttggtgca gccgggggg     480
tctctgagtg tctcctgtgc agcctctgga agcatcgcaa gaccaggtgc catggcctgg     540
taccgccagg ctccagggaa ggagcgcgag ttggtcgcgt ctattacgcc tggtggtctt     600
acaaactatg cggactccgt gacgggccga ttcaccattt ccagagacaa cgccaagagg     660
acggtgtatc tgcagatgaa cagcctccaa cccgaggaca cggccgtcta ttactgtcat     720
gcacgaataa ttcccctagg acttgggtcc gaatacaggg accactgggg ccaggggact     780
caggtcaccg tctcctcagc gcaccacagc gaagacccct cg                       822

<210> SEQ ID NO 105
<211> LENGTH: 286

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Ala Glu Ser Gly Gly Gly Leu Val Gln Pro Gly Gly
1               5                   10                  15

Ser Leu Gly Leu Ser Cys Val Val Ala Ser Glu Arg Ser Ile Asn Asn
            20                  25                  30

Tyr Gly Met Gly Trp Tyr Arg Gln Ala Pro Gly Lys Gln Arg Glu Leu
        35                  40                  45

Val Ala Gln Ile Ser Ser Gly Thr Thr Asn Tyr Ala Asp Ser Val
    50                  55                  60

Glu Gly Arg Phe Thr Ile Ser Arg Asp Asn Val Lys Lys Met Val His
65                  70                  75                  80

Leu Gln Val Asn Ser Leu Lys Pro Glu Asp Thr Ala Val Tyr Tyr Cys
                85                  90                  95

Asn Ser Leu Leu Arg Thr Phe Ser Trp Gly Gln Gly Thr Gln Val Thr
            100                 105                 110

Val Ser Ser Glu Pro Lys Thr Pro Lys Pro Gln Ala Ile Ala Gly Gly
        115                 120                 125

Gly Gly Ser Gly Gly Gly Ser Gly Gly Gly Ser Leu Gln Gly
    130                 135                 140

Gln Val Gln Leu Ala Glu Ser Gly Gly Gly Leu Val Gln Ala Gly
145                 150                 155                 160

Gly Ser Leu Arg Leu Ser Cys Ala Ala Ser Gly Arg Thr Phe Ser Gly
                165                 170                 175

Tyr Ala Met Gly Trp Phe Arg Gln Ala Pro Gly Lys Glu Arg Glu Phe
            180                 185                 190

Val Ala Asp Ile Ser Trp Ser Gly His Asn Thr Tyr Tyr Gly Asp Ser
        195                 200                 205

Val Lys Gly Arg Phe Thr Ile Ser Arg Asp Thr Ala Lys Asn Thr Val
    210                 215                 220

Tyr Leu Gln Met Asn Ser Leu Lys Pro Glu Asp Thr Ala Val Tyr Tyr
225                 230                 235                 240

Cys Ala Ala Glu Gly Ala Arg Thr His Leu Ser Asp Ser Tyr Tyr Phe
                245                 250                 255

Pro Gly Leu Trp Ala Glu Pro Val Gly Tyr Trp Gly Gln Gly Thr
            260                 265                 270

Gln Val Thr Val Ser Ser Glu Pro Lys Thr Pro Lys Pro Gln
        275                 280                 285

<210> SEQ ID NO 106
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
caggtgcagc tggcggagtc gggcggaggc ttggtgcagc ctgggggtc tctgggactc        60 tcctgtgtag tcgcctctga agaagcatc aataattatg catgggctg gtaccgccag        120 gctccaggga agcagcgcga gttggtcgcg caaattagta gtggtggtac cacaaattat      180

-continued

```
gcagactccg tagagggccg attcaccatc tccagagaca acgtcaagaa aatggtgcat      240
cttcaagtga acagcctgaa acctgaggac acggccgtct attactgtaa ttcgctactc      300 cgaactttt cctggggcca ggggacccag gtcaccgtct cctcggaacc caagacacca      360
aaaccacaag cgatcgctgg tggaggcggt tcaggcggag gtggctctgg cggtggcggt      420
tccctgcagg gtcaggtgca gctcgcggag tcgggtgggg aggactggt gcaggctggg      480 ggctctctga gactcctg tgcagcctct ggacgcacct tcagtggcta tgccatgggc       540
tggttccgcc aggctccggg gaaggagcgt gagtttgtag ccgatattag ctggagtggt      600
cataacacgt actatggaga ctccgtgaag ggccgattca ccatctccag agacaccgcc      660
aagaacacgg tgtatctgca aatgaacagc ctgaaacctg aggacacggc cgtttattac      720
tgtgcagcgg agggggcccg tacacacctt agtgatagtt actacttccc gggcctctgg      780
gccgaacccc ccgtgggcta ctggggccag gggacccagg tcactgtctc ctcagaaccc      840
aagacaccaa aaccacaa                                                    858
```

<210> SEQ ID NO 107
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Gln Val Gln Leu Val Glu Ser Gly Gly Gly Ser Val Gln Ala Gly Gly
 1               5                  10                  15

Ser Leu Arg Leu Thr Cys Thr Gly Ser Gly Arg Ser Phe Ala Leu Tyr
            20                  25                  30

Tyr Met Ala Trp Phe Arg Gln Ala Pro Gly Lys Glu Arg Glu Phe Val
        35                  40                  45

Ala Ala Ile Ser His Asn Ser Leu Ser Ala Ile Val Ala Asp Ser Leu
    50                  55                  60

Lys Gly Arg Phe Thr Ile Ser Arg Asp Asn Ala Arg Asn Gln Val Val
65                  70                  75                  80

Leu Gln Met Asn Ser Leu Lys Pro Glu Asp Thr Ala Val Tyr Tyr Cys
                85                  90                  95

Ala Ala Asp Phe Ser Pro Ser Thr Tyr Asn Thr Asn Tyr Tyr Arg Thr
               100                 105                 110

Gly Ser Tyr Gln Tyr Trp Gly Gln Gly Thr Gln Val Thr Val Ser Ser
           115                 120                 125

Glu Pro Lys Thr Pro Lys Pro Gln
       130                 135
```

<210> SEQ ID NO 108
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
caggtgcagc tggtggagtc ggggggagga tcggtgcagg ctggggctc tctgagactc       60 acctgtacag gctctggacg cagtttcgcg ctctattaca tggcctggtt ccgccaggct     120
ccagggaagg agcgtgagtt tgtagcagct atcagccaca attcgttaag cgcaatcgtt     180
```

```
gcagactccc taaagggccg attcaccatc tccagagaca acgccagaaa ccaggtggtt    240
ctacaaatga acagcctgaa acctgaggac acggccgttt attactgtgc agcagacttt    300
tcgccctcga cctataatac aaattactac cgcaccggtt cgtatcagta ttggggccag    360
gggacccagg tcaccgtctc ctcagaaccc aagacaccaa aaccacaa               408
```

<210> SEQ ID NO 109
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Gln Val Gln Leu Val Glu Thr Gly Gly Gly Leu Val Gln Ala Gly Gly
1               5                   10                  15

Ser Leu Gly Leu Ser Cys Ala Ala Ser Gly Leu Ser Phe Asn Trp Tyr
            20                  25                  30

Asp Val Gly Trp Phe Arg Gln Ala Pro Gly Lys Glu Arg Glu Phe Val
        35                  40                  45

Ala Ser Arg Ser Ser Gly Gly Gly Ser Thr Tyr Tyr Gly Asp Ser Val
    50                  55                  60

Lys Gly Arg Phe Ser Ile Ser Thr Asp Asn Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Asp Trp Thr Gly Arg Ala Gly Phe Ser Val Gly Tyr Tyr Arg
            100                 105                 110

Pro Asp Glu Tyr Asp Tyr Trp Gly Gln Gly Thr Gln Val Thr Val Ser
        115                 120                 125

Glu Glu Pro Lys Thr Pro Lys Pro Gln
    130                 135
```

<210> SEQ ID NO 110
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
caggtgcagc tggtggagac gggaggagga ttggtgcagg ctgggggctc tctgggactc     60
tcctgtgcag cctctggact gtcctttaat tggtatgacg tgggctggtt ccgccaggct    120
ccagggaagg agcgtgagtt tgtagcgtct cgtagctcgg gtggtggtag tacatattat    180
ggagactccg tgaagggccg attcagcatc tccacagaca atgccaagaa cacggcgtat    240
ctgcaaatga acagcctaaa acctgaggac acggccgttt actactgtgc agcagattgg    300
acaggccgcg caggcttcag tgttggttac taccggcccg atgagtatga ctactggggc    360
cagggacccc aggtcaccgt ctccgaagaa cccaagacac caaaaccaca a             411
```

<210> SEQ ID NO 111
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Glu Thr Gly Gly Gly Leu Val Gln Pro Gly Gly
1               5                   10                  15

Ser Leu Arg Leu Ser Cys Val Ala Ser Gly Phe Thr Leu Asp Ser Tyr
            20                  25                  30

Ala Ile Gly Trp Phe Arg Gln Ala Pro Gly Lys Glu Arg Glu Gly Val
        35                  40                  45

Ser Cys Met Ser Ser Gly Asp Gly Ser Thr Tyr Tyr Thr Asn Ser Val
    50                  55                  60

Lys Gly Arg Phe Thr Ile Ser Arg Asp Asn Ala Gln Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gly Phe Asp Tyr Cys Ser Ala Tyr Val Pro Gly Arg Gly
            100                 105                 110

Met Asn Tyr Ser Gly Lys Gly Thr Leu Val Thr Val Ser Ser Glu Pro
        115                 120                 125

Lys Thr Pro Lys Pro Gln
    130

<210> SEQ ID NO 112
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
caggtgcagc tggtggagac ggggggaggc ttggtgcagc ctggggggtc tctgagactc      60
tcctgtgtag cctctggatt cactttggat tcatatgcca taggctggtt ccgccaggcc     120
ccagggaagg agcgtgaggg ggtctcatgt atgagtagtg gtgatggtag cacatactat     180
acaaactccg tgaagggccg attcaccatc tccagagaca acgcccagaa cacggtgtat     240
ctgcaaatga acagcctgaa acctgaggac acagccgttt attactgtgc agcagatggg     300
tttgactatt gttcagctta tgtgcccggg agaggcatga actactcggg caaagggacc     360
ctggtcaccg tctcctcaga acccaagaca ccaaaaccac aa                        402

<210> SEQ ID NO 113
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Glu Thr Gly Gly Gly Leu Val Gln Pro Gly Gly
1               5                   10                  15

Ser Leu Arg Leu Ser Cys Ala Gly Ser Gly Phe Thr Leu Asp Asn Tyr
            20                  25                  30

Ala Val Gly Trp Phe Arg Gln Ala Pro Gly Lys Glu Arg Glu Gly Val
        35                  40                  45

Ser Cys Ile Ser Ser Ser Asp Asp Asn Thr Asp Tyr Ser Asp Ser Val
    50                  55                  60

Lys Gly Arg Phe Thr Ile Ser Arg Asp Asn Ala Lys Asp Thr Val Tyr

```
                65                  70                  75                  80
Leu Gln Met Asn Ser Leu Lys Pro Glu Asp Thr Ala Ile Tyr Tyr Cys
                    85                  90                  95

Ala Ala Glu Ser Pro Thr Phe Gly Phe Ser Cys Thr Val Ala Thr Asp
                100                 105                 110

Pro Tyr Asp Tyr Trp Gly Gln Gly Thr Gln Val Thr Val Ser Ser Glu
            115                 120                 125

Pro Lys Thr Pro Lys Pro Gln
        130                 135

<210> SEQ ID NO 114
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
caggtgcagc tggtggagac gggtggaggc ttggtgcagc ctgggggggtc tctgagactc      60 tcctgtgcag gctctggatt cactttggat aattatgccg tcggctggtt ccgccaggcc     120
ccagggaagg agcgtgaggg ggtctcatgt attagtagta gtgatgataa cactgactat     180
tcagactccg tgaagggccg attcaccatc tccagagaca cgccaagga cacggtctat     240 ctgcaaatga acagcctgaa acctgaggac acagcgattt attactgtgc agcagaaagc     300
ccgacgttcg ggttcagctg tacggtagcc actgatccat atgactactg gggccagggg     360
acccaggtca ccgtctcctc agaacccaag acaccaaaac cacaa                     405

<210> SEQ ID NO 115
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Gly Tyr
            20                  25                  30

Ala Ala Gly Trp Phe Arg Gln Ala Pro Gly Lys Glu Arg Glu Leu Val
        35                  40                  45

Ser Trp Ile Ser Ser Thr Asp Gly Ser Thr Tyr Tyr Ala Ala Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                    85                  90                  95

Thr Ala Gly Leu Gly Leu Asp Val Ser Asp Tyr Val Tyr Asp Tyr Trp
                100                 105                 110

Gly Gln Gly Thr Gln Val Thr Val Ser Ser Glu Pro Lys Thr Pro Lys
            115                 120                 125

Pro Gln
    130

<210> SEQ ID NO 116
```

<210> SEQ ID NO 116
<211> LENGTH: 390
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 116

```
caggtgcagc tggtggagac ggggggaggc ttggtgcagc ctgggggtc tctgaggctc      60
tcctgtgcag cctctggatt cactttggat ggctatgccg caggctggtt ccgccaggcc    120
ccagggaagg agcgtgagtt ggtctcatgg attagtagca ctgatggtag cacatactat    180
gcagcctccg tgaagggccg attcaccgtc tccagagaca cgccaagaa cacggtgtat    240
ctacaaatga acagcctgaa acctgaggac acagccgttt attactgtac agcaggtcta    300
gggcttgacg ttagcgacta tgtatatgac tactggggcc aggggaccca ggtcaccgtc    360
tcctcagaac ccaagacacc aaaaccacaa                                     390
```

<210> SEQ ID NO 117
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 117

```
Gln Val Gln Leu Val Glu Ser Gly Gly Leu Val Gln Pro Gly Gly Ser
1               5                   10                  15

Leu Arg Leu Ser Cys Ala Ala Ser Gly Phe Thr Leu Asp Tyr Tyr Gly
            20                  25                  30

Ile Gly Trp Val Arg Gln Ala Pro Gly Lys Glu Arg Glu Glu Val Ser
        35                  40                  45

Cys Ile Thr Ser Gly Gly Leu Thr Asn Tyr Pro Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Ile
                85                  90                  95

Asp Arg Val Gly Val Cys Ala Met Glu Asp Phe Gly Ser Trp Gly Gln
            100                 105                 110

Gly Thr Gln Val Thr Val Ser Ser Glu Pro Lys Thr Pro Lys Pro Gln
        115                 120                 125
```

<210> SEQ ID NO 118
<211> LENGTH: 384
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118

```
caggtgcagc tggtggagtc gggcggcttg gtgcagcctg ggggtctct gagactctcc      60
tgtgcagcct ctggattcac tttgattat atggcatag ctgggtccg ccaggcccca       120
gggaaggagc gtgaggaggt ctcatgtatt actagtggtg gtctcacaaa ctatccagac   180
tccgtgaagg gccgattcac catctccaga gacaacgcca gaacacagt gtatctgcaa    240
atgaacagcc tgaaacctga ggacacggcc gtttattact gtgcaatcga ccgtgtggga   300
```

```
gtatgcgcga tggaggactt tggttcctgg ggccagggga cccaggtcac cgtctcctcg    360
gaacccaaga caccaaaacc acaa                                           384
```

<210> SEQ ID NO 119
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gln Val Gln Leu Val Glu Thr Gly Gly Gly Leu Val Gln Ala Gly Asp
1               5                   10                  15

Ser Leu Arg Leu Ser Cys Ala Ala Ser Gly Arg Thr Phe Asn Tyr Tyr
            20                  25                  30

Ala Met Ala Trp Phe Arg Gln Ala Pro Gly Lys Glu Arg Glu Phe Val
        35                  40                  45

Ala Phe Ile Asn Trp Ser Gly Asp Ser Thr Tyr Tyr Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Ser Cys
                85                  90                  95

Ala Ala Glu Phe Gly Thr Phe Ser Tyr Leu Gln Gly Asp Asp Tyr Ser
            100                 105                 110

Tyr Trp Gly Gln Gly Thr Gln Val Thr Val Ser Ser Glu Pro Lys Thr
        115                 120                 125

Pro Lys Pro Gln
    130
```

<210> SEQ ID NO 120
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
caggtgcagc tggtggagac aggtggagga ttggtgcagg ctggggactc tctgagactc    60
tcctgtgcag cctctggacg caccttcaat tactatgcca tggcctggtt ccgccaggcc   120
ccaggaaagg agcgtgaatt tgtagcattt attaactgga gcggcgatag tacatactat   180
gcaggctccg tgaagggccg attcaccatc tccagagaca acgccaagaa cacggtgtat   240
ctgcaaatga acaacctgaa acctgaggac acggccgttt attcctgtgc agcagaattc   300
ggtacatttt cctacttgca aggcgatgac tatagctact ggggccaggg gacccaggtc   360
accgtctcct cagaacccaa gacaccaaaa ccacaa                              396
```

<210> SEQ ID NO 121
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Gln Val Gln Leu Val Glu Ser Gly Gly Gly Leu Val Gln Ala Gly Gly
```

```
                1               5                  10                  15
            Ser Leu Arg Leu Ser Cys Ala Ala Ser Gly Arg Ser Phe Ser Ser Tyr
                           20                  25                  30

Arg Met Gly Trp Phe Arg Gln Ala Pro Gly Lys Glu Arg Glu Leu Val
                           35                  40                  45

Ala Gly Ile Ser Trp Ser Gly Ser Ser Thr Trp Tyr Ala Asp Ser Val
                50                          55                  60

Lys Gly Arg Phe Thr Ile Ser Arg Asp Asn Ala Lys Asn Thr Val Tyr
             65                          70                  75                  80

Leu Gln Met Asn Ser Leu Lys Pro Glu Asp Thr Ala Val Tyr Tyr Cys
                                    85                  90                  95

Ala Ala Asp Gly Leu Gly Thr Asp Trp Ser Asp Ala Ile Trp Asp Tyr
                                100                 105                 110

Trp Gly Gln Gly Thr Gln Val Thr Val Ser Ser Glu Pro Lys Thr Pro
                           115                 120                 125

Lys Pro Gln
                130

<210> SEQ ID NO 122
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
caggtgcagc tggtggagtc tggaggagga ttggtgcagg ctgggggctc tctgagactc       60
tcctgtgcag cctctggacg cagcttcagt agctatcgca tgggctggtt ccgccaggct      120
ccagggaagg agcgtgagct tgtagcaggt attagctgga gtggaagtag tacatggtat      180
gcagactccg tgaagggccg attcaccatc tccagagaca acgccaagaa cacggtgtat      240
ctgcaaatga acagcctgaa acccgaggac acggccgttt attactgtgc agcagatggg      300
ctagggacgg attggagcga tgccatatgg gactactggg gccagggac ccaggtcacc      360 gtctcctcag aacccaagac accaaaacca caa                                  393

<210> SEQ ID NO 123
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Val Gln Leu Val Glu Ser Gly Gly Gly Leu Val Gln Ala Gly Gly
             1               5                  10                  15

Ser Leu Arg Leu Ser Cys Ala Ala Ser Gly Arg Asn Phe Ser His Tyr
                           20                  25                  30

Ala Met Gly Trp Phe Arg Gln Ala Pro Gly Lys Ala Arg Glu Phe Val
                           35                  40                  45

Ala Thr Ile Asn Arg Asp Gly Asp Ser Thr Tyr Tyr Thr Asn Ser Val
                50                          55                  60

Lys Gly Arg Phe Thr Ile Ser Arg Glu Asn Ala Lys Asn Thr Gly Tyr
             65                          70                  75                  80

Leu Gln Met Asn Ser Leu Lys Pro Glu Asp Thr Ala Val Tyr Tyr Cys
                                    85                  90                  95
```

Gly Val Gln Tyr Ser Trp Ser Gly Thr Ser Ile Tyr Trp Arg Glu Tyr
                100                 105                 110

Glu Tyr Ala Tyr Trp Gly Gln Gly Ala Gln Val Thr Val Ser Ser Glu
            115                 120                 125

Pro Lys Thr Pro Lys Pro Gln
        130                 135

<210> SEQ ID NO 124
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
caggtgcagc tggtggagtc ggggggagga ttggtgcagg ctggggggctc tctgagactc      60 tcctgtgcag cctctggacg caatttcagt cactatgcca tgggctggtt ccgccaggct     120
ccagggaagg gcgtgagtt tgtagcaact attaaccggg atggtgatag cacatactat     180
acgaactccg tgaagggccg attcaccatc tccagagaga cgccaagaa cacgggatat     240 ctgcaaatga acagcctgaa acctgaggac acggccgttt attactgtgg agtacaatac     300
tcgtggtcgg gtacaagtat ttactggagg gagtatgagt atgcctactg gggccagggg     360
gcccaggtca ccgtctcctc agaacccaag acaccaaaac cacaa                     405

<210> SEQ ID NO 125
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe His Ala Tyr
            20                  25                  30

Tyr Met Ser Trp Val Arg Gln Ala Pro Gly Lys Gly Leu Glu Trp Val
        35                  40                  45

Ser His Ile Gly Asn Gly Gly Ile Ile Thr Arg Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Thr Leu Gly Thr Arg Asp Asp Leu Gly Pro Glu Arg Gly Gln Gly Thr
            100                 105                 110

Gln Val Thr Val Ser Ser Glu Pro Lys Thr Pro Lys Pro Gln
        115                 120                 125

<210> SEQ ID NO 126
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 126

```
caggtgcagc tggtggagtc gggtggaggc ttggtgcagc ctgggggtc tctgagactc      60
tcctgtgcag cctctggatt cccttccat gcctactaca tgagctgggt ccgccaggct     120
ccaggaaagg ggctcgagtg gtctcccat attggcaatg gtggtattat tacacgctat     180
gcagactccg tgaagggccg gttcaccatc tccagagaca acgccaagaa cacgctgtat    240
ctgcaaatga ccaacctgaa acctgaggac acggccctgt attattgtac ctgggggacc    300
cgcgacgacc tggggcctga gagggccag gggacccagg tcaccgtctc ctcagaaccc    360
aagacaccaa aaccacaa                                                   378
```

<210> SEQ ID NO 127
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Gln Val Gln Leu Val Glu Ser Gly Gly Gly Leu Val Gln Pro Gly Gly
1               5                   10                  15

Ser Leu Arg Leu Ser Cys Ala Ala Ser Glu Gly Ile Phe Ser Val Asp
            20                  25                  30

Ala Met Gly Trp Tyr Arg Gln Val Pro Gly Lys Gln Arg Glu Leu Val
        35                  40                  45

Ala Arg Ile Thr Arg Gly Gly Ser Ile Ile Tyr Ala Asp Ser Val Lys
    50                  55                  60

Gly Arg Phe Thr Ile Ser Arg Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Arg Leu Tyr Arg Gly Thr Leu Thr Phe Gly Gln Gly Thr Gln Val Thr
            100                 105                 110

Val Ser Ser Ala His His Ser Glu Asp Pro Ser
        115                 120
```

<210> SEQ ID NO 128
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
caggtgcagc tcgtggagtc gggtggaggc ttggtgcagc ctgggggtc tctgagactc      60
tcctgtgcag cctctgaggg aatcttcagt gttgatgcca tgggctggta ccgccaggtt    120
ccagggaagc agcgcgagtt ggtcgcacga attcccgtg tggtagcat aatttatgca     180
gactccgtga agggccgatt caccatctcc agagacagcg ccaagaacac ggtgtatctg    240
caaatgaaca gcctgaaacc tgaggacacg gccgtctatt actgtaatcg cctttatagg    300
ggtaccctaa cgttcggcca ggggacccag gtcaccgtct cctcagcgca ccacagcgaa    360
gaccctcg                                                             369
```

<210> SEQ ID NO 129
<211> LENGTH: 129

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Gln Val Gln Leu Val Glu Thr Gly Gly Gly Leu Val Gln Ala Gly Gly
1               5                   10                  15
Ser Leu Arg Leu Ser Cys Ala Ala Ser Gly Arg Thr Phe Ser Ile Tyr
            20                  25                  30
Ala Met Gly Trp Phe Arg Gln Ala Pro Gly Arg Glu Arg Glu Phe Val
        35                  40                  45
Ala Ser Ile Ser Arg Met Gly Trp Ser Thr Tyr Tyr Gly Asp Ser Val
    50                  55                  60
Lys Gly Arg Phe Thr Ala Ser Arg Asp Asn Ala Lys Asn Thr Leu Tyr
65                  70                  75                  80
Leu Gln Met Asn Ser Leu Glu Leu Glu Asp Thr Ala Val Tyr Phe Cys
                85                  90                  95
Ala Ala Ser Ala Ser Ala Leu Arg Val Asn Gln Trp Asp Tyr Trp Gly
            100                 105                 110
Gln Gly Thr Gln Val Thr Val Ser Ser Glu Pro Lys Thr Pro Lys Pro
        115                 120                 125
Gln
```

<210> SEQ ID NO 130
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
caggtgcagc tggtggagac cggcggagga ttggtgcagg ctgggggctc tctgagactc      60
tcctgtgcag cctctggacg caccttcagt atctatgcca tgggctggtt ccgccaggct     120
ccagggaggg agcgtgagtt tgtagcgtct attagtcgga tgggttggag cacatattat     180
ggggactccg tgaagggccg attcaccgcc tccagagaca acgccaagaa cacgctgtat     240
ctacaaatga acagcctcga acttgaggac acggccgtat attttgtgc ggcatctgcg     300
agtgcgttac gagttaatca gtgggactac tggggccagg ggacccaggt caccgtctcc     360
tcagaaccca agacaccaaa accacaa                                        387
```

<210> SEQ ID NO 131
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Leu Asp Ser Tyr
            20                  25                  30
Ala Ile Gly Trp Phe Arg Gln Ala Pro Gly Lys Glu Arg Glu Gly Val
        35                  40                  45
```

```
Ala Cys Ile Ser Ala Ser Gly Ser Gly Thr Asp Tyr Val Asp Ser Val
         50                  55                  60
Lys Gly Arg Phe Thr Val Ser Arg Asp Gln Ala Lys Ser Met Val Phe
 65                  70                  75                  80
Leu Gln Met Asn Asn Met Lys Pro Glu Asp Ala Ala Val Tyr Tyr Cys
                 85                  90                  95
Ala Ala Asp Tyr Arg Pro Arg Pro Leu Pro Ile Gln Ala Pro Cys Thr
                100                 105                 110
Met Thr Gly Gly Asn Tyr Trp Gly Gln Gly Thr Gln Val Thr Val Ser
            115                 120                 125
Ser Glu Pro Lys Thr Pro Lys Pro Gln Ala Ile Ala Gly Gly Gly Gly
130                 135                 140
Ser Gly Gly Gly Ser Gly Gly Gly Ser Leu Gln Gly Gln Val
145                 150                 155                 160
Gln Leu Val Glu Ser Gly Gly Leu Val Gln Ala Gly Gly Ser Leu
                165                 170                 175
Arg Leu Ser Cys Ala Ala Ser Ile Leu Thr Tyr Asp Leu Asp Tyr Tyr
            180                 185                 190
Tyr Ile Gly Trp Val Arg Gln Ala Pro Gly Lys Glu Arg Glu Gly Val
            195                 200                 205
Ser Cys Ile Ser Ser Thr Asp Gly Ala Thr Tyr Tyr Ala Asp Ser Val
210                 215                 220
Lys Gly Arg Phe Thr Ile Ser Arg Asn Asn Ala Lys Asn Thr Val Tyr
225                 230                 235                 240
Leu Gln Met Asn Asn Leu Lys Pro Glu Asp Thr Ala Ile Tyr Tyr Cys
                245                 250                 255
Ala Ala Ala Pro Leu Ala Gly Arg Tyr Cys Pro Ala Ser His Glu Tyr
            260                 265                 270
Gly Tyr Trp Gly Gln Gly Thr Gln Val Thr Val Ser Ser Ala His His
            275                 280                 285
Ser Glu Asp Pro Ser
            290

<210> SEQ ID NO 132
<211> LENGTH: 879
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
caggtgcagc tcgtggagtc agggggaggc ttggtgcagc ctgggggggtc tctgagactc       60
tcctgtgcag cctctggatt cactttagat agttatgcaa taggctggtt ccgccaggcc      120
ccagggaagg agcgtgaggg ggtcgcatgt attagtgcta gtggtagtgg cacggactat      180
gtagactccg tgaagggccg attcaccgtc tccagagacc aggccaagag catggtgttt      240
ctgcaaatga acaacatgaa acctgaggac gcagccgttt attactgtgc agcagattat      300
cggccgaggc ccctgccgat tcaggcgccg tgtacaatga caggtggcaa ctactgggc       360
caggggaccc aggtcaccgt ctcctcagaa cccaagacac aaaaccaca gcgatcgct        420
ggtggaggcg gttcaggcgg aggtggctct ggcggtggcg gttccctgca gggtcaggtg      480
cagctcgtgg agtccggtgg aggcttggtg caggctgggg gtctctgag actctcctgt       540
gcagcctcta tactcactta tgatttggat tattattaca taggctgggt ccgccaggcc      600
```

```
ccagggaagg agcgtgaggg ggtctcatgt attagtagta ctgatggtgc cacatactat    660
gcagactccg tgaagggccg attcaccatc tccagaaaca acgccaagaa cacggtgtat    720
ctgcaaatga acaacctaaa acctgaggac acagccattt attattgtgc agcagccccc    780
ctggctgggc gctactgtcc cgcctcgcat gagtatggct actggggtca ggggacccag    840
gtcaccgtct cgtcagcgca ccacagcgaa gacccctcg                            879
```

<210> SEQ ID NO 133
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (160)..(160)
<223> OTHER INFORMATION: Any amino acid
<220> FEATURE:
<221> NAME/KEY: MOD_RES
<222> LOCATION: (163)..(163)
<223> OTHER INFORMATION: Any amino acid

<400> SEQUENCE: 133

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Ser Tyr
            20                  25                  30

Ala Ile Gly Trp Phe Arg Gln Ala Pro Gly Lys Glu Arg Glu Gly Val
        35                  40                  45

Ala Cys Ile Ser Ala Ser Gly Ser Gly Thr Asp Tyr Val Asp Ser Val
    50                  55                  60

Lys Gly Arg Phe Thr Val Ser Arg Asp Gln Ala Lys Ser Met Val Phe
65                  70                  75                  80

Leu Gln Met Asn Asn Met Lys Pro Glu Asp Ala Ala Val Tyr Tyr Cys
                85                  90                  95

Ala Ala Asp Tyr Arg Pro Arg Pro Leu Pro Ile Gln Ala Pro Cys Thr
            100                 105                 110

Met Thr Gly Gly Asn Tyr Trp Gly Gln Gly Thr Gln Val Thr Val Ser
        115                 120                 125

Ser Glu Pro Lys Thr Pro Lys Pro Gln Ala Ile Ala Gly Gly Gly Gly
    130                 135                 140

Ser Gly Gly Gly Gly Ser Gly Gly Gly Gly Ser Leu Gln Gly Gln Xaa
145                 150                 155                 160

Gln Leu Xaa Glu Ser Gly Gly Gly Leu Val Gln Ala Gly Gly Ser Leu
                165                 170                 175

Arg Leu Ser Cys Ala Ala Ser Glu Phe Arg Ala Glu His Phe Ala Val
            180                 185                 190

Gly Trp Phe Arg Gln Ala Pro Gly Lys Glu Arg Glu Gly Val Ser Cys
        195                 200                 205

Val Asp Ala Ser Gly Asp Ser Thr Ala Tyr Ala Asp Ser Val Lys Gly
    210                 215                 220

Arg Phe Thr Ile Ser Arg Asp Asn Asn Lys Asn Val Tyr Leu Gln
225                 230                 235                 240

Met Asp Ser Leu Glu Pro Glu Asp Thr Gly Asp Tyr Tyr Cys Gly Ala
                245                 250                 255

Ser Tyr Phe Thr Val Cys Ala Lys Ser Met Arg Lys Ile Glu Tyr Arg
            260                 265                 270
```

-continued

Tyr Trp Gly Gln Gly Thr Gln Val Thr Val Ser Ser Glu Pro Lys Thr
          275                 280                 285

Pro Lys Pro Gln
    290

<210> SEQ ID NO 134
<211> LENGTH: 876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
caggtgcagc tcgtggagtc agggggaggc ttggtgcagc ctgggggtc tctgagactc      60 tcctgtgcag cctctggatt cactttagat agttatgcaa taggctggtt ccgccaggcc    120
ccagggaagg agcgtgaggg ggtcgcatgt attagtgcta gtggtagtgg cacggactat    180
gtagactccg tgaagggccg attcaccgtc tccagagacc aggccaagag catggtgttt    240
ctgcaaatga acaacatgaa acctgaggac gcagccgttt attactgtgc agcagattat    300
cggccgaggc ccctgccgat tcaggcgccg tgtacaatga caggtggcaa ctactggggc    360
caggggaccc aggtcaccgt ctcctcagaa cccaagacac caaaaccaca agcgatcgct    420
ggtggaggcg gttcaggcgg aggtggctct ggcggtggcg gttccctgca gggtcagktg    480
cagctsgygg agtccggtgg aggcttggtg caggctgggg ggtctctgag actctcctgt    540
gcagcctctg aattccgtgc ggagcatttt gccgtgggct ggttccgcca ggccccaggg    600
aaggagcgtg aggggggtctc atgtgtagac gcgagtggtg atagtacagc atatgcggac    660
tctgtgaagg gccgattcac catctccaga gacaacaaca gaacgtagt gtatctgcaa    720 atggacagcc tggaacctga agacacagga gattattatt gtggagcctc gtactttact    780
gtctgcgcca agagcatgcg gaaaattgaa tataggtact ggggccaggg gacccaggtc    840
accgtctcct cagaacccaa gacaccaaaa ccacaa                              876

<210> SEQ ID NO 135
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Val Glu Ser Gly Gly Gly Leu Val Gln Ala Gly Gly
1               5                   10                  15

Ser Leu Arg Leu Ser Cys Ala Ala Ser Ile Leu Thr Tyr Asp Leu Asp
            20                  25                  30

Tyr Tyr Tyr Ile Gly Trp Val Arg Gln Ala Pro Gly Lys Glu Arg Glu
        35                  40                  45

Gly Val Ser Cys Ile Ser Ser Thr Asp Gly Ala Thr Tyr Tyr Ala Asp
    50                  55                  60

Ser Val Lys Gly Arg Phe Thr Ile Ser Arg Asn Asn Ala Lys Asn Thr
65                  70                  75                  80

Val Tyr Leu Gln Met Asn Asn Leu Lys Pro Glu Asp Thr Ala Ile Tyr
                85                  90                  95

Tyr Cys Ala Ala Ala Pro Leu Ala Gly Arg Tyr Cys Pro Ala Ser His
            100                 105                 110

```
Glu Tyr Gly Tyr Trp Gly Gln Gly Thr Gln Val Thr Val Ser Ser Ala
        115                 120                 125
His His Ser Glu Asp Pro Ser Ala Ile Ala Gly Gly Gly Ser Gly
    130                 135                 140
Gly Gly Gly Ser Gly Gly Gly Ser Leu Gln Gly Gln Val Gln Leu
145                 150                 155                 160
Val Glu Ser Gly Gly Gly Leu Val Gln Pro Gly Gly Ser Leu Arg Leu
                165                 170                 175
Ser Cys Glu Ala Ser Gly Phe His Leu Glu His Phe Ala Val Gly Trp
            180                 185                 190
Phe Arg Gln Ala Pro Gly Lys Glu Arg Glu Gly Val Ser Cys Ile Ser
        195                 200                 205
Ala Ser Gly Asp Ser Thr Thr Tyr Ala Asp Ser Val Lys Gly Arg Ser
    210                 215                 220
Thr Ile Ser Lys Asp Asn Ala Lys Asn Ala Val Tyr Leu Gln Met Asp
225                 230                 235                 240
Ser Leu Arg Pro Glu Asp Thr Gly Asp Tyr Tyr Cys Ala Ala Ser His
                245                 250                 255
Phe Ser Val Cys Gly Lys Asn Ile Arg Lys Ile Glu Tyr Arg Tyr Trp
            260                 265                 270
Gly Gln Gly Thr Pro Val Thr Val Ser Ser Glu Pro Lys Thr Pro Lys
        275                 280                 285
Pro Gln
    290

<210> SEQ ID NO 136
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
caggtgcagc tggtggagtc cggtggaggc ttggtgcagg ctggggggtc tctgagactc      60
tcctgtgcag cctctatact cacttatgat ttggattatt attacatagg ctgggtccgc     120
caggccccag ggaaggagcg tgaggggtc tcatgtatta gtagtactga tggtgccaca      180
tactatgcag actccgtgaa ggccgattc accatctcca gaaacaacgc caagaacacg      240
gtgtatctgc aaatgaacaa cctaaaacct gaggacacag ccatttatta ttgtgcagca     300
gcccccctgg ctgggcgcta ctgtcccgcc tcgcatgagt atggctactg gggtcagggg     360
acccaggtca ccgtctcgtc agcgcaccac agcgaagacc cctcggcgat cgctggtgga     420
ggcggttcag gcggaggtgg ctctggcggt ggcggttccc tgcagggtca ggtgcagctg     480
gtggagtctg gtggaggctt ggtgcagcct gggggggtctc tgagactctc ctgtgaagcc     540
tcaggattcc atttggagca ttttgccgta ggctggttcc gccaggcccc agggaaggag     600
cgtgaggggg tctcatgtat aagcgcgagt ggtgatagta caacgtatgc agactccgtg     660
aagggccgat ccaccatctc caagacaac gccaagaacg cggtgtatct gcaaatggac     720
agcctgagac ccgaggacac aggcgattat tactgtgcag cctcgcactt cagtgtctgc     780
ggcaagaaca ttcggaaaat tgagtatagg tactggggcc aggggacccc ggtcaccgtc     840
tcctcagaac ccaagacacc aaaaccacaa                                      870
```

```
<210> SEQ ID NO 137
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Glu Ser Gly Gly Gly Leu Val Gln Ala Gly
1               5                   10                  15

Ser Leu Arg Leu Ser Cys Ala Ala Ser Ile Leu Thr Tyr Asp Leu Asp
            20                  25                  30

Tyr Tyr Tyr Ile Gly Trp Val Arg Gln Ala Pro Gly Lys Glu Arg Glu
                35                  40                  45

Gly Val Ser Cys Ile Ser Ser Thr Asp Gly Ala Thr Tyr Tyr Ala Asp
    50                  55                  60

Ser Val Lys Gly Arg Phe Thr Ile Ser Arg Asn Asn Ala Lys Asn Thr
65                  70                  75                  80

Val Tyr Leu Gln Met Asn Asn Leu Lys Pro Glu Asp Thr Ala Ile Tyr
                85                  90                  95

Tyr Cys Ala Ala Ala Pro Leu Ala Gly Arg Tyr Cys Pro Ala Ser His
                100                 105                 110

Glu Tyr Gly Tyr Trp Gly Gln Gly Thr Gln Val Thr Val Ser Ser Ala
            115                 120                 125

His His Ser Glu Asp Pro Ser Ala Ile Ala Gly Gly Gly Ser Gly
        130                 135                 140

Gly Gly Gly Ser Gly Gly Gly Ser Leu Gln Gly Val Gln Leu
145                 150                 155                 160

Ala Glu Ser Gly Gly Gly Leu Val Gln Ala Gly Gly Ser Leu Arg Leu
                165                 170                 175

Ser Cys Ala Ala Ser Glu Phe Arg Ala Glu His Phe Ala Val Gly Trp
            180                 185                 190

Phe Arg Gln Ala Pro Gly Lys Glu Arg Glu Gly Val Ser Cys Val Asp
        195                 200                 205

Ala Ser Gly Asp Ser Thr Ala Tyr Ala Asp Ser Val Lys Gly Arg Phe
210                 215                 220

Thr Ile Ser Arg Asp Asn Asn Lys Asn Val Val Tyr Leu Gln Met Asp
225                 230                 235                 240

Ser Leu Glu Pro Glu Asp Thr Gly Asp Tyr Tyr Cys Gly Ala Ser Tyr
                245                 250                 255

Phe Thr Val Cys Ala Lys Ser Met Arg Lys Ile Glu Tyr Arg Tyr Trp
            260                 265                 270

Gly Gln Gly Thr Gln Val Thr Val Ser Ser Glu Pro Lys Thr Pro Lys
        275                 280                 285

Pro Gln
    290

<210> SEQ ID NO 138
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
caggtgcagc tggtggagtc cggtggaggc ttggtgcagg ctgggggtc tctgagactc      60
```

```
tcctgtgcag cctctatact cacttatgat ttggattatt attacatagg ctgggtccgc    120
caggccccag ggaaggagcg tgaggggtc tcatgtatta gtagtactga tggtgccaca     180
tactatgcag actccgtgaa gggccgattc accatctcca gaaacaacgc caagaacacg    240
gtgtatctgc aaatgaacaa cctaaaacct gaggacacag ccattttatta ttgtgcagca   300 gccccctgg ctgggcgcta ctgtcccgcc tcgcatgagt atggctactg ggtcagggg     360 acccaggtca ccgtctcgtc agcgcaccac agcgaagacc cctcggcgat cgctggtgga   420
ggcggttcag gcggaggtgg ctctggcggt ggcggttccc tgcagggtca ggtgcagctg   480
gcggagtccg gtgaggctt ggtgcaggct gggggtctc tgagactctc ctgtgcagcc    540
tctgaattcc gtgcggagca ttttgccgtg gctggttcc gccaggcccc agggaaggag   600
cgtgaggggg tctcatgtgt agacgcgagt ggtgatagta cagcatatgc ggactctgtg   660
aagggccgat tcaccatctc cagagacaac aacaagaacg tagtgtatct gcaaatggac   720
agcctggaac ctgaagacac aggagattat tattgtggag cctcgtactt tactgtctgc   780
gccaagagca tgcggaaaat tgaatatagg tactgggggcc aggggaccca ggtcaccgtc   840
tcctcagaac ccaagacacc aaaaccacaa                                    870
```

<210> SEQ ID NO 139
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 139

```
Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Ser Tyr Ala Met Gly
            20                  25                  30

Trp Phe Arg Gln Gly Pro Gly Lys Glu Arg Glu Phe Val Ala Thr Ile
        35                  40                  45

Ser Trp Ser Ser Thr Asn Thr Trp Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Ala Ala Ser
                85                  90                  95

His Arg Phe Ser Asp Tyr Pro Met Arg Ser Glu Asp Gly Met Asp Tyr
            100                 105                 110

Trp Gly Lys Gly Thr Leu Val Thr Val Ser Ser Glu Pro Lys Thr Pro
        115                 120                 125

Lys Pro Gln Ala Ile Ala Gly Gly Gly Ser Gly Gly Gly Gly Ser
    130                 135                 140

Gly Gly Gly Gly Ser Leu Gln Gly Gln Val Gln Leu Val Glu Thr Gly
145                 150                 155                 160

Gly Gly Leu Val Gln Ala Gly Gly Ser Leu Arg Leu Ser Cys Ala Ala
                165                 170                 175

Ser Gly Arg Thr Phe Ser Ser Tyr Ser Met Gly Trp Phe Arg Gln Ala
            180                 185                 190

Pro Gly Lys Glu Arg Glu Tyr Val Ala Ala Val Asn Ser Asn Gly Asp
        195                 200                 205
```

```
Ser Thr Phe Tyr Ala Asp Ser Ile Lys Gly Arg Phe Thr Val Ser Arg
    210                 215                 220
Asp Ala Ala Lys Asn Thr Val Tyr Leu Gln Met Asn Ser Leu Lys Pro
225                 230                 235                 240
Glu Asp Thr Ala Leu Tyr Tyr Cys Ala Ala Val Tyr Gly Arg Tyr Thr
                245                 250                 255
Tyr Gln Ser Pro Lys Ser Tyr Glu Tyr Trp Gly Gln Gly Thr Gln Val
                260                 265                 270
Thr Val Ser Ser Glu Pro Lys Thr Pro Lys Pro Gln
            275                 280
```

<210> SEQ ID NO 140
<211> LENGTH: 852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
caggtgcagc tggtggagac gggggggagga ttggtgcagg ctgggggctc tctgagactc    60
tcctgtgcag cctctggacg cagttatgcc atgggctggt tccgccaggg tccagggaag   120
gagcgtgagt ttgtagccac tatcagttgg agtagtacta acacatggta tgcagattcc   180
gtgaagggcc gattcaccat ctctagagac aacgccaaga acacggtgta tctgcaaatg   240
aacagcctga acctgaggac acggctgtt tattactgtg cagcgagcca tcgttttagc   300
gactatccca tgaggtcaga ggacggcatg gactactggg gcaaagggac cctggtcacc   360
gtctcctcag aacccaagac accaaaacca aagcgatcg ctggtggagg cggttcaggc   420
ggaggtggct ctggcggtgg cggttccctg cagggtcagg tgcagctggt ggagacggga   480
ggaggattgg tgcaggctgg gggctctctg agactctcgt gtgcagcctc tggacgcacc   540
ttcagtagct attccatggg ctggttccgc caggctccag ggaaggagcg tgagtatgta   600
gcagcagtta actccaatgg cgacagtaca ttctatgccg actccattaa gggccgattc   660
accgtctcca gagacgccgc caagaacaca gtctatctgc aaatgaacag cctgaaacct   720
gaggacacgg cccttttatta ctgtgcagct gtctacggta gatacactta ccagtcccca   780
aaatcgtatg agtactgggg ccagggggacc caggtcaccg tctcctcaga acccaagaca   840
ccaaaaccac aa                                                      852
```

<210> SEQ ID NO 141
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

```
Gln Val Gln Leu Val Glu Thr Gly Gly Gly Leu Val Gln Ala Gly Gly
1               5                   10                  15
Ser Leu Arg Leu Ser Cys Ala Ala Ser Gly Arg Ser Tyr Ala Met Gly
            20                  25                  30
Trp Phe Arg Gln Gly Pro Gly Lys Glu Arg Glu Phe Val Ala Thr Ile
        35                  40                  45
Ser Trp Ser Ser Thr Asn Thr Trp Tyr Ala Asp Ser Val Lys Gly Arg
    50                  55                  60
```

Phe Thr Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Ala Ala Ser
             85                  90                  95

His Arg Phe Ser Asp Tyr Pro Met Arg Ser Glu Asp Gly Met Asp Tyr
            100                 105                 110

Trp Gly Lys Gly Thr Leu Val Thr Val Ser Ser Glu Pro Lys Thr Pro
        115                 120                 125

Lys Pro Gln Ala Ile Ala Gly Gly Gly Ser Gly Gly Gly Gly Gly Ser
    130                 135                 140

Gly Gly Gly Gly Ser Leu Gln Gly Gln Val Gln Leu Val Glu Thr Gly
145                 150                 155                 160

Gly Gly Leu Val Lys Pro Gly Gly Ser Leu Arg Leu Ser Cys Val Val
                165                 170                 175

Ser Gly Phe Thr Phe Asp Asp Tyr Arg Met Ala Trp Val Arg Gln Ala
            180                 185                 190

Pro Gly Lys Glu Leu Glu Trp Val Ser Ser Ile Asp Ser Trp Ser Ile
        195                 200                 205

Asn Thr Tyr Tyr Glu Asp Ser Val Lys Gly Arg Phe Thr Ile Ser Thr
    210                 215                 220

Asp Asn Ala Lys Asn Thr Leu Tyr Leu Gln Met Ser Ser Leu Lys Pro
225                 230                 235                 240

Glu Asp Thr Ala Val Tyr Tyr Cys Ala Ala Glu Asp Arg Leu Gly Val
                245                 250                 255

Pro Thr Ile Asn Ala His Pro Ser Lys Tyr Asp Tyr Asn Tyr Trp Gly
            260                 265                 270

Gln Gly Thr Gln Val Thr Val Ser Ser Glu Pro Lys Thr Pro Lys Pro
        275                 280                 285

Gln

<210> SEQ ID NO 142
<211> LENGTH: 867
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
caggtgcagc tggtggagac ggggggagga ttggtgcagg ctgggggctc tctgagactc      60
tcctgtgcag cctctggacg cagttatgcc atgggctggt tccgccaggg tccaggaag     120 gagcgtgagt ttgtagccac tatcagttgg agtagtacta acacatggta tgcagattcc    180
gtgaagggcc gattcaccat ctctagagac aacgccaaga acacgtgta tctgcaaatg     240 aacagcctga aacctgagga cacggctgtt tattactgtg cagcgagcca tcgttttagc    300
gactatccca tgaggtcaga ggacggcatg gactactggg gcaaaggac cctggtcacc    360 gtctcctcag aacccaagac accaaaacca aagcgatcg ctggtggagg cggttcaggc    420
ggaggtggct ctggcggtgg cggttccctg cagggtcagg tgcagctggt ggagactggt    480
ggaggcttgg tgaagcctgg gggttctctg agactctcct gtgtagtctc cggattcact    540
tttgatgatt atcgcatggc ttgggtccgc caggctccag ggaaggagct ggagtgggtg    600
tccagtatag atagttggag tatcaacaca tactatgaag actccgtgaa gggccggttc    660
accatctcca cagacaacgc caagaataca ctgtatctgc aaatgagcag cctgaaacct    720

```
gaggacacgg ccgtgtatta ctgtgcagca gaggaccgct taggtgtacc gactattaac    780
gcccacccct tcaaaatatga ttataactac tgggggcagg ggacccaggt caccgtctcc    840
tcagaaccca agacaccaaa accacaa                                         867
```

<210> SEQ ID NO 143
<211> LENGTH: 290
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

```
Gln Leu Gln Leu Val Glu Thr Gly Gly Gly Leu Val Lys Pro Gly Gly
1               5                   10                  15

Ser Leu Arg Leu Ser Cys Val Val Ser Gly Phe Thr Phe Asp Asp Tyr
            20                  25                  30

Arg Met Ala Trp Val Arg Gln Ala Pro Gly Lys Glu Leu Glu Trp Val
        35                  40                  45

Ser Ser Ile Asp Ser Trp Ser Ile Asn Thr Tyr Tyr Glu Asp Ser Val
    50                  55                  60

Lys Gly Arg Phe Thr Ile Ser Thr Asp Asn Ala Lys Asn Thr Leu Tyr
65                  70                  75                  80

Leu Gln Met Ser Ser Leu Lys Pro Glu Asp Thr Ala Val Tyr Tyr Cys
                85                  90                  95

Ala Ala Glu Asp Arg Leu Gly Val Pro Thr Ile Asn Ala His Pro Ser
            100                 105                 110

Lys Tyr Asp Tyr Asn Tyr Trp Gly Gln Gly Thr Gln Val Thr Val Ser
        115                 120                 125

Ser Glu Pro Lys Thr Pro Lys Pro Gln Ala Ile Ala Gly Gly Gly Gly
    130                 135                 140

Ser Gly Gly Gly Gly Ser Gly Gly Gly Gly Ser Leu Gln Gly Gln Val
145                 150                 155                 160

Gln Leu Val Glu Thr Gly Gly Gly Leu Val Gln Ala Gly Gly Ser Leu
                165                 170                 175

Arg Leu Ser Cys Ala Ala Ser Gly Arg Thr Phe Ser Ser Tyr Ser Met
            180                 185                 190

Gly Trp Phe Arg Gln Ala Pro Gly Lys Glu Arg Glu Tyr Val Ala Ala
        195                 200                 205

Val Asn Ser Asn Gly Asp Ser Thr Phe Tyr Ala Asp Ser Ile Lys Gly
    210                 215                 220

Arg Phe Thr Val Ser Arg Asp Ala Ala Lys Asn Thr Val Tyr Leu Gln
225                 230                 235                 240

Met Asn Ser Leu Lys Pro Glu Asp Thr Ala Leu Tyr Tyr Cys Ala Ala
                245                 250                 255

Val Tyr Gly Arg Tyr Thr Tyr Gln Ser Pro Lys Ser Tyr Glu Tyr Trp
            260                 265                 270

Gly Gln Gly Thr Gln Val Thr Val Ser Ser Glu Pro Lys Thr Pro Lys
        275                 280                 285

Pro Gln
    290
```

<210> SEQ ID NO 144
<211> LENGTH: 870
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 144
cagttgcagc tcgtggagac tggtggaggc ttggtgaagc ctgggggttc tctgagactc      60
tcctgtgtag tctccggatt cactttgat gattatcgca tggcttgggt ccgccaggct     120
ccagggaagg agctggagtg ggtgtccagt atagatagtt ggagtatcaa cacatactat    180
gaagactccg tgaagggccg gttcaccatc tccacagaca acgccaagaa tacactgtat    240
ctgcaaatga gcagcctgaa acctgaggac acggccgtgt attactgtgc agcagaggac    300
cgcttaggtg taccgactat taacgcccac ccttcaaaat atgattataa ctactggggg    360
caggggaccc aggtcaccgt ctcctcagaa cccaagacac caaaaccaca agcgatcgct    420
ggtggaggcg gttcaggcgg aggtggctct ggcggtggcg gttccctgca gggtcaggtg    480
cagctggtgg agacgggagg aggattggtg caggctgggg gctctctgag actctcgtgt    540
gcagcctctg gacgcacctt cagtagctat tccatgggct ggttccgcca ggctccaggg    600
aaggagcgtg agtatgtagc agcagttaac tccaatggcg acagtacatt ctatgccgac    660
tccattaagg gccgattcac cgtctccaga gacgccgcca agaacacagt ctatctgcaa    720
atgaacagcc tgaaacctga ggacacggcc ctttattact gtgcagctgt ctacggtaga    780
tacacttacc agtccccaaa atcgtatgag tactggggcc aggggaccca ggtcaccgtc    840
tcctcagaac ccaagacacc aaaaccacaa                                     870

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Gly Gly Ser Gly Gly Gly Gly Ser Gly Gly Gly Gly Ser
1               5                   10                  15

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Ile Cys Leu Pro Arg Trp Gly Cys Leu Trp Glu Asp
1               5                   10

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Gly Gly Ser
1               5
```

<210> SEQ ID NO 148
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ser Gly Gly Gly Leu Val Gln Pro Gly Gly Ser Leu Arg Leu Ser Cys
1               5                   10                  15

Ala Ala Ser Gly Ser Ser Phe Ser Arg Tyr Ala Met Arg Trp Tyr Arg
            20                  25                  30

Gln Ala Pro Gly Lys Gln Arg Glu Leu Val Ala Asn Ile Asn Ser Arg
        35                  40                  45

Gly Thr Ser Asn Tyr Ala Asp Ser Val Lys Gly Arg Phe Thr Ile Ser
    50                  55                  60

Arg Asp Asn Ala Lys Asn Thr Val Tyr Leu Gln Met Asn Ser Leu Lys
65                  70                  75                  80

Pro Glu Asp Thr Ala Val Tyr Tyr Cys Asn Ala Glu Trp Leu Gly Arg
                85                  90                  95

Ser Glu Pro Ser Trp Gly Gln Thr Gln Val Thr Val Ser Ser
            100                 105                 110

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ser Gly Gly Gly Leu Val Gln Pro Gly Gly Ser Leu Arg Leu Ser Cys
1               5                   10                  15

Ala Ala Ser Gly Phe Ile Phe Ser Leu Tyr Thr Met Arg Trp His Arg
            20                  25                  30

Gln Ala Pro Gly Lys Glu Arg Glu Leu Val Ala Thr Ile Thr Ser Ala
        35                  40                  45

Thr Gly Ile Thr Asn Tyr Ala Asp Ser Val Lys Gly Arg Phe Ile Ile
    50                  55                  60

Ser Arg Asp Asp Ala Lys Lys Thr Gly Tyr Leu Gln Met Asn Ser Leu
65                  70                  75                  80

Lys Pro Glu Asp Thr Ala Val Tyr Tyr Cys Asn Ala Val Arg Thr Thr
                85                  90                  95

Val Ser Arg Asp Tyr Trp Gly Gln Gly Thr Gln Val Thr Val Ser Ser
            100                 105                 110

<210> SEQ ID NO 150
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ser Gly Gly Gly Leu Val Gln Pro Gly Gly Ser Leu Arg Leu Ser Cys
1               5                   10                  15

Ala Ala Ser Gly Ile Ile Phe Ser Ile Tyr Thr Met Gly Trp Tyr Arg
            20                  25                  30

Gln Ala Pro Gly Lys Gln Arg Glu Leu Val Ala Ile Pro Ser Gly
            35                  40                  45

Pro Ser Ala Asn Ala Thr Asp Ser Val Gly Gly Arg Phe Thr Ile Thr
 50                  55                  60

Arg Asp Asn Ala Glu Asn Thr Val Tyr Leu Gln Met Asn Asp Leu Lys
 65                  70                  75                  80

Pro Glu Asp Thr Ala Val Tyr Tyr Cys Asn Ala Arg Arg Gly Pro Gly
                 85                  90                  95

Ile Lys Asn Tyr Trp Gly Gln Gly Thr Gln Val Thr Val Ser Ser
            100                 105                 110

<210> SEQ ID NO 151
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ser Gly Gly Gly Leu Val Gln Pro Gly Gly Ser Leu Ser Val Ser Cys
1               5                   10                  15

Ala Ala Ser Gly Ser Ile Ala Arg Pro Gly Ala Met Ala Trp Tyr Arg
            20                  25                  30

Gln Ala Pro Gly Lys Glu Arg Glu Leu Val Ala Ser Ile Thr Pro Gly
            35                  40                  45

Gly Leu Thr Asn Tyr Ala Asp Ser Val Thr Gly Arg Phe Thr Ile Ser
 50                  55                  60

Arg Asp Asn Ala Lys Arg Thr Val Tyr Leu Gln Met Asn Ser Leu Gln
 65                  70                  75                  80

Pro Glu Asp Thr Ala Val Tyr Tyr Cys His Ala Arg Ile Ile Pro Leu
                 85                  90                  95

Gly Leu Gly Ser Glu Tyr Arg Asp His Trp Gly Gln Gly Thr Gln Val
            100                 105                 110

Thr Val Ser Ser
        115

<210> SEQ ID NO 152
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Thr Gly Gly Leu Val Gln Pro Gly Gly Ser Leu Arg Leu Ser Cys Ala
1               5                   10                  15

Ala Ser Gly Leu Thr Phe Ser Ser Thr Ala Met Ala Trp Phe Arg Gln
            20                  25                  30

Ala Pro Gly Lys Glu Arg Glu Phe Val Ala Arg Ile Ser Gly Ala Gly
            35                  40                  45

Ile Thr Ile Tyr Tyr Ser Asp Ser Val Lys Asp Arg Phe Thr Ile Ser
 50                  55                  60

Arg Asn Asn Val Glu Asn Thr Val Tyr Leu Gln Met Asn Ser Leu Lys
 65                  70                  75                  80

Thr Glu Asp Thr Ala Val Tyr Tyr Cys Ala Ala Arg Arg Asn Thr Tyr
                 85                  90                  95

```
Thr Ser Asp Tyr Asn Ile Pro Ala Arg Tyr Pro Tyr Trp Gly Gln Gly
                100                 105                 110

Thr Gln Val Thr Val Ser Ser
        115

<210> SEQ ID NO 153
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Thr Gly Gly Leu Val Gln Pro Gly Gly Ser Leu Arg Leu Ser Cys Ala
1               5                   10                  15

Ala Ser Arg Ser Thr Thr Ala Thr Ile Tyr Ser Met Asn Trp Tyr Arg
                20                  25                  30

Gln Ala Pro Gly Lys Gln Arg Glu Leu Val Ala Gly Met Thr Ser Asp
            35                  40                  45

Gly Gln Thr Asn Tyr Ala Thr Ser Val Lys Gly Arg Phe Thr Ile Ser
        50                  55                  60

Arg Asp Asn Ala Lys Asn Thr Val Tyr Leu Ile Met Asn Ser Leu Lys
65                  70                  75                  80

Leu Glu Asp Thr Ala Val Tyr Tyr Cys Tyr Val Lys Pro Trp Arg Leu
                85                  90                  95

Gln Gly Trp Asp Tyr Trp Gly Gln Gly Thr Gln Val Thr Val Ser Ser
            100                 105                 110

<210> SEQ ID NO 154
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ser Gly Gly Gly Leu Val Gln Pro Gly Gly Ser Leu Arg Leu Ser Cys
1               5                   10                  15

Ala Ala Pro Glu Ser Ile Val Asn Ser Arg Thr Met Ala Trp Tyr Arg
                20                  25                  30

Gln Ala Pro Gly Lys Gln Arg Glu Arg Val Ala Thr Ile Thr Thr Ala
            35                  40                  45

Gly Ser Pro Asn Tyr Ala Asp Ser Val Lys Gly Arg Phe Ala Ile Ser
        50                  55                  60

Arg Asp Asn Ala Lys Asn Thr Val Tyr Leu Gln Met Asn Ser Leu Lys
65                  70                  75                  80

Pro Glu Asp Thr Ala Val Tyr Tyr Cys Asn Thr Leu Leu Ser Thr Leu
                85                  90                  95

Pro Tyr Gly Gln Gly Thr Gln Val Thr Val Ser Ser
            100                 105

<210> SEQ ID NO 155
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 155

Ser Gly Gly Gly Leu Val Gln Pro Gly Ser Leu Gly Leu Ser Cys
1               5                   10                  15

Val Val Ala Ser Glu Arg Ser Ile Asn Asn Tyr Gly Met Gly Trp Tyr
            20                  25                  30

Arg Gln Ala Pro Gly Lys Gln Arg Glu Leu Val Ala Gln Ile Ser Ser
        35                  40                  45

Gly Gly Thr Thr Asn Tyr Ala Asp Ser Val Glu Gly Arg Phe Thr Ile
    50                  55                  60

Ser Arg Asp Asn Val Lys Lys Met Val His Leu Gln Val Asn Ser Leu
65                  70                  75                  80

Lys Pro Glu Asp Thr Ala Val Tyr Tyr Cys Asn Ser Leu Leu Arg Thr
                85                  90                  95

Phe Ser Trp Gly Gln Gly Thr Gln Val Thr Val Ser Ser
            100                 105

<210> SEQ ID NO 156
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Thr Gly Gly Gly Leu Val Gln Pro Gly Gly Ser Leu Arg Leu Ser Cys
1               5                   10                  15

Ala Ala Ser Gly Phe Thr Phe Ser Ser Tyr Arg Met Ser Trp Tyr Arg
            20                  25                  30

Gln Ala Ala Gly Lys Glu Arg Asp Val Val Ala Thr Ile Thr Ala Asn
        35                  40                  45

Gly Val Pro Thr Gly Tyr Ala Asp Ser Val Met Gly Arg Phe Thr Ile
    50                  55                  60

Ser Arg Asp Asn Ala Lys Asn Thr Val Tyr Leu Glu Met Asn Ser Leu
65                  70                  75                  80

Asn Pro Glu Asp Thr Ala Val Tyr Tyr Cys Asn Ala Pro Arg Leu His
                85                  90                  95

Thr Ser Val Gly Tyr Trp Gly Gln Gly Thr Gln Val Thr Val Ser Ser
            100                 105                 110

<210> SEQ ID NO 157
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ser Gly Gly Gly Leu Val Gln Ala Gly Asn Ser Leu Arg Leu Ser Cys
1               5                   10                  15

Thr Ala Ser Gly Val Ile Phe Ser Ile Tyr Thr Met Gly Trp Phe Arg
            20                  25                  30

Gln Ala Pro Gly Lys Glu Arg Glu Phe Val Ala Ala Ile Gly Val Ala
        35                  40                  45

Asp Gly Thr Ala Leu Val Ala Asp Ser Val Thr Gly Arg Phe Thr Ile
    50                  55                  60
```

```
Ser Arg Asp Asn Ala Lys Asn Thr Val Tyr Leu His Met Asn Ser Leu
 65                  70                  75                  80

Lys Pro Glu Asp Thr Ala Val Tyr Ser Cys Ala Ala Tyr Leu Ser Pro
                 85                  90                  95

Arg Val Gln Ser Pro Tyr Ile Thr Asp Ser Arg Tyr Gln Leu Trp Gly
            100                 105                 110

Gln Gly Thr Gln Val Thr Val Ser Ser
            115                 120
```

<210> SEQ ID NO 158
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Thr Gly Gly Gly Leu Val Gln Ala Gly Gly Ser Leu Arg Leu Ser Cys
 1               5                  10                  15

Ala Ala Ser Gly Arg Tyr Ala Met Gly Trp Phe Arg Gln Ala Pro Gly
                 20                  25                  30

Lys Glu Arg Glu Phe Val Ala Thr Ile Ser Arg Ser Gly Ala Ile Arg
             35                  40                  45

Glu Tyr Ala Asp Ser Val Lys Gly Arg Phe Thr Ile Ser Arg Asp Gly
 50                  55                  60

Ala Glu Asn Thr Val Tyr Leu Glu Met Asn Ser Leu Lys Pro Asp Asp
 65                  70                  75                  80

Thr Ala Ile Tyr Val Cys Ala Glu Gly Arg Gly Ala Thr Phe Asn Pro
                 85                  90                  95

Glu Tyr Ala Tyr Trp Gly Gln Gly Thr Gln Val Thr Val Ser Ser
            100                 105                 110
```

<210> SEQ ID NO 159
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
Thr Gly Gly Gly Leu Val Gln Ala Gly Gly Ser Leu Arg Leu Ser Cys
 1               5                  10                  15

Ser Ala Ser Gly Leu Thr Phe Gly Asn Tyr Ala Met Gly Trp Phe Arg
                 20                  25                  30

Gln Ala Pro Gly Lys Glu Arg Glu Phe Val Ala Ser Ile Ser Arg Ser
             35                  40                  45

Gly Ser Asn Thr Trp Tyr Ala Glu Pro Leu Lys Gly Arg Phe Ala Ile
 50                  55                  60

Ser Arg Asp Asn Asp Lys Asn Ala Leu Tyr Leu Gln Met Asn Ser Leu
 65                  70                  75                  80

Lys Pro Glu Asp Thr Ala Val Tyr Tyr Cys Ala Gly Gly Ser Tyr Asn
                 85                  90                  95

Ser Asp Trp Trp Asn Tyr Met Tyr Trp Gly Gln Gly Thr Gln Val Thr
            100                 105                 110

Val Ser Ser
       115
```

<210> SEQ ID NO 160
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

Ser Gly Gly Gly Leu Val Gln Ala Gly Gly Ser Leu Arg Leu Ser
1               5                   10                  15

Cys Ala Ala Ser Gly Arg Thr Phe Ser Gly Tyr Ala Met Gly Trp Phe
                20                  25                  30

Arg Gln Ala Pro Gly Lys Glu Arg Glu Phe Val Ala Asp Ile Ser Trp
            35                  40                  45

Ser Gly His Asn Thr Tyr Tyr Gly Asp Ser Val Lys Gly Arg Phe Thr
50                  55                  60

Ile Ser Arg Asp Thr Ala Lys Asn Thr Val Tyr Leu Gln Met Asn Ser
65                  70                  75                  80

Leu Lys Pro Glu Asp Thr Ala Val Tyr Tyr Cys Ala Ala Gly Ala
                85                  90                  95

Arg Thr His Leu Ser Asp Ser Tyr Tyr Phe Pro Gly Leu Trp Ala Glu
            100                 105                 110

Pro Pro Val Gly Tyr Trp Gly Gln Gly Thr Gln Val Thr Val Ser Ser
        115                 120                 125

<210> SEQ ID NO 161
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 161

Thr Gly Gly Gly Leu Val Gln Ala Gly Gly Thr Leu Arg Leu Ser Cys
1               5                   10                  15

Ala Ala Ser Gly Arg Thr Phe Ser Tyr Tyr Ile Gly Trp Phe Arg
                20                  25                  30

Gln Glu Pro Gly Lys Glu Arg Glu Phe Val Ala Ser Ile Gly Trp Thr
            35                  40                  45

Asp Asp Asn Thr Tyr Tyr Ala Asp Ser Val Lys Gly Arg Phe Thr Ile
        50                  55                  60

Ser Arg Asp Asn Ala Glu Thr Thr Ala Tyr Leu Gln Met Ser Gly Leu
65                  70                  75                  80

Lys Pro Glu Asp Thr Ala Val Tyr Tyr Cys Ala Ala Asp Tyr Gly Ser
                85                  90                  95

Gly Ile Arg Ala Trp Tyr Asn Trp Ile Tyr Trp Gly Gln Gly Thr Gln
            100                 105                 110

Val Thr Val Ser Ser
        115

<210> SEQ ID NO 162
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 162

Thr Gly Gly Gly Leu Val Gln Pro Gly Ser Leu Arg Leu Ser Cys
1               5                   10                  15

Ala Ala Ser Gly Ala Thr Leu Asp Thr Tyr Ile Ile Thr Trp Phe Arg
            20                  25                  30

Gln Ala Pro Gly Lys Glu Arg Glu Ala Val Ser Cys Ile Asn Arg Ser
        35                  40                  45

Gly Ser Thr Thr Tyr Ser Asp Ser Val Lys Gly Arg Phe Thr Ile Ser
    50                  55                  60

Arg Asp Asn Ala Gln Lys Thr Val Tyr Leu Gln Met Asn Ser Leu Asn
65                  70                  75                  80

Pro Glu Asp Thr Ala Ile Tyr Tyr Cys Ala Ala Asp Ala Ser Tyr Arg
                85                  90                  95

Thr Cys Gly Gly Ser Trp Trp Asn Trp Ala Tyr Trp Gly Gln Gly Thr
            100                 105                 110

Gln Val Thr Val Ser Ser
        115

<210> SEQ ID NO 163
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ser Gly Gly Gly Ser Val Gln Pro Gly Gly Ser Leu Arg Leu Ser Cys
1               5                   10                  15

Ala Ala Ser Gly Phe Thr Phe Ser Ser Tyr Thr Met Ser Trp Val Arg
            20                  25                  30

Gln Ala Pro Gly Lys Gly Ile Glu Trp Val Ser Asp Ile Asn Gly Gly
        35                  40                  45

Gly Asp Arg Thr Asp Tyr Ala Asp Ser Val Lys Gly Arg Phe Thr Ile
    50                  55                  60

Ser Arg Asp Asn Ala Arg Asn Thr Leu Tyr Leu Gln Met Asn Ser Leu
65                  70                  75                  80

Gln Pro Glu Asp Thr Ala Val Tyr Tyr Cys Ala Lys Asp Leu Ser Tyr
                85                  90                  95

Val Ser Gly Thr Tyr Phe Ala Asn Asp Trp Gly Gln Gly Thr Gln Val
            100                 105                 110

Thr Val Ser Ser
        115

<210> SEQ ID NO 164
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ser Gly Gly Gly Leu Val Gln Pro Gly Gly Ser Leu Arg Leu Ser Cys
1               5                   10                  15

Thr Ala Ser Gly Ile Ile Phe Asp Tyr Tyr Ser Val Asp Trp Tyr Arg
            20                  25                  30

Gln Ala Pro Gly Lys Glu Arg Glu Leu Val Ala Thr Ile Thr Gly Asp

```
                35                  40                  45
Gly Ser Pro Asn Tyr Ala Asp Ser Val Lys Gly Arg Phe Thr Ile Ser
         50                  55                  60
Arg Asp Asn Ala Lys Lys Thr Val Tyr Leu Gln Met Asn Gly Leu Lys
 65                  70                  75                  80
Pro Glu Glu Thr Ala Val Tyr Tyr Cys His Ala Lys Arg Thr Ile Gly
                 85                  90                  95
Thr Lys Ser Glu Tyr Trp Gly Gln Gly Thr Gln Val Thr Val Ser Ser
                100                 105                 110
```

<210> SEQ ID NO 165
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Thr Gly Gly Gly Leu Val Gln Ala Gly Gly Ser Leu Arg Leu Ser Cys
 1               5                  10                  15
Leu Ala Ser Arg Met Ser Phe Ser Arg Arg Pro Met Ala Trp Tyr Arg
                20                  25                  30
Gln Ala Pro Gly Lys Gln Arg Glu Arg Val Ala Thr Ile Ser Ser Phe
                35                  40                  45
Gly Asp Thr Thr Asn Tyr Thr Asp Ser Val Glu Gly Arg Phe Thr Ile
         50                  55                  60
Ser Arg Asp Asn Ala Lys Asn Thr Met Tyr Leu Gln Met Asn Ser Leu
 65                  70                  75                  80
Lys Pro Asp Asp Thr Ala Val Tyr Tyr Cys Asn Thr Leu Leu Ala Thr
                 85                  90                  95
Tyr Ala Trp Gly Gln Gly Thr Gln Val Thr Val Ser Ser
                100                 105
```

<210> SEQ ID NO 166
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Ser Gly Gly Gly Leu Val Gln Ala Gly Gly Ser Leu Arg Leu Ser Cys
 1               5                  10                  15
Ala Ala Ser Gly Arg Thr Phe Ser Ser Tyr Val Met Gly Trp Phe Arg
                20                  25                  30
Gln Ala Pro Gly Lys Glu Arg Glu Phe Val Ala Ala Ile Ser Arg Asn
                35                  40                  45
Gly Gly Lys Thr Tyr Tyr Ala Asp Ser Val Lys Gly Arg Phe Thr Ile
         50                  55                  60
Ser Arg Asp Gly Thr Glu Asn Thr Val Tyr Leu Gln Met Asn Ser Leu
 65                  70                  75                  80
Lys Pro Glu Asp Thr Ala Val Tyr Tyr Cys Ala Ala Val Ala Ala
                 85                  90                  95
Ser Ala Glu Phe Val Thr Ala Arg Ser Asn Phe Tyr Glu Tyr Trp Gly
                100                 105                 110
Gln Gly Thr Gln Val Thr Val Ser Ser
```

```
                115                  120
```

<210> SEQ ID NO 167
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Ala Glu Ser Gly Gly
            180                 185                 190

Gly Leu Val Gln Pro Gly Gly Ser Leu Gly Leu Ser Cys Val Val Ala
        195                 200                 205

Ser Glu Arg Ser Ile Asn Asn Tyr Gly Met Gly Trp Tyr Arg Gln Ala
210                 215                 220

Pro Gly Lys Gln Arg Glu Leu Val Ala Gln Ile Ser Ser Gly Gly Thr
225                 230                 235                 240

Thr Asn Tyr Ala Asp Ser Val Glu Gly Arg Phe Thr Ile Ser Arg Asp
                245                 250                 255

Asn Val Lys Lys Met Val His Leu Gln Val Asn Ser Leu Lys Pro Glu
            260                 265                 270

Asp Thr Ala Val Tyr Tyr Cys Asn Ser Leu Leu Arg Thr Phe Ser Trp
        275                 280                 285

Gly Gln Gly Thr Gln Val Thr Val Ser Ser Glu Pro Lys Thr Pro Lys
    290                 295                 300

Pro Gln Ala Ile Ala Gly Gly Gly Ser Gly Gly Gly Gly Ser Gly
305                 310                 315                 320

Gly Gly Gly Ser Leu Gln Gly Gln Val Gln Leu Val Glu Ser Gly Gly
                325                 330                 335

Gly Leu Val Gln Pro Gly Gly Ser Leu Ser Val Ser Cys Ala Ala Ser
            340                 345                 350
```

Gly Ser Ile Ala Arg Pro Gly Ala Met Ala Trp Tyr Arg Gln Ala Pro
            355                 360                 365

Gly Lys Glu Arg Glu Leu Val Ala Ser Ile Thr Pro Gly Gly Leu Thr
        370                 375                 380

Asn Tyr Ala Asp Ser Val Thr Gly Arg Phe Thr Ile Ser Arg Asp Asn
385                 390                 395                 400

Ala Lys Arg Thr Val Tyr Leu Gln Met Asn Ser Leu Gln Pro Glu Asp
                405                 410                 415

Thr Ala Val Tyr Tyr Cys His Ala Arg Ile Ile Pro Leu Gly Leu Gly
            420                 425                 430

Ser Glu Tyr Arg Asp His Trp Gly Gln Gly Thr Gln Val Thr Val Ser
        435                 440                 445

Ser Ala His His Ser Glu Asp Pro Ser Ala Arg Gln Gly Ala Pro Val
    450                 455                 460

Pro Tyr Pro Asp Pro Leu Glu Pro Arg Gly Gly Ser Asp Ile Cys
465                 470                 475                 480

Leu Pro Arg Trp Gly Cys Leu Trp Glu Asp
            485                 490

<210> SEQ ID NO 168
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Gln Val Gln Leu Ala Glu Ser Gly Gly
            180                 185                 190

Gly Leu Val Gln Pro Gly Gly Ser Leu Gly Leu Ser Cys Val Val Ala
        195                 200                 205

Ser Glu Arg Ser Ile Asn Asn Tyr Gly Met Gly Trp Tyr Arg Gln Ala
    210                 215                 220

Pro Gly Lys Gln Arg Glu Leu Val Ala Gln Ile Ser Ser Gly Gly Thr
225                 230                 235                 240

Thr Asn Tyr Ala Asp Ser Val Glu Gly Arg Phe Thr Ile Ser Arg Asp
            245                 250                 255

Asn Val Lys Met Val His Leu Gln Val Asn Ser Leu Lys Pro Glu
        260                 265                 270

Asp Thr Ala Val Tyr Tyr Cys Asn Ser Leu Leu Arg Thr Phe Ser Trp
        275                 280                 285

Gly Gln Gly Thr Gln Val Thr Val Ser Ser Glu Pro Lys Thr Pro Lys
            290                 295                 300

Pro Gln Ala Ile Ala Gly Gly Gly Ser Gly Gly Gly Ser Gly
305                 310                 315                 320

Gly Gly Gly Ser Leu Gln Gly Gln Val Gln Leu Ala Glu Ser Gly Gly
            325                 330                 335

Gly Leu Val Gln Ala Gly Gly Ser Leu Arg Leu Ser Cys Ala Ala
        340                 345                 350

Ser Gly Arg Thr Phe Ser Gly Tyr Ala Met Gly Trp Phe Arg Gln Ala
        355                 360                 365

Pro Gly Lys Glu Arg Glu Phe Val Ala Asp Ile Ser Trp Ser Gly His
        370                 375                 380

Asn Thr Tyr Tyr Gly Asp Ser Val Lys Gly Arg Phe Thr Ile Ser Arg
385                 390                 395                 400

Asp Thr Ala Lys Asn Thr Val Tyr Leu Gln Met Asn Ser Leu Lys Pro
            405                 410                 415

Glu Asp Thr Ala Val Tyr Tyr Cys Ala Ala Gly Ala Arg Thr His
        420                 425                 430

Leu Ser Asp Ser Tyr Tyr Phe Pro Gly Leu Trp Ala Glu Pro Pro Val
        435                 440                 445

Gly Tyr Trp Gly Gln Gly Thr Gln Val Thr Val Ser Ser Glu Pro Lys
    450                 455                 460

Thr Pro Lys Pro Gln Pro Ala Arg Gln Gly Ala Pro Val Pro Tyr Pro
465                 470                 475                 480

Asp Pro Leu Glu Pro Arg Gly Gly Ser Asp Ile Cys Leu Pro Arg
            485                 490                 495

Trp Gly Cys Leu Trp Glu Asp
            500

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 169

His His His His His His
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
Ser Gly Ser Ile Ala Arg Pro Gly Ala
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Ile Thr Pro Gly Gly Leu Thr Asn
1               5

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

His Ala Arg Ile Ile Pro Leu Gly Leu Gly Ser Glu Tyr Arg Asp His
1               5                   10                  15

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ser Glu Arg Ser Ile Asn Asn Tyr Gly
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Ile Ser Ser Gly Gly Thr Thr Asn
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asn Ser Leu Leu Arg Thr Phe Ser
1               5

<210> SEQ ID NO 176
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 176

Ser Gly Leu Thr Phe Gly Asn Tyr Ala
1               5

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Ile Ser Arg Ser Gly Ser Asn Thr Trp
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Gly Gly Ser Tyr Asn Ser Asp Trp Trp Asn Tyr Met Tyr
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Gly Arg Thr Phe Ser Gly Tyr Ala
1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Ile Ser Trp Ser Gly His Asn Thr Tyr
1               5                   10

<210> SEQ ID NO 181
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Glu Gly Ala Arg Thr His Leu Ser Asp Ser Tyr Tyr Phe Pro Gly
1               5                   10                  15
```

Leu Trp Ala Glu Pro Pro Val Gly Tyr
            20                  25

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Gly Arg Thr Phe Thr Ser Tyr Tyr
1               5

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ile Gly Trp Thr Asp Asp Asn Thr Tyr
1               5                   10

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ala Asp Tyr Gly Ser Gly Ile Arg Ala Trp Tyr Asn Trp Ile Tyr
1               5                   10                  15

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Gly Ala Thr Leu Asp Thr Tyr Ile Ile
1               5                   10

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Ile Asn Arg Ser Gly Ser Thr Thr
1               5

<210> SEQ ID NO 187
<211> LENGTH: 18
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 187

Ala Ala Asp Ala Ser Tyr Arg Thr Cys Gly Gly Ser Trp Trp Asn Trp
1               5                   10                  15

Ala Tyr

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Gly Phe Thr Phe Ser Ser Tyr Thr
1               5

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Ile Asn Gly Gly Gly Asp Arg Thr Asp
1               5                   10

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Lys Asp Leu Ser Tyr Val Ser Gly Thr Tyr Phe Ala Asn Asp
1               5                   10                  15

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gly Ile Ile Phe Asp Tyr Tyr Ser Val
1               5                   10

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Thr Ile Thr Gly Asp Gly Ser Pro Asn
1               5

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

His Ala Lys Arg Thr Ile Gly Thr Lys Ser Glu Tyr
1               5                   10

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Arg Met Ser Phe Ser Arg Arg Pro
1               5

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Ile Ser Ser Phe Gly Asp Thr Thr Asn
1               5                   10

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asn Thr Leu Leu Ala Thr Tyr Ala
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Gly Arg Thr Phe Ser Ser Tyr Val
1               5

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Ile Ser Arg Asn Gly Gly Lys Thr Tyr
1               5                   10

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Ala Ala Val Ala Ala Ser Ala Glu Phe Val Thr Ala Arg Ser Asn
1               5                   10                  15

Phe Tyr Glu Tyr
            20

<210> SEQ ID NO 200
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T or S
<220> FEATURE:
<221> NAME/KEY: MOD_RES
<222> LOCATION: (5)..(5)
<223> OTHER INFORMATION: G or absent
<220> FEATURE:
<221> NAME/KEY: MOD_RES
<222> LOCATION: (6)..(6)
<223> OTHER INFORMATION: L or S
<220> FEATURE:
<221> NAME/KEY: MOD_RES
<222> LOCATION: (9)..(9)
<223> OTHER INFORMATION: A or P
<220> FEATURE:
<221> NAME/KEY: MOD_RES
<222> LOCATION: (14)..(14)
<223> OTHER INFORMATION: R, S or G
<220> FEATURE:
<221> NAME/KEY: MOD_RES
<222> LOCATION: (15)..(15)
<223> OTHER INFORMATION: L or V
<220> FEATURE:
<221> NAME/KEY: MOD_RES
<222> LOCATION: (18)..(18)
<223> OTHER INFORMATION: A, V, S, T or L

<400> SEQUENCE: 200

Xaa Gly Gly Gly Xaa Xaa Val Gln Xaa Gly Gly Ser Leu Xaa Xaa Ser
1               5                   10                  15

Cys Xaa

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, T, S or D

```
<220> FEATURE:
<221> NAME/KEY: MOD_RES
<222> LOCATION: (3)..(3)
<223> OTHER INFORMATION: F, Y or V
<220> FEATURE:
<221> NAME/KEY: MOD_RES
<222> LOCATION: (6)..(6)
<223> OTHER INFORMATION: A or E
<220> FEATURE:
<221> NAME/KEY: MOD_RES
<222> LOCATION: (10)..(10)
<223> OTHER INFORMATION: E, Q or G
<220> FEATURE:
<221> NAME/KEY: MOD_RES
<222> LOCATION: (11)..(11)
<223> OTHER INFORMATION: R or I
<220> FEATURE:
<221> NAME/KEY: MOD_RES
<222> LOCATION: (13)..(13)
<223> OTHER INFORMATION: F, L, A, W or R

<400> SEQUENCE: 201

Xaa Trp Xaa Arg Gln Xaa Pro Gly Lys Xaa Xaa Glu Xaa Val
1               5                   10

<210> SEQ ID NO 202
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: G, A, S or T
<220> FEATURE:
<221> NAME/KEY: MOD_RES
<222> LOCATION: (3)..(3)
<223> OTHER INFORMATION: D or E
<220> FEATURE:
<221> NAME/KEY: MOD_RES
<222> LOCATION: (4)..(4)
<223> OTHER INFORMATION: S or P
<220> FEATURE:
<221> NAME/KEY: MOD_RES
<222> LOCATION: (5)..(5)
<223> OTHER INFORMATION: V or L
<220> FEATURE:
<221> NAME/KEY: MOD_RES
<222> LOCATION: (6)..(6)
<223> OTHER INFORMATION: K, T or E
<220> FEATURE:
<221> NAME/KEY: MOD_RES
<222> LOCATION: (10)..(10)
<223> OTHER INFORMATION: T or A
<220> FEATURE:
<221> NAME/KEY: MOD_RES
<222> LOCATION: (15)..(15)
<223> OTHER INFORMATION: T, N or G
<220> FEATURE:
<221> NAME/KEY: MOD_RES
<222> LOCATION: (16)..(16)
<223> OTHER INFORMATION: A, V, D or T
<220> FEATURE:
<221> NAME/KEY: MOD_RES
<222> LOCATION: (17)..(17)
<223> OTHER INFORMATION: K, E, Q or R
<220> FEATURE:
<221> NAME/KEY: MOD_RES
<222> LOCATION: (18)..(18)
<223> OTHER INFORMATION: N, R, K or T
<220> FEATURE:
<221> NAME/KEY: MOD_RES
<222> LOCATION: (19)..(19)
<223> OTHER INFORMATION: T, A or M
<220> FEATURE:
```

```
<221> NAME/KEY: MOD_RES
<222> LOCATION: (20)..(20)
<223> OTHER INFORMATION: V, L, A or M
<220> FEATURE:
<221> NAME/KEY: MOD_RES
<222> LOCATION: (21)..(21)
<223> OTHER INFORMATION: Y or H
<220> FEATURE:
<221> NAME/KEY: MOD_RES
<222> LOCATION: (24)..(24)
<223> OTHER INFORMATION: M or V
<220> FEATURE:
<221> NAME/KEY: MOD_RES
<222> LOCATION: (25)..(25)
<223> OTHER INFORMATION: N or S
<220> FEATURE:
<221> NAME/KEY: MOD_RES
<222> LOCATION: (26)..(26)
<223> OTHER INFORMATION: S or G
<220> FEATURE:
<221> NAME/KEY: MOD_RES
<222> LOCATION: (28)..(28)
<223> OTHER INFORMATION: K, Q or N
<220> FEATURE:
<221> NAME/KEY: MOD_RES
<222> LOCATION: (30)..(30)
<223> OTHER INFORMATION: E or D
<220> FEATURE:
<221> NAME/KEY: MOD_RES
<222> LOCATION: (31)..(31)
<223> OTHER INFORMATION: D or E
<220> FEATURE:
<221> NAME/KEY: MOD_RES
<222> LOCATION: (34)..(34)
<223> OTHER INFORMATION: V or I

<400> SEQUENCE: 202

Tyr Xaa Xaa Xaa Xaa Xaa Gly Arg Phe Xaa Ile Ser Arg Asp Xaa Xaa
1               5                   10                  15

Xaa Xaa Xaa Xaa Xaa Leu Gln Xaa Xaa Xaa Leu Xaa Pro Xaa Xaa Thr
            20                  25                  30

Ala Xaa Tyr Tyr
        35

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gln Gly Thr Gln Val Thr Val Ser Ser
1               5                   10

<210> SEQ ID NO 204
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Gly Gly Gly Gly Leu Val Gln Ala Gly Gly Ser Leu Arg Leu Ser
1               5                   10                  15

Cys Ala

<210> SEQ ID NO 205
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Trp Phe Arg Gln Ala Pro Gly Lys Glu Arg Glu Phe Val
1               5                   10

<210> SEQ ID NO 206
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Tyr Gly Asp Ser Val Lys Gly Arg Phe Thr Ile Ser Arg Asp Thr Ala
1               5                   10                  15

Lys Asn Thr Val Tyr Leu Gln Met Asn Ser Leu Lys Pro Glu Asp Thr
            20                  25                  30

Ala Val Tyr Tyr
        35

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Gly Gly Gly Leu Val Gln Pro Gly Gly Ser Leu Ser Val Ser Cys
1               5                   10                  15

Ala

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Gly Gly Gly Leu Val Gln Pro Gly Gly Ser Leu Gly Leu Ser Cys
1               5                   10                  15

Val

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Gly Gly Gly Leu Val Gln Ala Gly Gly Ser Leu Arg Leu Ser Cys
1               5                   10                  15

Ser
```

```
<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Gly Gly Gly Leu Val Gln Ala Gly Gly Thr Leu Arg Leu Ser Cys
1               5                   10                  15

Ala

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Gly Gly Gly Leu Val Gln Pro Gly Gly Ser Leu Arg Leu Ser Cys
1               5                   10                  15

Ala

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Gly Gly Gly Ser Val Gln Pro Gly Gly Ser Leu Arg Leu Ser Cys
1               5                   10                  15

Ala

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Gly Gly Gly Leu Val Gln Pro Gly Gly Ser Leu Arg Leu Ser Cys
1               5                   10                  15

Thr

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Gly Gly Gly Leu Val Gln Ala Gly Gly Ser Leu Arg Leu Ser Cys
1               5                   10                  15
```

Leu

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Gly Gly Gly Leu Val Gln Ala Gly Gly Ser Leu Arg Leu Ser Cys
1               5                   10                  15

Ala

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Trp Tyr Arg Gln Ala Pro Gly Lys Glu Arg Glu Leu Val
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Trp Tyr Arg Gln Ala Pro Gly Lys Gln Arg Glu Leu Val
1               5                   10

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Trp Phe Arg Gln Glu Pro Gly Lys Glu Arg Glu Phe Val
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Trp Phe Arg Gln Ala Pro Gly Lys Glu Arg Glu Ala Val
1               5                   10

<210> SEQ ID NO 220
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 220

Ser Trp Val Arg Gln Ala Pro Gly Lys Gly Ile Glu Trp Val
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asp Trp Tyr Arg Gln Ala Pro Gly Lys Glu Arg Glu Leu Val
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Trp Tyr Arg Gln Ala Pro Gly Lys Gln Arg Glu Arg Val
1               5                   10

<210> SEQ ID NO 223
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Tyr Ala Asp Ser Val Thr Gly Arg Phe Thr Ile Ser Arg Asp Asn Ala
1               5                   10                  15

Lys Arg Thr Val Tyr Leu Gln Met Asn Ser Leu Gln Pro Glu Asp Thr
                20                  25                  30

Ala Val Tyr Tyr
        35

<210> SEQ ID NO 224
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Tyr Ala Asp Ser Val Glu Gly Arg Phe Thr Ile Ser Arg Asp Asn Val
1               5                   10                  15

Lys Lys Met Val His Leu Gln Val Asn Ser Leu Lys Pro Glu Asp Thr
                20                  25                  30

Ala Val Tyr Tyr
        35

<210> SEQ ID NO 225
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Tyr Ala Glu Pro Leu Lys Gly Arg Phe Ala Ile Ser Arg Asp Asn Asp
1               5                   10                  15

Lys Asn Ala Leu Tyr Leu Gln Met Asn Ser Leu Lys Pro Glu Asp Thr
            20                  25                  30

Ala Val Tyr Tyr
        35

<210> SEQ ID NO 226
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Tyr Ala Asp Ser Val Lys Gly Arg Phe Thr Ile Ser Arg Asp Asn Ala
1               5                   10                  15

Glu Thr Thr Ala Tyr Leu Gln Asn Ser Gly Leu Lys Pro Glu Asp Thr
            20                  25                  30

Ala Val Tyr Tyr
        35

<210> SEQ ID NO 227
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Tyr Ser Asp Ser Val Lys Gly Arg Phe Thr Ile Ser Arg Asp Asn Ala
1               5                   10                  15

Gln Lys Thr Val Tyr Leu Gln Met Asn Ser Leu Asn Pro Glu Asp Thr
            20                  25                  30

Ala Ile Tyr Tyr
        35

<210> SEQ ID NO 228
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Tyr Ala Asp Ser Val Lys Gly Arg Phe Thr Ile Ser Arg Asp Asn Ala
1               5                   10                  15

Arg Asn Thr Leu Tyr Leu Gln Met Asn Ser Leu Gln Pro Glu Asp Thr
            20                  25                  30

Ala Val Tyr Tyr
        35
```

```
<210> SEQ ID NO 229
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Tyr Ala Asp Ser Val Lys Gly Arg Phe Thr Ile Ser Arg Asp Asn Ala
1               5                   10                  15

Lys Lys Thr Val Tyr Leu Gln Met Asn Gly Leu Lys Pro Glu Glu Thr
            20                  25                  30

Ala Val Tyr Tyr
            35

<210> SEQ ID NO 230
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Tyr Thr Asp Ser Val Glu Gly Arg Phe Thr Ile Ser Arg Asp Asn Ala
1               5                   10                  15

Lys Asn Thr Met Tyr Leu Gln Met Asn Ser Leu Lys Pro Asp Asp Thr
            20                  25                  30

Ala Val Tyr Tyr
            35

<210> SEQ ID NO 231
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Tyr Ala Asp Ser Val Lys Gly Arg Phe Thr Ile Ser Arg Asp Gly Thr
1               5                   10                  15

Glu Asn Thr Val Tyr Leu Gln Met Asn Ser Leu Lys Pro Glu Asp Thr
            20                  25                  30

Ala Val Tyr Tyr
            35

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Gly Ser Ser Phe Ser Arg Tyr Ala
1               5

<210> SEQ ID NO 233
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 233

Ser Gly Phe Ile Phe Ser Leu Tyr Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Gly Ile Ile Phe Ser Ile Tyr Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Gly Leu Thr Phe Ser Ser Thr Ala
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Arg Ser Thr Thr Ala Thr Ile Tyr Ser
1               5                   10

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Pro Glu Ser Ile Val Asn Ser Arg Thr
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Gly Phe Thr Phe Ser Ser Tyr Arg
1               5

```
<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Gly Val Ile Phe Ser Ile Tyr Thr
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ser Gly Arg Tyr Ala
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asn Ile Asn Ser Arg Gly Thr Ser Asn
1               5

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Thr Ile Thr Ser Ala Thr Gly Ile Thr Asn
1               5                   10

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Ile Pro Ser Gly Pro Ser Ala Asn
1               5

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244
```

```
Arg Ile Ser Gly Ala Gly Ile Thr Ile Tyr
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Met Thr Ser Asp Gly Gln Thr Asn
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Ile Thr Thr Ala Gly Ser Pro Asn
1               5

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Ile Thr Ala Asn Gly Val Pro Thr Gly
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Ile Gly Val Ala Asp Gly Thr Ala Leu
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Ile Ser Arg Ser Gly Ala Ile Arg Glu
1               5                   10

<210> SEQ ID NO 250
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 250

Asn Ala Glu Trp Leu Gly Arg Ser Glu Pro Ser
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asn Ala Val Arg Thr Thr Val Ser Arg Asp Tyr
1               5                   10

<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asn Ala Arg Arg Gly Pro Gly Ile Lys Asn Tyr
1               5                   10

<210> SEQ ID NO 253
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ala Ala Arg Arg Asn Thr Tyr Thr Ser Asp Tyr Asn Ile Pro Ala Arg
1               5                   10                  15

Tyr Pro Tyr

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Tyr Val Lys Pro Trp Arg Leu Gln Gly Trp Asp Tyr
1               5                   10

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asn Thr Leu Leu Ser Thr Leu Pro
```

```
<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asn Ala Pro Arg Leu His Thr Ser Val Gly Tyr
1               5                   10

<210> SEQ ID NO 257
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ala Ala Tyr Leu Ser Pro Arg Val Gln Ser Pro Tyr Ile Thr Asp Ser
1               5                   10                  15

Arg Tyr Gln Leu
            20

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Glu Gly Arg Gly Ala Thr Phe Asn Pro Glu Tyr Ala Tyr
1               5                   10

<210> SEQ ID NO 259
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Ala Glu Gly Ala Arg Thr His Leu Ser Asp Ser Tyr Tyr Phe Pro
1               5                   10                  15

Gly Leu Trp Ala Glu Pro Pro Val Gly Tyr
            20                  25
```